(12) United States Patent
Doyon

(10) Patent No.: US 12,378,549 B2
(45) Date of Patent: Aug. 5, 2025

(54) CRISPR-cas9 SYSTEM AND USES THEREOF

(71) Applicant: UNIVERSITÉ LAVAL, Québec (CA)

(72) Inventor: Yannick Doyon, Québec (CA)

(73) Assignee: UNIVERSITÉ LAVAL, Quebec (CA)

( * ) Notice: Subject to any disclaimer, the term of this patent is extended or adjusted under 35 U.S.C. 154(b) by 1031 days.

(21) Appl. No.: 17/054,008

(22) PCT Filed: May 10, 2019

(86) PCT No.: PCT/CA2019/050629
§ 371 (c)(1),
(2) Date: Nov. 9, 2020

(87) PCT Pub. No.: WO2019/213776
PCT Pub. Date: Nov. 14, 2019

(65) Prior Publication Data
US 2022/0119809 A1    Apr. 21, 2022

Related U.S. Application Data

(60) Provisional application No. 62/670,135, filed on May 11, 2018.

(51) Int. Cl.
*C12N 15/11* (2006.01)
*C12N 9/22* (2006.01)

(52) U.S. Cl.
CPC ............. *C12N 15/111* (2013.01); *C12N 9/22* (2013.01); *C12N 2310/122* (2013.01); *C12N 2310/20* (2017.05)

(58) Field of Classification Search
None
See application file for complete search history.

(56) References Cited

U.S. PATENT DOCUMENTS

2016/0355797 A1   12/2016  Konermann et al.
2017/0121693 A1*   5/2017  Liu ........................... A61P 3/00

FOREIGN PATENT DOCUMENTS

EP          3705490 B1    3/2024
WO      2016/089433 A1    6/2016

OTHER PUBLICATIONS

Nishimasu et al. Crystal Structure of *Staphylococcus aureus* Cas9. Cell. Aug. 27, 2015; 162(5):1113-26. (Year: 2015).*
Chimeric. NCI Dictionary of Cancer Terms. National Cancer Institute (accessed at: https://web.archive.org/web/20180423080722/ https://www.cancer.gov/publications/dictionaries/cancer-terms/def/chimeric) (Year: 2018).*

(Continued)

*Primary Examiner* — Marcia S Noble
*Assistant Examiner* — Briana N Ebbinghaus
(74) *Attorney, Agent, or Firm* — Lavery, de Billy, L.L.P.; S. Serge Shahinian

(57) ABSTRACT

Methods and products are described herein for the modification of nucleic acids using a CRISPR/Cas9 system. Also described herein are uses of such methods and products for the modification of a target nucleic acid in a cell, in vitro or in vivo. Such methods and products may also be used for prevention or treatment of a condition associated with a target polynucleotide.

6 Claims, 50 Drawing Sheets
Specification includes a Sequence Listing.

(56) References Cited

OTHER PUBLICATIONS

Derived. Dictionary.com (accessed at https://www.dictionary.com/browse/derived on Aug. 1, 2024) (Year: 2024).*
Komor, A.C., Badran, A.H. & Liu, D.R. CRISPR-Based Technologies for the Manipulation of Eukaryotic Genomes. Cell 169, 559 (2017).
Jinek, M. et al. A programmable dual-RNA-guided DNA endonuclease in adaptive bacterial immunity. Science 337, 816-821 (2012).
Koonin, E.V., Makarova, K.S. & Zhang, F. Diversity, classification and evolution of CRISPR-Cas systems. Curr Opin Microbiol 37, 67-78 (2017).
Shmakov, S. et al. Diversity and evolution of class 2 CRISPR-Cas systems. Nat Rev Microbiol 15, 169-182 (2017).
Hille, F. et al. The Biology of CRISPR-Cas: Backward and Forward. Cell 172, 1239-1259 (2018).
Esvelt, K.M. et al. Orthogonal Cas9 proteins for RNA-guided gene regulation and editing. Nat Methods 10, 1116-1121 (2013).
Ran, F.A. et al. In vivo genome editing using *Staphylococcus aureus* Cas9. Nature 520, 186-191 (2015).
Chen, F. et al. Targeted activation of diverse CRISPR-Cas systems for mammalian genome editing via proximal CRISPR targeting. Nat Commun 8, 14958 (2017).
Anderson, E.M. et al. Lactobacillus gasseri CRISPR-Cas9 characterization In Vitro reveals a flexible mode of protospacer-adjacent motif recognition. PLoS One 13, e0192181 (2018).
Zetsche, B. et al. Cpf1 is a single RNA-guided endonuclease of a class 2 CRISPR-Cas system. Cell 163, 759-771 (2015).
Colella, P., Ronzitti, G. & Mingozzi, F. Emerging Issues in AAV-Mediated In Vivo Gene Therapy. Mol Ther Methods Clin Dev 8, 87-104 (2018).
Friedland, A.E. et al. Characterization of *Staphylococcus aureus* Cas9: a smaller Cas9 for all-in-one adeno-associated virus delivery and paired nickase applications. Genome Biol 16, 257 (2015).
Kim, E. et al. In vivo genome editing with a small Cas9 orthologue derived from Campylobacter jejuni. Nat Commun 8, 14500 (2017).
Ibraheim, R. et al. All-in-One Adeno-associated Virus Delivery and Genome Editing by Neisseria meningitidis Cas9 in vivo. bioRxiv (2018).
Mir, A., Edraki, A., Lee, J. & Sontheimer, E.J. Type II-C CRISPR-Cas9 Biology, Mechanism, and Application. ACS Chem Biol 13, 357-365 (2018).
Anguela, X.M. et al. Robust ZFN-mediated genome editing in adult hemophilic mice. Blood 122, 3283-3287 (2013).
Li, H. et al. In vivo genome editing restores haemostasis in a mouse model of haemophilia. Nature 475, 217-221 (2011).
Sharma, R. et al. In vivo genome editing of the albumin locus as a platform for protein replacement therapy. Blood 126, 1777-1784 (2015).
Nami, F. et al. Strategies for In Vivo Genome Editing in Nondividing Cells. Trends Biotechnol (2018).
He Z, Proudfoot C, Mileham A, J., McLaren DG, Whitelaw BA, Lillico SG. Highly efficient targeted chromosome deletions using CRISPR/Cas9. Biotechnology and Bioengineering. 112(5): 1060-4 (2015).
Byrne SM, Ortiz L, Mali P, Aach J, Church GM. Multi-kilobase homozygous targeted gene replacement in human induced pluripotent stem cells. Nucleic Acids Res. 43(3):e21 (2015).
Schneller, J.L., Lee, C.M., Bao, G. & Venditti, C.P. Genome editing for inborn errors of metabolism: advancing towards the clinic. BMC Med 15, 43 (2017).
Au, C.H. & Suh, Y. In vivo genome editing in animals using AAV-CRISPR system: applications to translational research of human disease. F1000Res 6, 2153 (2017).
Bolotin, A. et al. Complete sequence and comparative genome analysis of the dairy bacterium *Streptococcus thermophilus*. Nat Biotechnol 22, 1554-1558 (2004).
Barrangou, R. & Horvath, P. A decade of discovery: CRISPR functions and applications. Nat Microbiol 2, 17092 (2017).
Bolotin, A., Quinquis, B., Sorokin, A. & Ehrlich, S.D. Clustered regularly interspaced short palindrome repeats (CRISPRs) have spacers of extrachromosomal origin. Microbiology 151, 2551-2561 (2005).
Barrangou, R. et al. CRISPR provides acquired resistance against viruses in prokaryotes. Science 315, 1709-1712 (2007).
Horvath, P. et al. Diversity, activity, and evolution of CRISPR loci in *Streptococcus thermophilus*. J Bacteriol 190, 1401-1412 (2008).
Deveau, H. et al. Phage response to CRISPR-encoded resistance in *Streptococcus thermophilus*. J Bacteriol 190, 1390-1400 (2008).
Garneau, J.E. et al. The CRISPR/Cas bacterial immune system cleaves bacteriophage and plasmid DNA. Nature 468, 67-71 (2010).
Briner, A.E. et al. Guide RNA functional modules direct Cas9 activity and orthogonality. Mol Cell 56, 333-339 (2014).
Hynes, A.P. et al. An anti-CRISPR from a virulent *Streptococcal phage* inhibits *Streptococcus pyogenes* Cas9. Nat Microbiol 2, 1374-1380 (2017).
Chari, R., Mali, P., Moosburner, M. & Church, G.M. Unraveling CRISPR-Cas9 genome engineering parameters via a library-on-library approach. Nat Methods 12, 823-826 (2015).
Kleinstiver, B.P. et al. Engineered CRISPR-Cas9 nucleases with altered PAM specificities. Nature 523, 481-485 (2015).
Agudelo, D. et al. Marker-free coselection for CRISPR-driven genome editing in human cells. Nat Methods 14, 615-620 (2017).
Dalvai, M. et al. A Scalable Genome-Editing-Based Approach for Mapping Multiprotein Complexes in Human Cells. Cell Rep 13, 621-633 (2015).
Guschin, D.Y. et al. A rapid and general assay for monitoring endogenous gene modification. Methods Mol Biol 649, 247-256 (2010).
Brinkman, E.K., Chen, T., Amendola, M. & van Steensel, B. Easy quantitative assessment of genome editing by sequence trace decomposition. Nucleic Acids Res 42, e168 (2014).
Haeussler, M. et al. Evaluation of off-target and on-target scoring algorithms and integration into the guide RNA selection tool CRISPOR. Genome Biol 17, 148 (2016).
Tomoeda, K. et al. Mutations in the 4-hydroxyphenylpyruvic acid dioxygenase gene are responsible for tyrosinemia type III and hawkinsinuria. Mol Genet Metab 71, 506-510 (2000).
Ruetschi, U. et al. Mutations in the 4-hydroxyphenylpyruvate dioxygenase gene (HPD) in patients with tyrosinemia type II. Hum Genet 106, 654-662 (2000).
Russell, S. et al. Efficacy and safety of voretigene neparvovec (AAV2-hRPE65v2) in patients with RPE65-mediated Inherited retinal dystrophy: a randomised, controlled, open-label, phase 3 trial. Lancet 390, 849-860 (2017).
George, L.A. et al. Hemophilia B Gene Therapy with a High-Specific-Activity Factor IX Variant. N Engl J Med 377, 2215-2227 (2017).
Nathwani, A.C. et al. Long-term safety and efficacy of factor IX gene therapy in hemophilia B. N Engl J Med 371, 1994-2004 (2014).
McKay, T.R. et al. Perinatal gene transfer to the liver. Curr Pharm Des 17, 2528-2541 (2011).
Wang, L. et al. AAV8-mediated hepatic gene transfer in infant rhesus monkeys (*Macaca mulatta*). Mol Ther 19, 2012-2020 (2011).
Wang, L., Wang, H., Bell, P., McMenamin, D. & Wilson, J.M. Hepatic gene transfer in neonatal mice by adeno-associated virus serotype 8 vector. Hum Gene Ther 23, 533-539 (2012).
Yang, Y. et al. A dual AAV system enables the Cas9-mediated correction of a metabolic liver disease in newborn mice. Nat Biotechnol 34, 334-338 (2016).
Morrow, G. & Tanguay, R.M. Biochemical and Clinical Aspects of Hereditary Tyrosinemia Type 1. Adv Exp Med Biol 959, 9-21 (2017).
Grompe, M. Fah Knockout Animals as Models for Therapeutic Liver Repopulation. Adv Exp Med Biol 959, 215-230 (2017).
Endo, F. et al. Complete rescue of lethal albino c14COS mice by null mutation of 4-hydroxyphenylpyruvate dioxygenase and induction of apoptosis of hepatocytes in these mice by in vivo retrieval of the tyrosine catabolic pathway. J Biol Chem 272, 24426-24432 (1997).

(56) References Cited

OTHER PUBLICATIONS

Pankowicz, F.P. et al. Reprogramming metabolic pathways in vivo with CRISPR/Cas9 genome editing to treat hereditary tyrosinaemia. Nat Commun 7, 12642 (2016).
Nathwani, A.C. et al. Self-complementary adeno-associated virus vectors containing a novel liver-specific human factor X expression cassette enable highly efficient transduction of murine and nonhuman primate liver. Blood 107, 2653-2661 (2006).
McIntosh, J. et al. Therapeutic levels of FVIII following a single peripheral vein administration of rAAV vector encoding a novel human factor VIII variant. Blood 121, 3335-3344 (2013).
Pawluk, A., Davidson, A.R. & Maxwell, K.L. Anti-CRISPR: discovery, mechanism and function. Nat Rev Microbiol 16, 12-17 (2018).
Shin, J. et al. Disabling Cas9 by an anti-CRISPR DNA mimic. Sci Adv 3, e1701620 (2017).
Rauch, B.J. et al. Inhibition of CRISPR-Cas9 with Bacteriophage Proteins. Cell 168, 150-158 e110 (2017).
Rousseau, B.A., Hou, Z., Gramelspacher, M.J. & Zhang, Y. Programmable RNA Cleavage and Recognition by a Natural CRISPR-Cas9 System from Neisseria meningitidis. Mol Cell 69, 906-914 e904 (2018).
Strutt, S.C., Torrez, R.M., Kaya, E., Negrete, O.A. & Doudna, J.A. RNA-dependent RNA targeting by CRISPR-Cas9. Elife 7 (2018).
Zhang, Y., Rajan, R., Seifert, H.S., Mondragon, A. & Sontheimer, E.J. DNase H Activity of Neisseria meningitidis Cas9. Mol Cell 60, 242-255 (2015).
Stephenson, A.A., Raper, A.T. & Suo, Z. Bidirectional Degradation of DNA Cleavage Products Catalyzed by CRISPR/Cas9. J Am Chem Soc 140, 3743-3750 (2018).
Ma, E., Harrington, L.B., O'Connell, M.R., Zhou, K. & Doudna, J.A. Single-Stranded DNA Cleavage by Divergent CRISPR-Cas9 Enzymes. Mol Cell 60, 398-407 (2015).
Dugar, G. et al. CRISPR RNA-Dependent Binding and Cleavage of Endogenous RNAs by the Campylobacter jejuni Cas9. Mol Cell 69, 893-905 e897 (2018).
Chen, J.S. et al. CRISPR-Cas12a target binding unleashes indiscriminate single-stranded DNase activity. Science (2018).
Boettcher, M. et al. Dual gene activation and knockout screen reveals directional dependencies in genetic networks. Nat Biotechnol 36, 170-178 (2018).
Fonfara, I. et al. Phylogeny of Cas9 determines functional exchangeability of dual-RNA and Cas9 among orthologous type II CRISPR-Cas systems. Nucleic Acids Res 42, 2577-2590 (2014).
Goudy, K.S., Annoni, A., Naldini, L. & Roncarolo, M.G. Manipulating Immune Tolerance with Micro-RNA Regulated Gene Therapy. Frontiers in microbiology 2, 221 (2011).
Charlesworth, C.T. et al. Identification of Pre-Existing Adaptive Immunity to Cas9 Proteins in Humans. bioRxiv (2018).
Moreno, A.M. et al. Exploring protein orthogonality in immune space: a case study with AAV and Cas9 orthologs. bioRxiv (2018).
Wagner, D.L. et al. High prevalence of S. pyogenes Cas9-specific T cell sensitization within the adult human population—A balanced effector/regulatory T cell response. bioRxiv (2018).
Chew, W.L. et al. A multifunctional AAV-CRISPR-Cas9 and its host response. Nat Methods 13, 868-874 (2016).
Muller, M. et al. *Streptococcus thermophilus* CRISPR-Cas9 Systems Enable Specific Editing of the Human Genome. Mol Ther 24, 636-644 (2016).
Karvelis, T., Gasiunas, G. & Siksnys, V. Methods for decoding Cas9 protospacer adjacent motif (PAM) sequences: A brief overview. Methods 121-122, 3-8 (2017).
Leenay, R.T. & Beisel, C.L. Deciphering, Communicating, and Engineering the CRISPR PAM. J Mol Biol 429, 177-191 (2017).
Rock, J.M. et al. Programmable transcriptional repression in mycobacteria using an orthogonal CRISPR interference platform. Nat Microbiol 2, 16274 (2017).
Makarova, K. et al. Comparative genomics of the lactic acid bacteria. Proc Natl Acad Sci U S A 103, 15611-15616 (2006).
Chen, H., Choi, J. & Bailey, S. Cut site selection by the two nuclease domains of the Cas9 RNA-guided endonuclease. J Biol Chem 289, 13284-13294 (2014).
Hu, J.H. et al. Evolved Cas9 variants with broad PAM compatibility and high DNA specificity. Nature 556, 57-63 (2018).
Kleinstiver, B.P. et al. Broadening the targeting range of *Staphylococcus aureus* CRISPR-Cas9 by modifying PAM recognition. Nat Biotechnol 33, 1293-1298 (2015).
Chatterjee, P., Jakimo, N. & Jacobson, J.M. Divergent PAM Specificity of a Highly-Similar SpCas9 Ortholog. bioRxiv (2018).
Gray, S.J. et al. Production of recombinant adeno-associated viral vectors and use in in vitro and in vivo administration Curr Protoc Neurosci Chapter 4, Unit 4 17 (2011).
Aurnhammer, C. et al. Universal real-time PCR for the detection and quantification of adeno-associated virus serotype 2-derived inverted terminal repeat sequences. Hum Gene Ther Methods 23, 18-28 (2012).
Grompe, M. et al. Loss of fumarylacetoacetate hydrolase is responsible for the neonatal hepatic dysfunction phenotype of lethal albino mice. Genes Dev 7, 2298-2307 (1993).
Yardeni, T., Eckhaus, M., Morris, H.D., Huizing, M. & Hoogstraten-Miller, S. Retro-orbital injections in mice. Lab Anim (NY) 40, 155-160 (2011).
Cyr, D., Giguere, R., Villain, G., Lemieux, B. & Drouin, R. A GC/MS validated method for the nanomolar range determination of succinylacetone in amniotic fluid and plasma: an analytical tool for tyrosinemia type I. J Chromatogr B Analyt Technol Biomed Life Sci 832, 24-29 (2006).
Chatterjee, P., Jakimo, N. & Jacobson, J.M. Minimal PAM specificity of a highly similar SpCas9 ortholog. Sci Adv 4, eaau0766 (2018).
International Search Report and Written Opinion dated Aug. 9, 2019 in respect of PCT/CA2019/050629.
International Preliminary Report on Patentability dated Nov. 17, 2020 in respect of PCT/CA2019/050629.
Ma et al., Engineer chimeric Cas9 to expand PAM recognition based on evolutionary information, Nature Communications 10(1): 1-9 (2019).

* cited by examiner

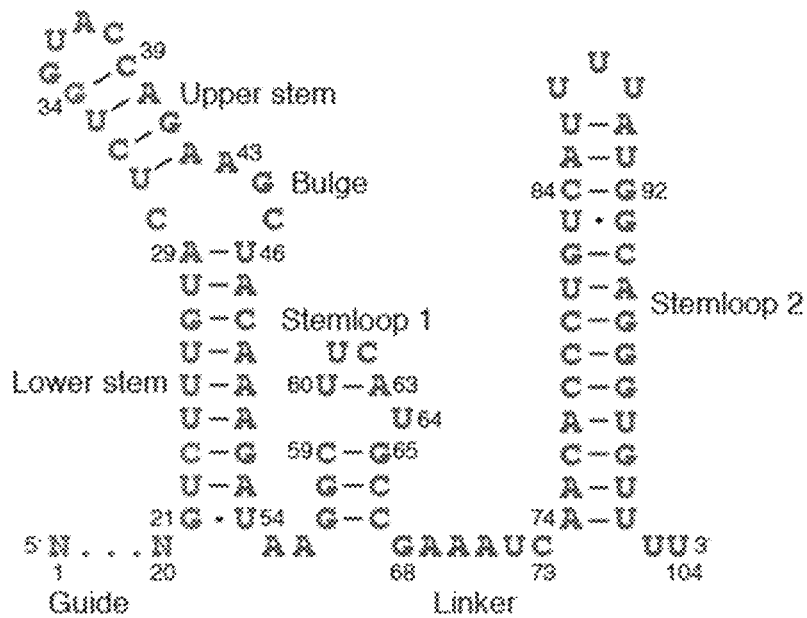
FIGs. 1a-1c b c d a

*Hpd* exon 8 (G2)

TGGCCGTTTCTTACCTGGATTCGAGGCCCCAACATACAAGGATACC
 G   R   F   L   P   G   F   E   A   P   T   Y   K   D   T
ACCGGCAAAGAATGGACCTAAGCTCCGGGGTTGTATGTTCCTATGG
     NAAGAAN      Target (20 bp)

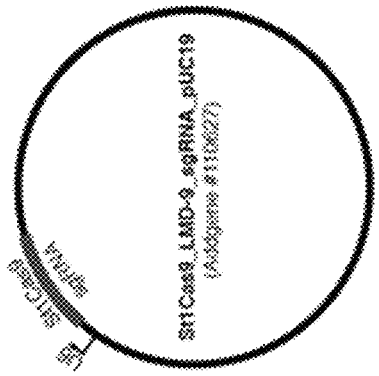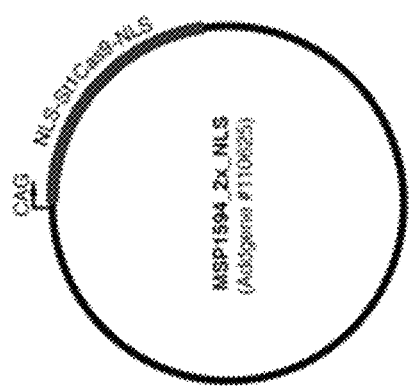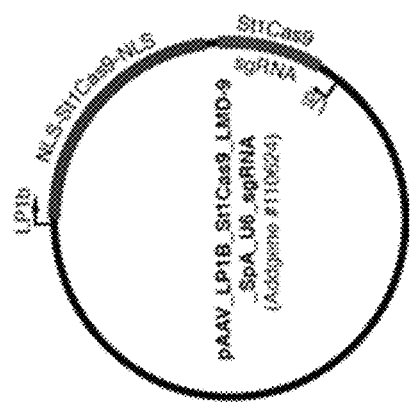
FIG. 11

| FANCF | | | | |
|---|---|---|---|---|
| | Editing efficacy (%) | | | |
| sgRNA | Dose (ng) | | | |
| | ctrl (-) | 50 | 100 | 250 |
| v0 | 0 | 4 | 7 | 22 |
| v1 | 0 | 21 | 38 | 67 |

FIG. 12

| EMX1 | | | | |
|---|---|---|---|---|
| | Editing efficacy (%) | | | |
| sgRNA | Dose (ng) | | | |
| | ctrl (-) | 50 | 100 | 250 |
| v0 | 0 | 4 | 7 | 32 |
| v1 | 0 | 40 | 54 | 85 |

FIG. 13

| RUNX1 | | | | |
|---|---|---|---|---|
| | Editing efficacy (%) | | | |
| sgRNA | Dose (ng) | | | |
| | ctrl (-) | 50 | 100 | 250 |
| v0 | 0 | 12 | 22 | 53 |
| v1 | 0 | 66 | 76 | 90 |

FIG. 14

| Target | sgRNA | | |
|---|---|---|---|
| | ctrl (-) | v0 | v1 |
| EMX1 | 0 | 24 | 62 |
| FANCF | 0 | 16 | 34 |
| RUNX1 | 0 | 30 | 81 |

FIG. 15

St1Cas9 (LMD-9) DNA
<u>SV40 NLS</u>
*ST1CAS9 SEQUENCE*
linkers

ATGggcgccCCAAAGAAGAAGCGGAAGGTCggtatccacggagtcccagcagccAGCGACCTGGTGCTGGGCCTGGACAT
CGGCATCGGCAGCGTGGGCGTGGGCATCCTGAACAAGGTGACCGGCGAGATCATCCACAAGAACAGTCGCATCTTCCCTG
CTGCTCAGGCTGAGAACAACCTGGTGCGCCGCACCAACCGCCAGGGTCGCCGGCTTGCTCGCCGCAAGAAGCACCGGCGC
GTGCGCCTGAACCGCCTGTTCGAGGAGAGCGGCCTGATCACCGACTTCACCAAGATCAGCATCAACCTGAACCCCTACCA
GCTGCGCGTGAAGGGCCTGACCGACGAGCTGAGCAACGAGGAGCTGTTCATCGCCCTGAAGAACATGGTGAAGCACCGCG
GCATCAGCTACCTGGACGACGCCAGCGACGACGGCAACAGCAGCGTGGGCGACTACGCCCAGATCGTGAAGGAGAACAGC
AAGCAGCTGGAGACCAAGACCCCCGGCCAGATCCAGCTGGAGCGCTACCAGACCTACGGCCAGCTGCGCGGCGACTTCAC
CGTGGAGAAGGACGGCAAGAAGCACCGCCTGATCAACGTGTTCCCCACCAGCGCCTACCGCAGCGAGGCCCTGCGCATCC
TGCAGACCCAGCAGGAGTTCAACCCCCAGATCACCGACGAGTTCATCAACCGCTACCTGGAGATCCTGACCGGCAAGCGC
AAGTACTACCACGGCCCCGGCAACGAGAAGAGCCGCACCGACTACGGCCGCTACCGCACCAGCGGCGAGACCCTGGACAA
CATCTTCGGCATCCTGATCGGCAAGTGCACCTTCTACCCCGACGAGTTCCGCGCCGCCAAGGCCAGCTACACCGCCCAGG
AGTTCAATCTGCTGAACGACCTGAACAACCTGACCGTGCCCACCGAGACCAAGAAGCTGAGCAAGGAGCAGAAGAACCAG
ATCATCAACTACGTGAAGAACGAGAAGGCTATGGGCCCCGCCAAGCTGTTCAAGTACATCGCCAAGCTGCTGAGCTGCGA
CGTGGCCGACATCAAGGGCTACCGCATCGACAAGAGCGGCAAGGCCGAGATCCACACCTTCGAGGCCTACCGCAAGATGA
AGACCCTGGAGACCCTGGACATCGAGCAGATGGACCGAGAGACCCTGGACAAGCTGGCCTACGTGCTGACCCTGAACACC
GAGCGCGAGGGCATCCAGGAGGCCCTGGAGCACGAGTTCGCCGACGGCAGCTTCAGCCAGAAACAGGTGGACGAGCTGGT
GCAGTTCCGCAAGGCCAACAGCAGCATCTTCGGCAAGGGCTGGCACAACTTCAGCGTGAAGCTGATGATGGAGCTGATCC
CCGAGCTGTACGAGACCAGCGAGGAGCAGATGACCATCCTGACCCGCCTGGGCAAGCAGAAGACCACCAGCAGCAGCAAC
AAGACCAAGTACATCGACGAGAAGCTGCTGACCGAGGAGATCTACAACCCCGTGGTGGCCAAGAGCGTGCGCCAGGCCAT
CAAGATCGTGAACGCCGCCATCAAGGAGTACGGCGACTTCGACAACATCGTGATCGAGATGGCCCGCGAGACCAACGAGG
ACGACGAGAAGAAGGCCATCCAGAAGATCCAGAAGGCCAACAAGGACGAGAAGGACGCCGCCATGCTGAAGGCCGCCAAC
CAGTACAACGGCAAGGCCGAGCTGCCCCACAGCGTGTTCCACGGCCACAAGCAGCTGGCCACCAAGATCCGCCTGTGGCA
CCAGCAGGGCGAGCGCTGCCTGTACACCGGCAAGACCATCAGCATCCACGACCTGATCAACAACAGCAACCAGTTCGAGG
TGGACCACATCCTGCCCCTGAGCATCACCTTCGACGACAGCCTGGCCAACAAGGTGCTGGTGTACGCCACCGCCAACCAG
GAGAAGGGCCAGCGCACCCCCTACCAGGCCCTGGACAGCATGGACGACGCCTGGAGCTTCCGCGAGCTGAAGGCCTTCGT
GCGCGAGAGCAAGACCCTGAGCAACAAGAAGAAGGAGTATCTGCTGACCGAGGAGGACATCAGCAAGTTCGACGTGCGCA
AGAAGTTCATCGAGCGCAACCTGGTGGACACCCGCTACGCCAGCCGCGTGGTGCTGAACGCCCTGCAGGAGCACTTCCGC
GCCCACAAGATCGACACCAAGGTGAGCGTGGTGCGCGGCCAGTTCACCAGCCAGCTGCGCCGCCACTGGGGCATCGAGAA
GACCCGCGACACCTACCACCACCACGCCGTGGACGCCCTGATCATTGCGGCTTCTAGCCAGCTGAACCTGTGGAAGAAGC
AGAAGAACACCCTGGTGAGCTACAGCGAGGACCAGCTGCTGGACATCGAGACCGGCGAGCTGATCAGCGACGACGAGTAC
AAGGAGAGCGTGTTCAAGGCCCCCTACCAGCACTTCGTGGACACCCTGAAGAGCAAGGAGTTCGAGGACAGCATCCTGTT
CAGCTACCAGGTGGACAGCAAGTTCAACCGCAAGATCAGCGACGCCACCATCTACGCCACCCGCCAGGCCAAGGTGGGCA
AGGACAAGGCCGACGAGACCTACGTGCTGGGCAAGATCAAGGACATCTACACCCAGGACGGCTACGACGCCTTCATGAAG
ATCTACAAGAAGGACAAGAGCAAGTTCCTGATGTACCGCCACGACCCCAGACCTTCGAGAAGGTGATCGAGCCCATCCT
GGAGAACTACCCCAACAAGCAGATCAACGAGAAAGGCAAGGAGGTGCCCTGCAACCCCTTCCTGAAGTACAAGGAGGAGC
ACGGCTACATCCGCAAGTACAGCAAGAAGGGCAACGGCCCCGAGATCAAGAGCCTGAAGTACTACGACAGCAAGCTGGGC
AACCACATCGACATCACCCCCAAGGACAGCAACAACAAGGTGGTGCTGCAGAGCGTGAGCCCCTGGCGCCGACGTGTA
CTTCAACAAGACCACCGGCAAGTACGAGATCCTGGGGCTGAAGTACGCCGATCTGCAGTTTGAGAAAGGCACAGGCACCT
ACAAGATCAGCCAGGAGAAGTACAACGACATCAAGAAGAAGGAGGGCGTGGACAGCGACAGCGAGTTCAAGTTCACCCTG
TACAAGAACGACCTTCTGCTGGTGAAGGACACCGAGACCAAGGAGCAACAGCTGTTCCGCTTCCTGAGCCGCACCATGCC
CAAGCAGAAGCACTACGTGGAGCTGAAGCCCTACGACAAGCAGAAGTTCGAGGGCGGCGAGGCCCTGATCAAGGTGCTGG
GCAACGTGGCCAACAGCGGCCAGTGCAAGAAGGGCCTGGGCAAGAGCAACATCAGCATCTACAAGGTGCGCACCGACGTG
CTGGGCAACCAGCACATCATCAAGAACGAGGGCGACAAGCCCAAGTTGGACTTCagcagggctgacCCCAAGAAGAAGAG
GAAGGTGTGA

FIG. 16

St1Cas9 (LMD-9) protein

<u>SV40 NLS</u>

*ST1CAS9 SEQUENCE* linkers

Mga<u>PKKKRKV</u>gihgvpaa*SDLVLGLDIGIGSVGVGILNKVTGEIIHKNSRIFPAAQAENNLVRRTNRQGRRLARRKKHRR*

*VRLNRLFEESGLITDFTKISINLNPYQLRVKGLTDELSNEELFIALKNMVKHRGISYLDDASDDGNSSVGDYAQIVKENS*

*KQLETKTPGQIQLERYQTYGQLRGDFTVEKDGKKHRLINVFPTSAYRSEALRILQTQQEFNPQITDEFINRYLEILTGKR*

*KYYHGPGNEKSRTDYGRYRTSGETLDNIFGILIGKCTFYPDEFRAAKASYTAQEFNLLNDLNNLTVPTETKKLSKEQKNQ*

*IINYVKNEKAMGPAKLFKYIAKLLSCDVADIKGYRIDKSGKAEIHTFEAYRKMKTLETLDIEQMDRETLDKLAYVLTLNT*

*EREGIQEALEHEFADGSFSQKQVDELVQFRKANSSIFGKGWHNFSVKLMMELIPELYETSEEQMTILTRLGKQKTTSSSN*

*KTKYIDEKLLTEEIYNPVVAKSVRQAIKIVNAAIKEYGDFDNIVIEMARETNEDDEKKAIQKIQKANKDEKDAAMLKAAN*

*QYNGKAELPHSVFHGHKQLATKIRLWHQQGERCLYTGKTISIHDLINNSNQFEVDHILPLSITFDDSLANKVLVYATANQ*

*EKGQRTPYQALDSMDDAWSFRELKAFVRESKTLSNKKKEYLLTEEDISKFDVRKKFIERNLVDTRYASRVVLNALQEHFR*

*AHKIDTKVSVVRGQFTSQLRRHWGIEKTRDTYHHHAVDALIIAASSQLNLWKKQKNTLVSYSEDQLLDIETGELISDDEY*

*KESVFKAPYQHFVDTLKSKEFEDSILFSYQVDSKFNRKISDATIYATRQAKVGKDKADETYVLGKIKDIYTQDGYDAFMK*

*IYKKDKSKFLMYRHDPQTFEKVIEPILENYPNKQINEKGKEVPCNPFLKYKEEHGYIRKYSKKGNGPEIKSLKYYDSKLG*

*NHIDITPKDSNNKVVLQSVSPWRADVYFNKTTGKYEILGLKYADLQFEKGTGTYKISQEKYNDIKKKEGVDSDSEFKFTL*

*YKNDLLLVKDTETKEQQLFRFLSRTMPKQKHYVELKPYDKQKFEGGEALIKVLGNVANSGQCKKGLGKSNISIYKVRTDV*

*LGNQHIIKNEGDKPKLDF*srad<u>PKKKRKV</u>

FIG. 17

NLS-St1Cas9 LMD-9/LMG18311 Hybrid-NLS ORF DNA sequence
<u>SV40 NLS</u>
*ST1CAS9 SEQUENCE*
LINKERS ATGGGCGCC<u>CCAAAGAAGAAGCGGAAGGTC</u>GGTATCCACGGAGTCCCAGCAGCC*AGCGAC*
*CTGGTGCTGGGCCTGGACATCGGCATCGGCAGCGTGGGCGTGGGCATCCTGAACAAGGTG*
*ACCGGCGAGATCATCCACAAGAACAGTCGCATCTTCCCTGCTGCTCAGGCTGAGAACAAC*
*CTGGTGCGCCGCACCAACCGCCAGGGTCGCCGGCTTGCTCGCCGCAAGAAGCACCGGCGC*
*GTGCGCCTGAACCGCCTGTTCGAGGAGAGCGGCCTGATCACCGACTTCACCAAGATCAGC*
*ATCAACCTGAACCCCTACCAGCTGCGCGTGAAGGGCCTGACCGACGAGCTGAGCAACGAG*
*GAGCTGTTCATCGCCCTGAAGAACATGGTGAAGCACCGCGGCATCAGCTACCTGGACGAC*
*GCCAGCGACGACGGCAACAGCAGCGTGGGCGACTACGCCCAGATCGTGAAGGAGAACAGC*
*AAGCAGCTGGAGACCAAGACCCCCGGCCAGATCCAGCTGGAGCGCTACCAGACCTACGGC*
*CAGCTGCGCGGCGACTTCACCGTGGAGAAGGACGGCAAGAAGCACCGCCTGATCAACGTG*
*TTCCCCACCAGCGCCTACCGCAGCGAGGCCCTGCGCATCCTGCAGACCCAGCAGGAGTTC*
*AACCCCCAGATCACCGACGAGTTCATCAACCGCTACCTGGAGATCCTGACCGGCAAGCGC*
*AAGTACTACCACGGCCCCGGCAACGAGAAGAGCCGCACCGACTACGGCCGCTACCGCACC*
*AGCGGCGAGACCCTGGACAACATCTTCGGCATCCTGATCGGCAAGTGCACCTTCTACCCC*
*GACGAGTTCCGCGCCGCCAAGGCCAGCTACACCGCCCAGGAGTTCAATCTGCTGAACGAC*
*CTGAACAACCTGACCGTGCCCACCGAGACCAAGAAGCTGAGCAAGGAGCAGAAGAACCAG*
*ATCATCAACTACGTGAAGAACGAGAAGGCTATGGGCCCCGCCAAGCTGTTCAAGTACATC*
*GCCAAGCTGCTGAGCTGCGACGTGGCCGACATCAAGGGCTACCGCATCGACAAGAGCGGC*
*AAGGCCGAGATCCACACCTTCGAGGCCTACCGCAAGATGAAGACCCTGGAGACCCTGGAC*
*ATCGAGCAGATGGACCGAGAGACCCTGGACAAGCTGGCCTACGTGCTGACCCTGAACACC*
*GAGCGCGAGGGCATCCAGGAGGCCCTGGAGCACGAGTTCGCCGACGGCAGCTTCAGCCAG*
*AAACAGGTGGACGAGCTGGTGCAGTTCCGCAAGGCCAACAGCAGCATCTTCGGCAAGGGC*
*TGGCACAACTTCAGCGTGAAGCTGATGATGGAGCTGATCCCCGAGCTGTACGAGACCAGC*
*GAGGAGCAGATGACCATCCTGACCCGCCTGGGCAAGCAGAAGACCACCAGCAGCAGCAAC*
*AAGACCAAGTACATCGACGAGAAGCTGCTGACCGAGGAGATCTACAACCCCGTGGTGGCC*
*AAGAGCGTGCGCCAGGCCATCAAGATCGTGAACGCCGCCATCAAGGAGTACGGCGACTTC*
*GACAACATCGTGATCGAGATGGCCCGCGAGACCAACGAGGACGACGAGAAGAAGGCCATC*
*CAGAAGATCCAGAAGGCCAACAAGGACGAGAAGGACGCCGCCATGCTGAAGGCCGCCAAC*
*CAGTACAACGGCAAGGCCGAGCTGCCCCACAGCGTGTTCCACGGCCACAAGCAGCTGGCC*
*ACCAAGATCCGCCTGTGGCACCAGCAGGGCGAGCGCTGCCTGTACACCGGCAAGACCATC*
*AGCATCCACGACCTGATCAACAACAGCAACCAGTTCGAGGTGGACCACATCCTGCCCCTG*
*AGCATCACCTTCGACGACAGCCTGGCCAACAAGGTGCTGGTGTACGCCACCGCCAACCAG*
*GAGAAGGGCCAGCGCACCCCCTACCAGGCCCTGGACAGCATGGACGACGCCTGGAGCTTC*
*CGCGAGCTGAAGGCCTTCGTGCGCGAGAGCAAGACCCTGAGCAACAAGAAGAAGGAGTAT*
*CTGCTGACCGAGGAGGACATCAGCAAGTTCGACGTGCGCAAGAAGTTCATCGAGCGCAAC*

FIG. 23a

```
CTGGTGGACACCCGCTACGCCAGCCGCGTGGTGCTGAACGCCCTGCAGGAGCACTTCCGC
GCCCACAAGATCGACACCAAGGTGAGCGTGGTGCGCGGCCAGTTCACCAGCCAGCTGCGC
CGCCACTGGGGCATCGAGAAGACCCGCGACACCTACCACCACCACGCCGTGGACGCCCTG
ATCATTGCGGCTTCTAGCCAGCTGAACCTGTGGAAGAAGCAGAAGAACACCCTGGTGAGC
TACAGCGAGGAGCAGCTGCTGGACATCGAGACCGGCGAGCTGATCAGCGACGACGAGTAC
AAGGAGAGCGTGTTCAAGGCCCCCTACCAGCACTTCGTGGACACCCTGAAGAGCAAGGAG
TTCGAGGACAGCATCCTGTTCAGCTACCAGGTGGACAGCAAGTTCAACCGCAAGATCAGC
GACGCCACCATCTACGCCACCCGCCAGGCCAAGGTGGGCAAGGACAAGAAGGACGAGACC
TACGTGCTGGGCAAGATCAAGGACATCTACACCCAGGACGGCTACGACGCCTTCATGAAG
ATCTACAAGAAGGACAAGAGCAAGTTCCTGATGTACCGCCACGACCCCAGACCTTCGAG
AAGGTGATCGAGCCCATCCTGGAGAACTACCCCAACAAGCAGATGAACGAGAAAGGCAAG
GAGGTGCCCTGCAACCCCTTCCTGAAGTACAAGGAGGAGCACGGCTACATCCGCAAGTAC
AGCAAGAAGGGCAACGGCCCCGAGATCAAGAGCCTGAAGTACTACGACAGCAAGCTGCTG
GGCAACCCCATCGACATCACCCCCGAAAACAGCAAGAACAAGGTGGTGCTGCAGAGCCTT
AAGCCCTGGCGCACCGACGTGTACTTCAACAAGAACACCGGCAAGTACGAGATCCTGGGG
CTGAAGTACGCCGATCTGCAGTTTGAGAAAAAGACAGGCACCTACAAGATCAGCCAGGAG
AAGTACAACGGCATCATGAAGGAGGAGGGCGTGGACAGCGACAGCGAGTTCAAGTTCACC
CTGTACAAGAACGACCTTCTGCTGGTGAAGGACACCGAGACCAAGGAGCAACAGCTGTTC
CGCTTCCTGAGCCGCACCATGCCCAACGTGAAGTACTACGTGGAGCTGAAGCCCTACAGC
AAGGACAAGTTCGAGAAGAACGAGAGCCTGATCGAGATCCTGGGCAGCGCCGACAAGAGC
GGCAGGTGCATCAAGGGCCTGGGCAAGAGCAACATCAGCATCTACAAGGTGCGCACCGAC
GTGCTGGGCAACCAGCACATCATCAAGAACGAGGGCGACAAGCCCAAGTTGGACTTCAGC
AGGGCTGACCCCAAGAAGAAGAGGAAGGTGGGATCC
```

FIG 23b

NLS-St1Cas9 LMD-9/LMG18311 Hybrid-NLS AA sequence
<u>SV40 NLS</u>
*ST1CAS9 SEQUENCE*
LINKERS MGA<u>PKKKRKV</u>GIHGVPAA*SDLVLGLDIGIGSVGVGILNKVTGEIIHKNSRIFPAAQAENNLVRRTNRQGRRLA*
*RRKKHRRVRLNRLFEESGLITDFTKISINLNPYQLRVKGLTDELSNEELFIALKNMVKHRGISYLDDASDDGN*
*SSVGDYAQIVKENSKQLETKTPGQIQLERYQTYGQLRGDFTVEKDGKKHRLINVFPTSAYRSEALRILQTQQE*
*FNPQITDEFINRYLEILTGKRKYYHGPGNEKSRTDYGRYRTSGETLDNIFGILIGKCTFYPDEFRAAKASYTA*
*QEFNLLNDLNNLTVPTETKKLSKEQKNQIINYVKNEKAMGPAKLFKYIAKLLSCDVADIKGYRIDKSGKAEIH*
*TFEAYRKMKTLETLDIEQMDRETLDKLAYVLTLNTEREGIQEALEHEFADGSFSQKQVDELVQFRKANSSIFG*
*KGWHNFSVKLMMELIPELYETSEEQMTILTRLGKQKTTSSSNKTKYIDEKLLTEEIYNPVVAKSVRQAIKIVN*
*AAIKEYGDFDNIVIEMARETNEDDEKKAIQKIQKANKDEKDAAMLKAANQYNGKAELPHSVFHGHKQLATKIR*
*LWHQQGERCLYTGKTISIHDLINNSNQFEVDHILPLSITFDDSLANKVLVYATANQEKGQRTPYQALDSMDDA*
*WSFRELKAFVRESKTLSNKKKEYLLTEEDISKFDVRKKFIERNLVDTRYASRVVLNALQEHFRAHKIDTKVSV*
*VRGQFTSQLRRHWGIEKTRDTYHHHAVDALIIAASSQLNLWKKQKNTLVSYSEEQLLDIETGELISDDEYKES*
*VFKAPYQHFVDTLKSKEFEDSILFSYQVDSKFNRKISDATIYATRQAKVGKDKKDETYVLGKIKDIYTQDGYD*
*AFMKIYKKDKSKFLMYRHDPQTFEKVIEPILENYPNKQMNEKGKEVPCNPFLKYKEEHGYIRKYSKKGNGPEI*
*KSLKYYDSKLLGNPIDITPENSKNKVVLQSLKPWRTDVYFNKNTGKYEILGLKYADLQFEKKTGTYKISQEKY*
*NGIMKEEGVDSDSEFKFTLYKNDLLLVKDTETKEQQLFRFLSRTMPNVKYYVELKPYSKDKFEKNESLIEILG*
*SADKSGRCIKGLGKSNISIYKVRTDVLGNQHIIKNEGDKPKLDF*SRAD<u>PKKKRKV</u>GS

FIG. 24

NLS-St1Cas9 LMD-9/CNRZ1066 Hybrid-NLS ORF DNA sequence
SV40 NLS
ST1CAS9 SEQUENCE
LINKERS ATGGGCGCCCCAAAGAAGAAGCGGAAGGTCGGTATCCACGGAGTCCCAGCAGCCAGCGAC
CTGGTGCTGGGCCTGGACATCGGCATCGGCAGCGTGGGCGTGGGCATCCTGAACAAGGTG
ACCGGCGAGATCATCCACAAGAACAGTCGCATCTTCCCTGCTGCTCAGGCTGAGAACAAC
CTGGTGCGCCGCACCAACCGCCAGGGTCGCCGGCTTGCTCGCCGCAAGAAGCACCGGCGC
GTGCGCCTGAACCGCCTGTTCGAGGAGAGCGGCCTGATCACCGACTTCACCAAGATCAGC
ATCAACCTGAACCCCTACCAGCTGCGCGTGAAGGGCCTGACCGACGAGCTGAGCAACGAG
GAGCTGTTCATCGCCCTGAAGAACATGGTGAAGCACCGCGGCATCAGCTACCTGGACGAC
GCCAGCGACGACGGCAACAGCAGCGTGGGCGACTACGCCCAGATCGTGAAGGAGAACAGC
AAGCAGCTGGAGACCAAGACCCCGGCCAGATCCAGCTGGAGCGCTACCAGACCTACGGC
CAGCTGCGCGGCGACTTCACCGTGGAGAAGGACGGCAAGAAGCACCGCCTGATCAACGTG
TTCCCCACCAGCGCCTACCGCAGCGAGGCCCTGCGCATCCTGCAGACCCAGCAGGAGTTC
AACCCCCAGATCACCGACGAGTTCATCAACCGCTACCTGGAGATCCTGACCGGCAAGCGC
AAGTACTACCACGGCCCCGGCAACGAGAAGAGCCGCACCGACTACGGCCGCTACCGCACC
AGCGGCGAGACCCTGGACAACATCTTCGGCATCCTGATCGGCAAGTGCACCTTCTACCCC
GACGAGTTCCGCGCCGCCAAGGCCAGCTACACCGCCCAGGAGTTCAATCTGCTGAACGAC
CTGAACAACCTGACCGTGCCCACCGAGACCAAGAAGCTGAGCAAGGAGCAGAAGAACCAG
ATCATCAACTACGTGAAGAACGAGAAGGCTATGGGCCCCGCCAAGCTGTTCAAGTACATC
GCCAAGCTGCTGAGCTGCGACGTGGCCGACATCAAGGGCTACCGCATCGACAAGAGCGGC
AAGGCCGAGATCCACACCTTCGAGGCCTACCGCAAGATGAAGACCCTGGAGACCCTGGAC
ATCGAGCAGATGGACCGAGAGACCCTGGACAAGCTGGCCTACGTGCTGACCCTGAACACC
GAGCGCGAGGGCATCCAGGAGGCCCTGGAGCACGAGTTCGCCGACGGCAGCTTCAGCCAG
AAACAGGTGGACGAGCTGGTGCAGTTCCGCAAGGCCAACAGCAGCATCTTCGGCAAGGGC
TGGCACAACTTCAGCGTGAAGCTGATGATGGAGCTGATCCCCGAGCTGTACGAGACCAGC
GAGGAGCAGATGACCATCCTGACCCGCCTGGGCAAGCAGAAGACCACCAGCAGCAGCAAC
AAGACCAAGTACATCGACGAGAAGCTGCTGACCGAGGAGATCTACAACCCCGTGGTGGCC
AAGAGCGTGCGCCAGGCCATCAAGATCGTGAACGCCGCCATCAAGGAGTACGGCGACTTC
GACAACATCGTGATCGAGATGGCCCGCGAGACCAACGAGGACGACGAGAAGAAGGCCATC
CAGAAGATCCAGAAGGCCAACAAGGACGAGAAGGACGCCGCCATGCTGAAGGCCGCCAAC
CAGTACAACGGCAAGGCCGAGCTGCCCCACAGCGTGTTCCACGGCCACAAGCAGCTGGCC
ACCAAGATCCGCCTGTGGCACCAGCAGGGCGAGCGCTGCCTGTACACCGGCAAGACCATC
AGCATCCACGACCTGATCAACAACAGCAACCAGTTCGAGGTGGACCACATCCTGCCCCTG
AGCATCACCTTCGACGACAGCCTGGCCAACAAGGTGCTGGTGTACGCCACCGCCAACCAG
GAGAAGGGCCAGCGCACCCCCTACCAGGCCCTGGACAGCATGGACGACGCCTGGAGCTTC
CGCGAGCTGAAGGCCTTCGTGCGCGAGAGCAAGACCCTGAGCAACAAGAAGAAGGAGTAT
CTGCTGACCGAGGAGGACATCAGCAAGTTCGACGTGCGCAAGAAGTTCATCGAGCGCAAC
CTGGTGGACACCCGCTACGCCAGCCGCGTGGTGCTGAACGCCCTGCAGGAGCACTTCCGC
GCCCACAAGATCGACACCAAGGTGAGCGTGGTGCGCGGCCAGTTCACCAGCCAGCTGCGC
CGCCACTGGGGCATCGAGAAGACCCGCGACACCTACCACCACCACGCCGTGGACGCCCTG
ATCATTGCGGCTTCTAGCCAGCTGAACCTGTGGAAGAAGCAGAAGAACACCCTGGTGAGC
TACAGCGAGGAGCAGCTGCTGGACATCGAGACCGGCGAGCTGATCAGCGACGACGAGTAC

FIG. 25a

```
AAGGAGAGCGTGTTCAAGGCCCCCTACCAGCACTTCGTGGACACCCTGAAGAGCAAGGAG
TTCGAGGACAGCATCCTGTTCAGCTACCAGGTGGACAGCAAGTTCAACCGCAAGATCAGC
GACGCCACCATCTACGCCACCCGCCAGGCCAAGGTGGGCAAGGACAAGAAGGACGAGACC
TACGTGCTGGGCAAGATCAAGGACATCTACACCCAGGACGGCTACGACGCCTTCATGAAG
ATCTACAAGAAGGACAAGAGCAAGTTCCTGATGTACCGCCACGACCCCCAGACCTTCGAG
AAGGTGATCGAGCCCATCCTGGAGAACTACCCCAACAAGCAGATGAACGAGAAAGGCAAG
GAGGTGCCCTGCAACCCCTTCCTGAAGTACAAGGAGGAGCACGGCTACATCCGCAAGTAC
AGCAAGAAGGGCAACGGCCCCGAGATCAAGAGCCTGAAGTACTACGACAGCAAGCTGCTG
GGCAACCCCATCGACATCACCCCCGAAAACAGCAAGAACAAGGTGGTGCTGCAGAGCCTT
AAGCCCTGGCGCACCGACGTGTACTTCAACAAGGCCACCGGCAAGTACGAGATCCTGGGG
CTGAAGTACGCCGATCTGCAGTTTGAGAAAGGCACAGGCACCTACAAGATCAGCCAGGAG
AAGTACAACGACATCAAGAAGAAGGAGGGCGTGGACAGCGACAGCGAGTTCAAGTTCACC
CTGTACAAGAACGACCTTCTGCTGGTGAAGGACACCGAGACCAAGGAGCAACAGCTGTTC
CGCTTCCTGAGCCGCACCCTGCCCAAGCAGAAGCACTACGTGGAGCTGAAGCCCTACGAC
AAGCAGAAGTTCGAGGGCGGCGAGGCCCTGATCAAGGTGCTGGGCAACGTGGCCAACGGC
GGCCAGTGCATCAAGGGCCTGGCCAAGAGCAACATCAGCATCTACAAGGTGCGCACCGAC
GTGCTGGGCAACCAGCACATCATCAAGAACGAGGGCGACAAGCCCAAGTTGGACTTCAGC
AGGGCTGACCCCAAGAAGAAGAGGAAGGTGGGATCC
```

FIG. 25b

NLS-St1Cas9 LMD-9/CNRZ1066 Hybrid-NLS AA sequence
<u>SV40 NLS</u>
*ST1CAS9 SEQUENCE*
LINKERS MGA<u>PKKKRKV</u>GIHGVPAA*SDLVLGLDIGIGSVGVGILNKVTGEIIHKNSRIFPAAQAENNLVRRTNRQGRRLA
RRKKHRRVRLNRLFEESGLITDFTKISINLNPYQLRVKGLTDELSNEELFIALKNMVKHRGISYLDDASDDGN
SSVGDYAQIVKENSKQLETKTPGQIQLERYQTYGQLRGDFTVEKDGKKHRLINVFPTSAYRSEALRILQTQQE
FNPQITDEFINRYLEILTGKRKYYHGPGNEKSRTDYGRYRTSGETLDNIFGILIGKCTFYPDEFRAAKASYTA
QEFNLLNDLNNLTVPTETKKLSKEQKNQIINYVKNEKAMGPAKLFKYIAKLLSCDVADIKGYRIDKSGKAEIH
TFEAYRKMKTLETLDIEQMDRETLDKLAYVLTLNTEREGIQEALEHEFADGSFSQKQVDELVQFRKANSSIFG
KGWHNFSVKLMMELIPELYETSEEQMTILTRLGKQKTTSSSNKTKYIDEKLLTEEIYNPVVAKSVRQAIKIVN
AAIKEYGDFDNIVIEMARETNEDDEKKAIQKIQKANKDEKDAAMLKAANQYNGKAELPHSVFHGHKQLATKIR
LWHQQGERCLYTGKTISIHDLINNSNQFEVDHILPLSITFDDSLANKVLVYATANQEKGQRTPYQALDSMDDA
WSFRELKAFVRESKTLSNKKKEYLLTEEDISKFDVRKKFIERNLVDTRYASRVVLNALQEHFRAHKIDTKVSV
VRGQFTSQLRRHWGIEKTRDTYHHHAVDALIIAASSQLNLWKKQKNTLVSYSEEQLLDIETGELISDDEYKES
VFKAPYQHFVDTLKSKEFEDSILFSYQVDSKFNRKISDATIYATRQAKVGKDKKDETYVLGKIKDIYTQDGYD
AFMKIYKKDKSKFLMYRHDPQTFEKVIEPILENYPNKQMNEKGKEVPCNPFLKYKEEHGYIRKYSKKGNGPEI
KSLKYYDSKLLGNPIDITPENSKNKVVLQSLKPWRTDVYFNKATGKYEILGLKYADLQFEKGTGTYKISQEKY
NDIKKKEGVDSDSEFKFTLYKNDLLLVKDTETKEQQLFRFLSRTLPKQKHYVELKPYDKQKFEGGEALIKVLG
NVANGGQCIKGLAKSNISIYKVRTDVLGNQHIIKNEGDKPKLDFSRADPKKKRKV*GS

FIG. 26

NLS-St1Cas9 LMD-9/TH1477 Hybrid-NLS ORF DNA sequence
<u>SV40 NLS</u>
*ST1CAS9 SEQUENCE*
LINKERS ATGGGCGCCCC<u>AAAGAAGAAGCGGAAGGT</u>CGGTATCCACGGAGTCCCAGCAGCCAGCGACCTGGTGC
*TGGGCCTGGACATCGGCATCGGCAGCGTGGGCGTGGGCATCCTGAACAAGGTGACCGGCGAGATCAT
CCACAAGAACAGTCGCATCTTCCCTGCTGCTCAGGCTGAGAACAACCTGGTGCGCCGCACCAACCGC
CAGGGTCGCCGGCTTGCTCGCCGCAAGAAGCACCGGCGCGTGCGCCTGAACCGCCTGTTCGAGGAGA
GCGGCCTGATCACCGACTTCACCAAGATCAGCATCAACCTGAACCCCTACCAGCTGCGCGTGAAGGG
CCTGACCGACGAGCTGAGCAACGAGGAGCTGTTCATCGCCCTGAAGAACATGGTGAAGCACCGCGGC
ATCAGCTACCTGGACGACGCCAGCGACGACGGCAACAGCAGCGTGGGCGACTACGCCCAGATCGTGA
AGGAGAACAGCAAGCAGCTGGAGACCAAGACCCCGGCCAGATCCAGCTGGAGCGCTACCAGACCTA
CGGCCAGCTGCGCGGCGACTTCACCGTGGAGAAGGACGGCAAGAAGCACCGCCTGATCAACGTGTTC
CCCACCAGCGCCTACCGCAGCGAGGCCCTGCGCATCCTGCAGACCCAGCAGGAGTTCAACCCCCAGA
TCACCGACGAGTTCATCAACCGCTACCTGGAGATCCTGACCGGCAAGCGCAAGTACTACCACGGCCC
CGGCAACGAGAAGAGCCGCACCGACTACGGCCGCTACCGCACCAGCGGCGAGACCCTGGACAACATC
TTCGGCATCCTGATCGGCAAGTGCACCTTCTACCCCGACGAGTTCCGCGCCGCCAAGGCCAGCTACA
CCGCCCAGGAGTTCAATCTGCTGAACGACCTGAACAACCTGACCGTGCCCACCGAGACCAAGAAGCT
GAGCAAGGAGCAGAAGAACCAGATCATCAACTACGTGAAGAACGAGAAGGCTATGGGCCCCGCCAAG
CTGTTCAAGTACATCGCCAAGCTGCTGAGCTGCGA*
CGTGGCCGACATCAAGGGCTACCGCATCGACAAGAGCGGCAAGGCCGAGATCCACACCTTCGAGGCC
TACCGCAAGATGAAGACCCTGGAGACCCTGGACATCGAGCAGATGGACCGAGAGACCCTGGACAAGC
TGGCCTACGTGCTGACCCTGAACACCGAGCGCGAGGGCATCCAGGAGGCCCTGGAGCACGAGTTCGC
CGACGGCAGCTTCAGCCAGAAACAGGTGGACGAGCTGGTGCAGTTCCGCAAGGCCAACAGCAGCATC
TTCGGCAAGGGCTGGCACAACTTCAGCGTGAAGCTGATGATGGAGCTGATCCCCGAGCTGTACGAGA
CCAGCGAGGAGCAGATGACCATCCTGACCCGCCTGGGCAAGCAGAAGACCACCAGCAGCAGCAACAA
GACCAAGTACATCGACGAGAAGCTGCTGACCGAGGAGATCTACAACCCCGTGGTGGCCAAGAGCGTG
CGCCAGGCCATCAAGATCGTGAACGCCGCCATCAAGGAGTACGGCGACTTCGACAACATCGTGATCG
AGATGGCCCGCGAGACCAACGAGGACGACGAGAAGAAGGCCATCCAGAAGATCCAGAAGGCCAACAA
GGACGAGAAGGACGCCGCCATGCTGAAGGCCGCCAACCAGTACAACGGCAAGGCCGAGCTGCCCCAC
AGCGTGTTCCACGGCCACAAGCAGCTGGCCACCAAGATCCGCCTGTGGCACCAGCAGGGCGAGCGCT
GCCTGTACACCGGCAAGACCATCAGCATCCACGACCTGATCAACAACAGCAACCAGTTCGAGGTGGA
CCACATCCTGCCCCTGAGCATCACCTTCGACGACAGCCTGGCCAACAAGGTGCTGGTGTACGCCACC
GCCAACCAGGAGAAGGGCCAGCGCACCCCCTACCAGGCCCTGGACAGCATGGACGACGCCTGGAGCT
TCCGCGAGCTGAAGGCCTTCGTGCGCGAGAGCAAGACCCTGAGCAACAAGAAGAAGGAGTATCTGCT
GACCGAGGAGGACATCAGCAAGTTCGACGTGCGCA
AGAAGTTCATCGAGCGCAACCTGGTGGACACCCGCTACGCCAGCCGCGTGGTGCTGAACGCCCTGCA
GGAGCACTTCCGCGCCCACAAGATCGACACCAAGGTGAGCGTGGTGCGCGGCCAGTTCACCAGCCAG
CTGCGCCGCCACTGGGGCATCGAGAAGACCCGCGACACCTACCACCACCACGCCGTGGACGCCCTGA
TCATTGCGGCTTCTAGCCAGCTGAACCTGTGGAAGAAGCAGAAGAACACCCTGGTGAGC

FIG. 27a

```
TACAGCGAGGACCAGCTGCTGGACATCGAGACCGGCGAGCTGATCAGCGACGACGAGTACAAGGAGA
GCGTGTTCAAGGCCCCCTACCAGCACTTCGTGGACACCCTGAAGAGCAAGGAGTTCGAGGACAGCAT
CCTGTTCAGCTACCAGGTGGACAGCAAGTTCAACCGCAAGATCAGCGACGCCACCATCTACGCCACC
CGCCAGGCCAAGGTGGGCAAGGACAAGGCCGACGAGACCTACGTGCTGGGCAAGATCAAGGACATCT
ACACCCAGGACGGCTACGACGCCTTCATGAAGATCTACAAGAAGGACAAGAGCAAGTTCCTGATGTA
CCGCCACGACCCCAGACCTTCGAGAAGGTGATCGAGCCCATCCTGGAGAACTACCCCAACAAGCAG
ATCAACGAGAAAGGCAAGGAGGTGCCCTGCAACCCCTTCCTGAAGTACAAGGAGGAGCACGGCTACA
TCCGCAAGTACAGCAAGAAGGGCAACGGCCCCGAGATCAAGAGCCTGAAGTACTACGACAGCAAGCT
GGGCAACCACATCGACATCACCCCCAAGGACAGCAACAACAAGGTGGTGCTGCAGAGCGTGAGCCCC
TGGCGCGCCGACGTGTACTTCAACAAGAACACCGGCAAGTACGAGATCCTGGGGCTGAAGTACAGCG
ATATGCAGTTTGAGAAAGGCACAGGCAAGTACAGCATCAGCAAGGAGCAGTACGAGAACATCAAGGT
GCGCGAGGGCGTGGACGAGAACAGCGAGTTCAAGTTCACCCTG
TACAAGAACGACCTTCTGCTGCTGAAGGACAGCGAGAACGGCGAGCAAATCCTGCTGCGCTTCACCA
GCCGCAACGACACCAGCAAGCACTACGTGGAGCTGAAGCCCTACAACCGCCAGAAGTTCGAGGGCAG
CGAGTACCTGATCAAGAGCCTGGGCACCGTGGTGAAGGGCGGCAGGTGCATCAAGGGCCTGGGCAAG
AGCAACATCAGCATCTACAAGGTGCGCACCGACGTGCTGGGCAACCAGCACATCATCAAGAACGAGG
GCGACAAGCCCAAGTTGGACTTCAGCAGGGCTGACCCAAGAAGAAGAGGAAGGTGGGATCC
```

FIG. 27b

NLS-St1Cas9 LMD-9/TH1477 Hybrid-NLS AA sequence
<u>SV40 NLS</u>
*ST1CAS9 SEQUENCE*
LINKERS

```
MGAPKKKRKVGIHGVPAASDLVLGLDIGIGSVGVGILNKVTGEIIHKNSRIFPAAQAENNLVRRTNRQGRRLA
RRKKHRRVRLNRLFEESGLITDFTKISINLNPYQLRVKGLTDELSNEELFIALKNMVKHRGISYLDDASDDGN
SSVGDYAQIVKENSKQLETKTPGQIQLERYQTYGQLRGDFTVEKDGKKHRLINVFPTSAYRSEALRILQTQQE
FNPQITDEFINRYLEILTGKRKYYHGPGNEKSRTDYGRYRTSGETLDNIFGILIGKCTFYPDEFRAAKASYTA
QEFNLLNDLNNLTVPTETKKLSKEQKNQIINYVKNEKAMGPAKLFKYIAKLLSCDVADIKGYRIDKSGKAEIH
TFEAYRKMKTLETLDIEQMDRETLDKLAYVLTLNTEREGIQEALEHEFADGSFSQKQVDELVQFRKANSSIFG
KGWHNFSVKLMMELIPELYETSEEQMTILTRLGKQKTTSSSNKTKYIDEKLLTEEIYNPVVAKSVRQAIKIVN
AAIKEYGDFDNVIEMARETNEDDEKKAIQKIQKANKDEKDAAMLKAANQYNGKAELPHSVFHGHKQLATKIR
LWHQQGERCLYTGKTISIHDLINNSNQFEVDHILPLSITFDDSLANKVLVYATANQEKGQRTPYQALDSMDDA
WSFRELKAFVRESKTLSNKKKEYLLTEEDISKFDVRKKFIERNLVDTRYASRVVLNALQEHFRAHKIDTKVSV
VRGQFTSQLRRHWGIEKTRDTYHHHAVDALIIAASSQLNLWKKQKNTLVSYSEDQLLDIETGELISDDEYKES
VFKAPYQHFVDTLKSKEFEDSILFSYQVDSKFNRKISDATIYATRQAKVGKDKADETYVLGKIKDIYTQDGYD
AFMKIYKKDKSKFLMYRHDPQTFEKVIEPILENYPNKQINEKGKEVPCNPFLKYKEEHGYIRKYSKKGNGPEI
KSLKYYDSKLGNHIDITPKDSNNKVVLQSVSPWRADVYFNKNTGKYEILGLKYSDMQFEKGTGKYSISKEQYE
NIKVREGVDENSEFKFTLYKNDLLLLKDSENGEQILLRFTSRNDTSKHYVELKPYNRQKFEGSEYLIKSLGTV
VKGGRCIKGLGKSNISIYKVRTDVLGNQHIIKNEGDKPKLDFSRADPKKKRKVGS
```

FIG. 28

NLS-rAPOBEC1-St1Cas9 LMD-9-NLS-2xUGI-NLS-3xHA ORF DNA sequence
<u>NLS</u>
rAPOBEC1
*St1Cas9 ORF*
*UGI*
<u>*3xHA*</u>

ATGAAACGGACAGCCGACGGAAGCGAGTTCGAGTCA<u>CCAAAGAAGAAGCGGAAAGTC</u>TCCTCAGAGACTGGGC
CTGTCGCCGTCGATCCAACCCTGCGCCGCCGGATTGAACCTCACGAGTTTGAAGTGTTCTTTGACCCCGGGA
GCTGAGAAAGGAGACATGCCTGCTGTACGAGATCAACTGGGGAGGCAGGCACTCCATCTGGAGGCACACCTCT
CAGAACACAAATAAGCACGTGGAGGTGAACTTCATCGAGAAGTTTACCACAGAGCGGTACTTCTGCCCCAATA
CCAGATGTAGCATCACATGGTTTCTGAGCTGGTCCCCTTGCGGAGAGTGTAGCAGGGCCATCACCGAGTTCCT
GTCCAGATATCCACACGTGACACTGTTTATCTACATCGCCAGGCTGTATCACCACGCAGACCCAAGGAATAGG
CAGGGCCTGCGCGATCTGATCAGCTCCGGCGTGACCATCCAGATCATGACAGAGCAGGAGTCCGGCTACTGCT
GGCGGAACTTCGTGAATTATTCTCCTAGCAACGAGGCCCACTGGCCTAGGTACCCACACCTGTGGGTGCGCCT
GTACGTGCTGGAGCTGTATTGCATCATCCTGGGCCTGCCCCCTTGTCTGAATATCCTGCGGAGAAAGCAGCCC
CAGCTGACCTTCTTTACAATCGCCCTGCAGTCTTGTCACTATCAGAGGCTGCCACCCCACATCCTGTGGGCCA
CAGGCCTGAAGTCTGGAGGATCTAGCGGAGGCTCCTCTGGCAGCGAGACACCAGGAACAAGCGAGTCAGCAAC
*ACCAGAGAGCAGTGGCGGCAGCAGCGGCGGCAGCAGCGACCTGGTGCTGGGCCTGGCTATCGGCATCGGCAGC*
*GTGGGCGTGGGCATCCTGAACAAGGTGACCGGCGAGATCATCCACAAGAACAGTCGCATCTTCCTGCTGCTC*
*AGGCTGAGAACAACCTGGTGCGCCGCACCAACCGCCAGGGTCGCCGGCTTGCTCGCCGCAAGAAGCACCGGCG*
*CGTGCGCCTGAACCGCCTGTTCGAGGAGAGCGGCCTGATCACCGACTTCACCAAGATCAGCATCAACCTGAAC*
*CCCTACCAGCTGCGCGTGAAGGGCCTGACCGACGAGCTGAGCAACGAGGAGCTGTTCATCGCCCTGAAGAACA*
*TGGTGAAGCACCGCGGCATCAGCTACCTGGACGACGCCAGCGACGACGGCAACAGCAGCGTGGGCGACTACGC*
*CCAGATCGTGAAGGAGAACAGCAAGCAGCTGGAGACCAAGACCCCCGGCCAGATCCAGCTGGAGCGCTACCAG*
*ACCTACGGCCAGCTGCGCGGCGACTTCACCGTGGAGAAGGACGGCAAGAAGCACCGCCTGATCAACGTGTTCC*
*CCACCAGCGCCTACCGCAGCGAGGCCCTGCGCATCCTGCAGACCCAGCAGGAGTTCAACCCCCAGATCACCGA*
*CGAGTTCATCAACCGCTACCTGGAGATCCTGACCGGCAAGCGCAAGTACTACCACGGCCCCGGCAACGAGAAG*
*AGCCGCACCGACTACGGCCGCTACCGCACCAGCGGCGAGACCCTGGACAACATCTTCGGCATCCTGATCGGCA*
*AGTGCACCTTCTACCCCGACGAGTTCCGCGCCGCCAAGGCCAGCTACACCGCCCAGGAGTTCAATCTGCTGAA*
*CGACCTGAACAACCTGACCGTGCCCACCGAGACCAAGAAGCTGAGCAAGGAGCAGAAGAACCAGATCATCAAC*
*TACGTGAAGAACGAGAAGGCTATGGGCCCCGCCAAGCTGTTCAAGTACATCGCCAAGCTGCTGAGCTGCGACG*
*TGGCCGACATCAAGGGCTACCGCATCGACAAGAGCGGCAAGGCCGAGATCCACACCTTCGAGGCCTACCGCAA*
*GATGAAGACCCTGGAGACCCTGGACATCGAGCAGATGGACCGAGAGACCCTGGACAAGCTGGCCTACGTGCTG*
*ACCCTGAACACCGAGCGCGAGGGCATCCAGGAGGCCCTGGAGCACGAGTTCGCCGACGGCAGCTTCAGCCAGA*
*AACAGGTGGACGAGCTGGTGCAGTTCCGCAAGGCCAACAGCAGCATCTTCGGCAAGGGCTGGCACAACTTCAG*
*CGTGAAGCTGATGATGGAGCTGATCCCCGAGCTGTACGAGACCAGCGAGGAGCAGATGACCATCCTGACCCGC*
*CTGGGCAAGCAGAAGACCACCAGCAGCAGCAACAAGACCAAGTACATCGACGAGAAGCTGCTGACCGAGGAGA*
*TCTACAACCCCGTGGTGGCCAAGAGCGTGCGCCAGGCCATCAAGATCGTGAACGCCGCCATCAAGGAGTACGG*
*CGACTTCGACAACATCGTGATCGAGATGGCCCGCGAGACCAACGAGGACGACGAGAAGAAGGCCATCCAGAAG*
*ATCCAGAAGGCCAACAAGGACGAGAAGGACGCCGCCATGCT*

FIG. 29a

```
GAAGGCCGCCAACCAGTACAACGGCAAGGCCGAGCTGCCCCACAGCGTGTTCCACGGCCACAAGCAGCTGGCC
ACCAAGATCCGCCTGTGGCACCAGCAGGGCGAGCGCTGCCTGTACACCGGCAAGACCATCAGCATCCACGACC
TGATCAACAACAGCAACCAGTTCGAGGTGGACCACATCCTGCCCCTGAGCATCACCTTCGACGACAGCCTGGC
CAACAAGGTGCTGGTGTACGCCACCGCCAACCAGGAGAAGGGCCAGCGCACCCCCTACCAGGCCCTGGACAGC
ATGGACGACGCCTGGAGCTTCCGCGAGCTGAAGGCCTTCGTGCGCGAGAGCAAGACCCTGAGCAACAAGAAGA
AGGAGTATCTGCTGACCGAGGAGGACATCAGCAAGTTCGACGTGCGCAAGAAGTTCATCGAGCGCAACCTGGT
GGACACCGCTACGCCAGCCGCGTGGTGCTGAACGCCCTGCAGGAGCACTTCGCGCCCACAAGATCGACACC
AAGGTGAGCGTGGTGCGCGGCCAGTTCACCAGCCAGCTGCGCCGCCACTGGGGCATCGAGAAGACCCGCGACA
CCTACCACCACCACGCCGTGGACGCCCTGATCATTGCGGCTTCTAGCCAGCTGAACCTGTGGAAGAAGCAGAA
GAACACCCTGGTGAGCTACAGCGAGGACCAGCTGCTGGACATCGAGACCGGCGAGCTGATCAGCGACGACGAG
TACAAGGAGAGCGTGTTCAAGGCCCCCTACCAGCACTTCGTGGACACCCTGAAGAGCAAGGAGTTCGAGGACA
GCATCCTGTTCAGCTACCAGGTGGACAGCAAGTTCAACCGCAAGATCAGCGACGCCACCATCTACGCCACCCG
CCAGGCCAAGGTGGGCAAGGACAAGGCCGACGAGACCTACGTGCTGGGCAAGATCAAGGACATCTACACCCAG
GACGGCTACGACGCCTTCATGAAGATCTACAAGAAGGACAAGAGCAAGTTCCTGATGTACCGCCACGACCCCC
AGACCTTCGAGAAGGTGATCGAGCCCATCCTGGAGAACTACCCCAACAAGCAGATCAACGAGAAAGGCAAGGA
GGTGCCCTGCAACCCCTTCCTGAAGTACAAGGAGGAGCACGGCTACATCCGCAAGTACAGCAAGAAGGGCAAC
GGCCCCGAGATCAAGAGCCTGAAGTACTACGACAGCAAGCTGGGCAACCACATCGACATCACCCCCAAGGACA
GCAACAACAAGGTGGTGCTGCAGAGCGTGAGCCCCTGGCGCGCCGACGTGTACTTCAACAAGACCACCGGCAA
GTACGAGATCCTGGGGCTGAAGTACGCCGATCTGCAGTTTGAGAAAGGCACAGGCACCTACAAGATCAGCCAG
GAGAAGTACAACGACATCAAGAAGAAGGAGGGCGTGGACAGCGACAGCGAGTTCAAGTTCACCCTGTACAAGA
ACGACCTTCTGCTGGTGAAGGACACCGAGACCAAGGAGCAACAGCTGTTCCGCTTCCTGAGCCGCACCATGCC
CAAGCAGAAGCACTACGTGGAGCTGAAGCCCTACGACAAGCAGAAGTTCGAGGGCGGCGAGGCCCTGATCAAG
GTGCTGGGCAACGTGGCCAACAGCGGCCAGTGCAAGAAGGGCCTGGGCAAGAGCAACATCAGCATCTACAAGG
TGCGCACCGACGTGCTGGGCAACCAGCACATCATCAAGAACGAGGGCGACAAGCCCAAGTTGGACTTCAGCAG
GGCTGACCCCAAGAAGAAGAGGAAGGTGGGATCTAGCGGCGGGAGCGGCGGGAGCGGGGGAGCACTAATCTG
AGCGACATCATTGAGAAGGAGACTGGGAAACAGCTGGTCATTCAGGAGTCCATCCTGATGCTGCCTGAGGAGG
TGGAGGAAGTGATCGGCAACAAGCCAGAGTCTGACATCCTGGTGCACACCGCCTACGACGAGTCCACAGATGA
GAATGTGATGCTGCTGACCTCTGACGCCCCCGAGTATAAGCCTTGGGCCCTGGTCATCCAGGATTCTAACGGC
GAGAATAAGATCAAGATGCTGAGCGGAGGATCCGGAGGATCTGGAGGCAGCACCAACCTGTCTGACATCATCG
AGAAGGAGACAGGCAAGCAGCTGGTCATCCAGGAGAGCATCCTGATGCTGCCCGAAGAAGTCGAAGAAGTGAT
CGGAAACAAGCCTGAGAGCGATATCCTGGTCCATACCGCCTACGACGAGAGTACCGACGAAAATGTGATGCTG
CTGACATCCGACGCCCCAGAGTATAAGCCCTGGGCTCTGGTCATCCAGGATTCCAACGGAGAGAACAAAATCA
AAATGCTGTCTGGCGGCTCAAAAAGAACCGCCGACGGCAGCGAATTCGAGCCCAAGAAGAAGAGGAAAGTCGG
ATCCTACCCATACGATGTTCCAGATTACGCTTATCCCTACGACGTGCCTGATTATGCATACCCATATGATGTC
CCCGACTATGCC
```

FIG. 29b

NLS-rAPOBEC1-St1Cas9 LMD-9-NLS-2xUGI-NLS-3xHA AA sequence

<u>NLS</u>
rAPOBEC1
*St1Cas9 ORF*
UGI
<u>*3xHA*</u>

MKRTADGSEFE<u>SPKKKRKV</u>SSETGPVAVDPTLRRRIEPHEFEVFFDPRELRKETCLLYEINWGGRHSIWRHTS
QNTNKHVEVNFIEKFTTERYFCPNTRCSITWFLSWSPCGECSRAITEFLSRYPHVTLFIYIARLYHHADPRNR
QGLRDLISSGVTIQIMTEQESGYCWRNFVNYSPSNEAHWPRYPHLWVRLYVLELYCIILGLPPCLNILRRKQP
QLTFFTIALQSCHYQRLPPHILWATGLKSGGSSGGSSGSETPGTSESATPESSGGSSGGS*SDLVLGLAIGIGS*
*VGVGILNKVTGEIIHKNSRIFPAAQAENNLVRRTNRQGRRLARRKKHRRVRLNRLFEESGLITDFTKISINLN*
*PYQLRVKGLTDELSNEELFIALKNMVKHRGISYLDDASDDGNSSVGDYAQIVKENSKQLETKTPGQIQLERYQ*
*TYGQLRGDFTVEKDGKKHRLINVFPTSAYRSEALRILQTQQEFNPQITDEFINRYLEILTGKRKYYHGPGNEK*
*SRTDYGRYRTSGETLDNIFGILIGKCTFYPDEFRAAKASYTAQEFNLLNDLNNLTVPTETKKLSKEQKNQIIN*
*YVKNEKAMGPAKLFKYIAKLLSCDVADIKGYRIDKSGKAEIHTFEAYRKMKTLETLDIEQMDRETLDKLAYVL*
*TLNTEREGIQEALEHEFADGSFSQKQVDELVQFRKANSSIFGKGWHNFSVKLMMELIPELYETSEEQMTILTR*
*LGKQKTTSSSNKTKYIDEKLLTEEIYNPVVAKSVRQAIKIVNAAIKEYGDFDNIVIEMARETNEDDEKKAIQK*
*IQKANKDEKDAAMLKAANQYNGKAELPHSVFHGHKQLATKIRLWHQQGERCLYTGKTISIHDLINNSNQFEVD*
*HILPLSITFDDSLANKVLVYATANQEKGQRTPYQALDSMDDAWSFRELKAFVRESKTLSNKKKEYLLTEEDIS*
*KFDVRKKFIERNLVDTRYASRVVLNALQEHFRAHKIDTKVSVVRGQFTSQLRRHWGIEKTRDTYHHHAVDALI*
*IAASSQLNLWKKQKNTLVSYSEDQLLDIETGELISDDEYKESVFKAPYQHFVDTLKSKEFEDSILFSYQVDSK*
*FNRKISDATIYATRQAKVGKDKADETYVLGKIKDIYTQDGYDAFMKIYKKDKSKFLMYRHDPQTFEKVIEPIL*
*ENYPNKQINEKGKEVPCNPFLKYKEEHGYIRKYSKKGNGPEIKSLKYYDSKLGNHIDITPKDSNNKVVLQSVS*
*PWRADVYFNKTTGKYEILGLKYADLQFEKGTGTYKISQEKYNDIKKKEGVDSDSEFKFTLYKNDLLLVKDTET*
*KEQQLFRFLSRTMPKQKHYVELKPYDKQKFEGGEALIKVLGNVANSGQCKKGLGKSNISIYKVRTDVLGNQHI*
*IKNEGDKPKLDF*SRADPKKKRKVGSSGGSGGSGGS*TNLSDIIEKETGKQLVIQESILMLPEEVEEVIGNKPES*
*DILVHTAYDESTDENVMLLTSDAPEYKPWALVIQDSNGENKIKML*SGGSGGSGGS*TNLSDIIEKETGKQLVIQ*
*ESILMLPEEVEEVIGNKPESDILVHTAYDESTDENVMLLTSDAPEYKPWALVIQDSNGENKIKML*SGGSKRTA
DGSEFE<u>PKKKRKV</u>GS<u>*YPYDVPDYAYPYDVPDYAYPYDVPDYA*</u>

FIG. 30

NLS-rAPOBEC1-St1Cas9 LMD-9/LMG18311-NLS-2xUGI-NLS-3xHA ORF DNA sequence
<u>NLS</u>
rAPOBEC1
*St1Cas9 ORF*
UGI
<u>*3xHA*</u>

ATGAAACGGACAGCCGACGGAAGCGAGTTCGAGTCA<u>CCAAAGAAGAAGCGGAAAGTC</u>TCCTCAGAGACTGGGC
CTGTCGCCGTCGATCCAACCCTGCGCCGCCGGATTGAACCTCACGAGTTTGAAGTGTTCTTTGACCCCGGGA
GCTGAGAAAGGAGACATGCCTGCTGTACGAGATCAACTGGGGAGGCAGGCACTCCATCTGGAGGCACACCTCT
CAGAACACAAATAAGCACGTGGAGGTGAACTTCATCGAGAAGTTTACCACAGAGCGGTACTTCTGCCCCAATA
CCAGATGTAGCATCACATGGTTTCTGAGCTGGTCCCCTTGCGGAGAGTGTAGCAGGGCCATCACCGAGTTCCT
GTCCAGATATCCACACGTGACACTGTTTATCTACATCGCCAGGCTGTATCACCACGCAGACCCAAGGAATAGG
CAGGGCCTGCGCGATCTGATCAGCTCCGGCGTGACCATCCAGATCATGACAGAGCAGGAGTCCGGCTACTGCT
GGCGGAACTTCGTGAATTATTCTCCTAGCAACGAGGCCCACTGGCCTAGGTACCCACACCTGTGGGTGCGCCT
GTACGTGCTGGAGCTGTATTGCATCATCCTGGGCCTGCCCCCTTGTCTGAATATCCTGCGGAGAAAGCAGCCC
CAGCTGACCTTCTTTACAATCGCCCTGCAGTCTTGTCACTATCAGAGGCTGCCACCCCACATCCTGTGGGCCA
CAGGCCTGAAG*TCTGGAGGATCTAGCGGAGGCTCCTCTGGCAGCGAGACACCAGGAACAAGCGAGTCAGCAAC*
*ACCAGAGAGCAGTGGCGGCAGCAGCGGCGGCAGCAGCGACCTGGTGCTGGGCCTGGCTATCGGCATCGGCAGC*
*GTGGGCGTGGGCATCCTGAACAAGGTGACCGGCGAGATCATCCACAAGAACAGTCGCATCTTCCCTGCTGCTC*
*AGGCTGAGAACAACCTGGTGCGCCGCACCAACCGCCAGGGTCGCCGGCTTGCTCGCCGCAAGAAGCACCGGCG*
*CGTGCGCCTGAACCGCCTGTTCGAGGAGAGCGGCCTGATCACCGACTTCACCAAGATCAGCATCAACCTGAAC*
*CCCTACCAGCTGCGCGTGAAGGGCCTGACCGACGAGCTGAGCAACGAGGAGCTGTTCATCGCCCTGAAGAACA*
*TGGTGAAGCACCGCGGCATCAGCTACCTGGACGACGCCAGCGACGACGGCAACAGCAGCGTGGGCGACTACGC*
*CCAGATCGTGAAGGAGAACAGCAAGCAGCTGGAGACCAAGACCCCCGGCCAGATCCAGCTGGAGCGCTACCAG*
*ACCTACGGCCAGCTGCGCGGCGACTTCACCGTGGAGAAGGACGGCAAGAAGCACCGCCTGATCAACGTGTTCC*
*CCACCAGCGCCTACCGCAGCGAGGCCCTGCGCATCCTGCAGACCCAGCAGGAGTTCAACCCCCAGATCACCGA*
*CGAGTTCATCAACCGCTACCTGGAGATCCTGACCGGCAAGCGCAAGTACTACCACGGCCCCGGCAACGAGAAG*
*AGCCGCACCGACTACGGCCGCTACCGCACCAGCGGCGAGACCCTGGACAACATCTTCGGCATCCTGATCGGCA*
*AGTGCACCTTCTACCCCGACGAGTTCCGCGCCGCCAAGGCCAGCTACACCGCCCAGGAGTTCAATCTGCTGAA*
*CGACCTGAACAACCTGACCGTGCCCACCGAGACCAAGAAGCTGAGCAAGGAGCAGAAGAACCAGATCATCAAC*
*TACGTGAAGAACGAGAAGGCTATGGGCCCCGCCAAGCTGTTCAAGTACATCGCCAAGCTGCTGAGCTGCGACG*
*TGGCCGACATCAAGGGCTACCGCATCGACAAGAGCGGCAAGGCCGAGATCCACACCTTCGAGGCCTACCGCAA*
*GATGAAGACCCTGGAGACCCTGGACATCGAGCAGATGGACCGAGAGACCCTGGACAAGCTGGCCTACGTGCTG*
*ACCCTGAACACCGAGCGCGAGGGCATCCAGGAGGCCCTGGAGCACGAGTTCGCCGACGGCAGCTTCAGCCAGA*
*AACAGGTGGACGAGCTGGTGCAGTTCCGCAAGGCCAACAGCAGCATCTTCGGCAAGGGCTGGCACAACTTCAG*
*CGTGAAGCTGATGATGGAGCTGATCCCCGAGCTGTACGAGACCAGCGAGGAGCAGATGACCATCCTGACCCGC*
*CTGGGCAAGCAGAAGACCACCAGCAGCAGCAACAAGACCAAGTACATCGACGAGAAGCTGCTGACCGAGGAGA*
*TCTACAACCCCGTGGTGGCCAAGAGCGTGCGCCAGGCCATCAAGATCGTGAACGCCGCCATCAAGGAGTACGG*
*CGACTTCGACAACATCGTGATCGAGATGGCCCGCGAGACCAACGAGGACGACGAGAAGAAGGCCATCCAGAAG*
*ATCCAGAAGGCCAACAAGGACGAGAAGGACGCCGCCATGCTGAAGGCCGCCAACCAGTACAACGGCAAGGCC*
*GAGCTGCCCCACAGCGTGTTCCACGGCCACAAGCAGCTG*

FIG. 31a

```
GCCACCAAGATCCGCCTGTGGCACCAGCAGGGCGAGCGCTGCCTGTACACCGGCAAGACCATCAGCATCCACG
ACCTGATCAACAACAGCAACCAGTTCGAGGTGGACCACATCCTGCCCCTGAGCATCACCTTCGACGACAGCCT
GGCCAACAAGGTGCTGGTGTACGCCACCGCCAACCAGGAGAAGGGCCAGCGCACCCCCTACCAGGCCCTGGAC
AGCATGGACGACGCCTGGAGCTTCCGCGAGCTGAAGGCCTTCGTGCGCGAGAGCAAGACCCTGAGCAACAAGA
AGAAGGAGTATCTGCTGACCGAGGAGGACATCAGCAAGTTCGACGTGCGCAAGAAGTTCATCGAGCGCAACCT
GGTGGACACCCGCTACGCCAGCCGCGTGGTGCTGAACGCCCTGCAGGAGCACTTCCGCGCCCACAAGATCGAC
ACCAAGGTGAGCGTGGTGCGCGGCCAGTTCACCAGCCAGCTGCGCCGCCACTGGGGCATCGAGAAGACCCGCG
ACACCTACCACCACCACGCCGTGGACGCCCTGATCATTGCGGCTTCTAGCCAGCTGAACCTGTGGAAGAAGCA
GAAGAACACCCTGGTGAGCTACAGCGAGGAGCAGCTGCTGGACATCGAGACCGGCGAGCTGATCAGCGACGAC
GAGTACAAGGAGAGCGTGTTCAAGGCCCCCTACCAGCACTTCGTGGACACCCTGAAGAGCAAGGAGTTCGAGG
ACAGCATCCTGTTCAGCTACCAGGTGGACAGCAAGTTCAACCGCAAGATCAGCGACGCCACCATCTACGCCAC
CCGCCAGGCCAAGGTGGGCAAGGACAAGAAGGACGAGACCTACGTGCTGGGCAAGATCAAGGACATCTACACC
CAGGACGGCTACGACGCCTTCATGAAGATCTACAAGAAGGACAAGAGCAAGTTCCTGATGTACCGCCACGACC
CCCAGACCTTCGAGAAGGTGATCGAGCCCATCCTGGAGAACTACCCCAACAAGCAGATGAACGAGAAAGGCAA
GGAGGTGCCCTGCAACCCCTTCCTGAAGTACAAGGAGGAGCACGGCTACATCCGCAAGTACAGCAAGAAGGGC
AACGGCCCCGAGATCAAGAGCCTGAAGTACTACGACAGCAAGCTGCTGGGCAACCCCATCGACATCACCCCCG
AAAACAGCAAGAACAAGGTGGTGCTGCAGAGCCTTAAGCCCTGGCGCACCGACGTGTACTTCAACAAGAACAC
CGGCAAGTACGAGATCCTGGGGCTGAAGTACGCCGATCTGCAGTTTGAGAAAAGACAGGCACCTACAAGATC
AGCCAGGAGAAGTACAACGGCATCATGAAGGAGGAGGGCGTGGACAGCGACAGCGAGTTCAAGTTCACCCTGT
ACAAGAACGACCTTCTGCTGGTGAAGGACACCGAGACCAAGGAGCAACAGCTGTTCCGCTTCCTGAGCCGCAC
CATGCCCAACGTGAAGTACTACGTGGAGCTGAAGCCCTACAGCAAGGACAAGTTCGAGAAGAACGAGAGCCTG
ATCGAGATCCTGGGCAGCGCCGACAAGAGCGGCAGGTGCATCAAGGGCCTGGGCAAGAGCAACATCAGCATCT
ACAAGGTGCGCACCGACGTGCTGGGCAACCAGCACATCATCAAGAACGAGGGCGACAAGCCCAAGTTGGACTT
CAGCAGGGCTGACCCCAAGAAGAAGAGGAAGGTGGGATCTAGCGGCGGGAGCGGCGGGAGCGGGGGAGC**ACT
AATCTGAGCGACATCATTGAGAAGGAGACTGGGAAACAGCTGGTCATTCAGGAGTCCATCCTGATGCTGCCTG
AGGAGGTGGAGGAAGTGATCGGCAACAAGCCAGAGTCTGACATCCTGGTGCACACCGCCTACGACGAGTCCAC
AGATGAGAATGTGATGCTGCTGACCTCTGACGCCCCGAGTATAAGCCTTGGGCCCTGGTCATCCAGGATTCT
AACGGCGAGAATAAGATCAAGATGCTGAGCGGAGGATCCGGAGGATCTGGAGGCAGCACCAACCTGTCTGACA
TCATCGAGAAGGAGACAGGCAAGCAGCTGGTCATCCAGGAGAGCATCCTGATGCTGCCCGAAGAAGTCGAAGA
AGTGATCGGAAACAAGCCTGAGAGCGATATCCTGGTCCATACCGCCTACGACGAGAGTACCGACGAAAATGTG
ATGCTGCTGACATCCGACGCCCCAGAGTATAAGCCCTGGGCTCTGGTCATCCAGGATTCCAACGGAGAGAACA
AAATCAAAATGCTG**TCTGGCGGCTCAAAAAGAACCGCCGACGGCAGCGAATTCGAGCCCAAGAAGAAGAGGAA
AGTCGGATCC***TACCCATACGATGTTCCAGATTACGCTTATCCCTACGACGTGCCTGATTATGCATACCCATAT
GATGTCCCCGACTATGCC***
```

FIG. 31b

NLS-rAPOBEC1-St1Cas9 LMD-9/LMG18311-NLS-2xUGI-NLS-3xHA AA sequence
<u>NLS</u>
rAPOBEC1
*St1Cas9 ORF*
UGI
*<u>3xHA</u>*

MKRTADGSEFES<u>PKKKRKV</u>SSETGPVAVDPTLRRRIEPHEFEVFFDPRELRKETCLLYEINWGGRHSIWRHTS
QNTNKHVEVNFIEKFTTERYFCPNTRCSITWFLSWSPCGECSRAITEFLSRYPHVTLFIYIARLYHHADPRNR
QGLRDLISSGVTIQIMTEQESGYCWRNFVNYSPSNEAHWPRYPHLWVRLYVLELYCIILGLPPCLNILRRKQP
QLTFFTIALQSCHYQRLPPHILWATGLKSGGSSGGSSGSETPGTSESATPESSGGSSGGS*SDLVLGLAIGIGS*
*VGVGILNKVTGEIIHKNSRIFPAAQAENNLVRRTNRQGRRLARRKKHRRVRLNRLFEESGLITDFTKISINLN*
*PYQLRVKGLTDELSNEELFIALKNMVKHRGISYLDDASDDGNSSVGDYAQIVKENSKQLETKTPGQIQLERYQ*
*TYGQLRGDFTVEKDGKKHRLINVFPTSAYRSEALRILQTQQEFNPQITDEFINRYLEILTGKRKYYHGPGNEK*
*SRTDYGRYRTSGETLDNIFGILIGKCTFYPDEFRAAKASYTAQEFNLLNDLNNLTVPTETKKLSKEQKNQIIN*
*YVKNEKAMGPAKLFKYIAKLLSCDVADIKGYRIDKSGKAEIHTFEAYRKMKTLETLDIEQMDRETLDKLAYVL*
*TLNTEREGIQEALEHEFADGSFSQKQVDELVQFRKANSSIFGKGWHNFSVKLMMELIPELYETSEEQMTILTR*
*LGKQKTTSSSNKTKYIDEKLLTEEIYNPVVAKSVRQAIKIVNAAIKEYGDFDNIVIEMARETNEDDEKKAIQK*
*IQKANKDEKDAAMLKAANQYNGKAELPHSVFHGHKQLATKIRLWHQQGERCLYTGKTISIHDLINNSNQFEVD*
*HILPLSITFDDSLANKVLVYATANQEKGQRTPYQALDSMDDAWSFRELKAFVRESKTLSNKKKEYLLTEEDIS*
*KFDVRKKFIERNLVDTRYASRVVLNALQEHFRAHKIDTKVSVVRGQFTSQLRRHWGIEKTRDTYHHHAVDALI*
*IAASSQLNLWKKQKNTLVSYSEEQLLDIETGELISDDEYKESVFKAPYQHFVDTLKSKEFEDSILFSYQVDSK*
*FNRKISDATIYATRQAKVGKDKKDETYVLGKIKDIYTQDGYDAFMKIYKKDKSKFLMYRHDPQTFEKVIEPIL*
*ENYPNKQMNEKGKEVPCNPFLKYKEEHGYIRKYSKKGNGPEIKSLKYYDSKLLGNPIDITPENSKNKVVLQSL*
*KPWRTDVYFNKNTGKYEILGLKYADLQFEKKTGTYKISQEKYNGIMKEEGVDSDSEFKFTLYKNDLLLVKDTE*
*TKEQQLFRFLSRTMPNVKYYVELKPYSKDKFEKNESLIEILGSADKSGRCIKGLGKSNISIYKVRTDVLGNQH*
*IIKNEGDKPKLDFS*RADPKKKRKVGSSGGSGGSGGS*TNLSDIIEKETGKQLVIQESILMLPEEVEEVIGNKPE*
*SDILVHTAYDESTDENVMLLTSDAPEYKPWALVIQDSNGENKIKML*SGGSGGSGGS*TNLSDIIEKETGKQLVI*
*QESILMLPEEVEEVIGNKPESDILVHTAYDESTDENVMLLTSDAPEYKPWALVIQDSNGENKIKML*SGGSKRT
ADGSEFE<u>PKKKRKV</u>GS*<u>YPYDVPDYAYPYDVPDYAYPYDVPDYA</u>*

FIG. 32

NLS-rAPOBEC1-St1Cas9 LMD-9/CNRZ1066-NLS-2xUGI-NLS-3xHA ORF DNA sequence
<u>NLS</u>
rAPOBEC1
*St1Cas9 ORF*
*UGI*
<u>*3xHA*</u>

ATGAAACGGACAGCCGACGGAAGCGAGTTCGAGTCA<u>CCAAAGAAGAAGCGGAAAGTC</u>TCCTCAGAGACTGGGC
CTGTCGCCGTCGATCCAACCCTGCGCCGCCGGATTGAACCTCACGAGTTTGAAGTGTTCTTTGACCCCGGGA
GCTGAGAAAGGAGACATGCCTGCTGTACGAGATCAACTGGGGAGGCAGGCACTCCATCTGGAGGCACACCTCT
CAGAACACAAATAAGCACGTGGAGGTGAACTTCATCGAGAAGTTTACCACAGAGCGGTACTTCTGCCCCAATA
CCAGATGTAGCATCACATGGTTTCTGAGCTGGTCCCCTTGCGGAGAGTGTAGCAGGGCCATCACCGAGTTCCT
GTCCAGATATCCACACGTGACACTGTTTATCTACATCGCCAGGCTGTATCACCACGCAGACCCAAGGAATAGG
CAGGGCCTGCGCGATCTGATCAGCTCCGGCGTGACCATCCAGATCATGACAGAGCAGGAGTCCGGCTACTGCT
GGCGGAACTTCGTGAATTATTCTCCTAGCAACGAGGCCCACTGGCCTAGGTACCCACACCTGTGGGTGCGCCT
GTACGTGCTGGAGCTGTATTGCATCATCCTGGGCCTGCCCCCTTGTCTGAATATCCTGCGGAGAAAGCAGCCC
CAGCTGACCTTCTTTACAATCGCCCTGCAGTCTTGTCACTATCAGAGGCTGCCACCCCACATCCTGTGGGCCA
CAGGCCTGAAGTCTGGAGGATCTAGCGGAGGCTCCTCTGGCAGCGAGACACCAGGAACAAGCGAGTCAGCAAC
ACCAGAGAGCAGTGGCGGCAGCAGCGGCGGCAGCAGCGACCTGGTGCTGGGCCTGGCTATCGGCATCGGCAGC
GTGGGCGTGGGCATCCTGAACAAGGTGACCGGCGAGATCATCCACAAGAACAGTCGCATCTTCCCTGCTGCTC
AGGCTGAGAACAACCTGGTGCGCCGCACCAACCGCCAGGGTCGCCGGCTTGCTCGCCGCAAGAAGCACCGGCG
CGTGCGCCTGAACCGCCTGTTCGAGGAGAGCGGCCTGATCACCGACTTCACCAAGATCAGCATCAACCTGAAC
CCCTACCAGCTGCGCGTGAAGGGCCTGACCGACGAGCTGAGCAACGAGGAGCTGTTCATCGCCCTGAAGAACA
TGGTGAAGCACCGCGGCATCAGCTACCTGGACGACGCCAGCGACGACGGCAACAGCAGCGTGGGCGACTACGC
CCAGATCGTGAAGGAGAACAGCAAGCAGCTGGAGACCAAGACCCCCGGCCAGATCCAGCTGGAGCGCTACCAG
ACCTACGGCCAGCTGCGCGGCGACTTCACCGTGGAGAAGGACGGCAAGAAGCACCGCCTGATCAACGTGTTCC
CCACCAGCGCCTACCGCAGCGAGGCCCTGCGCATCCTGCAGACCCAGCAGGAGTTCAACCCCCAGATCACCGA
CGAGTTCATCAACCGCTACCTGGAGATCCTGACCGGCAAGCGCAAGTACTACCACGGCCCCGGCAACGAGAAG
AGCCGCACCGACTACGGCCGCTACCGCACCAGCGGCGAGACCCTGGACAACATCTTCGGCATCCTGATCGGCA
AGTGCACCTTCTACCCCGACGAGTTCCGCGCCGCCAAGGCCAGCTACACCGCCCAGGAGTTCAATCTGCTGAA
CGACCTGAACAACCTGACCGTGCCCACCGAGACCAAGAAGCTGAGCAAGGAGCAGAAGAACCAGATCATCAAC
TACGTGAAGAACGAGAAGGCTATGGGCCCCGCCAAGCTGTTCAAGTACATCGCCAAGCTGCTGAGCTGCGACG
TGGCCGACATCAAGGGCTACCGCATCGACAAGAGCGGCAAGGCCGAGATCCACACCTTCGAGGCCTACCGCAA
GATGAAGACCCTGGAGACCCTGGACATCGAGCAGATGGACCGAGAGACCCTGGACAAGCTGGCCTACGTGCTG
ACCCTGAACACCGAGCGCGAGGGCATCCAGGAGGCCCTGGAGCACGAGTTCGCCGACGGCAGCTTCAGCCAGA
AACAGGTGGACGAGCTGGTGCAGTTCCGCAAGGCCAACAGCAGCATCTTCGGCAAGGGCTGGCACAACTTCAG
CGTGAAGCTGATGATGGAGCTGATCCCCGAGCTGTACGAGACCAGCGAGGAGCAGATGACCATCCTGACCCGC
CTGGGCAAGCAGAAGACCACCAGCAGCAGCAACAAGACCAAGTACATCGACGAGAAGCTGCTGACCGAGGAGA
TCTACAACCCCGTGGTGGCCAAGAGCGTGCGCCAGGCCATCAAGATCGTGAACGCCGCCATCAAGGAGTACGG
CGACTTCGACAACATCGTGATCGAGATGGCCCGCGAGACCAACGAGGACGACGAGAAGAAGGCCATCCAGAAG
ATCCAGAAGGCCAACAAGGACGAGAAGGACGCCGCCATGCTGAAGGCCGCCAACCAGTACAACGGCAAGGCCG
AGCTGCCCCACAGCGTGTTCCACGGCCACAAGCAGCTGGCCACCAAGATCCGCCTGTGGCACCAGCAGGGCGA
GCGCTGCCTGTACACCGGCAAGACCATCAGCATCC

FIG. 33a

```
ACGACCTGATCAACAACAGCAACCAGTTCGAGGTGGACCACATCCTGCCCCTGAGCATCACCTTCGACGACAG
CCTGGCCAACAAGGTGCTGGTGTACGCCACCGCCAACCAGGAGAAGGGCCAGCGCACCCCCTACCAGGCCCTG
GACAGCATGGACGACGCCTGGAGCTTCCGCGAGCTGAAGGCCTTCGTGCGCGAGAGCAAGACCCTGAGCAACA
AGAAGAAGGAGTATCTGCTGACCGAGGAGGACATCAGCAAGTTCGACGTGCGCAAGAAGTTCATCGAGCGCAA
CCTGGTGGACACCCGCTACGCCAGCCGCGTGGTGCTGAACGCCCTGCAGGAGCACTTCCGCGCCCACAAGATC
GACACCAAGGTGAGCGTGGTGCGCGGCCAGTTCACCAGCCAGCTGCGCCGCACTGGGCATCGAGAAGACCC
GCGACACCTACCACCACCACGCCGTGGACGCCCTGATCATTGCGGCTTCTAGCCAGCTGAACCTGTGGAAGAA
GCAGAAGAACACCCTGGTGAGCTACAGCGAGGAgCAGCTGCTGGACATCGAGACCGGCGAGCTGATCAGCGAC
GACGAGTACAAGGAGAGCGTGTTCAAGGCCCCCTACCAGCACTTCGTGGACACCCTGAAGAGCAAGGAGTTCG
AGGACAGCATCCTGTTCAGCTACCAGGTGGACAGCAAGTTCAACCGCAAGATCAGCGACGCCACCATCTACGC
CACCCGCCAGGCCAAGGTGGGCAAGGACAAGaagGACGAGACCTACGTGCTGGGCAAGATCAAGGACATCTAC
ACCCAGGACGGCTACGACGCCTTCATGAAGATCTACAAGAAGGACAAGAGCAAGTTCCTGATGTACCGCCACG
ACCCCCAGACCTTCGAGAAGGTGATCGAGCCCATCCTGGAGAACTACCCCAACAAGCAGATgAACGAGAAAGG
CAAGGAGGTGCCCTGCAACCCCTTCCTGAAGTACAAGGAGGAGCACGGCTACATCCGCAAGTACAGCAAGAAG
GGCAACGGCCCCGAGATCAAGAGCCTGAAGTACTACGACAGCAAGCTGctgGGCAACCcCATCGACATCACCC
CCgAaaACAGCAAgAACAAGGTGGTGCTGCAGAGCcTtAagCCCTGGCGCaCCGACGTGTACTTCAACAAGgC
CACCGGCAAGTACGAGATCCTGGGGCTGAAGTACGCCGATCTGCAGTTTGAGAAAGGCACAGGCACCTACAAG
ATCAGCCAGGAGAAGTACAACGACATCAAGAAGAAGGAGGGCGTGGACAGCGACAGCGAGTTCAAGTTCACCC
TGTACAAGAACGACCTTCTGCTGGTGAAGGACACCGAGACCAAGGAGCAACAGCTGTTCCGCTTCCTGAGCCG
CACCCTGCCCAAGCAGAAGCACTACGTGGAGCTGAAGCCCTACGACAAGCAGAAGTTCGAGGGCGGCGAGGCC
CTGATCAAGGTGCTGGGCAACGTGGCCAACgGCGGCCAGTGCAtcAAGGGCCTGGcCAAGAGCAACATCAGCA
TCTACAAGGTGCGCACCGACGTGCTGGGCAACCAGCACATCATCAAGAACGAGGGCGACAAGCCCAAGTTGGA
CTTCAGCAGGGCTGACCCCAAGAAGAAGAGGAAGGTGGGATCTAGCGGCGGGAGCGGCGGGAGCGGGGGAGC
ACTAATCTGAGCGACATCATTGAGAAGGAGACTGGGAAACAGCTGGTCATTCAGGAGTCCATCCTGATGCTGC
CTGAGGAGGTGGAGGAAGTGATCGGCAACAAGCCAGAGTCTGACATCCTGGTGCACACCGCCTACGACGAGTC
CACAGATGAGAATGTGATGCTGCTGACCTCTGACGCCCCCGAGTATAAGCCTTGGGCCCTGGTCATCCAGGAT
TCTAACGGCGAGAATAAGATCAAGATGCTGAGCGGAGGATCCGGAGGATCTGGAGGCAGCACCAACCTGTCTG
ACATCATCGAAGGAGACAGGCAAGCAGCTGGTCATCCAGGAGAGCATCCTGATGCTGCCCGAAGAAGTCGA
AGAAGTGATCGGAAACAAGCCTGAGAGCGATATCCTGGTCCATACCGCCTACGACGAGAGTACCGACGAAAAT
GTGATGCTGCTGACATCCGACGCCCCAGAGTATAAGCCCTGGGCTCTGGTCATCCAGGATTCCAACGGAGAGA
ACAAAATCAAAATGCTGTCTGGCGGCTCAAAAAGAACCGCCGACGGCAGCGAATTCGAGCCCAAGAAGAAGAG
GAAAGTCGGATCCTACCCATACGATGTTCCAGATTACGCTTATCCCTACGACGTGCCTGATTATGCATACCCA
TATGATGTCCCCGACTATGCC
```

FIG. 33b

NLS-rAPOBEC1-St1Cas9 LMD-9/CNRZ1066-NLS-2xUGI-NLS-3xHA AA sequence
<u>NLS</u>
rAPOBEC1
*St1Cas9 ORF*
UGI
<u>*3xHA*</u>

MKRTADGSEFES<u>PKKKRKV</u>SSETGPVAVDPTLRRRIEPHEFEVFFDPRELRKETCLLYEINWGGRHSIWRHTS
QNTNKHVEVNFIEKFTTERYFCPNTRCSITWFLSWSPCGECSRAITEFLSRYPHVTLFIYIARLYHHADPRNR
QGLRDLISSGVTIQIMTEQESGYCWRNFVNYSPSNEAHWPRYPHLWVRLYVLELYCIILGLPPCLNILRRKQP
QLTFFTIALQSCHYQRLPPHILWATGLKSGGSSGGSSGSETPGTSESATPESSGGSSGGS*SDLVLGLAIGIGS
VGVGILNKVTGEIIHKNSRIFPAAQAENNLVRRTNRQGRRLARRKKHRRVRLNRLFEESGLITDFTKISINLN
PYQLRVKGLTDELSNEELFIALKNMVKHRGISYLDDASDDGNSSVGDYAQIVKENSKQLETKTPGQIQLERYQ
TYGQLRGDFTVEKDGKKHRLINVFPTSAYRSEALRILQTQQEFNPQITDEFINRYLEILTGKRKYYHGPGNEK
SRTDYGRYRTSGETLDNIFGILIGKCTFYPDEFRAAKASYTAQEFNLLNDLNNLTVPTETKKLSKEQKNQIIN
YVKNEKAMGPAKLFKYIAKLLSCDVADIKGYRIDKSGKAEIHTFEAYRKMKTLETLDIEQMDRETLDKLAYVL
TLNTEREGIQEALEHEFADGSFSQKQVDELVQFRKANSSIFGKGWHNFSVKLMMELIPELYETSEEQMTILTR
LGKQKTTSSSNKTKYIDEKLLTEEIYNPVVAKSVRQAIKIVNAAIKEYGDFDNIVIEMARETNEDDEKKAIQK
IQKANKDEKDAAMLKAANQYNGKAELPHSVFHGHKQLATKIRLWHQQGERCLYTGKTISIHDLINNSNQFEVD
HILPLSITFDDSLANKVLVYATANQEKGQRTPYQALDSMDDAWSFRELKAFVRESKTLSNKKKEYLLTEEDIS
KFDVRKKFIERNLVDTRYASRVVLNALQEHFRAHKIDTKVSVVRGQFTSQLRRHWGIEKTRDTYHHHAVDALI
IAASSQLNLWKKQKNTLVSYSEEQLLDIETGELISDDEYKESVFKAPYQHFVDTLKSKEFEDSILFSYQVDSK
FNRKISDATIYATRQAKVGKDKKDETYVLGKIKDIYTQDGYDAFMKIYKKDKSKFLMYRHDPQTFEKVIEPIL
ENYPNKQMNEKGKEVPCNPFLKYKEEHGYIRKYSKKGNGPEIKSLKYYDSKLLGNPIDITPENSKNKVVLQSL
KPWRTDVYFNKATGKYEILGLKYADLQFEKGTGTYKISQEKYNDIKKKEGVDSDSEFKFTLYKNDLLLVKDTE
TKEQQLFRFLSRTLPKQKHYVELKPYDKQKFEGGEALIKVLGNVANGGQCIKGLAKSNISIYKVRTDVLGNQH
IIKNEGDKPKLDFS*RADPKKKRKVGSSGGSGGSGGS**TNLSDIIEKETGKQLVIQESILMLPEEVEEVIGNKPE
SDILVHTAYDESTDENVMLLTSDAPEYKPWALVIQDSNGENKIKMLSGGSGGSGGSTNLSDIIEKETGKQLVI
QESILMLPEEVEEVIGNKPESDILVHTAYDESTDENVMLLTSDAPEYKPWALVIQDSNGENKIKML**SGGSKRT
ADGSEFE<u>PKKKRKV</u>GS<u>*YPYDVPDYAYPYDVPDYAYPYDVPDYA*</u>

FIG. 34

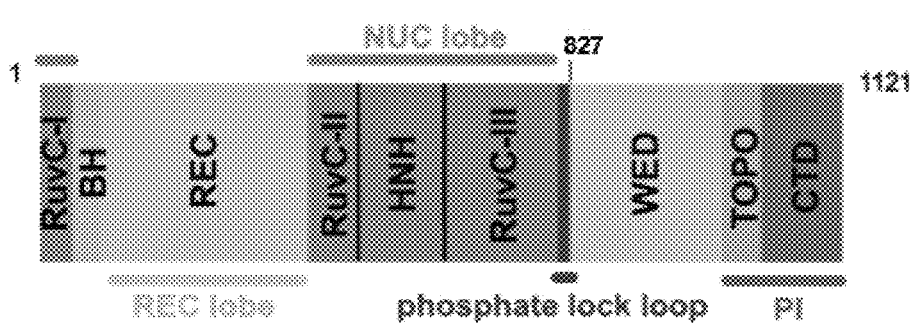

FIG. 35a

```
              1         10        20        30        40        50        60
LMD-9   IYATRQAKVGKDK DETYVLGKIKDIYTQDGYDAFMKIYKKDKSKFLMYRHDPQTFEKVI
LMG     IYATRQAKVGKDK DETYVLGKIKDIYTQDGYDAFMKIYKKDKSKFLMYRHDPQTFEKVI
CNRZ    IYATRQAKVGKDK DETYVLGKIKDIYTQDGYDAFMKIYKKDKSKFLMYRHDPQTFEKVI
TH1477  IYATRQAKVGKDK DETYVLGKIKDIYTQDGYDAFMKIYKKDKSKFLMYRHDPQTFEKVI 70        80        90       100       110
LMD-9   EPILENYPNKQ  NEKGKEVPCNPFLKYKEEHGYIRKYSKKGNGPEIKSLKYYDSK LGN
LMG     EPILENYPNKQ  NEKGKEVPCNPFLKYKEEHGYIRKYSKKGNGPEIKSLKYYDSK LGN
CNRZ    EPILENYPNKQ  NEKGKEVPCNPFLKYKEEHGYIRKYSKKGNGPEIKSLKYYDSK LGN
TH1477  EPILENYPNKQ  NEKGKEVPCNPFLKYKEEHGYIRKYSKKGNGPEIKSLKYYDSK LGN 120       130       140       150       160       170
LMD-9   IDITP   S NKVVLQS  PWR DVYFNK TGKYEILGLKY DLQFEKGTGTY ISQ KYN
LMG     IDITP     NKVVLQS  PWR DVYFNK TGKYEILGLKYADLQFEK TGTY ISQ KYN
CNRZ    IDITP   S NKVVLQS LNPWR DVYFNK TGKYEILGLKYADLQFEKGTGTY ISQ KYN
TH1477  IDITP     NKVVLQS LNPWR DVYFNK TGKYEILGLKY DLQFEKGT Y IS   Y 180       190       200       210       220       230
LMD-9    IKK EGVDSDSEFKFTLYKNDLLL KD  TKEQ L RF SRT  K  K YVELKPY K K
LMG      I N EGVDSDSEFKFTLYKNDLLL KD  TKEQ L RF SR   H  K YVELKPY K K
CNRZ     IKK EGVDSDSEFKFTLYKNDLLL KD  TKEQ L RF SRT  H  K YVELKPY KQK
TH1477    K  RGVD  SEFKFTLYKNDLLL KD   EQ L RF SR      K YVELKPY  GK 240       250       260       270       280       290
LMD-9   PEG E LIK LG VAN G CIKGL KSNISIYKVRTDVLGNQHIIKNEGDKPKLDF
LMG     PE  E LI  LG  DK  G CIKGL KSNISIYKVRTDVLGNQHIIKNEGDKPKLDF
CNRZ    PEG E LIK LG VAN G CIKGL KSNISIYKVRTDVLGNQHIIKNEGDKPKLDF
TH1477  PEG E LIK LG V K G CIKGL KSNISIYKVRTDVLGNQHIIKNEGDKPKLDF
```

FIG. 35b

CRISPR-cas9 SYSTEM AND USES THEREOF

CROSS-REFERENCE TO RELATED APPLICATIONS

The present application is a National Stage Application of PCT Application No. PCT/CA2019/050629 filed on May 10, 2019 and published in English under PCT Article 21 (2), which claims the benefit of U.S. Provisional Application Ser. No. 62/670,135 filed on May 11, 2018. All documents above are incorporated herein by reference in their entirety.

SEQUENCE LISTING

Pursuant to 37 C.F.R. 1.821 (c), a sequence listing is submitted herewith as an ASCII compliant text file named "G11229_441_SeqList.txt", created on Sep. 5, 2024 and having a size of about 343,000 bytes. The computer readable form of the sequence listing is incorporated herein by reference in its entirety.

TECHNICAL FIELD

The present disclosure generally relates to the modification of nucleic acids, and more particularly to the to the modification of nucleic acids using a CRISPR/Cas9 system.

BACKGROUND ART

Clustered regularly interspaced short palindromic repeats (CRISPR) and CRISPR-associated (Cas) proteins are components of prokaryotic adaptive immune systems that have been harnessed for robust genome editing[1]. Type II-based tools rely on a large multidomain endonuclease, Cas9, guided to its DNA target by an engineered single-guide RNA (sgRNA) chimera[2,3,4]. The Cas9-sgRNA binary complex finds its target through recognition of a short sequence called the protospacer adjacent motif (PAM) and subsequent base pairing of the guide RNA with the DNA to generate a specific double-strand break (DSB)[1,5]. While *Streptococcus pyogenes* (SpCas9) remains the most widely used Cas9 variant for genome engineering, other RNA-guided nucleases have also been identified[4,6]. However, certain bacterial CRISPR/Cas enzymes were found to be inactive in human cells despite being accurately reprogrammed for DNA binding and cleavage in vitro[7-10]. An even greater challenge has been implementation in vivo, examples including the use of the type II-A Cas9 from *Staphylococcus aureus* (SaCas9) for in vivo editing using recombinant Adeno-Associated Virus (rAAV) vectors[7,11,12], as well as Cas9s from *Campylobacter jejuni* and *Neisseria meningitidis*[13-15].

In vivo genome editing offers the possibility to generate phenotypes in animal models in order to better recapitulate the interactions between cell types and organs. In addition, it can be contemplated as a novel class of human therapeutics that enables precise molecular correction of genetic defects underlying diseases. As such, it has for example been shown that rAAV- and zinc-finger nuclease (ZFN)-mediated liver targeting can correct disease phenotypes in neonatal and adult mouse models, a process currently under clinical investigation[16-19].

There is therefore a need for further development of robust and wide-ranging CRISPR-based technologies, for example for in vivo editing.

The present description refers to a number of documents, the content of which is herein incorporated by reference in their entirety.

SUMMARY OF THE DISCLOSURE

The present disclosure generally relates to the modification of nucleic acids, and more particularly to the to the modification of nucleic acids using a CRISPR/Cas9 system. Methods and products are described herein for the modification of nucleic acids using a CRISPR/Cas9 system. Also described herein are uses of such methods and products for the modification of a target nucleic acid in a cell, in vitro or in vivo. Such methods and products may also be used for prevention or treatment of a condition associated with a target polynucleotide.

In various aspects and embodiments, the present disclosure provides the following items 1 to 136:

1. A sgRNA for modification of a target polynucleotide in a cell, comprising:
    (a) a guide segment comprising a guide sequence corresponding to a region of the target polynucleotide;
    (b) a first hairpin-forming segment located 3' to the guide sequence, the first hairpin hairpin-forming segment being capable of forming a hairpin comprising a stem portion and a loop portion, wherein the stem portion does not comprise a sequence corresponding to an RNA polymerase III termination signal.
2. The sgRNA of item 1, wherein the stem portion does not comprise more than 4 consecutive uracil nucleotides.
3. The sgRNA of item 1, wherein the stem portion does not comprise more than 3 consecutive uracil nucleotides.
4. The sgRNA of item 1, wherein the stem portion comprises a first stem portion and a second stem portion, wherein the first stem portion does not comprise a sequence corresponding to an RNA polymerase III termination signal.
5. The sgRNA of item 4, wherein the first stem portion does not comprise more than 4 consecutive uracil nucleotides.
6. The sgRNA of item 5, wherein the first stem portion does not comprise more than 3 consecutive uracil nucleotides.
7. The sgRNA of any one of items 4 to 6, wherein the first stem portion and second stem portion are separated by a first bulge portion.
8. The sgRNA of any one of items 1 to 8, wherein the loop portion comprises or consists of a sequence of 3 to 6 nucleotides.
9. The sgRNA of item 8, wherein the loop portion comprises or consists of a sequence of 3 to 5 nucleotides.
10. The sgRNA of item 9, wherein the loop portion comprises or consists of a sequence of 4 nucleotides.
11. The sgRNA of item 10, wherein the loop portion comprises or consists of the nucleotide sequence $N^1N^2N^3N^4$, wherein $N^1$, $N^2$, and $N^3$ are each independently A, C, G or U, and $N^4$ is C or G.
12. The sgRNA of item 10 or 11, wherein the loop portion comprises or consists of the nucleotide sequence $N^1N^2N^3N^4$, wherein $N^1$, $N^3$, and $N^4$ are each independently A, C, G or U, and $N^2$ is U, G or A.
13. The sgRNA of item 11 or 12, wherein $N^1$ is G.
14. The sgRNA of any one of items 11 to 13, wherein $N^2$ is U.
15. The sgRNA of any one of items 11 to 14, wherein $N^3$ is A.
16. The sgRNA of any one of items 11 to 15, wherein $N^4$ is C.
17. The sgRNA of any one of items 10 to 16, wherein the loop portion comprises or consists of the nucleotide sequence GUAC.
18. The sgRNA of any one of items 4 to 17, wherein the second stem portion comprises or consists of a hybrid of 4 nucleotide pairs.

19. The sgRNA of item 18, wherein the fourth pair of the hybrid of the second stem portion, distal to the first stem portion, is a G-C pair.
20. The sgRNA of item 18 or 19, wherein the hybrid of the second stem portion comprises or consists of the sequence 5'-UCUG-3' hybridized to the sequence 5'-CAGA-3'.
21. The sgRNA of any one of items 4 to 20, wherein the first stem portion comprises or consists of a hybrid of at least 5 nucleotide pairs.
22. The sgRNA of any one of items 4 to 21, wherein the first stem portion comprises or consists of a hybrid of not more than 12 nucleotide pairs.
23. The sgRNA of item 21 or 22, wherein the first stem portion comprises or consists of a hybrid of 6 to 10 nucleotide pairs.
24. The sgRNA of item 23, wherein the first stem portion comprises or consists of a hybrid of 7 to 9 nucleotide pairs.
25. The sgRNA of item 24, wherein the first stem portion comprises or consists of a hybrid of 8 nucleotide pairs.
26. The sgRNA of any one of items 4 to 25, wherein the first stem portion does not comprise a mismatch.
27. The sgRNA of any one of items 4 to 26, wherein the hybrid of the first stem portion comprises or consists of the sequence 5'-UCUUUGUA-3' hybridized to the sequence 5'-UACAAAGA-3'.
28. The sgRNA of any one of items 4 to 24, wherein the first stem portion comprises a single mismatch.
29. The sgRNA of item 28, wherein the hybrid of the first stem portion comprises or consists of the sequence 5'-GUCUUUGUA-3' hybridized to the sequence 5'-UACAAAGAU-3'.
30. The sgRNA of any one of items 1 to 29, further comprising one or more additional hairpin-forming segments located 3' to the first hairpin-forming segment.
31. The sgRNA of item 30, further comprising one or more linker segments located between the first hairpin-forming segment and additional hairpin-forming segments, and/or between the additional hairpin-forming segments.
32. A nucleic acid comprising a nucleotide sequence encoding the sgRNA of any one of items 1 to 31.
33. A vector comprising the nucleic acid of item 32.
34. The vector of item 33, further comprising a nucleotide sequence encoding a CRISPR nuclease.
35. The vector of item 34, wherein the CRISPR nuclease is a Cas9 enzyme.
36. The vector of item 34 or 35, wherein the CRISPR nuclease is derived from non-pathogenic bacteria.
37. The vector of any one of items 34 to 36, wherein the CRISPR nuclease is a *Streptococcus thermophilus* Cas9 nuclease.
38. The vector of any one of items 34 to 37, wherein the CRISPR nuclease is a type II Cas9 nuclease.
39. The vector of any one of items 34 to 38, wherein the CRISPR nuclease is a *Streptococcus thermophilus* type II-A CRISPR1-Cas9 (St1Cas9).
40. The vector of any one of items 34 to 39, wherein the CRISPR nuclease further comprises one or more nuclear localization signal (NLS) and the vector further comprises one or more nucleotide sequences encoding the one or more NLSs.
41. The vector of item 40, wherein the CRISPR nuclease comprises a first NLS at its amino terminal end and a second NLS at its carboxy terminal end, and the vector comprises NLS-encoding nucleotide sequences flanking the CRISPR nuclease-encoding nucleotide sequence.
42. The vector of item 33, further comprising a promoter operably-linked to the nucleotide sequence encoding the sgRNA.
43. The vector of any one of items 34 to 41, further comprising one or more promoters operably-linked to the nucleotide sequence encoding the sgRNA and or the nucleotide sequence encoding the CRISPR nuclease.
44. The vector of item 43, wherein the nucleotide sequence encoding the sgRNA and or the nucleotide sequence encoding the CRISPR nuclease are both operably linked to a single promoter.
45. The vector of item 43, wherein the nucleotide sequence encoding the sgRNA is operably linked to a first promoter and the nucleotide sequence encoding the CRISPR nuclease is operably linked to a second promoter, wherein the first and second promoters may be the same or different.
46. The vector of item 45, wherein (i) the first promoter and the nucleotide sequence encoding the sgRNA and (ii) the second promoter and the nucleotide sequence encoding the CRISPR nuclease are in the same orientation within the vector.
47. The vector of item 45, wherein (i) the first promoter and the nucleotide sequence encoding the sgRNA and (ii) the second promoter and the nucleotide sequence encoding the CRISPR nuclease are in opposite orientations within the vector.
48. The vector of any one of items 33 to 47, wherein the vector is a viral vector.
49. The vector of item 48, wherein the vector is an adeno-associated virus (AAV) vector.
50. A host cell comprising the nucleic acid of item 32 or the vector of any one of items 33 to 49.
51. A composition comprising the sgRNA of any one of items 1 to 31, the nucleic acid of item 32, the vector of any one of items 33 to 49, or the host cell of item 50.
52. The composition of item 51, further comprising a pharmaceutically acceptable carrier.
53. A system comprising the sgRNA of any one of items 1 to 31, the nucleic acid of item 32, the vector of any one of items 33 to 49, the host cell of item 50, and/or the composition of claim 51 or 52.
54. A system comprising the vector of item 33 and a further vector comprising a nucleotide sequence encoding a CRISPR nuclease.
55. The system of item 54, wherein the CRISPR nuclease is as defined in any one of items 35 to 41.
56. The system of item 54 or 55, wherein the vector of item 33 further comprises a promoter operably-linked to the nucleotide sequence encoding the sgRNA and further vector further comprises a promoter operably-linked to the nucleotide sequence encoding the CRISPR nuclease.
57. A method of modifying a target polynucleotide in a cell, comprising contacting the cell with the sgRNA of any one of items 1 to 31, the nucleic acid of item 32, the vector of any one of items 33 to 49, the composition of item 51 or 52 and/or 5 the system of any one of items 53 to 56.
58. The method of item 57, which is an in vitro method.
59. The method of item 57, which is an in vivo method and the cell is in a subject.
60. Use of the sgRNA of any one of items 1 to 31, the nucleic acid of item 32, the vector of any one of items 33 to 49, the composition of item 51 or 52 and/or the system of any one of items 53 to 56, for modifying a target polynucleotide in a cell.
61. Use of the sgRNA of any one of items 1 to 31, the nucleic acid of item 32, the vector of any one of items 33 to 49, the composition of item 51 or 52 and/or the system of any one of items 53 to 56, for the preparation of a medicament for modifying a target polynucleotide in a cell.

62. The sgRNA of any one of items 1 to 31, the nucleic acid of item 32, the vector of any one of items 33 to 49, the composition of item 51 or 52 and/or the system of any one of items 53 to 56, for use in modifying a target polynucleotide in a cell.

63. A method of preventing or treating a condition associated with a target polynucleotide in a subject in need thereof, comprising administering to the subject an effective amount the sgRNA of any one of items 1 to 31, the nucleic acid of item 32, the vector of any one of items 33 to 49, the composition of item 51 or 52 and/or the system of any one of items 53 to 56.

64. The method of item 63, wherein the condition is a metabolic condition.

65. The method of item 63 or 64, wherein the condition is a hepatic condition.

66. Use of the sgRNA of any one of items 1 to 31, the nucleic acid of item 32, the vector of any one of items 33 to 49, the composition of item 51 or 52 and/or the system of any one of items 53 to 56, for preventing or treating a condition associated with a target polynucleotide in a subject.

67. Use of the sgRNA of any one of items 1 to 31, the nucleic acid of item 32, the vector of any one of items 33 to 49, the composition of item 51 or 52 and/or the system of any one of items 53 to 56, for the preparation of a medicament for preventing or treating a condition associated with a target polynucleotide in a subject.

68. The use of item 66 or 67, wherein the condition is a metabolic condition.

69. The use of any one of items 66 to 68, wherein the condition is a hepatic condition.

70. The sgRNA of any one of items 1 to 31, the nucleic acid of item 32, the vector of any one of items 33 to 49, the composition of item 51 or 52 and/or the system of any one of items 53 to 56, for use in preventing or treating a condition associated with a target polynucleotide in a subject.

71. The sgRNA, nucleic acid, vector, composition and/or system for use of item 70, wherein the condition is a metabolic condition.

72. The sgRNA, nucleic acid, vector, composition and/or system for use of item 70 or 71, wherein the condition is a hepatic condition.

73. The sgRNA of any one of items 1 to 31, the nucleic acid of item 32, the vector of any one of items 33 to 49, the host cell of item 50, the composition of item 51 or 52 and/or the system of any one of items 53 to 56, for use as a medicament.

74. An isolated CRISPR nuclease polypeptide comprising a first domain and a second domain C-terminal to the first domain, wherein the first domain comprises a guide RNA-binding domain and a nuclease domain, and the second domain comprises a WED domain and a PAM-interacting domain, wherein the first and second domains are derived from different bacterial strains.

75. The isolated polypeptide of item 74, wherein the first and second domains are derived from non-pathogenic bacteria.

76. The isolated polypeptide of item 74 or 75, wherein the first and second domains are derived from different bacterial species.

77. The isolated polypeptide of item 74 or 75, wherein the first and second domains are derived from different strains of the same bacterial species.

78. The isolated polypeptide of item 77, wherein the first and second domains are derived from different strains of *Streptococcus thermophilus*.

79. The isolated polypeptide of any one of items 74 to 78, wherein the CRISPR nuclease is a type II Cas9 nuclease.

80. The isolated polypeptide of any one of items 74 to 79, wherein the CRISPR nuclease is a *Streptococcus thermophilus* type II-A CRISPR1-Cas9 (St1Cas9).

81. The isolated polypeptide of any one of items 74 to 80, further comprising one or more nuclear localization signal (NLS).

82. The isolated polypeptide of item 81, comprising a first NLS N-terminal to the first domain and a second NLS C-terminal to the second domain.

83. The isolated polypeptide of any one of items 74 to 82, further comprising a cytidine deaminase domain or an adenosine deaminase domain.

84. The isolated polypeptide of item 83, comprising a cytidine deaminase domain.

85. The isolated polypeptide of item 84, wherein the cytidine deaminase is an APOBEC cytidine deaminase.

86. The isolated polypeptide of item 84, wherein the cytidine deaminase domain comprises the amino acid sequence of SEQ ID NO: 50, or a functional fragment thereof, or a functional variant thereof.

87. The isolated polypeptide of item 84 or 85, further comprising a uracil DNA glycosylase inhibitor (UGI) domain.

88. The isolated polypeptide of item 87, wherein the UGI domain comprises the amino acid sequence of SEQ ID NO: 51, or a functional fragment thereof, or a functional variant thereof.

89. The isolated polypeptide of any one of items 74 to 88, wherein the first domain is derived from *Streptococcus thermophilus* LMD-9, LMG18311, CNRZ1066 or TH1477.

90. The isolated polypeptide of any one of items 74 to 89, wherein the second domain is derived from *Streptococcus thermophilus* LMD-9, LMG18311, CNRZ1066 or TH1477.

91. The isolated polypeptide of any one of items 74 to 90, wherein the first domain is derived from *Streptococcus thermophilus* LMD-9 and the second domain is derived from *Streptococcus thermophilus* LMG18311, CNRZ1066 or TH1477.

92. The isolated polypeptide of any one of items 74 to 90, wherein the first domain is derived from *Streptococcus thermophilus* LMG18311 and the second domain is derived from *Streptococcus thermophilus* LMD-9, CNRZ1066 or TH1477.

93. The isolated polypeptide of any one of items 74 to 90, wherein the first domain is derived from *Streptococcus thermophilus* CNRZ1066 and the second domain is derived from *Streptococcus thermophilus* LMG18311, LMD-9 or TH1477.

94. The isolated polypeptide of any one of items 74 to 90, wherein the first domain is derived from *Streptococcus thermophilus* TH1477 and the second domain is derived from *Streptococcus thermophilus* LMG18311, CNRZ1066 or LMD-9.

95. The isolated polypeptide of any one of items 74 to 88, wherein the first domain comprises the amino acid sequence of SEQ ID NO: 264, 265, 266, or 267, or a functional fragment of any thereof, or a functional variant of any thereof.

96. The isolated polypeptide of any one of items 74 to 88, wherein the second domain comprises the amino acid sequence of SEQ ID NO: 260, 261, 262, or 263, or a functional fragment of any thereof, or a functional variant of any thereof.

97. The isolated polypeptide of any one of items 74 to 88, 95 and 96, wherein the first domain comprises the amino acid sequence of SEQ ID NO: 264, or a functional fragment of any thereof, or a functional variant of any thereof, and the second domain comprises the amino acid sequence of SEQ ID NO: 261, 262, or 263, or a functional fragment of any thereof, or a functional variant of any thereof.

98. The isolated polypeptide of any one of items 74 to 88, 95 and 96, wherein the first domain comprises the amino acid sequence of SEQ ID NO: 265, or a functional fragment of any thereof, or a functional variant of any thereof, and the second domain comprises the amino acid sequence of SEQ ID NO: 260, 262, or 263, or a functional fragment of any thereof, or a functional variant of any thereof.

99. The isolated polypeptide of any one of items 74 to 88, 95 and 96, wherein the first domain comprises the amino acid sequence of SEQ ID NO: 266, or a functional fragment of any thereof, or a functional variant of any thereof, and the second domain comprises the amino acid sequence of SEQ ID NO: 260, 261, or 263, or a functional fragment of any thereof, or a functional variant of any thereof.

100. The isolated polypeptide of any one of items 74 to 88, 95 and 96, wherein the first domain comprises the amino acid sequence of SEQ ID NO: 267, or a functional fragment of any thereof, or a functional variant of any thereof, and the second domain comprises the amino acid sequence of SEQ ID NO: 260, 261, or 262, or a functional fragment of any thereof, or a functional variant of any thereof.

101. The isolated polypeptide of any one of items 74 to 100, the first domain is connected to the second domains via a linker region.

102. The isolated polypeptide of any one of items 74 to 101, wherein the polypeptide is capable of binding a PAM that is different from the PAM bound by a CRISPR nuclease from which the first domain is derived.

103. The isolated polypeptide of any one of items 74 to 102, wherein the polypeptide binds a PAM comprising the sequence NNAGAA, NNGGAA, NNACAA, NNGCAA, NNGAAA or NNAAAA.

104. A nucleic acid comprising a nucleotide sequence encoding the isolated polypeptide of any one of items 74 to 103.

105. A vector comprising the nucleic acid of item 104.

106. The vector of item 105, further comprising a nucleotide sequence encoding an sgRNA.

107. The vector of item 106, wherein the sgRNA is the sgRNA of any one of items 1 to 31.

108. The vector of any one of items 105 to 107, further comprising one or more promoters operably-linked to the nucleotide sequence encoding the polypeptide and/or the nucleotide sequence encoding the sgRNA.

109. The vector of item 108, wherein the nucleotide sequence encoding the polypeptide and the nucleotide sequence encoding the sgRNA are both operably linked to a single promoter.

110. The vector of item 108, wherein the nucleotide sequence encoding the sgRNA is operably linked to a first promoter and the nucleotide sequence encoding the polypeptide is operably linked to a second promoter, wherein the first and second promoters may be the same or different.

111. The vector of item 110, wherein (i) the first promoter and the nucleotide sequence encoding the sgRNA and (ii) the second promoter and the nucleotide sequence encoding the CRISPR nuclease are in the same orientation within the vector.

112. The vector of item 110, wherein (i) the first promoter and the nucleotide sequence encoding the sgRNA and (ii) the second promoter and the nucleotide sequence encoding the CRISPR nuclease are in opposite orientations within the vector.

113. The vector of any one of items 105 to 112, wherein the vector is a viral vector.

114. The vector of item 113, wherein the vector is an adeno-associated virus (AAV) vector.

115. A host cell comprising the nucleic acid of item 104 or the vector of any one of items 105-113.

116. A composition comprising the polypeptide according to any one of items 74 to 103, the nucleic acid of item 104, the vector of any one of items 105 to 112, or the host cell of item 115.

117. The composition of item 116, further comprising a pharmaceutically or biologically acceptable carrier.

118. A system comprising the polypeptide according to any one of items 74 to 103, the nucleic acid of item 104, the vector of any one of items 105 to 112, the host cell of item 115, and/or the composition of item 116 or 117.

119. A system comprising the vector of item 105 and a further vector comprising a nucleotide sequence encoding an sgRNA.

120. A method of modifying a target polynucleotide in a cell, comprising contacting the cell with the polypeptide according to any one of items 74 to 103, the nucleic acid of item 104, the vector of any one of items 105 to 112, the host cell of item 115, and/or the composition of item 116 or 117, and/or the system of item 118 or 119.

121. The method of item 120, which is an in vitro method.

122 The method of item 120, which is an in vivo method and the cell is in a subject.

123. Use of the polypeptide according to any one of items 74 to 103, the nucleic acid of item 104, the vector of any one of items 105 to 112, the host cell of item 115, and/or the composition of item 116 or 117, and/or the system of item 118 or 119, for modifying a target polynucleotide in a cell.

124. Use of the polypeptide according to any one of items 74 to 103, the nucleic acid of item 104, the vector of any one of items 105 to 112, the host cell of item 115, and/or the composition of item 116 or 117, and/or the system of item 118 or 119, for the preparation of a medicament for modifying a target polynucleotide in a cell.

125. The polypeptide according to any one of items 74 to 103, the nucleic acid of item 104, the vector of any one of items 105 to 112, the host cell of item 115, and/or the composition of item 116 or 117, and/or the system of item 118 or 119, for use in modifying a target polynucleotide in a cell.

126. A method of preventing or treating a condition associated with a target polynucleotide in a subject in need thereof, comprising administering to the subject an effective amount the polypeptide according to any one of items 74 to 103, the nucleic acid of item 104, the vector of any one of items 105 to 112, the host cell of item 115, and/or the composition of item 116 or 117, and/or the system of item 118 or 119.

127. The method of item 126, wherein the condition is a metabolic condition.

128. The method of item 126 or 127, wherein the condition is a hepatic condition.

129. Use of the polypeptide according to any one of items 74 to 103, the nucleic acid of item 104, the vector of any one of items 105 to 112, the host cell of item 115, and/or the composition of item 116 or 117, and/or the system of item 118 or 119, for preventing or treating a condition associated with a target polynucleotide in a subject.

130. Use of the polypeptide according to any one of items 74 to 103, the nucleic acid of item 104, the vector of any one of items 105 to 112, the host cell of item 115, and/or the composition of item 116 or 117, and/or the system of item 118 or 119, for the preparation of a medicament for preventing or treating a condition associated with a target polynucleotide in a subject.

131. The use of item 129 or 130, wherein the condition is a metabolic condition.

132. The use of any one of items 129 to 131, wherein the condition is a hepatic condition.

133. The polypeptide according to any one of items 74 to 103, the nucleic acid of item 104, the vector of any one of items 105 to 112, the host cell of item 115, and/or the composition of item 116 or 117, and/or the system of item 118 or 119, for use in preventing or treating a condition associated with a target polynucleotide in a subject.

134. The sgRNA, nucleic acid, vector, composition and/or system for use of item 133, wherein the condition is a metabolic condition.

135. The sgRNA, nucleic acid, vector, composition and/or system for use of item 133 or 134, wherein the condition is a hepatic condition.

136. The polypeptide according to any one of items 74 to 103, the nucleic acid of item 104, the vector of any one of items 105 to 112, the host cell of item 115, and/or the composition of item 116 or 117, and/or the system of item 118 or 119, for use as a medicament.

Other objects, advantages and features of the present disclosure will become more apparent upon reading of the following non-restrictive description of specific embodiments thereof, given by way of example only with reference to the accompanying drawings.

BRIEF DESCRIPTION OF DRAWINGS

In the appended drawings:

FIG. 10: Amino acid sequence alignment of St1Cas9 from different strains (SEQ ID NOs: 16-19 corresponding to LMD_9, LMG_18311, CNRZ_1066, and TH1477, respectively). Identical residues are highlighted in black. The position of the WED and PAM-interacting domain (PI) are indicated by arrows. This region of the protein has diverged the most as compared to the N-terminal segment. In SaCas9, the PAM duplex is sandwiched between the WED and PI domains5. Alignment was performed with Clustal Omega6 and ESPript7.

FIG. 11: St1Cas9 vectors available from Addgene. Plasmids for in vitro genome editing (left to right): Mammalian expression vector for St1Cas9 LMD-9 (Addgene #110625); hU6-driven sgRNA expression plasmid for St1Cas9 LMD-9 (Addgene #110627); Dual expression vector for St1Cas9 LMD-9 and its sgRNA (Addgene #110626). Plasmid for in vivo genome editing: Single AAV vector with a liver-specific promoter to express St1Cas9 LMD-9 and its hU6-driven sgRNA (Addgene #110624). Cloning: The guide N (x) can vary in size between 18-22; Annealed oligonucleotides must have the indicated overhangs; sgRNA expression cassettes are linearized by digestion with BsmBI (guide sense and antisense sequences, SEQ ID NOs: 20-21).

FIG. 12: Total editing efficacy at FANCF as determined by the TIDE assay for FIG. 1.

FIG. 13: Total editing efficacy at EMX1 as determined by the TIDE assay for FIG. 1.

FIG. 14: Total editing efficacy at RUNX1 as determined by the TIDE assay for FIG. 1.

FIG. 15: Total editing efficacy as determined by the TIDE assay for FIG. 5.

FIG. 16: Nucleotide sequence of St1Cas9 of strain LMD-9 (SEQ ID NO: 22). SV40 NLS is uppercase and underlined SEQ ID NOs: 23-24); St1Cas9 sequence is in uppercase italic (SEQ ID NO: 25); linker regions are in lowercase (linkers flanking St1Cas9, SEQ ID NOs: 26-27).

FIG. 17: Amino acid sequence of St1Cas9 of strain LMD-9 (SEQ ID NO: 28). SV40 NLS is uppercase and underlined (SEQ ID NO: 29); St1Cas9 sequence is in uppercase italic (SEQ ID NO: 30); linker regions are in lowercase (linkers flanking St1Cas9, SEQ ID NOs: 31-32).

FIGS. 23a-23b: Nucleotide sequence of NLS-St1Cas9 LMD-9/LMG18311 Hybrid-NLS (SEQ ID NO: 33). SV40 NLS is uppercase and underlined (SEQ ID NOs: 23-24); St1Cas9 hybrid sequence is in uppercase italic (SEQ ID NO: 34); linker regions are in lowercase (linkers flanking St1Cas9 hybrid, SEQ ID NOs: 26-27).

FIG. 24: Amino acid sequence of NLS-St1Cas9 LMD-9/LMG18311 Hybrid-NLS (SEQ ID NO: 35). SV40 NLS is uppercase and underlined (SEQ ID NO: 29); St1Cas9 hybrid sequence is in uppercase italic (SEQ ID NO: 36); linker regions are in lowercase (linkers flanking St1Cas9, SEQ ID NOs: 31-32).

FIGS. 25a-25b: Nucleotide sequence of NLS-St1Cas9 LMD-9/CNRZ1066 Hybrid-NLS (SEQ ID NO: 37). SV40 NLS is uppercase and underlined SEQ ID NOs: 23-24); St1Cas9 hybrid sequence is in uppercase italic (SEQ ID NO: 38); linker regions are in lowercase (linkers flanking St1Cas9 hybrid, SEQ ID NOs: 26-27).

FIG. 26: Amino acid sequence of NLS-St1Cas9 LMD-9/CNRZ1066 Hybrid-NLS (SEQ ID NO: 30). SV40 NLS is uppercase and underlined (SEQ ID NO: 29); St1Cas9 hybrid sequence is in uppercase italic (SEQ ID NO: 40); linker regions are in lowercase (linkers flanking St1Cas9, SEQ ID NOs: 31-32).

FIGS. 27a-27b: Nucleotide sequence of NLS-St1Cas9 LMD-9/TH1477 Hybrid-NLS (SEQ ID NO: 41). SV40 NLS is uppercase and underlined SEQ ID NOs: 23-24); St1Cas9 hybrid sequence is in uppercase italic (SEQ ID NO: 42); linker regions are in lowercase (linkers flanking St1Cas9 hybrid, SEQ ID NOs: 26-27).

FIG. 28: Amino acid sequence of NLS-St1Cas9 LMD-9/TH1477 Hybrid-NLS (SEQ ID NO: 43). SV40 NLS is uppercase and underlined (SEQ ID NO: 29); St1Cas9 hybrid sequence is in uppercase italic (SEQ ID NO: 44); linker regions are in lowercase (linkers flanking St1Cas9, SEQ ID NOs: 31-32).

FIGS. 29a-29b: Nucleotide sequence of NLS-rAPOBEC1-St1Cas9 LMD-9-NLS-2×UGI-NLS-3×HA (SEQ ID NO: 45). SV40 NLS is uppercase and underlined SEQ ID NO: 23); rAPOBEC1 sequence is uppercase bold (SEQ ID NO: 46); St1Cas9 sequence is in uppercase italic (SEQ ID NO: 25); UGI sequence is in uppercase bold italic (SEQ ID NO: 47); 3×HA sequence is in uppercase bold italic underlined (SEQ ID NO: 48).

FIG. 30: Amino acid sequence of NLS-rAPOBEC1-St1Cas9 LMD-9-NLS-2×UGI-NLS-3×HA (SEQ ID NO: 49). SV40 NLS is uppercase and underlined SEQ ID NO: 23); rAPOBEC1 sequence is uppercase bold (SEQ ID NO: 50); St1Cas9 sequence is in uppercase italic (SEQ ID NO: 30); UGI sequence is in uppercase bold italic (SEQ ID NO: 51); 3×HA sequence is in uppercase bold italic underlined (SEQ ID NO: 52).

FIGS. 31a-31b: Nucleotide sequence of NLS-rAPOBEC1-St1Cas9 LMD-9/LMG18311-NLS-2×UGI-NLS-3×HA (SEQ ID NO: 53). SV40 NLS is uppercase and underlined SEQ ID NO: 23); rAPOBEC1 sequence is uppercase bold (SEQ ID NO: 47); St1Cas9 sequence is in uppercase italic (SEQ ID NO: 54); UGI sequence is in uppercase bold italic (SEQ ID NO: 48); 3×HA sequence is in uppercase bold italic underlined (SEQ ID NO: 49).

FIG. 32: Amino acid sequence of NLS-rAPOBEC1-St1Cas9 LMD-9/LMG18311-NLS-2×UGI-NLS-3×HA (SEQ ID NO: 55). SV40 NLS is uppercase and underlined SEQ ID NO: 23); rAPOBEC1 sequence is uppercase bold (SEQ ID NO: 51); St1Cas9 sequence is in uppercase italic (SEQ ID NO: 56); UGI sequence is in uppercase bold italic (SEQ ID NO: 52); 3×HA sequence is in uppercase bold italic underlined (SEQ ID NO: 53).

FIGS. 33a-33b: Nucleotide sequence of NLS-rAPOBEC1-St1Cas9 LMD-9/CNRZ1066-NLS-2×UGI-NLS-3×HA (SEQ ID NO: 57). SV40 NLS is uppercase and underlined SEQ ID NO: 23); rAPOBEC1 sequence is uppercase bold (SEQ ID NO: 47); St1Cas9 sequence is in uppercase italic (SEQ ID NO: 58); UGI sequence is in uppercase bold italic (SEQ ID NO: 48); 3×HA sequence is in uppercase bold italic underlined (SEQ ID NO: 49).

FIG. 34: Amino acid sequence of NLS-rAPOBEC1-St1Cas9 LMD-9/CNRZ1066-NLS-2×UGI-NLS-3×HA (SEQ ID NO: 59). SV40 NLS is uppercase and underlined SEQ ID NO: 23); rAPOBEC1 sequence is uppercase bold (SEQ ID NO: 51); St1Cas9 sequence is in uppercase italic (SEQ ID NO: 60); UGI sequence is in uppercase bold italic (SEQ ID NO: 52); 3×HA sequence is in uppercase bold italic underlined (SEQ ID NO: 53).

FIG. 35: Domain organization of St1Cas9 from *S. thermophilus* LMD-9. BH: bridge helix, CTD: C-terminal domain, PI: PAM-interacting domain, WED: wedge domain. (a) Schematic representation of St1Cas9 domains; (b) amino acid sequence alignment of the C-terminal regions (including WED and PAM-interacting domain (PI)—see FIG. 10) of St1Cas9 from different strains (SEQ ID NOs: 260-263 corresponding to C-terminal regions of LMD_9, LMG_18311, CNRZ_1066, and TH1477, respectively). Identical residues are highlighted in black.

DESCRIPTION OF ILLUSTRATIVE EMBODIMENTS

Described herein are reagents and methods for genetic modification using a CRISPR-Cas9 system. For example, CRISPR-based genetic modification is shown herein both in vitro and in vivo.

In an aspect, described herein are modified sgRNA architectures for CRISPR-based genetic modification. Therefore, in an aspect, described herein is an sgRNA, e.g., for modification of a target polynucleotide in a cell, comprising: (a) a guide segment comprising a guide sequence corresponding to a region of the target polynucleotide; (b) a first hairpin-forming segment located 3' to the guide sequence, the first hairpin hairpin-forming segment being capable of forming a hairpin comprising a stem portion and a loop portion, wherein the stem portion does not comprise a sequence corresponding to an RNA polymerase III termination signal. RNA polymerase III terminates at a poly(T) stretch, of typically 5-6 nucleotides in length. A poly(T) stretch on the target would correspond to a poly(U) in the sgRNA. Thus in an embodiment, the stem portion does not comprise more than 4 consecutive uracil nucleotides (U's), in a further embodiment, the stem portion does not comprise more than 3 consecutive U's.

In an embodiment the cell is a eukaryotic cell, in a further embodiment, a mammalian cell, in a further embodiment, a human cell. In further embodiments, the cell is a fungal (e.g., yeast), plant or animal cell.

A hairpin (or stem-loop) forms when the phosphodiester backbone folds back onto itself to form a double-helical tract (the stem), leaving unpaired nucleotides to form a single-stranded "loop" region.

The stem may be subdivided into first and second stem portions (e.g. lower and upper stem portions, when considering a hairpin illustrated in an upright orientation).

The first hairpin may optionally comprise a bulge portion separating the first and second stem portions. Bulges and internal loops for when two double-helical tracts are separated on either one or both strands, due to one or more unpaired nucleotides.

Figure 36A:
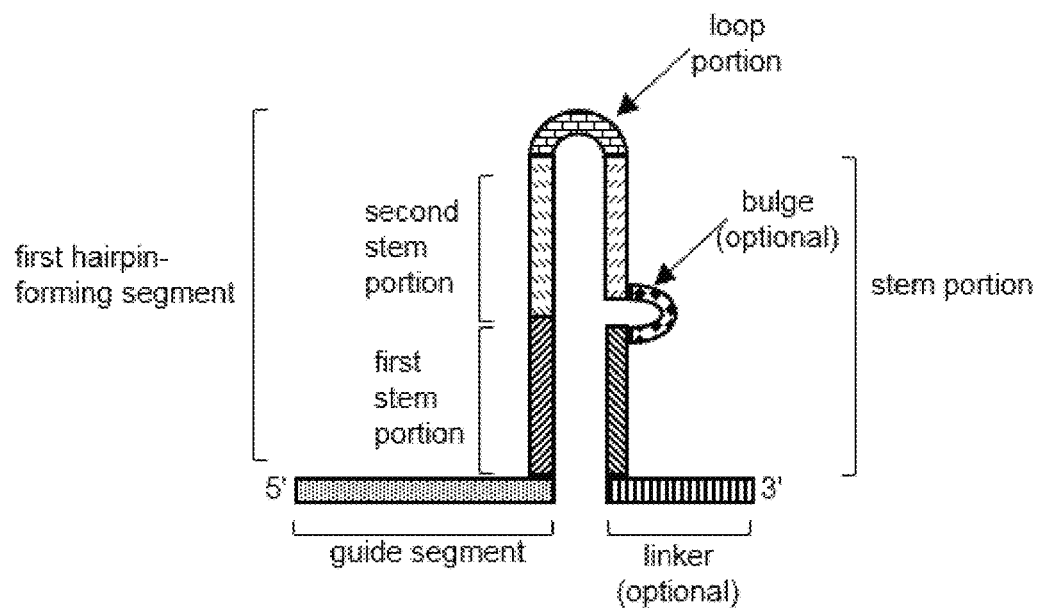
FIGS. 36a-36b: Schematic representation of an sgRNA according to an embodiment described herein, with a hairpin configuration shown in FIG. 36a and a linear configuration shown in FIG. 36b.
Figure 36B:
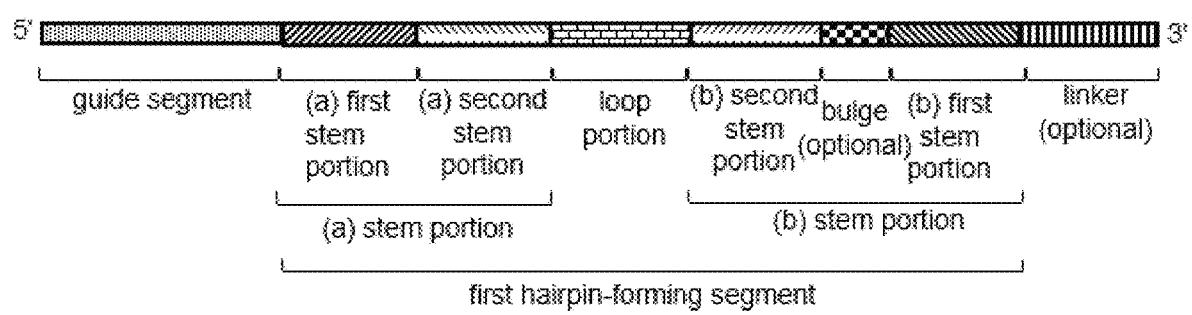

In an embodiment, such an sgRNA can be illustrated schematically as shown in FIG. 36a, with the optional bulge and linker shown, when it has adopted a hairpin configuration The same sgRNA in a linear configuration is shown in FIG. 36b.

In the schematic shown in FIG. 36, (a) and (b) denote the two strands of the stem portion, created when the single strand folds back onto itself to create a two-strand hybrid or duplex structure. Thus the (a) and (b) portions are at least partially complementary to each other to enable formation of the stem portion.

In an embodiment, a predicted secondary structure of an sgRNA is shown in FIG. 1b, with the "guide" corresponding to the guide segment, the "lower" and "upper" stems corresponding to the first and second stem portions, respectively, the "GUAC" loop corresponding to the loop portion, and also showing the bulge. In embodiments, further secondary structures may be formed downstream (3' to the first hairpin-forming segment), as shown in FIG. 1b as "stemloop 1" and "stemloop 2".

In embodiments, the loop portion comprises or consists of a sequence of 3 to 6 nucleotides, in a further embodiment, 3 to 5 nucleotides, in a further embodiment, 4 nucleotides.

In embodiments, such a loop comprises or consists of the nucleotide sequence $N^1N^2N^3N^4$, wherein $N^1$, $N^2$, and $N^3$ are each independently A, C, G or U, and $N^4$ is C or G. In a further embodiment, $N^1$, $N^3$, and $N^4$ are each independently A, C, G or U, and $N^2$ is U, G or A. In a further embodiment, $N^1$ is G. In a further embodiment, $N^2$ is U. In a further embodiment, $N^3$ is A. In a further embodiment, $N^4$ is C. In an embodiment, such a loop comprises or consists of the sequence GUAC.

In embodiments, the second stem portion comprises or consists of a hybrid of 4 nucleotide pairs. In an embodiment, the fourth pair of the hybrid of the second stem portion, distal to the first stem portion, is a G-C pair. In a further embodiment, the hybrid of the second stem portion comprises or consists of the sequence 5'-UCUG-3' hybridized to the sequence 5'-CAGA-3'.

In an embodiment, the first stem portion comprises or consists of a hybrid of at least 5 nucleotide pairs. In a further embodiment, the first stem portion comprises or consists of a hybrid of not more than 12 nucleotide pairs. In further embodiments, the first stem portion comprises or consists of a hybrid of 6 to 10, 7 to 9, 5, 6, 7, 8, 9, 10, 11 or 12 nucleotide pairs. In an embodiment, the hybrid of the first stem portion comprises or consists of the sequence 5'-UCUUUGUA-3' hybridized to the sequence 5'-UACAAAGA-3'. In an embodiment, the hybrid of the first stem portion comprises or consists of the sequence 5'-GUCUUUGUA-3' hybridized to the sequence 5'-UACAAAGAU-3'.

In an embodiment the first stem portion does not comprise a mismatch. In an embodiment, the first stem portion comprises one or more mismatches, in a further embodiment, 1-2 mismatches, in a further embodiment, a single mismatch.

As noted above, in embodiments, the sgRNA further comprises one or more additional hairpin-forming segments located 3' to the first hairpin-forming segment. In embodiments, the sgRNA further comprises one or more linker segments located between the first hairpin-forming segment and additional hairpin-forming segments, and/or between the additional hairpin-forming segments.

Also described herein are nucleic acids comprising a nucleotide sequence encoding an sgRNA described herein.

Also described herein are vectors comprising a nucleic acid described herein. In an embodiment, the vector further comprises a nucleotide sequence encoding a CRISPR nuclease. In an alternative arrangement, two vectors may be used, one for expression of the sgRNA and the other for expression of the CRISPR nuclease, however a single vector for expression of both the sgRNA and CRISPR nuclease is preferred, particularly for in vivo applications.

In an embodiment, the CRISPR nuclease is derived from non-pathogenic bacteria. In an embodiment, the CRISPR nuclease is a Cas9 nuclease, in a further embodiment, a Cas9 nuclease from a non-pathogenic bacterium. In a further embodiment, the Cas9 nuclease is a *Streptococcus thermophilus* Cas9 nuclease. In a further embodiment, the Cas9 nuclease is a *Streptococcus thermophilus* type II-A CRISPR1-Cas9 (St1Cas9). The distinctive functional PAM sequences (NNAGAA and NNGGAA) of St1Cas9 increase the targeting flexibility and combinatorial potential of CRISPR-based genome editing tools.

Also described herein are engineered hybrid CRISPR nucleases combining gRNA-binding and nuclease domains from one source with a PAM-interacting domain from another source. This strategy allows for example the modification of PAM specificity of a CRISPR nuclease.

Therefore, in an aspect, there is further provided an isolated CRISPR nuclease polypeptide comprising a first domain and a second domain C-terminal to the first domain, wherein the first domain comprises a guide RNA-binding domain and a nuclease domain, and the second domain comprises a WED domain and a PAM-interacting domain.

In embodiments, the first and second domains the first and second domains are derived from different sources, i.e., they do not occur together in the same CRISPR nuclease in nature. In an embodiment, the first and second domains are from different bacterial strains, in a further embodiment, from different bacterial species, in a further embodiment, from different strains of the same bacterial species. In an embodiment, the first and second domains are derived from different strains of *Streptococcus thermophilus*.

The CRISPR nucleases described herein may also be used in a base editing approach, by using the CRISPR/Cas9 system to modify a cytidine (C) into a thymidine (T) in a target nucleic acid, or to modify an adenosine (A) into an inosine (I), which is read as a guanine (G), in a target sequence. In such an approach, an sgRNA may be designed and used in combination with a Cas9 nuclease (e.g. a Cas9 nickase) fused with a cytidine deaminase enzyme C into a T) or to modify an A into an I (read as G) in a target nucleic acid. Thus in embodiments a CRISPR nuclease or polypeptide described herein may further comprise a cytidine deaminase domain or an adenosine deaminase domain. In an embodiment, the cytidine deaminase is an APOBEC cytidine deaminase (e.g., comprising the amino acid sequence of SEQ ID NO: 50, or a functional fragment thereof, or a functional variant thereof). Further, enhanced C to T base editing may be achieved by co-expressing a uracil DNA glycosylase inhibitor (UGI). Thus in an embodiment, embodiments a CRISPR nuclease or polypeptide described herein may be used in conjunction with or fused to a UGI domain (e.g. comprising the amino acid sequence of SEQ ID NO: 51, or a functional fragment thereof, or a functional variant thereof).

In embodiments, an engineered hybrid CRISPR nuclease may comprise gRNA-binding and nuclease domains from *Streptococcus thermophilus* LMD-9, LMG18311, CNRZ1066 or TH1477. In further embodiments, an engineered hybrid CRISPR nuclease may comprise a PAM-interacting domain from *Streptococcus thermophilus* LMD-9, LMG18311, CNRZ1066 or TH1477. In embodiments, an engineered hybrid CRISPR nuclease may comprise:

gRNA-binding and nuclease domains from *Streptococcus thermophilus* LMD-9 and a PAM-interacting domain derived from *Streptococcus thermophilus* LMG18311, CNRZ1066 or TH1477.

gRNA-binding and nuclease domains from *Streptococcus thermophilus* LMG18311 and a PAM-interacting domain derived from *Streptococcus thermophilus* LMD-9, CNRZ1066 or TH1477.

gRNA-binding and nuclease domains from *Streptococcus thermophilus* CNRZ1066 and a PAM-interacting domain derived from *Streptococcus thermophilus* LMG18311, LMD-9 or TH1477.

gRNA-binding and nuclease domains from *Streptococcus thermophilus* TH1477 and a PAM-interacting domain derived from *Streptococcus thermophilus* LMG18311, CNRZ1066 or LMD-9.

In embodiments, the domain comprising the gRNA-binding and nuclease domains comprises the amino acid sequence of SEQ ID NO: 264, 265, 266, or 267, or a functional fragment of any thereof, or a functional variant of any thereof. In embodiments, the domain comprising the gRNA-binding and nuclease domains comprises an amino acid sequence at least 80%, 85%, 90%, 91%, 92%, 93%, 94%, 95%, 96%, 97% or 98% identical to the amino acid sequence of SEQ ID NO: 264, 265, 266, or 267, which are embodiments of functional variants of SEQ ID NO: 264, 265, 266, and 267. In embodiments, the domain comprising the PAM-interacting domain comprises the amino acid sequence of SEQ ID NO: 260, 261, 262, or 263, or a functional fragment of any thereof, or a functional variant of any thereof. In embodiments, the domain comprising the PAM-interacting domain comprises an amino acid sequence at least 80%, 85%, 90%, 91%, 92%, 93%, 94%, 95%, 96%, 97% or 98% identical to the amino acid sequence of SEQ ID NO: 260, 261, 262, or 263, which are embodiments of functional variants of SEQ ID NO: 260, 261, 262, and 263.

In embodiments, one or more linker regions (e.g., one or more amino acids) may be used to connect any of the domains described herein.

Also described herein are engineered hybrid CRISPR nucleases combining gRNA-binding and nuclease domains from one source with a PAM-interacting domain from another source. This strategy allows for example the modification of PAM specificity of a CRISPR nuclease. Thus the engineered polypeptide may be capable of binding a PAM that is different from the PAM bound by a CRISPR nuclease from which gRNA-binding and nuclease domains are derived. In embodiments, the engineered polypeptide binds a PAM comprising the sequence NNAGAA, NNGGAA, NNACAA, NNGCAA, NNGAAA or NNAAAA.

In embodiments, the domain comprising the PAM-interacting domain is derived from LMD-9 (e.g., SEQ ID NO: 260, or a functional fragment of any thereof, or a functional variant of any thereof) and is specific for NNAGAA and NNGGAA PAMs. In embodiments, the domain comprising the PAM-interacting domain is derived from CNRZ1066 (e.g., SEQ ID NO: 262, or a functional fragment of any thereof, or a functional variant of any thereof) and is specific for NNACAA PAMs. In embodiments, the domain comprising the PAM-interacting domain is derived from LMG18311 (e.g., SEQ ID NO: 261, or a functional fragment of any thereof, or a functional variant of any thereof) and is specific for NNGCAA PAMs. In embodiments, the domain comprising the PAM-interacting domain is derived from TH1477 (e.g., SEQ ID NO: 263, or a functional fragment of any thereof, or a functional variant of any thereof) and is specific for NNGAAA PAMs.

In embodiments, CRISPR nuclease (Cas or other nuclease/nickase recombinant protein described herein) preferably comprises at least one Nuclear Localization Signal (NLS) to target the protein into the cell nucleus, and the vector further comprises one or more nucleotide sequences encoding the one or more NLS's. Accordingly, as used herein the expression "nuclear localization signal" or "NLS" refers to an amino acid sequence, which 'tags' a protein for import into the cell nucleus by nuclear transport. Typically, this signal consists of one or more short sequences of positively charged lysines or arginines exposed on the protein surface. Different nuclear localized proteins may share the same NLS. An NLS has the opposite function of a nuclear export signal, which targets proteins out of the nucleus. Classical NLSs can be further classified as either monopartite or bipartite. The first NLS to be discovered was the sequence PKKKRKV (SEQ ID NO: 29) in the SV40 Large T-antigen (a monopartite NLS). The NLS of nucleoplasmin, KR[PAATKKAGQA]KKKK (SEQ ID NO: 61), is the prototype of the ubiquitous bipartite signal: two clusters of basic amino acids, separated by a spacer of about 10 amino acids. The Cas9 protein exemplified herein is a Cas9 nuclease comprising one or more, preferably two, NLS sequences.

There are many other types of NLS, which are qualified as "non-classical", such as the acidic M9 domain of hnRNP A1, the sequence KIPIK in yeast transcription repressor Mata2, the complex signals of U snRNPs as well as a recently identified class of NLSs known as PY-NLSs. Thus, any type of NLS (classical or non-classical) may be used in accordance with the present disclosure as long as it targets the protein of interest into the nucleus of a target cell. In an embodiment, the NLS is derived from the simian virus 40 large T antigen. In an embodiment, the NLS of the recombinant protein of the present disclosure comprises or consists of the following amino acid sequence: SPKKKRKVEAS (SEQ ID NO: 62). In an embodiment the NLS comprises or consists of the sequence KKKRKV (SEQ ID NO: 63). In an embodiment, the NLS comprises or consists of the sequence SPKKKRKVEASPKKKRKV (SEQ ID NO: 64). In another embodiment, the NLS comprises or consists of the sequence KKKRK (SEQ ID NO: 65). In another embodiment, the NLS comprises comprises or consists of the sequence PKKKRKV (SEQ ID NO: 29).

In an embodiment, the CRISPR nuclease comprises a first NLS at its amino terminal end and a second NLS at its carboxy terminal end, and the vector comprises NLS-encoding nucleotide sequences flanking the CRISPR nuclease-encoding nucleotide sequence.

In embodiments, the vector further comprises one or more promoters operably-linked to the nucleotide sequence encoding the sgRNA and or the nucleotide sequence encoding the CRISPR nuclease. In an embodiment, the nucleotide sequence encoding the sgRNA and the nucleotide sequence encoding the CRISPR nuclease are both operably linked to a single promoter. In a further embodiment, the nucleotide sequence encoding the sgRNA is operably linked to a first promoter and the nucleotide sequence encoding the CRISPR nuclease is operably linked to a second promoter, wherein the first and second promoters may be the same or different. In the case where two promoters are used, (i) the first promoter and the nucleotide sequence encoding the sgRNA and (ii) the second promoter and the nucleotide sequence encoding the CRISPR nuclease may be in the same orientation within the vector, in a further embodiment, they may be in opposite orientations within the vector.

In an embodiment, the vector is a viral vector, such as an adeno-associated virus (AAV) vector.

Also described herein are host cells comprising the nucleic acid(s) or vector(s) described herein.

Also described herein is a composition comprising an sgRNA, nucleic acid, vector, CRISPR nuclease and/or host cell described herein, which may optionally further comprise a biologically or pharmaceutically acceptable carrier.

Also described herein is a system or combination comprising an sgRNA, nucleic acid, vector, CRISPR nuclease host cell, and/or composition described herein Also described herein are method of modifying a target polynucleotide in a cell, comprising contacting the cell with a sgRNA, nucleic acid, vector, CRISPR nuclease, host cell, composition and/or system or combination described herein.

In an embodiment, the method is an in vitro method. In a further embodiment, the method is an in vivo method and the cell is in a subject. In an embodiment, the method results in substantially no immune response in the subject.

Also described herein are a use of an sgRNA, nucleic acid, vector, CRISPR nuclease, host cell, composition and/or system or combination for modifying a target polynucleotide in a cell, or for the preparation of a composition or medicament for modifying a target polynucleotide in a cell. In an embodiment, the cell is in a subject and the use results in substantially no immune response in the subject.

The methods, uses and products described herein may be used to effect modifications in a target nucleic acid associated with a disease or condition, and therefore also provided herein are methods, uses and products for the prevention or treatment of a condition.

Therefore, also described herein is a method of treating a condition associated with a target polynucleotide in a subject in need thereof, comprising administering to the subject an effective amount an sgRNA, nucleic acid, vector, CRISPR nuclease, host cell, composition and/or system or combination described herein. In an embodiment, the method results in substantially no immune response in the subject.

Also described herein is a use of an sgRNA, nucleic acid, vector, CRISPR nuclease, host cell, composition and/or system or combination described herein, for use in preventing or treating a condition associated with a target polynucleotide in a subject, or for the preparation of a medicament for preventing or treating a condition associated with a target polynucleotide in a subject. In an embodiment, the use results in substantially no immune response in the subject.

Also described herein is an sgRNA, nucleic acid, vector, CRISPR nuclease, host cell, composition and/or system or combination described herein, for use as a medicament, e.g., for use in preventing or treating a condition described herein.

In embodiments, the condition is a metabolic condition, such as a condition affecting amino acid metabolism (e.g. tyrosine metabolism, e.g. a tyrosinemia). In an embodiment, the condition is a hepatic condition.

An "effective amount" includes a "therapeutically effective amount" and a "prophylactically effective amount". A "therapeutically effective amount" refers to an amount effective, at dosages and for periods of time necessary, to achieve the desired therapeutic result. A "prophylactically effective amount" refers to an amount effective, at dosages and for periods of time necessary, to achieve the desired prophylactic result, such as preventing or inhibiting the rate of onset or progression of a disease or condition. A prophylactically effective amount can be determined as described above for the therapeutically effective amount.

As used herein, the terms "subject" or "patient" are used interchangeably and are used to mean any animal, such as a mammal, including humans and non-human primates. In an embodiment, the above-mentioned subject is a mammal. In a further embodiment, the above-mentioned subject is a human.

Definitions

In order to provide clear and consistent understanding of the terms in the instant application, the following definitions are provided.

The use of the terms "a" and "an" and "the" and similar referents in the context of describing the subject matter disclosed herein (especially in the context of the following claims) are to be construed to cover both the singular and the plural, unless otherwise indicated herein or clearly contradicted by context.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, un-recited elements or method steps and are used interchangeably with the phrase "including but not limited to".

Recitation of ranges of values herein are merely intended to serve as a shorthand method of referring individually to each separate value falling within the range, unless otherwise indicated herein, and each separate value is incorporated into the specification as if it were individually recited herein. All subsets of values within the ranges are also incorporated into the specification as if they were individually recited herein. For example, for the recitation of numeric ranges herein, each intervening number there between with the same degree of precision is explicitly contemplated. For example, for the range of 18-20, the numbers 18, 19 and 20 are explicitly contemplated, and for the range 6.0-7.0, the number 6.0, 6.1, 6.2, 6.3, 6.4, 6.5, 6.6, 6.7, 6.8, 6.9, and 7.0 are explicitly contemplated.

All methods described herein can be performed in any suitable order unless otherwise indicated herein or otherwise clearly contradicted by context. Further, in embodiments various steps may be repeated, to for example increase recovery and purification.

The use of any and all examples, or exemplary language (e.g., "such as") provided herein, is intended merely to better illustrate the disclosure and does not pose a limitation on the scope of the disclosure unless otherwise claimed.

Any and all combinations and sub-combinations of the embodiments and features disclosed herein are encompassed by the present disclosure.

Unless otherwise defined herein, scientific and technical terms used in connection with the present disclosure shall have the meanings that are commonly understood by those of ordinary skill in the art. For example, any nomenclatures used in connection with, and techniques of, cell and tissue culture, molecular biology, immunology, microbiology, genetics and protein and nucleic acid chemistry and hybridization described herein are those that are well known and commonly used in the art. The meaning and scope of the terms should be clear; in the event however of any latent ambiguity, definitions provided herein take precedent over any dictionary or extrinsic definition. Further, unless otherwise required by context, singular terms shall include pluralities and plural terms shall include the singular.

Practice of the methods, as well as preparation and use of the products and compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of corresponding naturally-occurring amino acids.

As used herein, the term "non-conservative mutation" or "non-conservative substitution" in the context of polypeptides refers to a mutation in a polypeptide that changes an amino acid to a different amino acid with different biochemical properties (i.e., charge, hydrophobicity and/or size). Although there are many ways to classify amino acids, they are often sorted into six main groups on the basis of their structure and the general chemical characteristics of their R groups. (i) Aliphatic (Glycine, Alanine, Valine, Leucine, Isoleucine); (ii) Hydroxyl or Sulfur/Selenium-containing (also known as polar amino acids) (Serine, Cysteine, Selenocysteine, Threonine, Methionine); (iii) Cyclic (Proline); (iv) Aromatic (Phenylalanine, Tyrosine, Tryptophan); (v) Basic (Histidine, Lysine, Arginine) and (vi) Acidic and their Amide (Aspartate, Glutamate, Asparagine, Glutamine). Thus, a non-conservative substitution includes one that changes an amino acid of one group with another amino acid of another group (e.g., an aliphatic amino acid for a basic, a cyclic, an aromatic or a polar amino acid; a basic amino acid for an acidic amino acid, a negatively charged amino acid (aspartic acid or glutamic acid) for a positively charged amino acid (lysine, arginine or histidine) etc.

Conversely, a "conservative substitution" or "conservative mutations" in the context of polypeptides are mutations that change an amino acid to a different amino acid with similar biochemical properties (e.g. charge, hydrophobicity and size). For example, a leucine and isoleucine are both aliphatic, branched hydrophobes. Similarly, aspartic acid and glutamic acid are both small, negatively charged residues. Therefore, changing a leucine for an isoleucine (or vice versa) or changing an aspartic acid for a glutamic acid (or vice versa) are examples of conservative substitutions.

"Coding sequence" or "encoding nucleic acid" as used herein means the nucleic acids (RNA or DNA molecule) that comprise a nucleotide sequence which encodes a protein or sgRNA. The coding sequence can further include initiation and termination signals operably linked to regulatory elements including a promoter and polyadenylation signal capable of directing expression in the cells of an individual or mammal to which the nucleic acid is administered. The coding sequence may be codon optimized, e.g. for use in eukaryotic, mammalian and/or human cells.

In embodiments, recombinant expression vectors of the disclosure can comprise a polynucleotide of the present disclosure in a form suitable for expression of the polynucleotide in a host cell, which means that the recombinant expression vector includes one or more regulatory sequences, selected on the basis of the host cells to be used for expression, which is operably-linked to the nucleic acid sequence to be expressed. Within a recombinant expression vector, "operably-linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signal). Such regulatory sequences are described, for example, in Goeddel, Gene Expression Technology: Methods in Enzymology 185, Academic Press, San Diego, CA (1990). Regulatory sequences include those which direct constitutive expression of a nucleotide sequence in many types of host cells and those which direct expression of the nucleotide sequence only in a certain host cell (e.g., tissue-specific regulatory sequences). It will be appreciated by those skilled in the art that the design of the expression vector can depend on such factors as the choice of the host cell to be transformed, the level of expression of protein desired, etc. The expression vectors of the present disclosure can be introduced into host cells to thereby produce sgRNAs, proteins or peptides, encoded by polynucleotides as described herein.

"Complement" or "complementary" as used herein refers to Watson-Crick (e.g., A-T/U and C-G) or Hoogsteen base pairing between nucleotides or nucleotide analogs of nucleic acid molecules. "Complementarity" refers to a property shared between two nucleic acid sequences, such that when they are aligned antiparallel to each other, the nucleotide bases at each position will be complementary.

Sequence Similarity

"Homology" and "homologous" refers to sequence similarity between two peptides or two nucleic acid molecules. Homology can be determined by comparing each position in the aligned sequences. A degree of homology between nucleic acid or between amino acid sequences is a function of the number of identical or matching nucleotides or amino acids at positions shared by the sequences. As the term is used herein, a nucleic acid sequence is "substantially homologous" to another sequence if the two sequences are substantially identical and the functional activity of the sequences is conserved (as used herein, the term "homologous" does not infer evolutionary relatedness, but rather refers to substantial sequence identity, and thus is interchangeable with the terms "identity" "identical"). Two nucleic acid sequences are considered substantially identical if, when optimally aligned (with gaps permitted), they share at least about 50% sequence similarity or identity, or if the sequences share defined functional motifs. In alternative embodiments, sequence similarity in optimally aligned substantially identical sequences may be at least 60%, 70%, 75%, 80%, 85%, 90% or 95%. For the sake of brevity, the units (e.g., 66, 67 . . . 81, 82, . . . 91, 92% . . . ) have not systematically been recited but are considered, nevertheless, within the scope of the present disclosure.

Substantially complementary nucleic acids are nucleic acids in which the complement of one molecule is substantially identical to the other molecule. Two nucleic acid or protein sequences are considered substantially identical if, when optimally aligned, they share at least about 70% sequence identity. In alternative embodiments, sequence identity may for example be at least 75%, at least 80%, at least 85%, at least 90%, at least 95%, at least 96%, at least 98% or at least 99%. Optimal alignment of sequences for comparisons of identity may be conducted using a variety of algorithms, such as the local homology algorithm of Smith and Waterman, 1981, Adv. Appl. Math 2:482, the homology alignment algorithm of Needleman and Wunsch, 1970, J. Mol. Biol. 48:443, the search for similarity method of Pearson and Lipman (Pearson and Lipman 1988), and the computerized implementations of these algorithms (such as GAP, BESTFIT, FASTA and TFASTA in the Wisconsin Genetics Software Package, Genetics Computer Group, Madison, WI, U.S.A.). Sequence identity may also be determined using the BLAST algorithm, described in Altschul et al. (Altschul et al. 1990) 1990 (using the published default settings). Software for performing BLAST analysis may be available through the National Center for Biotechnology Information. The BLAST algorithm involves first identifying high scoring sequence pairs (HSPs) by identifying short words of length W in the query sequence that either match or satisfy some positive-valued threshold score T when aligned with a word of the same length in a database sequence. T is referred to as the neighborhood word score threshold. Initial neighborhood word hits act as seeds for initiating searches to find longer HSPs. The word hits are extended in both directions along each sequence for as far as the cumulative alignment score can be increased. Extension of the word hits in each direction is halted when the following parameters are met: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. One measure of the statistical similarity between two sequences using the BLAST algorithm is the smallest sum probability (P(N), which provides an indication of the probability by which a match between two nucleotide or amino acid sequences would occur by chance. In alternative embodiments of the disclosure, nucleotide or amino acid sequences are considered substantially identical if the smallest sum probability in a comparison of the test sequences is less than about 1, preferably less than about 0.1, more preferably less than about 0.01, and most preferably less than about 0.001.

An alternative indication that two nucleic acid sequences are substantially complementary is that the two sequences hybridize to each other under moderately stringent, or preferably stringent, conditions. Hybridization to filter-bound sequences under moderately stringent conditions may, for example, be performed in 0.5 M NaHPO4, 7% sodium dodecyl sulfate (SDS), 1 mM EDTA at 65° C., and washing in 0.2×SSC/0.1% SDS at 42° C. (Ausubel 2010). Alternatively, hybridization to filter-bound sequences under stringent conditions may, for example, be performed in 0.5 M NaHPO4, 7% SDS, 1 mM EDTA at 65° C., and washing in 0.1×SSC/0.1% SDS at 68° C. (Ausubel 2010). Hybridization conditions may be modified in accordance with known methods depending on the sequence of interest (Tijssen 1993). Generally, stringent conditions are selected to be about 5° C. lower than the thermal melting point for the specific sequence at a defined ionic strength and pH.

"Binding" refers to a sequence-specific, non-covalent interaction between macromolecules (e.g., between a protein and a nucleic acid or between a sgRNA and a target polynucleotide or between a sgRNA and a CRISPR nuclease (e.g., Cas9, Cpf1). Not all components of a binding interaction need be sequence-specific (e.g., contacts with phosphate residues in a DNA backbone), as long as the interaction as a whole is sequence-specific. "Affinity" refers to the strength of binding: increased binding affinity being correlated with a lower Kd.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

As used herein, "a nuclease-based modification" refers to a modification in a polynucleotide e.g., an endogenous gene locus or genomic sequence) which involves the introduction of a cut (e.g., a double-stranded break in the polynucleotide) which ultimately will trigger a repair mechanism by the cell involving (Non-homologous-end-joining) NHEJ or homologous recombination (HDR). The nuclease-based modification is made by site specific nucleases targeting the polynucleotide of interest (i.e., an endogenous gene locus or genomic sequence). Site-specific nucleases (engineered) are well known and include (but are not limited to) Zinc finger nucleases, meganucleases, Mega-Tals, CRISPR nucleases, TALENs, etc.

"Recombination" refers to a process of exchange of genetic information between two polynucleotides. For the purposes of this disclosure, "homologous recombination" (HR) refers to the specialized form of such exchange that takes place, for example, during repair of double-strand breaks in cells via homology-directed repair (HDR) mechanisms. This process requires nucleotide sequence homology, uses a "donor" or "patch" molecule as a template for repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to re-synthesize genetic information that will become part of the target, and/or related processes. Such specialized HR often results in an alteration of the sequence of the target molecule such that part or all of the sequence of the donor polynucleotide is incorporated into the target polynucleotide.

In the methods described herein, one or more targeted (site-specific) nucleases (e.g., sgRNA/CRISPR nuclease) create a double-stranded break in the target sequence (e.g., cellular chromatin) at a predetermined site. A "donor" polynucleotide, having homology to the nucleotide sequence in the region of the break, may be introduced into the cell if desired. The presence of the double-stranded break has been shown to facilitate integration of the donor sequence. The donor sequence may be physically integrated or, alternatively, the donor polynucleotide is used as a template for repair of the break via homologous recombination, resulting in the introduction of all or part of the nucleotide sequence as in the donor into the cellular chromatin. Thus, a first sequence in cellular chromatin can be altered and, in certain embodiments, can be converted into a sequence present in a donor polynucleotide. Thus, the use of the terms "replace" or "replacement" can be understood to represent replacement of one nucleotide sequence by another, (i.e., replacement of a sequence in the informational sense), and does not necessarily require physical or chemical replacement of one polynucleotide by another. In any of the methods described herein, additional sgRNA/CRISPR nucleases, pair zinc-finger, Meganucleases, Mega-Tals, and/or additional TALEN proteins can be used for additional double-stranded cleavage of additional target sites within the cell.

As used herein, the terms "donor" or "patch" nucleic acid are used interchangeably and refers to a nucleic acid that includes a fragment of the endogenous targeted gene of a cell (in some embodiments the entire targeted gene), but which includes desired modification(s) at specific nucleotides. The donor (patch) nucleic acid must be of sufficient size and similarity (e.g., in the right and left homology arms) to permit homologous recombination with the targeted gene. Preferably, the donor/patch nucleic acid is (or is flanked at the 5' end and at the 3' end by sequences) at least 80%, 85%, 90%, 91%, 92%, 93%, 94%, 95%, 96%, 97%, 98% identical to the endogenous targeted polynucleotide gene sequence. The patch nucleic acid may be provided for example as a ssODN, as a PCR product (amplicon) or within a vector. Preferably, the patch/donor nucleic acid will include modifications with respect to the endogenous gene which i) precludes it from being cut by a sgRNA once integrated in the genome of a cell and/or which facilitate the detection of the introduction of the patch nucleic acid by homologous recombination.

As used herein, a "targeted gene", "gene of interest" or "targeted polynucleotide" corresponds to the polynucleotide within a cell that will be modified by the introduction of the patch nucleic acid. It corresponds to an endogenous gene naturally present within a cell. The targeted gene may comprise one or more mutations associated with a risk of developing a disease or disorder which may be corrected by the introduction of the patch/donor nucleic acid (e.g., will be modified to correspond to the WT gene or to a form which is no longer associated with increased risk of developing a disease or condition). One or both alleles of a targeted gene may be corrected or modified within a cell in accordance with the present disclosure. Examples of target genes are described in Tables 3-6.

A "target polynucleotide" as used herein refers to any endogenous polynucleotide or nucleic acid present in the genome of a cell and encoding or not a known gene product. "Target gene" as used herein refers to any endogenous polynucleotide or nucleic acid present in the genome of a cell and encoding a known or putative gene product. The target gene or target polynucleotide further corresponds to the polynucleotide within a cell that will be modified by a nuclease of the present disclosure, alone or in combination with the introduction of one or more donor nucleic acid or patch nucleic acids. The target gene or target polynucleotide may be a mutated gene involved in a genetic disease.

"Promoter" as used herein means a synthetic or naturally-derived nucleic acid molecule which is capable of conferring, modulating or controlling (e.g., activating, enhancing and/or repressing) expression of a nucleic acid in a cell. A promoter may comprise one or more specific transcriptional regulatory sequences to further enhance or repress expression and/or to alter the spatial expression and/or temporal expression of same. A promoter may also comprise distal enhancer or repressor elements, which may be located as much as several thousand base pairs from the start site of transcription. A promoter may be derived from sources including viral, bacterial, fungal, plants, insects, and animals. A promoter may regulate the expression of a gene component constitutively or differentially with respect to cell, the tissue or organ in which expression occurs or, with respect to the developmental stage at which expression occurs, or in response to external stimuli such as physiological stresses, pathogens, metal ions, or inducing agents. Representative examples of promoters include the bacteriophage T7 promoter, bacteriophage T3 promoter, SP6 promoter, lac operator-promoter, tac promoter, SV40 late promoter, SV40 early promoter, RSV-LTR promoter, CMV IE promoter, SV40 early promoter or SV40 late promoter, CMV IE promoter, U6 promoter, a liver-specific promoter (e.g., LP1b; combining the human apolipoprotein E/C-I gene locus control region (ApoE-HCR) and a modified human α1 antitrypsin promoter (hAAT) coupled to an SV40 intron), human thyroxine binding globulin (TBG) promoter, CMV promoter, CAG promoter, CBH promoter, UbiC promoter, Ef1a promoter, H1 promoter, and 7SK promoter, any of which may be used to express one or more sgRNAs and/or a CRISPR nuclease in a cell. Sequences for the LP1b and TBG promoters are provided in Table 8.

"Vector" as used herein means a nucleic acid sequence containing an origin of replication. A vector may be a viral vector, bacteriophage, bacterial artificial chromosome or yeast artificial chromosome. A vector may be a DNA or RNA vector. A vector may be a self-replicating extrachromosomal vector, and preferably, is a DNA plasmid. For example, the vector may comprise nucleic acid sequence(s) that/which encode(s) a sgRNA, a donor (or patch) nucleic acid, and/or a CRISPR nuclease (e.g., Cas9 or Cpf1) of the present disclosure. A vector for expressing one or more sgRNA will comprise a "DNA" sequence of the sgRNA.

Nucleic acids encoding sgRNAs and CRISPR nucleases (e.g., Cas9) of the present disclosure may be delivered into cells using one or more various vectors such as viral vectors. Accordingly, preferably, the above-mentioned vector is a viral vector for introducing the gRNA and/or nuclease of the present disclosure in a target cell. Non-limiting examples of viral vectors include retrovirus, lentivirus, Herpes virus, adenovirus or Adeno Associated Virus, as well known in the art.

"Adeno-associated virus" or "AAV" as used interchangeably herein refers to a small virus belonging to the genus Dependovirus of the Parvoviridae family that infects humans and some other primate species. AAV is not currently known to cause disease and consequently the virus causes a very mild immune response.

In embodiments, the AAV vector preferably targets one or more cell types. Accordingly, the AAV vector may have enhanced cardiac, skeletal muscle, neuronal, liver, and/or pancreatic tissue (Langerhans cells) tropism. The AAV vector may be capable of delivering and expressing the at least one gRNA and nuclease of the present disclosure in the cell of a mammal. For example, the AAV vector may be an AAV-SASTG vector (Piacentino et al. (2012) Human Gene Therapy 23:635-646). The AAV vector may deliver gRNAs and nucleases to neurons, skeletal and cardiac muscle, and/or pancreas (Langerhans cells) in vivo. The AAV vector may be based on one or more of several capsid types, including AAVI, AAV2, AAV5, AAV6, AAV8, and AAV9. The AAV vector may be based on AAV2 pseudotype with alternative muscle-tropic AAV capsids, such as AAV2/1, AAV2/6, AAV2/7, AAV2/8, AAV2/9, AAV2.5 and AAVISASTG vectors that efficiently transduce skeletal muscle or cardiac muscle by systemic and local delivery. In an embodiment, the AAV vector is a AAV-DJ. In an embodiment, the AAV vector is a AAV-DJ8 vector. In an embodiment, the AAV vector is a AAV2-DJ8 vector. In an embodiment, the AAV vector is a AAV-PHP.B vector. In an embodiment, the AAV vector is a AAV-PHP.B, AAV-9 or AAV-DJ8 (PHP.B: PMID: 26829320, PMID: 27867348; AAV DJ-8; and AAV9: PMID: 27637390, PMID: 16713360).

In yet another aspect, the present disclosure provides a cell (e.g., a host cell) comprising the above-mentioned nucleic acid and/or vector. In embodiments, the host cell may be prokaryotic (e.g. bacteria) or eukaryotic (e.g., fungal (yeast), mammalian, murine, human). The disclosure further provides a recombinant expression system, vectors and host cells, such as those described above, for the expression/production of a recombinant protein, using for example culture media, production, isolation and purification methods well known in the art.

In another aspect, the present disclosure provides a composition (e.g., a pharmaceutical composition) comprising the above-mentioned gRNA, and/or CRISPR nuclease (e.g., Cas9), or nucleic acid(s) encoding same or vector(s) comprising such nucleic acid(s), or the above-mentioned host cells. In an embodiment, the composition further comprises one or more biologically or pharmaceutically acceptable carriers, excipients, and/or diluents.

As used herein, "pharmaceutically acceptable" (or "biologically acceptable") carriers, excipients, and/or diluents includes any and all solvents, dispersion media, coatings, antibacterial and antifungal agents, isotonic and absorption delaying agents, and the like that are physiologically compatible, and which can be used pharmaceutically or in biological systems. Such materials are characterized by the absence of (or limited) toxic or adverse biological effects in vivo. It refers to those compounds, compositions, and/or dosage forms which are, within the scope of sound medical judgment, suitable for use in contact with the biological fluids and/or tissues and/or organs of a subject (e.g., human, animal) without excessive toxicity, irritation, allergic response, or other problem or complication, commensurate with a reasonable benefit/risk ratio.

When the excipient serves as a diluent, it can be a solid, semisolid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders (see Remington: The Science and Practice of Pharmacy by Alfonso R. Gennaro, 2003, 21th edition, Mack Publishing Company). In embodiments, the carrier may be suitable for intra-neural, parenteral, intravenous, intraperitoneal, intramuscular, subcutaneous, sublingual or oral administration.

Some examples of suitable excipients include lactose, dextrose, sucrose, sorbitol, mannitol, starches, lecithin, phosphatidylcholine, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the disclosure can be formulated so as to provide quick sustained or delayed release of the active ingredient after administration to the patient by employing procedures known in the art.

Pharmaceutical compositions suitable for use in the disclosure include compositions wherein the active ingredients are contained in an effective amount to achieve the intended purpose (e.g., preventing, treating, ameliorating and/or inhibiting a disease or condition). The determination of an effective dose is well within the capability of those skilled in the art. For any compounds, the therapeutically effective dose can be estimated initially either in cell culture assays (e.g., cell lines) or in animal models, usually mice, rabbits, dogs or pigs. The animal model may also be used to determine the appropriate concentration range and route of administration. Such information can then be used to determine useful doses and routes for administration in humans. An effective dose or amount refers to that amount of one or more active ingredient(s), which is sufficient for treating a specific disease or condition. Therapeutic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between therapeutic and toxic effects is the therapeutic index, and it can be expressed as the ratio, $LD_{50}/ED_{50}$. Pharmaceutical compositions, which exhibit large therapeutic indices, are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration. The exact dosage will be determined by the practitioner, in light of factors related to the subject that requires treatment. Dosage and administration are adjusted to provide sufficient levels of the active moiety or to maintain the desired effect. Factors, which may be taken into account, include the severity of the disease state, general health of the subject, age, weight, and gender of the subject, diet, time and frequency of administration, drug combination(s), reaction sensitivities, and tolerance/response to therapy. Guidance as to particular dosages and methods of delivery is provided in the literature and generally available to practitioners in the art. In embodiments, dosages of an active ingredient of between about 0.01 and about 100 mg/kg body weight (in an embodiment, per day) may be used. In further embodiments, dosages of between about 0.5 and about 75 mg/kg body weight may be used. In further embodiments, dosages of between about 1 and about 50 mg/kg body weight may be used. In further embodiments, dosages of between about 10 and about 50 mg/kg body weight in further embodiments about 10, about 25 or about 50 mg/kg body weight, may be used.

The present disclosure further provides a kit or package comprising at least one container means having disposed therein at least one of the above-mentioned sgRNAs, nucleases, vectors, cells, systems, combinations or compositions. In an embodiment, the kit or package further comprises with instructions for use, such as for modification of a nucleotide sequence in a cell, or for the treatment of a condition associated with a target polynucleotide.

CRISPR System

CRISPR technology is a system for genome editing, e.g., for modification of a nucleic acid sequence, and may also be used for example to modify the expression of a specific gene.

This system stems from findings in bacterial and archaea which have developed adaptive immune defenses termed clustered regularly interspaced short palindromic repeats (CRISPR) systems, which use crRNAs and Cas proteins to degrade complementary sequences present in invading viral and plasmid DNA. The original CRISPR systems comprised a CRISPR RNA (crRNA) and a trans-activating crRNA (tracrRNA), which form a hybrid (which guides a CRISPR nuclease, e.g. a Cas9).

Engineered CRISPR systems use for example a synthetically reconstituted "guide RNA" ("sgRNA"), corresponding to a crRNA-tracrRNA fusion that obviates the need for RNase III and crRNA processing in general. The sgRNA comprises a "sgRNA guide sequence" or "sgRNA target sequence" and an RNA sequence (Cas recognition sequence)", which is necessary for CRISPR nuclease (e.g., Cas9) binding to the targeted gene. The sgRNA guide sequence is the sequence that confers specificity. It hybridizes with (i.e., it is complementary to) the opposite strand of a target sequence (i.e., it corresponds to the RNA sequence of a DNA target sequence). Other CRISPR systems using different CRISPR nucleases have been developed and are known in the art (e.g., using the Cpf1 nuclease instead of a Cas9 nuclease).

Because the original Cas9 nuclease combined with a sgRNA may produce off-target mutagenesis, one may alternatively use in accordance with the present disclosure a pair of specifically designed sgRNAs in combination with a Cas9 nickase or in combination with a dCas9-Folkl nuclease to cut both strands of DNA.

In embodiments, provided herein are CRISPR/nuclease-based engineered systems for use in modifying a target nucleic acid in cells. Introduction of DSBs can knockout a specific gene or allow modifying it by Homology Directed Repair (HDR), where one or more donor or patch nucleic acids comprising the desired modification(s) are provided to introduce the modification(s) by HDR. CRISPR/Cas9-induced DNA cleavage followed by Non-Homologous End Joining (NHEJ) repair has been used to generate loss-of-function alleles in protein-coding genes or to delete a very large DNA fragment (20, 21). The CRISPR-based engineered systems of the present disclosure are designed to (i) target and cleave a gene of interest) to generate gene variants (e.g., creating insertion(s) and/or deletions, also referred to as INDELS).

Accordingly, in an aspect, the present disclosure involves the design and preparation of one or more sgRNAs for inducing a DSB (or two single stranded breaks (SSB) in the case of a nickase) in a target gene of interest. In embodiments, the present disclosure also involves the design and preparation of one or more sgRNAs for inducing a DSB (or two SSBs in the case of a nickase) in a target polynucleotide located at a different locus within the genome of target cells. The sgRNAs and the nuclease are then used together to introduce the desired modification(s) (i.e., gene-editing events) by NHEJ or HDR within the genome of one or more target cells. When the desired modification(s) include specific point mutation(s) or insertions/deletion(s), one or more donor or patch nucleic acids comprising the desired modification(s) are provided to introduce the modification(s) by HDR.

sgRNAs

In order to cut DNA at a specific site, CRISPR nucleases require the presence of a sgRNA and a protospacer adjacent motif (PAM) on the targeted gene. The PAM immediately follows (i.e., is adjacent to) the sgRNA target sequence in the targeted polynucleotide gene sequence. The PAM is located at the 3' end or 5' end of the sgRNA target sequence (depending on the CRISPR nuclease used) but is not included in the sgRNA guide sequence. For example, the PAM for Cas9 CRISPR nucleases is located at the 3' end of the sgRNA target sequence on the target gene while the PAM for Cpf1 nucleases is located at the 5' end of the sgRNA target sequence on the target gene. Different CRISPR nucleases also require a different PAM. Accordingly, selection of a specific polynucleotide sgRNA target sequence is generally based on the CRISPR nuclease used. The PAM for the *Streptococcus pyogenes* Cas9 CRISPR system is 5'-NRG-3', where R is either A or G, and characterizes the specificity of this system in human cells. The PAM of *S. aureus* Cas9 is NNGRR. The *S. pyogenes* Type II system naturally prefers to use an "NGG" sequence, where "N" can be any nucleotide, but also accepts other PAM sequences, such as "NAG" in engineered systems. Similarly, the Cas9 derived from *Neisseria meningitidis* (NmCas9) normally has a native PAM of NNNNGATT, but has activity across a variety of PAMs, including a highly degenerate NNNNGNNN PAM. The PAM for AsCpf1 or LbCpf1 CRISPR nuclease is TTTN. In an embodiment, the PAM for a Cas9 protein used in accordance with the present disclosure is a NGG trinucleotide-sequence (Cas9). In another embodiment, the PAM for a Cpf1 CRISPR nuclease used in accordance with the present disclosure is a TTTN nucleotide sequence. In a preferred embodiment, the St1Cas9 may be used, which corresponds to the PAM sequences NNAGAA and NNGGAA. In embodiments, different St1Cas9 PAM sequences may be used, for example, inferred consensus PAM sequences for St1Cas9 from strains CNRZ1066 and LMG13811 are NNACAA(W) and NNGCAA(A), respectively[24, 26]. Table 1 below provides a list of non-limiting examples of CRISPR/nuclease systems with their respective PAM sequences.

Table 1: Non-exhaustive list of CRISPR-nuclease systems from different species (see. Mohanraju, P. et al., PMID 27493190; Shmakov, S et al., PMID: 26593719; and Zetsche, B. et al., PMID: 26422227). Also included are engineered variants recognizing alternative PAM sequences (see Kleinstiver, B P. et al., (Nature biotech 2015) PMID: 26524662 and Kleinstiver, B P. et al., (Nature 2015)).

| CRISPR nuclease | PAM Sequence |
| --- | --- |
| *Streptococcus pyogenes* (SP); SpCas9 | NGG + NAG |
| SpCas9 D1135E variant | NGG (reduced NAG binding) |
| SpCas9 VRER variant | NGCG |
| SpCas9 EQR variant | NGAG |
| SpCas9 VQR variant | NGAN or NGNG |
| *Staphylococcus aureus* (SA); SaCas9 | NNGRRT or NNGRR(N) |
| SaCas9 KKH variant | NNNRRT |
| *Neisseria meningitidis* (NM) | NNNNGATT |
| *Streptococcus thermophilus* (ST1) | NNAGAA and NNGGAA |
| *Treponema denticola* (TD) | NAAAAC |
| AsCpf1(*Acidominococcus*) | TTTN |
| AsCpf1 S542R/K607R | TYCV |
| AsCpf1 S542R/K548V/N552R | TATV |
| LbCpf1 (*Lachnospiraceae*) | TTTN |
| LbCpf1 G532R/K595R | TYCV |

As used herein, the expression "sgRNA" refers to a guide RNA which works in combination with a CRISPR nuclease to introduce a cut into DNA. The sgRNA comprises a sgRNA guide sequence and a "CRISPR nuclease recognition sequence".

As used herein, the expression "sgRNA guide sequence" refers to the corresponding RNA sequence of the "sgRNA target sequence". Therefore, it is the RNA sequence equivalent of the protospacer on the target polynucleotide gene sequence. It does not include the corresponding PAM sequence in the genomic DNA. It is the sequence that confers target specificity. The sgRNA guide sequence is linked to a CRISPR nuclease recognition sequence which binds to the nuclease (e.g., Cas9/Cpf1). The sgRNA guide sequence recognizes and binds to the targeted gene of interest. It hybridizes with (i.e., is complementary to) the opposite strand of a target gene sequence, which comprises the PAM (i.e., it hybridizes with the DNA strand opposite to the PAM). As noted above, the "PAM" is the nucleic acid sequence, that immediately follows (is contiguous to) the target sequence or target polynucleotide but is not in the sgRNA.

A "CRISPR nuclease recognition sequence" as used herein refers broadly to one or more RNA sequences (or RNA motifs) required for the binding and/or activity (including activation) of the CRISPR nuclease on the target gene. Some CRISPR nucleases require longer RNA sequences than other to function. Also, some CRISPR nucleases require multiple RNA sequences (motifs) to function while others only require a single short RNA sequence/motif. For example, Cas9 proteins require a tracrRNA sequence in addition to a crRNA sequence to function while Cpf1 only requires a crRNA sequence. Thus, unlike Cas9, which requires both crRNA sequence and a tracrRNA sequence (or a fusion or both crRNA and tracrRNA) to mediate interference, Cpf1 processes crRNA arrays independent of tracrRNA, and Cpf1-crRNA complexes alone cleave target DNA molecules, without the requirement for any additional RNA species (see Zetsche et al., PMID: 26422227).

The "CRISPR nuclease recognition sequence" included in the sgRNA described herein is thus selected based on the specific CRISPR nuclease used. It includes direct repeat sequences and any other RNA sequence known to be necessary for the selected CRISPR nuclease binding and/or activity. Various RNA sequences which can be fused to an RNA guide sequence to enable proper functioning of CRISPR nucleases (referred to herein as CRISPR nuclease recognition sequence) are well known in the art and can be used in accordance with the present disclosure. The "CRISPR nuclease recognition sequence" may thus include a crRNA sequence only (e.g., for AsCpf1 activity, such as the CRISPR nuclease recognition sequence UAAUUUC-UAC UCUUGUAGAU (SEQ ID NO: 268)) or may include additional sequences (e.g., tracrRNA sequence necessary for Cas9 activity). Furthermore, in accordance with the present disclosure and as well known in the art, RNA motifs necessary for CRISPR nuclease binding and activity may be provided separately (e.g., (i) RNA guide sequence-crRNA CRISPR recognition sequence" (also known as crRNA) in one RNA molecule and (ii) a tracrRNA CRISPR recognition sequence on another, separate RNA molecule. Alternatively, all necessary RNA sequences (motifs) may be fused together in a single RNA guide. The CRISPR recognition sequence is preferably fused directly to the sgRNA guide sequence (in 3' (e.g., Cas9) or 5' (Cpf1) depending on the CRISPR nuclease used) but may include a spacer sequence separating two RNA motifs. In embodiments, the CRISPR nuclease recognition sequence is a Cas9 recognition sequence having at least 65 nucleotides. In embodiments, the CRISPR nuclease recognition sequence is a Cas9 CRISPR nuclease recognition sequence having at least 85 nucleotides. In embodiments, the CRISPR nuclease recognition sequence is a Cpf1 recognition sequence (5' direct repeat) having about 19 nucleotides. In an embodiment, the CRISPR nuclease recognition sequence is a St1Cas9 recognition sequence. The sgRNA of the present disclosure may comprise any variant of the above noted sequences, provided that it allows for the proper functioning of the selected CRISPR nuclease (e.g., binding of the CRISPR nuclease protein to the gene of interest and/or target polynucleotide sequence(s)).

Together, the RNA guide sequence and CRISPR nuclease recognition sequence(s) provide both targeting specificity and scaffolding/binding ability for the CRISPR nuclease of the present disclosure. sgRNAs of the present disclosure do not exist in nature, i.e., is a non-naturally occurring nucleic acid(s).

A "target region", "target sequence" or "protospacer" in the context of sgRNAs and CRISPR system of the present disclosure are used herein interchangeably and refers to the region of the target gene, which is targeted by the CRISPR/nuclease-based system, without the PAM. It refers to the sequence corresponding to the nucleotides that precede the PAM (i.e., in 5' or 3' of the PAM, depending of the CRISPR nuclease) in the genomic DNA. It is the sequence that is included into a sgRNA expression construct (e.g., vector/plasmid/AAV). The CRISPR/nuclease-based system may include at least one (i.e., one or more) sgRNAs, wherein each sgRNA target different DNA sequences on the target gene. The target DNA sequences may be overlapping. The target sequence or protospacer is followed or preceded by a PAM sequence at an (3' or 5' depending on the CRISPR nuclease used) end of the protospacer. Generally, the target sequence is immediately adjacent (i.e., is contiguous) to the PAM sequence (it is located on the 5' end of the PAM for SpCas9-like nuclease and at the 3' end for Cpf1-like nuclease).

In embodiments, the sgRNA of the present disclosure comprises a "sgRNA guide sequence" or has a "sgRNA target sequence" which corresponds to the target sequence on the gene of interest or target polynucleotide sequence that is followed or preceded by a PAM sequence (is adjacent to a PAM). The sgRNA may comprise a "G" at the 5' end of its polynucleotide sequence. The presence of a "G" in 5' is preferred when the sgRNA is expressed under the control of the U6 promoter (Taeyoung KooJungjoon Lee and Jin-Soo Kim Mol Cells. 2015 Jun. 30; 38 (6): 475-481). The CRISPR/nuclease system of the present disclosure may use sgRNAs of varying lengths. The sgRNA may comprise a sgRNA guide sequence of at least at least a 10, at least 12 nts, at least a 13 nts, at least a 14 nts, at least a 15 nts, at least a 16 nts, at least a 17 nts, at least a 18 nts, at least a 19 nts, at least a 20 nts, at least a 21 nts, at least a 22 nts, at least a 23 nts, at least a 24 nts, at least a 25 nts, at least a 30 nts, or at least a 35 nts of a target sequence of a gene of interest or target polynucleotide (such target sequence is followed or preceded by a PAM in the gene of interest or target polynucleotide but is not part of the sgRNA). The length of the sgRNA is selected based on the specific CRISPR nuclease used. In embodiments, the "sgRNA guide sequence" or "sgRNA target sequence" may be at least 17 nucleotides (17, 18, 19, 20, 21, 22, 23) long, preferably between 17 and 30 nts long, more preferably between 17-22 nucleotides long. In embodiments, the sgRNA guide sequence is between 10-40, 10-30, 12-30, 15-30, 18-30, or 10-22 nucleotides long. In embodiments, the PAM sequence is "NGG", where "N" can be any nucleotide. In embodiments, the PAM sequence is "TTTN", where "N" can be any nucleotide. sgRNAs may target any region of a target gene which is immediately adjacent (contiguous, adjoining, in 5' or 3') to a PAM (e.g., NGG/TTTN or CCN/NAAA for a PAM that would be located on the opposite strand) sequence. In embodiments, the sgRNA of the present disclosure has a target sequence that is located in an exon (the sgRNA guide sequence consists of the RNA sequence of the target (DNA) sequence which is located in an exon). In embodiments, the sgRNA of the present disclosure has a target sequence that is located in an intron (the sgRNA guide sequence consists of the RNA sequence of the target (DNA) sequence which is located in an intron). In embodiments, the sgRNA may target any region (sequence) which is followed (or preceded, depending on the CRISPR nuclease used) by a PAM in the gene or target polynucleotide of interest.

Although a perfect match between the sgRNA guide sequence and the DNA sequence on the targeted gene is preferred, a mismatch between a sgRNA guide sequence and target sequence on the gene sequence of interest is also permitted as along as it still allows hybridization of the sgRNA with the complementary strand of the sgRNA target polynucleotide sequence on the targeted gene. A seed sequence of between 8-12 consecutive nucleotides in the sgRNA, which perfectly matches a corresponding portion of the sgRNA target sequence is preferred for proper recognition of the target sequence. The remainder of the guide sequence may comprise one or more mismatches. In general, sgRNA activity is inversely correlated with the number of mismatches. Preferably, the sgRNA of the present disclosure comprises 7 mismatches, 6 mismatches, 5 mismatches, 4 mismatches, 3 mismatches, more preferably 2 mismatches, or less, and even more preferably no mismatch, with the corresponding sgRNA target gene sequence (less the PAM). Preferably, the sgRNA nucleic acid sequence is at least 90%, 91%, 92%, 93%, 94%, 95%, 96%, 97%, 98% and 99% identical to the sgRNA target polynucleotide sequence in the gene of interest. Of course, the smaller the number of nucleotides in the sgRNA guide sequence the smaller the number of mismatches tolerated. The binding affinity is thought to depend on the sum of matching sgRNA-DNA combinations.

The number of sgRNAs administered to or expressed in a target cell in accordance with the methods of the present disclosure may be at least 1 sgRNA, at least 2 sgRNAs, at least 3 sgRNAs at least 4 sgRNAs, at least 5 sgRNAs, at least 6 sgRNAs, at least 7 sgRNAs, at least 8 sgRNAs, at least 9 sgRNAs, at least 10 sgRNAs, at least 11 sgRNAs, at least 12 sgRNAs, at least 13 sgRNAs, at least 14 sgRNAs, at least 15 sgRNAs, at least 16 sgRNAs, at least 17 sgRNAs, or at least 18 sgRNAs. The number of sgRNAs administered to or expressed in a cell may be between at least 1 sgRNA and 15 sgRNAs, 1 sgRNA and least 10 sgRNAs, 1 sgRNA and 8 sgRNAs, 1 sgRNA and 6 sgRNAs, 1 sgRNA and 4 sgRNAs, 1 sgRNA and sgRNAs, 2 sgRNA and 5 sgRNAs, or 2 sgRNAs and 3 sgRNAs.

CRISPR Nucleases

Recombinant dCas9-FoKI dimeric nucleases (RFNs) have been designed that can recognize extended sequences and edit endogenous genes with high efficiency in human cells. These nucleases comprise a dimerization-dependent wild type FokI nuclease domain fused to a catalytically inactive Cas9 (dCas9) protein. Dimers of the fusion proteins mediate sequence specific DNA cleavage when bound to target sites composed of two half-sites (each bound to a dCas9 (i.e., a Cas9 nuclease devoid of nuclease activity) monomer domain) with a spacer sequence between them. The dCas9-FoKI dimeric nucleases require dimerization for efficient genome editing activity and thus, use two sgRNAs for introducing a cut into DNA.

The recombinant CRISPR nuclease that may be used in accordance with the present disclosure is i) derived from a naturally occurring Cas; and ii) has a nuclease (or nickase) activity to introduce a DSB (or two SSBs in the case of a nickase) in cellular DNA when in the presence of appropriate sgRNA(s). Thus, as used herein, the term "CRISPR nuclease" refers to a recombinant protein which is derived from a naturally occurring Cas nuclease which has nuclease or nickase activity and which functions with the sgRNAs of the present disclosure to introduce DSBs (or one or two SSBs) in the targets of interest. In an embodiment, the CRISPR nuclease is St1Cas9. In further embodiments, the CRISPR nuclease is SpCas9 or Cpf1. In another embodiment, the CRISPR nuclease is a Cas9 protein having a nickase activity. As used herein, the term "Cas9 nickase" refers to a recombinant protein which is derived from a naturally occurring Cas9 and which has one of the two nuclease domains inactivated such that it introduces single stranded breaks (SSB) into the DNA. It can be either the RuvC or HNH domain. In a further embodiment, the Cas protein is a dCas9 protein fused with a dimerization-dependant FokI nuclease domain.

Exemplary CRISPR nucleases that may be used in accordance with the present disclosure are provided in Table 1 above.

CRISPR nucleases such as Cas9/nucleases cut 3-4 bp upstream of the PAM sequence. CRISPR nucleases such as Cpf1 on the other hand, generate a 5' overhang. The cut occurs 19 bp after the PAM on the targeted (+) strand and 23 bp on the opposite strand (Zetsche et al., 2015, PMID 26422227). There can be some off-target DSBs using wild-type Cas9. The degree of off-target effects depends on a number of factors, including: how closely homologous the off-target sites are compared to the on-target site, the specific site sequence, and the concentration of nuclease and guide RNA (sgRNA). These considerations only matter if the PAM sequence is immediately adjacent to the nearly homologous target sites. The mere presence of additional PAM sequences should not be sufficient to generate off target DSBs; there needs to be extensive homology of the protospacer followed or preceded by PAM.

Optimization of Codon Degeneracy

Because CRISPR nuclease proteins are (or are derived from) proteins normally expressed in bacteria, it may be advantageous to modify their nucleic acid sequences for optimal expression in eukaryotic cells (e.g., mammalian cells) when designing and preparing CRISPR nuclease recombinant proteins. Similarly, donor or patch nucleic acids of the present disclosure used to introduce specific modifications in the target polynucleotide may use codon degeneracy (e.g., to introduce new restriction sites for enabling easier detection of the targeted modification).

Accordingly, the following codon chart (Table 2) may be used, in a site-directed mutagenic scheme, to produce nucleic acids encoding the same or slightly different amino acid sequences of a given nucleic acid:

TABLE 2

Codons encoding the same amino acid

| Amino Acids | | | Codons |
|---|---|---|---|
| Alanine | Ala | A | GCA GCC GCG GCU |
| Cysteine | Cys | C | UGC UGU |
| Aspartic acid | Asp | D | GAC GAU |
| Glutamic acid | Glu | E | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUG AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | AGC AGU UCA UCC UCG UCU |
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

Mode(s) for Carrying Out the Invention

The present disclosure is illustrated in further details by the following non-limiting examples.

Example 1: Materials and Methods

Cell Culture and Transfection

K562 were obtained from the ATCC (CCL-243) and maintained at 37° C. under 5% $CO_2$ in RPMI medium supplemented with 10% FBS, penicillin-streptomycin and GlutaMAX™. Neuro-2a were obtained from the ATCC and maintained at 37° C. under 5% $CO_2$ in DMEM medium supplemented with 10% FBS, penicillin-streptomycin and GlutaMAX™. All cell lines are tested for absence of *mycoplasma* contamination. Cells ($2\times10^5$ per transfection) were transfected using the Amaxa 4D-Nucleofector (Lonza) per manufacturer's recommendations. K562 cell lines expressing SaCas9 and St1Cas9 from the AAVS1 safe harbor locus were generated as described[35, 36]. Briefly, simultaneous selection and cloning was performed for 10 days in methylcellulose-based semi-solid RPMI medium supplemented with 0.5 µg/ml puromycin starting 3 days post-transfection. Clones were picked and expanded in 96 wells for 3 days and transferred to 12-well plates for another 3 days before cells were harvested for western blot.

Genome Editing Vectors

Vectors for in vitro and in vivo genome editing with the CRISPR1-StCas9 LMD-9 system generated in this study are available from Addgene (FIG. 11). The CRISPOR39 web tool was used to design guide (spacer) sequences against mouse and human targets (Tables 3-6). DNA sequence for the spacers were modified at position 1 to encode a "G" due to the transcription initiation requirement of the human U6 promoter when required. Alternatively, the spacer length was increased to capture a naturally occurring "G". The mammalian expression vector for S. thermophilus CRISPR1 (StlCas9 LMD-9) fused to SV40 NLS sequences at the N- and C-terminus (MSP1594_2x_NLS; Addgene plasmid #110625) was constructed from MSP159434 (Addgene plasmid #65775). The U6-driven sgRNA expression plasmids for S. thermophilus CRISPR1 (StlCas9 LMD-9) (v1) (StlCas9_LMD-9_sgRNA_pUC19; Addgene plasmid #110627) and SaCas97 were synthesized as gBlocks™ gene fragments (Integrated DNA Technologies) and cloned into pUC19. BPK230134 (v0) (Addgene plasmid #65778) was used to compare StlCas9 sgRNA architectures. The single vector mammalian expression system containing a CAG promoter-driven StlCas9 LMD-9 and its U6-driven sgRNA (U6_sgRNA_CAG_hStlCas9_LMD9; Addgene plasmid #110626) was built from the above-described plasmids. The single vector rAAV-StlCas9 LMD-9 systems containing liver-specific promoters (Table 8) were assembled from the above-described components into a derivative of pX6027 (Addgene plasmid #61593) containing a deletion within the backbone to eliminate BsmBI restriction sites. The LP1b promoter was engineered by combining elements from previously described AAV expression cassettes[53, 54]. The most active version of this vector (v3) has the structure pAAV_LP1B_StlCas9_LMD-9_SpA_U6_sgRNA (Addgene plasmid #110624). To establish clonal K562 cell lines constitutively expressing C-terminally tagged SaCas9 and StlCas9 under the control of an hPGK1 promoter, the Cas9 ORFs from pX602 and MSP1594_2x_NLS were subcloned into AAVS1_Puro_PGK1_3×FLAG_Twin_Strep36 (Addgene plasmid #68375).

Surveyor Nuclease and TIDE Assays

Genomic DNA from 2.5E5 cells was extracted with 250 ml of QuickExtract™ DNA extraction solution (Epicentre) per the manufacturer's recommendations. The various loci were amplified by PCR using the primers described in Table 9. Assays were performed with the Surveyor™ mutation detection kit (Transgenomics) as described[35, 37]. Samples were separated on 10% PAGE gels in TBE buffer. Gels were imaged using a ChemiDoc™ MP (Bio-Rad) system and quantifications were performed using Image Lab™ software (Bio-Rad). TIDE analysis was performed using a significance cut-off value for decomposition of p<0.00138.

Recombinant Adeno-Associated Virus Production

Production of recombinant adeno-associated viral vectors was performed by the triple plasmid transfection method essentially as described[81]. Briefly, HEK293T17 cells were transfected using polyethylenimine (PEI, Polysciences) with helper plasmid pxx-680, the rep/cap hybrid plasmid pAAV2/8 and the rAAV vector plasmid. Twenty-four hours post-transfection, media was replaced with growth media without FBS, and cells were harvested 24 hours later. AAV particles were extracted from cell extracts by freeze/thaw cycles and purified on a discontinuous iodixanol gradient. Virus were resuspended in PBS 320 mM NaCl+10% sorbitol+0.002% pluronic acid, aliquoted and stored at −80° C. AAV were titrated by qPCR (Roche) using SYBR™ green and ITR primers as described[82]. Physical titer and purity was confirmed by separating similar volumes of AAV on a 10% SDS-PAGE stain free gel (Biorad) in Tris-Glycine-SDS buffer. ITR integrity was assessed following a BssHII digestion of the AAV plasmid. The vector core facility at the CERVO brain research center (Université Laval) produced the rAAV8s.

Animal Experiments

Fah$^{-/-}$ mice[83] on a C57BL/6 genetic background were group-housed and fed a standard chow diet (Harlan #2018SX) with free access to food and water. Fah$^{-/-}$ mice drinking water was supplemented with 7.5 mg (2-(2-nitro-4-trifluoromethylbenzoyl)-1,3-cyclohexanedione) (NTBC)/L and pH was adjusted to 7.0. Mice were exposed to a 12:12-h dark-light cycle and kept under an ambient temperature of 23±1° C. Animals were cared for and handled according to the Canadian Guide for the Care and Use of Laboratory Animals. The Université Laval Animal Care and Use Committee approved the procedures.

Two days old neonatal mice were injected intravenously in the retro-orbital sinus[84] with different doses of rAAV8 or saline in a total volume of 20 µL. Mice were weaned at 21 days of age and NTBC was removed 7 days later. Body weight and glycemia were monitored daily following NTBC removal. Mice were not fasted for measurement of glycemia, data collection occurred between 9-10 am. Animals were killed by cardiac puncture under anesthesia at predetermined time points or when weight loss reached 20% of body weight. Livers were snap frozen for downstream applications.

Urine Collection and Succinylacetone Quantification

Urine from groups of 3-4 mice was collected overnight in metabolic cages (Tecniplast) 15 days after NTBC removal. Urine was centrifuged at 2000 rpm for 5 minutes, aliquoted and frozen at −80° C. Succinylacetone was quantified in urine samples by a sensitive method using gas chromatography-mass spectrometry (GC-MS) as previously described[85]. The biochemical genetics laboratory at the Centre Hospitalier universitaire de Sherbrooke performed the analyses.

Example 2: Identification of an sgRNA Architecture Directing Robust DNA Cleavage by StlCas9 in Human Cells S. thermophilus encodes up to two type II-A systems (CRISPR1 and CRISPR3). While characterizing the interplay between StlCas9 and diverse Acr families isolated from phages infecting S. thermophilus[32], we were surprised by the substantial levels of editing achieved in human cells. This observation contrasts with early reports indicating that this ortholog was mildly active[7, 33].

Figure 1D:
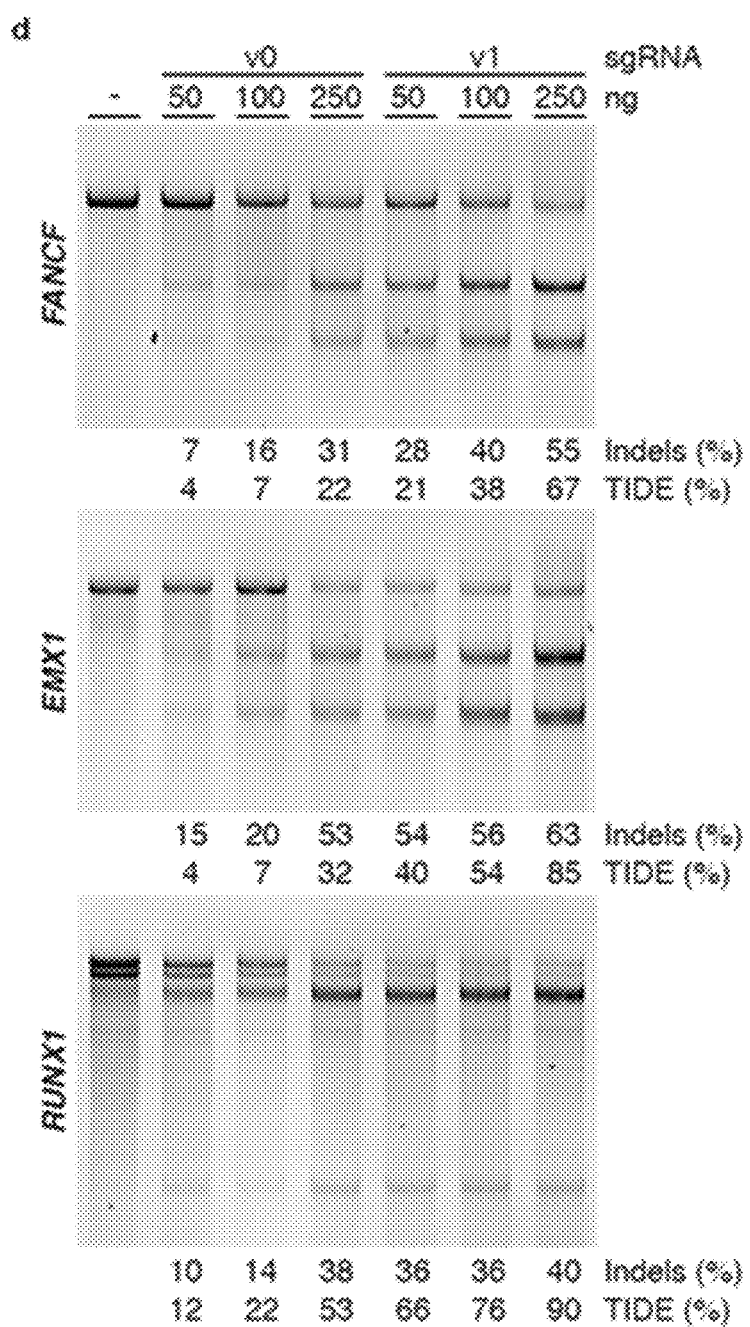
FIG. 1: Engineered CRISPR1-StCas9 system drives robust gene editing in human cells. (a) Schematic representation of St1Cas9 from the LMD-9 strain flanked by nuclear localization signals (NLS). (b) Nucleotide sequence, predicted secondary structure, and functional modules of St1Cas9 sgRNA (v1; SEQ ID NO: 1); crRNA (up to position 34; left side of lower stem, bulge and upper stem), loop (positions 35-38; connecting left and right sides of upper stem), tracrRNA (position 39 and onward; right side of lower stem, bulge and upper stem, as well as stemloop 1, linker and stemloop 2), mutated nucleotides (positions 23 and 34). (c) St1Cas9 target sites (FANCF: sense, SEQ ID NO: 2; antisense, SEQ ID NO: 3; EMX1: sense, SEQ ID NO: 66; antisense, SEQ ID NO: 67; RUNX1: sense, SEQ ID NO: 68; antisense, SEQ ID NO: 69) and PAM sequences in FANCF, EMX1, and RUNX1. (d) K562 cells stably expressing St1Cas9 were transfected with indicated sgRNA expression vectors at increasing doses and the Surveyor and TIDE assays were performed 3 days later to determine the frequency of indels, as indicated at the base of each lane. An expression vector encoding EGFP (−) was used as a negative control.

In the studies described herein, we made various modifications which we found were capable of increasing activity. First, we added an N-terminal nuclear localization signal (NLS) to a human codon-optimized expression construct[34] and established a K562 cell line stably expressing StlCas9 (LMD-9) from the AAVS1 safe harbor locus[35, 36] (FIGS. 1a and 5). StlCas9 (1121 aa) shares 17% and 37% identity with SpCas9 and SaCas9, respectively. Second, we adapted an sgRNA sequence used to monitor StlCas9 activity in the heterologous host Escherichia coli[31]. We substituted a wobble base pair present in the lower stem of the repeat:

anti-repeat region for a canonical Watson-Crick base pair in order to interrupt the RNA polymerase III termination signal (FIG. 1b). Then, we compared this sgRNA architecture (v1) to its counterpart containing a wild-type full length crRNA:tracrRNA duplex connected via a tetraloop (v0) by targeting EMX1, FANCF, and RUNX1[34] (FIGS. 1c and 5). St1Cas9-expressing cells were transfected with increasing amounts of each construct and the Surveyor nuclease assay was used to determine the frequency of indels characteristic of imprecise DSB repair by NHEJ[35, 37] (FIG. 1d). The spectrum and frequency of targeted mutations was also analyzed using the complementary TIDE (Tracking of Indels by DEcomposition) method38 (FIG. 1d and Table 3). Irrespective of the quantification method, the potency of sgRNA v1 was markedly superior. The increased activity was also observed when co-expressing St1Cas9 and its sgRNA transiently, a setting more typical of a genome editing experiment (FIG. 5). This analysis revealed that high gene disruption rates could be obtained under standard conditions using St1Cas9 in human cells.

Figures 2A, 2B, 2C:
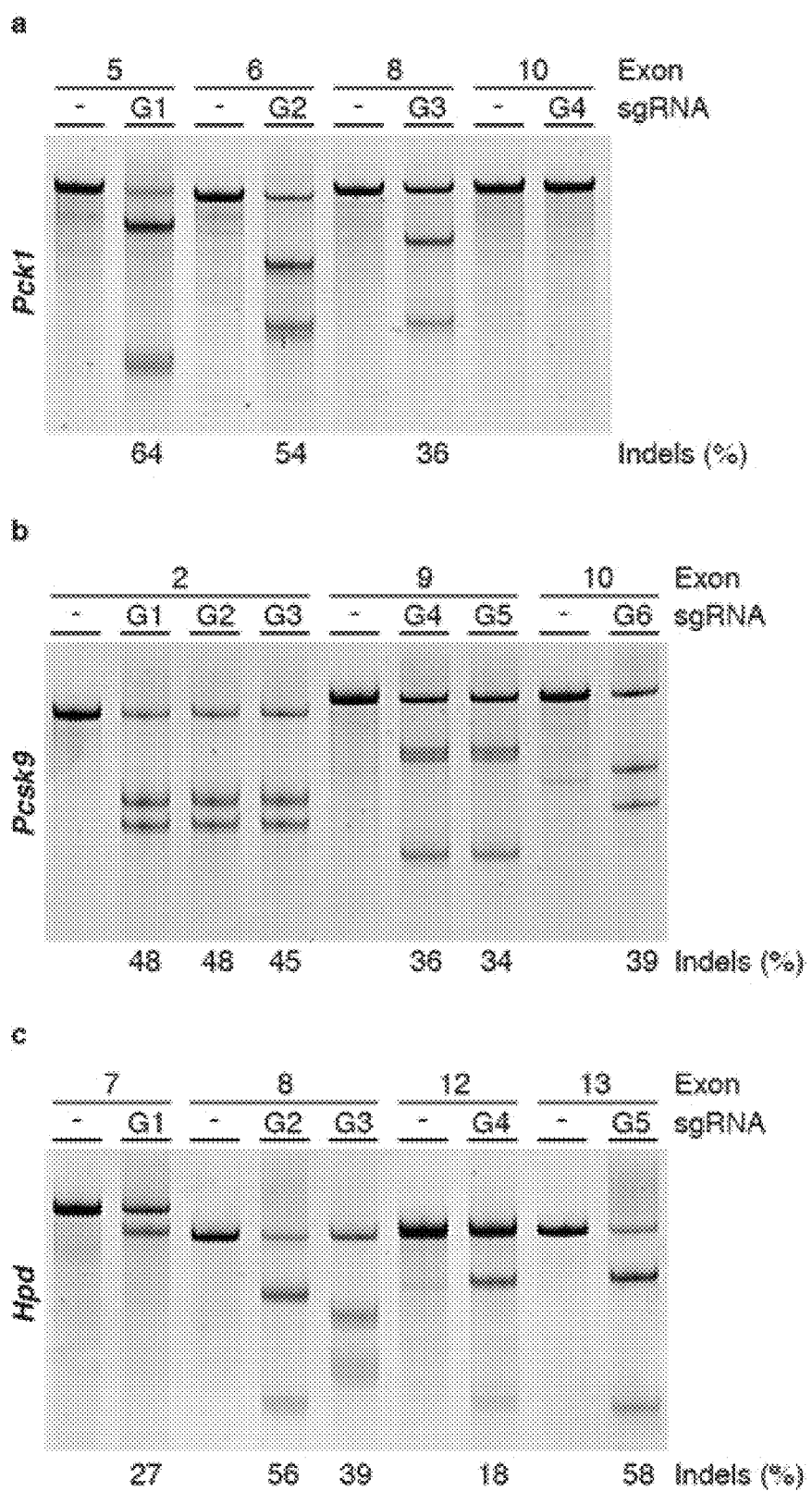
FIG. 2: Screening for active sgRNAs targeting genes affecting liver function in mouse cells. (a) Surveyor assays to determine St1Cas9 activity programmed with various sgRNAs targeting Pck1. Neuro-2a cells were transiently transfected with a single vector (0.5 µg) driving the expression of St1Cas9 and its sgRNA. Surveyor assays were performed 3 days later to determine the frequency of indels, as indicated at the base of each lane. An expression vector encoding EGFP (−) was used as a negative control. (b) Same as in (a) but targeting Pcsk9. (c) Same as in (a) but targeting Hpd.
Figure 3A:
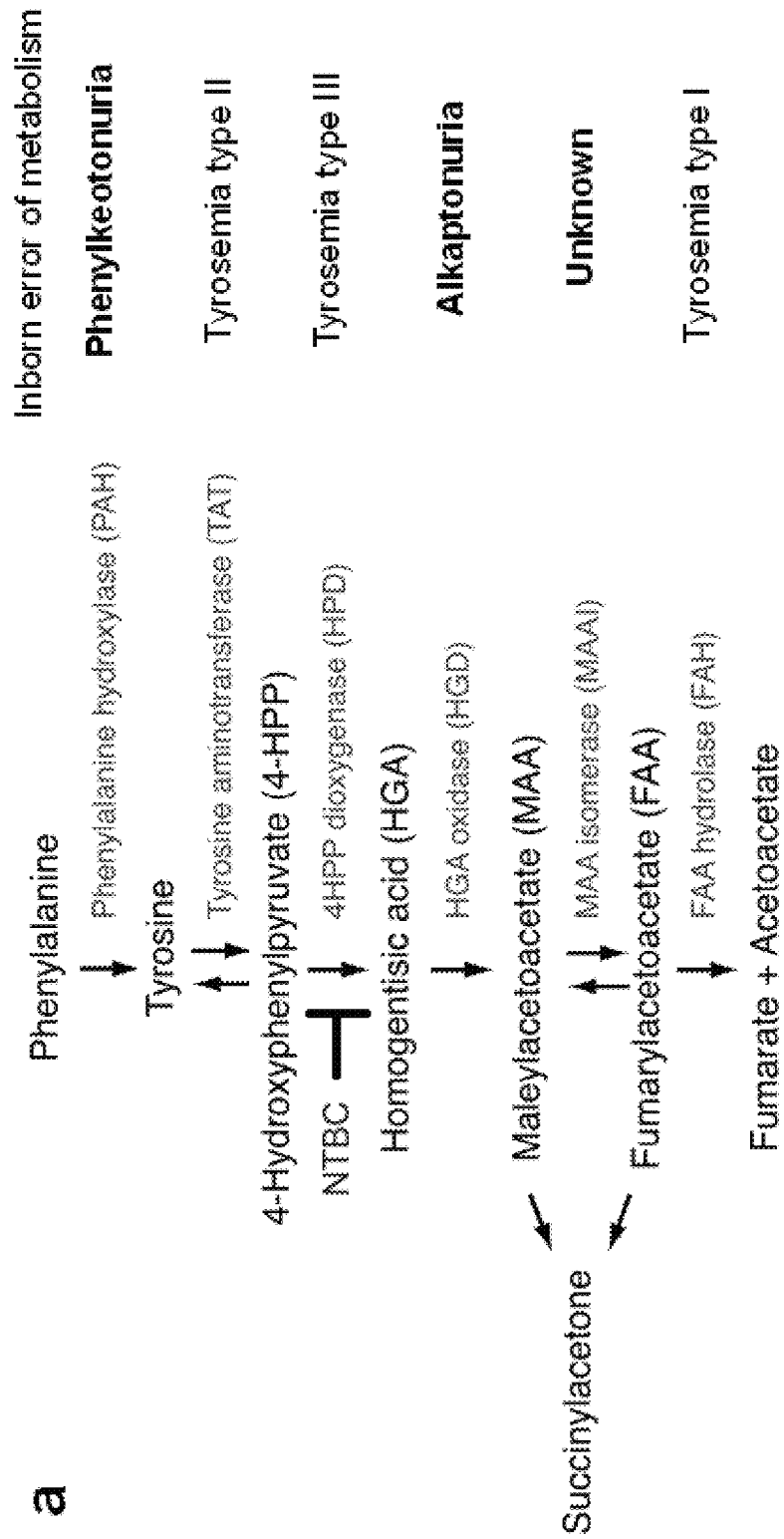
FIG. 3: In vivo metabolic pathway rewiring via rAAV8-mediated delivery of holo-St1Cas9. (a) The tyrosine degradation pathway and associated genetic disorders. (b) Experimental design for in vivo editing. Neonatal (2 days old) Fah/mice were injected with rAAV8-St1Cas9 or saline into the retro-orbital sinus, weaned at 21 days, and NTBC was removed at 30 days of age. Mice were assayed for phenotypic and metabolic correction and for gene disruption efficacy. Mice off NTBC were killed when they lost 20% of their body weight. (c) Schematic representations of the rAAV vector and St1Cas9 target site (G5) within exon 13 of Hpd. Target sequence (sense, SEQ ID NO: 4; antisense, SEQ ID NO: 5; amino acid, SEQ ID NO: 6), PAM and position of the I335M mutation (last amino acid shown, i.e. I of LLQI) causing type III tyrosinemia in humans are shown. Also annotated is the human thyroxine binding globulin (TBG) promoter, bovine growth hormone polyadenylation sequence (BGHpA) and hU6 promoter. Arrows indicate the direction of transcriptional unit. (d) Neonatal Fah$^{-/-}$ mice were injected into the retro-orbital sinus with either 5E10, 1E11, 2E11 or 4E11 vector genomes (vg) of rAAV8-St1Cas9 targeting Hpd exon 13 (G5) and killed 28 days following injection. Genomic DNA was extracted from whole liver samples and the Surveyor assay was used to determine the frequency of St1Cas9-induced gene disruption as the % Indels indicated at the base of each lane. Each lane represents a different mouse. A mouse injected with saline (−) was used as a negative control. (e) Survival analysis following NTBC removal in mice treated as described in (b). Number of mice per group (n) and rAAV doses (vg) is indicated. (f) Same as in (e) but body weight was measured daily. Solid lines designate the mean and error bars are represented by shaded areas and denote s.e.m. (g) Same as in (f) but glycemia was monitored in non-fasted mice. (h) Same as in (e) but succinylacetone levels in urine were determined 15 days following NTBC removal. Samples were collected from the indicated treatment groups over a 24 hours period using metabolic cages.
Figure 3B:
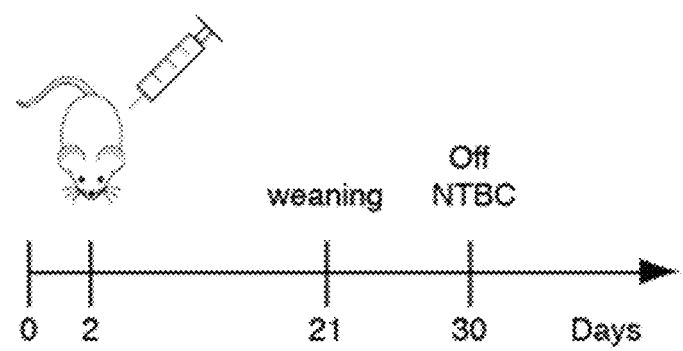
Figure 3C:
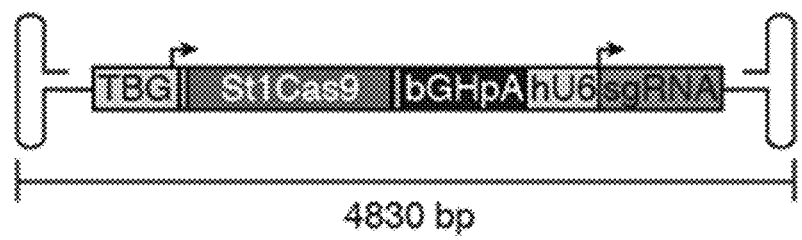
Figure 6A:
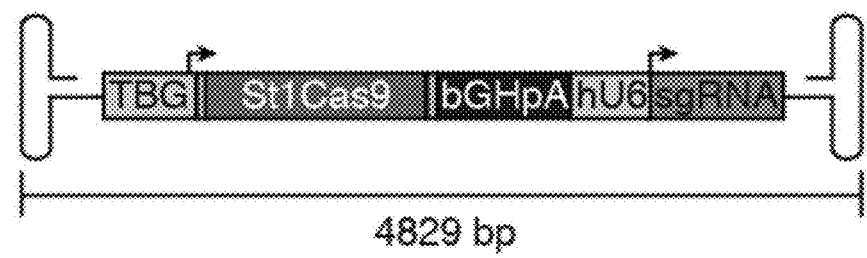
FIG. 6: In vivo metabolic pathway rewiring via rAAV8-mediated delivery of holo-St1Cas9. (a) Schematic representations of the rAAV vector and St1Cas9 target site (G2) within exon 8 of Hpd. Target sequence (sense, SEQ ID NO: 12; antisense, SEQ ID NO: 13; amino acid, SEQ ID NO: 14), PAM and position of the Y160C mutation causing type III tyrosinemia in humans are shown. Note that while this region of the protein is well conserved between human and mouse, a phenylalanine is found at this position in mouse, rat, pig, and *C. elegans*. Also annotated is the human thyroxine binding globulin (TBG) promoter, bovine growth hormone polyadenylation sequence (BGHpA) and hU6 promoter. Arrows indicate the direction of transcriptional unit. (b) Neonatal Fah−/− mice were injected into the retro-orbital sinus with 1E11 vector genomes (vg) of rAAV8-St1Cas9 targeting Hpd exon 8 (G2) and killed 28 days following injection. Genomic DNA was extracted from whole liver samples and the Surveyor assay was used to determine the frequency of St1Cas9-induced gene disruption as the % Indels indicated at the base of each lane. Each lane represents a different mouse. A mouse injected with saline (−) was used as a negative control. (c) Body weight was measured daily following NTBC removal in mice treated as in FIG. 3. Number of mice per group (n) is indicated. Dots designate the mean and error bars denote s.e.m. (d) Same as in (c) but glycemia was monitored in non-fasted mice.
Figure 6B:
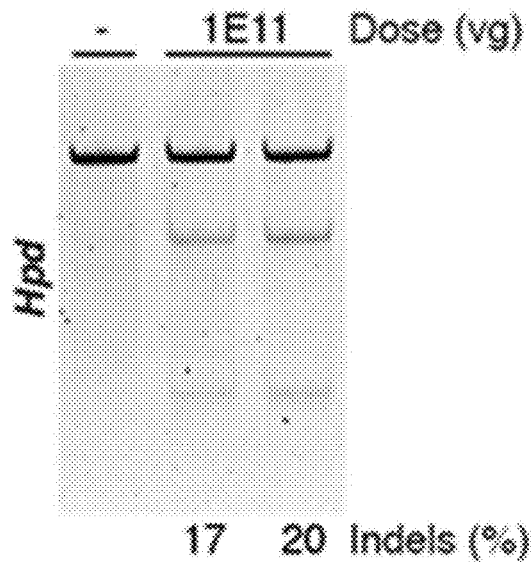
Figures 6C, 6D:
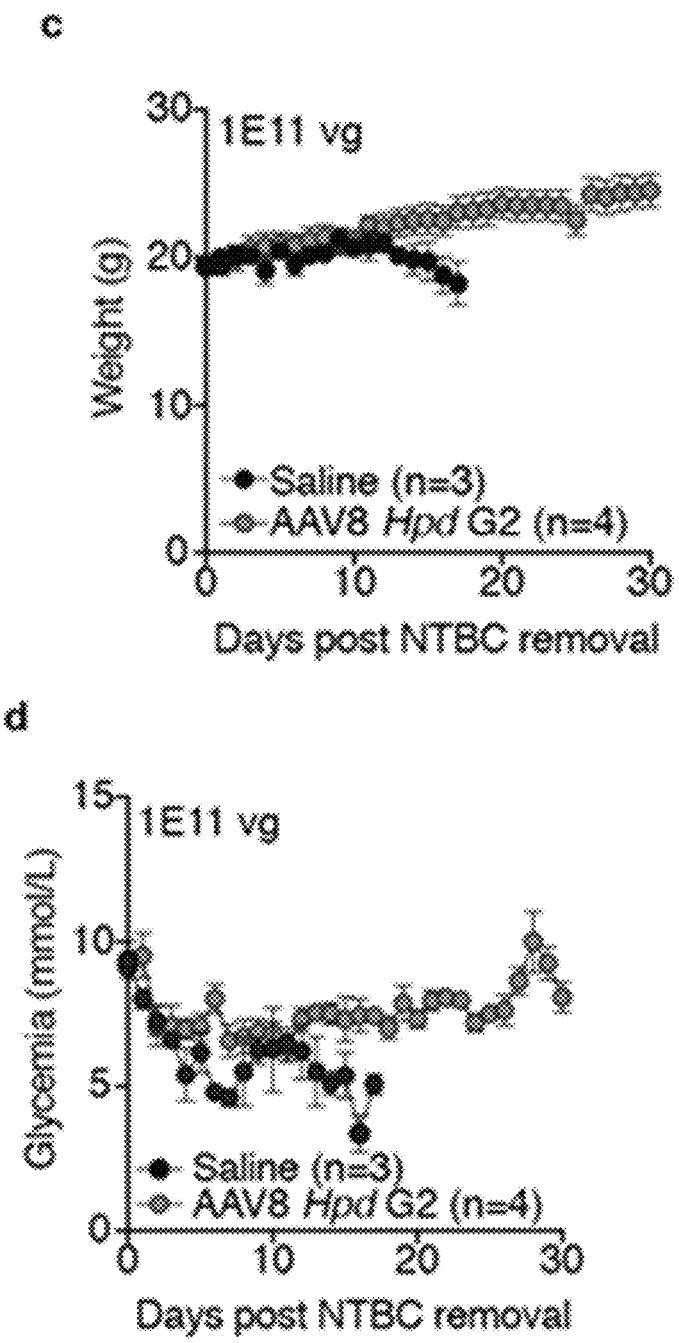

Example 3: Robust Editing of Target Genes Involved in Liver Metabolism by St1Cas9 in Mouse Cells We used CRISPOR39 to design sgRNAs against Pck1, Pcsk9, and Hpd, three genes affecting liver function when disrupted. When possible, we selected guides targeting essential protein domains and predicted to have few potential off-targets. Transient transfection of single vector constructs expressing both St1Cas9 and its sgRNA revealed strong cleavage activity (18% to >50% indels) at 14 out of 15 target sites highlighting the robustness of the system despite not relying on sgRNA design rules[33] (FIG. 2a-c). Of note, this screen identified highly active sgRNAs targeting in the vicinity of mutations found in human HPD[40, 41]. Deficiency of 4-hydroxyphenyl-pyruvate dioxygenase (HPD), the second enzyme in the tyrosine catabolic pathway, causes Tyrosinemia type III (Orphanet ORPHA: 69723) (FIG. 3a). Only three missense mutations are known to cause this rare disease (Prevalence <1/1,000,000) and we could target two of them with high efficacy (OMIM 276710) (FIGS. 3c and 6). Targeting the third mutation was not attempted due to the low specificity score of the guide. Taken together, these data suggest that St1Cas9 might enable in vivo genome editing if it could be packaged into a single rAAV particle alongside its sgRNA and the regulatory elements needed to drive its expression.

Figure 3D:
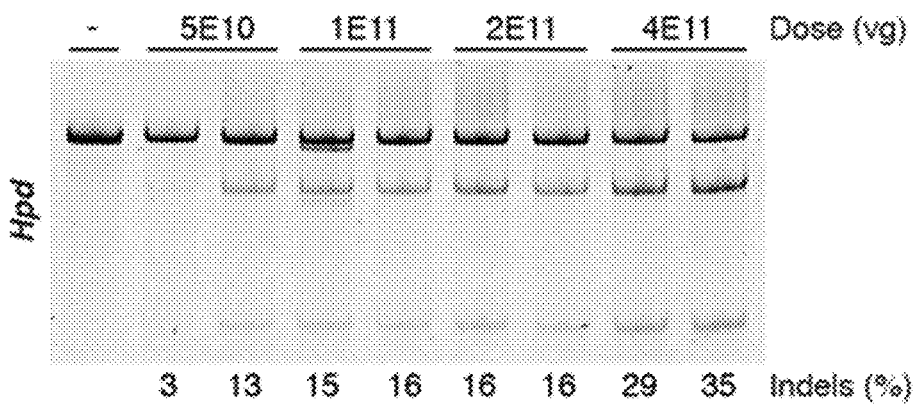

Example 4: Potent In Vivo Genome Editing Using an All-In-One rAAV Vector in Newborn Mice To deliver holo-St1Cas9 (St1Cas9+sgRNA) to the liver, we generated a hepatotropic rAAV serotype 8[11, 16-18] vector targeting Hpd exon 13 (aka AAV8-St1Cas9 Hpd G5) by mirroring the original SaCas9 vector architecture[7] (FIG. 3c). To test the cleavage activity of St1Cas9 in vivo, we injected mice at day 2 of life into the retro-orbital sinus with increasing amounts of vector and isolated total liver DNA at day 28 post injection (FIG. 3b). The titration showed that the degree of editing was substantial and dependent on the dose of AAV8-St1Cas9 (FIG. 3d).

Figure 3E:
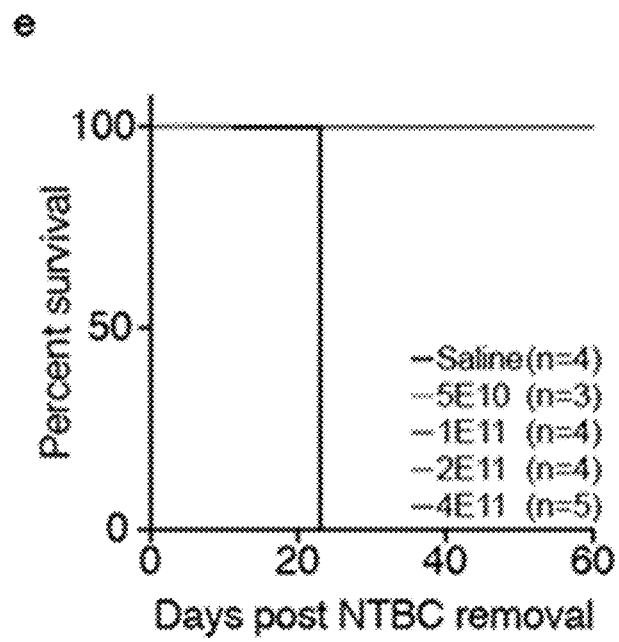
Figure 3F:
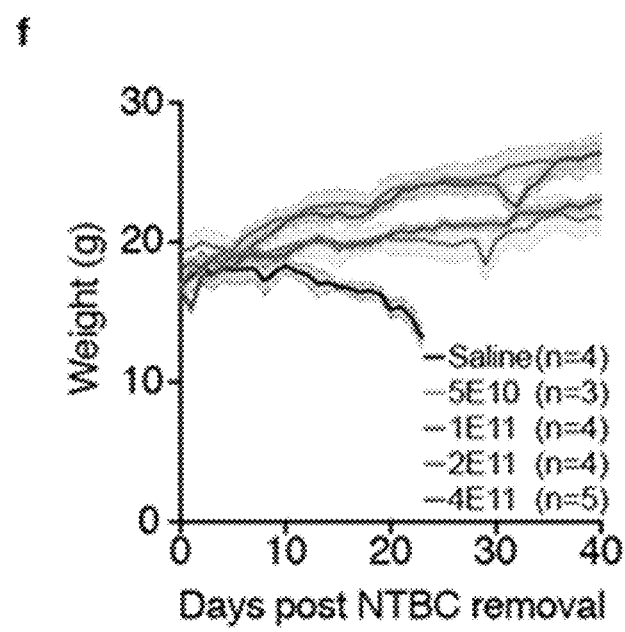
Figure 3G:
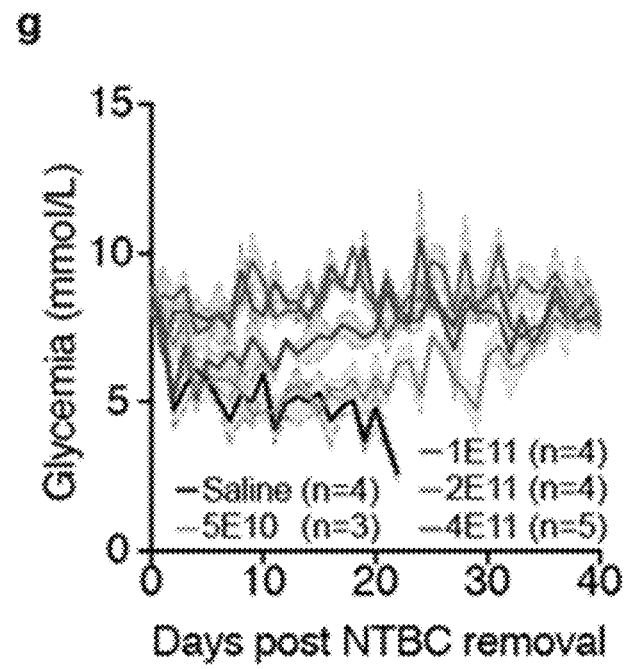
Figure 3H:
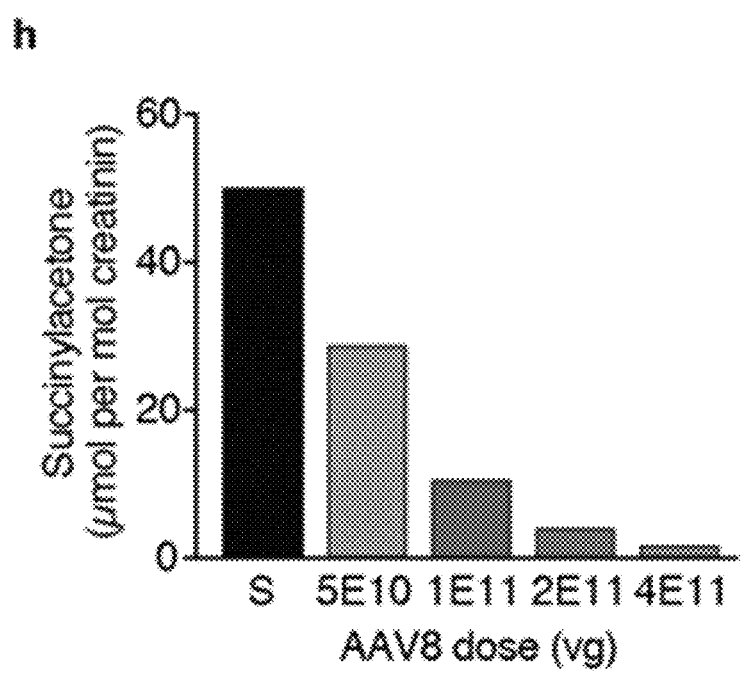

To test if AAV8-St1Cas9 can lead to phenotypic correction in vivo, we used a mouse model of hereditary tyrosinemia type I (HT-I) (OMIM 276700) (Orphanet ORPHA: 882), an autosomal recessive disease caused by a deficiency of fumarylacetoacetate hydrolase (FAH), the last enzyme of the tyrosine catabolic pathway (FIG. 3a). Of particular relevance to us, the incidence of HT-I reaches 1/1846 in a region of the province of Québec (Canada) while it is around 1/100,000 births worldwide[49]. Fah$^{-/-}$ mutant mice die as neonates with severe hepatic dysfunction and kidney damage due to the accumulation of toxic metabolites unless treated with nitisone (NTBC), a drug that inhibits Hpd upstream in the pathway (FIG. 3a)[50]. Similarly, genetic ablation of Hpd prevents liver damage and lethality[51, 52]. Fah$^{-/-}$ mutant pups maintained on NTBC were injected at day 2 of life with AAV8-St1Cas9 Hpd G5 and then the drug was withdrawn shortly after weaning (FIG. 3b). Systemic delivery via a single neonatal injection rescued lethality in all mice while saline-treated animals had to be killed after ~3 weeks as they lost weight (FIG. 3e,f). Likewise, glycemia was normalized in the treatment groups (FIG. 3g). Notably, the excretion of succinylacetone, a toxic metabolite and a diagnostic marker for HT-I, was inversely correlated with the dose of rAAV demonstrating metabolic correction (FIG. 3h). These observations were recapitulated when targeting Hpd exon 8 at a site corresponding to a mutation also found in human patients (FIG. 6). Therefore, rAAV-mediated delivery of St1Cas9 in vivo can correct a phenotype in neonatal mice by rewiring a metabolic pathway.

Figure 4A:
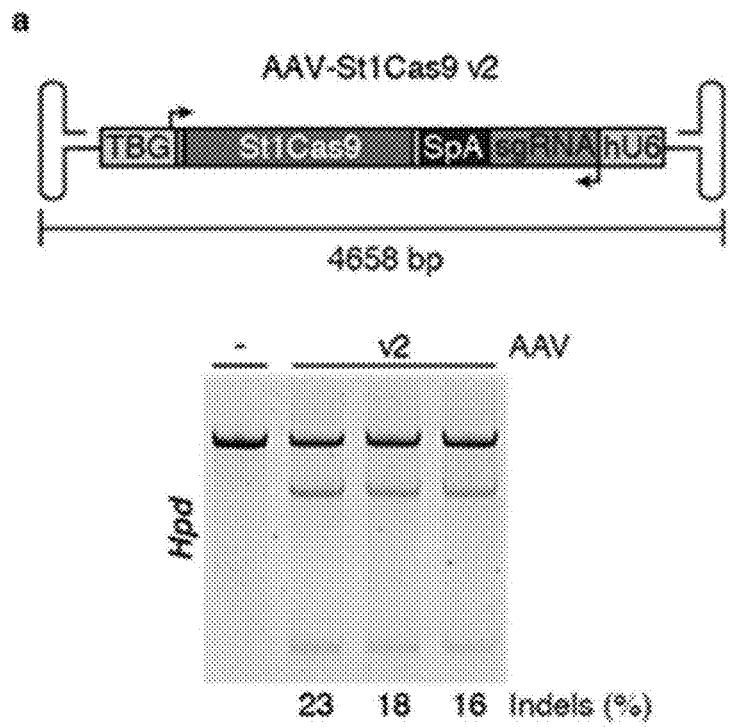
FIG. 4: Alternative rAAV-St1Cas9 vector architectures can further improve potency. (a) Schematic representations of the second-generation rAAV-St1Cas9 (v2) vector of similar size to the parent AAV genome (~4.7 kb). Annotated is the human thyroxine binding globulin (TBG) promoter, synthetic polyadenylation sequence (SpA) and hU6 promoter. Arrows indicate the direction of transcriptional unit. Neonatal (2 days old) Fah mice were injected with 2E11 vg rAAV8-St1Cas9 v2 targeting Hpd exon 13 (G5) or saline into the retro-orbital sinus and killed 13 days post injection. Genomic DNA was extracted from whole liver samples and the Surveyor assay was used to determine the frequency of St1Cas9-induced gene disruption as the % Indels indicated at the base of each lane. Each lane represents a different mouse. A mouse injected with saline (−) was used as a negative control. (b) Same as in (a) but the TBG promoter was swapped for the composite liver-specific LP1b promoter to generate rAAV8-St1Cas9 v3.
Figure 4B:
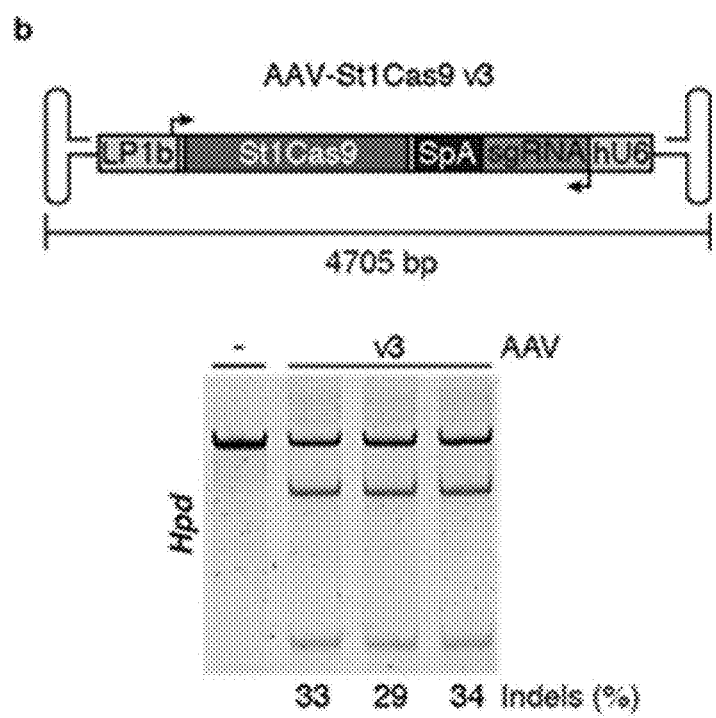
Figure 5A:
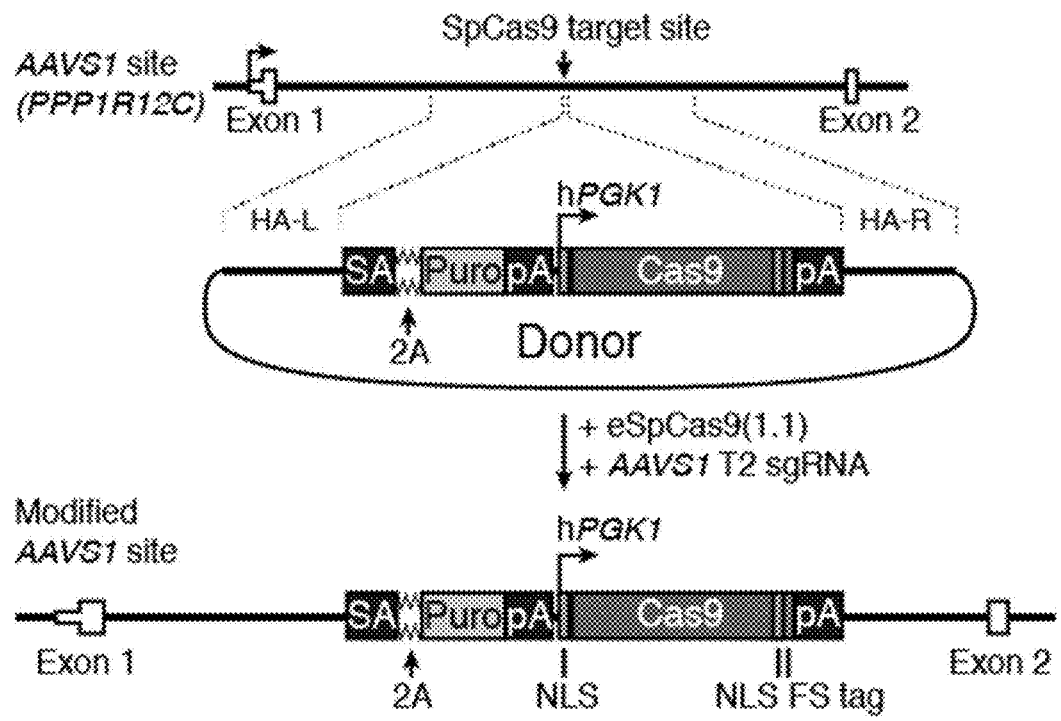
FIG. 5: Engineered CRISPR1-StCas9 system drives robust gene editing in human cells. (a) Schematic representation of the targeted integration of tagged St1Cas9 and SaCas9 to the AAVS1 safe harbor locus. The donor construct and the locus following cDNA addition are displayed. The first two exons of the PPP1R12C gene are shown as open boxes. Also annotated are the locations of the splice acceptor site (SA), 2A self-cleaving peptide sequence (2A), puromycin resistance gene (Puro), polyadenylation sequence (pA), human phosphoglycerate kinase 1 promoter (hPGK1), nuclear localization signals (NLS), and 3×FLAG-2×STREP tandem affinity tag (Tag), homology arms left and right (HA-L, HA-R) are respectively 800 and 840 bp. (b) Western blots showing Cas9-tag protein expression in K562 clones and cells expressing only the tag (Mock). The FLAG M2 antibody was used to detect Cas9 and the tubulin antibody was used as a loading control. (c) Alignment of previously described sgRNA sequences (SEQ ID NOs: 7-11) for St1Cas9. (d) K562 cells were transiently transfected with an St1Cas9 expression vector (0.5 µg) in addition to the indicated sgRNA expression plasmids (0.8 µg). Surveyor and TIDE assays were performed 3 days later to determine the frequency of indels, as indicated at the base of each lane. An expression vector encoding EGFP (−) was used as a negative control.
Figure 5B:
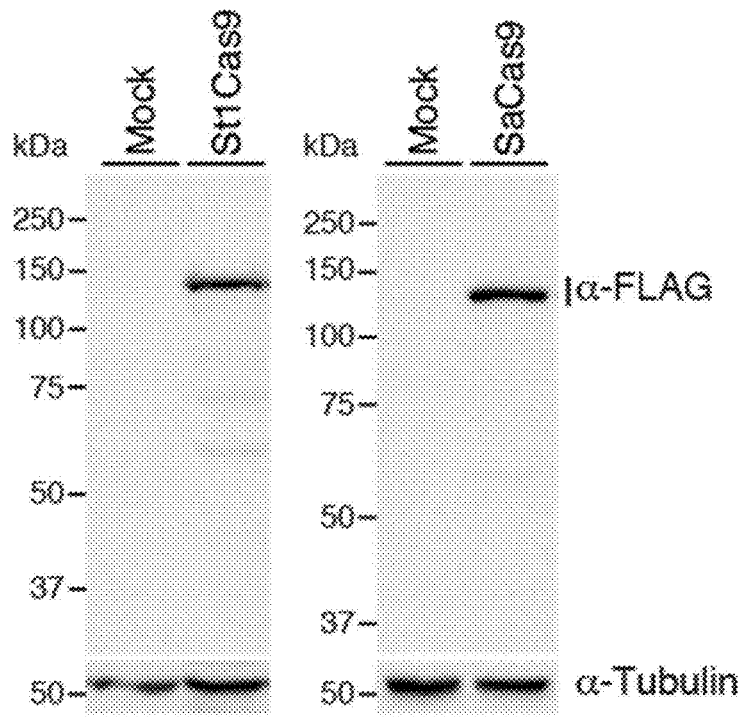
Figure 5C:
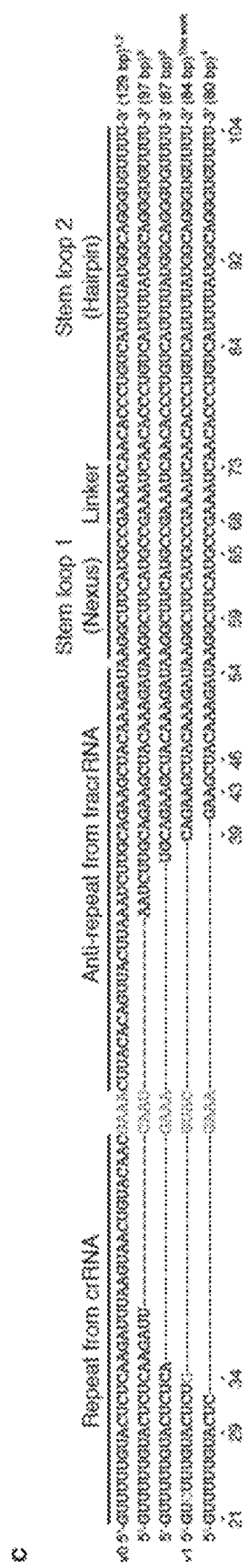
Figure 5D:
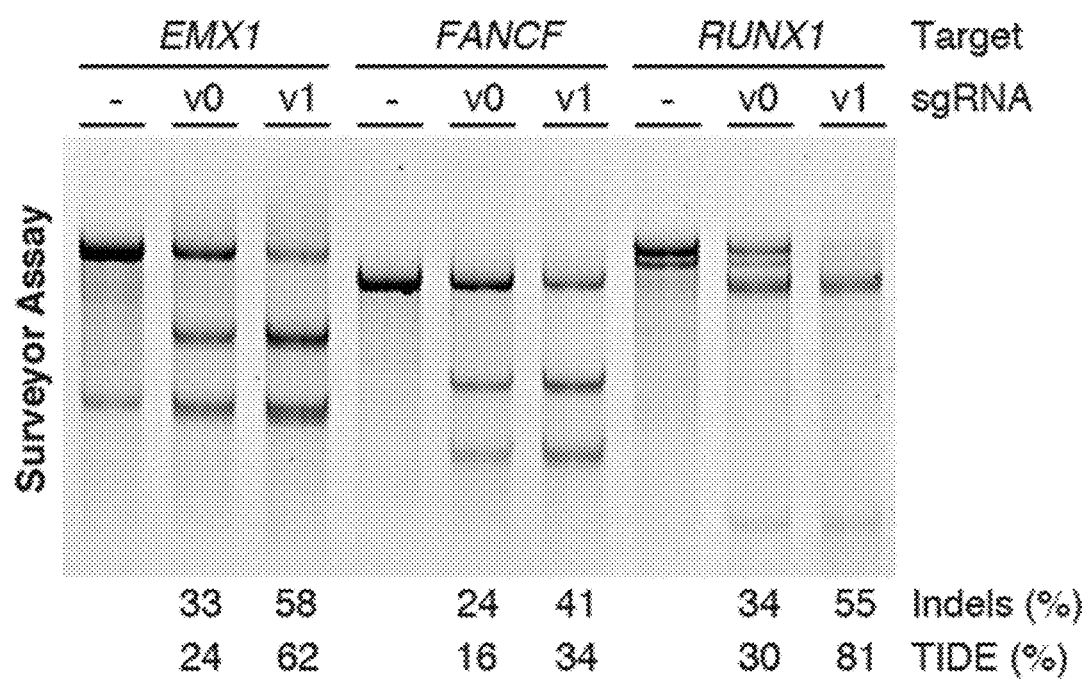

Lastly, we evaluated two additional vector architectures in order to minimize the size of rAAV and test the impact of the promoter on overall activity (FIG. 4). An rAAV vector (v3) containing an engineered liver-specific promoter (LP1b) combining the human apolipoprotein E/C-I gene locus control region (ApoE-HCR) and a modified human α1 antitrypsin promoter (hAAT) coupled to an SV40 intron and a synthetic polyadenylation element greatly improved efficacy as compared to the TBG promoter (FIG. 4a,b). These modifications also led to the creation of a vector of ~4.7 kb in size which was optimal for efficient packaging. Collectively, these data indicate that St1Cas9 is an efficient tool for in vivo genome editing.

Figures 7A, 7B:
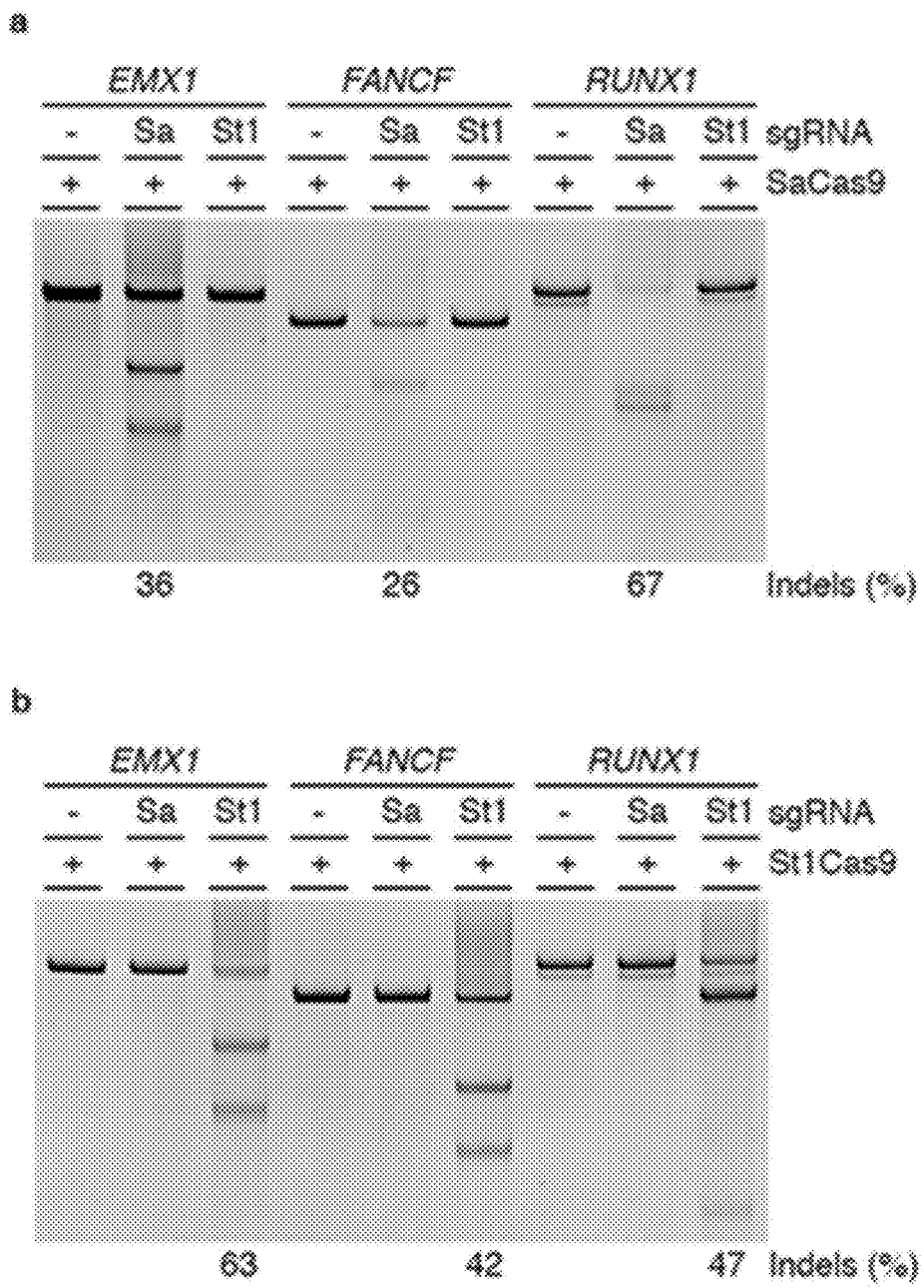
FIG. 7: sgRNAs for SaCas9 and St1Cas9 are not functionally interchangeable. (a) A stable K562 cell line constitutively expressing SaCas9 was transfected with expression vectors (0.25 µg) for its cognate sgRNA or the St1Cas9 sgRNA. The Surveyor assay was performed 3 days later to determine the frequency of indels, as indicated at the base of each lane. An expression vector encoding EGFP (−) was used as a negative control. (b) Same as in (a) but in a K562 cell line constitutively expressing St1Cas9. These data indicate that an sgRNA programmed to specify cleavage by St1Cas9 at one site cannot recruit and induce cutting by SaCas9 at this same site and vice-versa.

It is shown herein that St1Cas9 can be harnessed for robust and efficient genome editing in vitro and in vivo. While there is considerable interest in exploiting the diversity of Cas enzymes, but their implementation as genome editing tools is not a straightforward process7-10. Some enzymes simply fail to work and some choose their substrates promiscuously, necessitating thorough biochemical characterization 58-64. Moreover, sgRNAs for St1Cas9 and SaCas9 are not functionally interchangeable, which is likely due to their unique PAM specificity (FIG. 7).

Figure 8A:
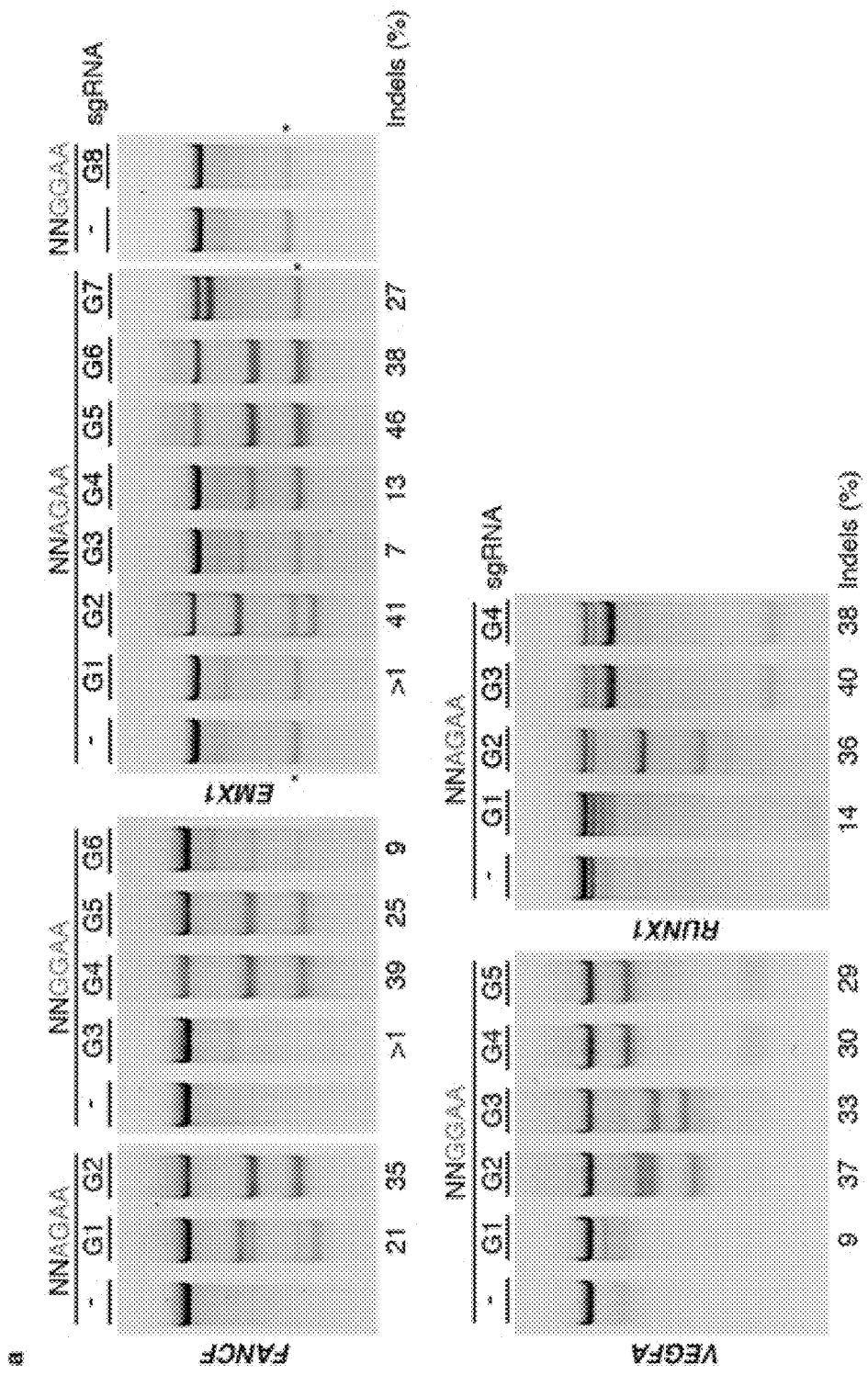
FIG. 8: St1Cas9 LMD-9 is functional at both NNAGAA and NNGGAA PAM sequences in human cells. (a) Surveyor assays to determine St1Cas9 activity programmed with various sgRNAs targeting FANCF, EMX1, VEGFA, and RUNX1 (Tables 3-4). K562 cells were transiently transfected with a single vector (1 µg) driving the expression of St1Cas9 and its sgRNA. Surveyor assays were performed 3 days later to determine the frequency of indels, as indicated at the base of each lane. An expression vector encoding EGFP (−) was used as a negative control. *Indicates a non-specific PCR amplification product that generates a signal in the Surveyor assay. This signal was subtracted from all quantifications. (b) sgRNAs specifying cleavage by St1Cas9 at PAMs with an NN linker were modified to test their functionality with an NNN linker (Tables 3, 6). Cleavage activity was determined as in (a).
Figure 8B:
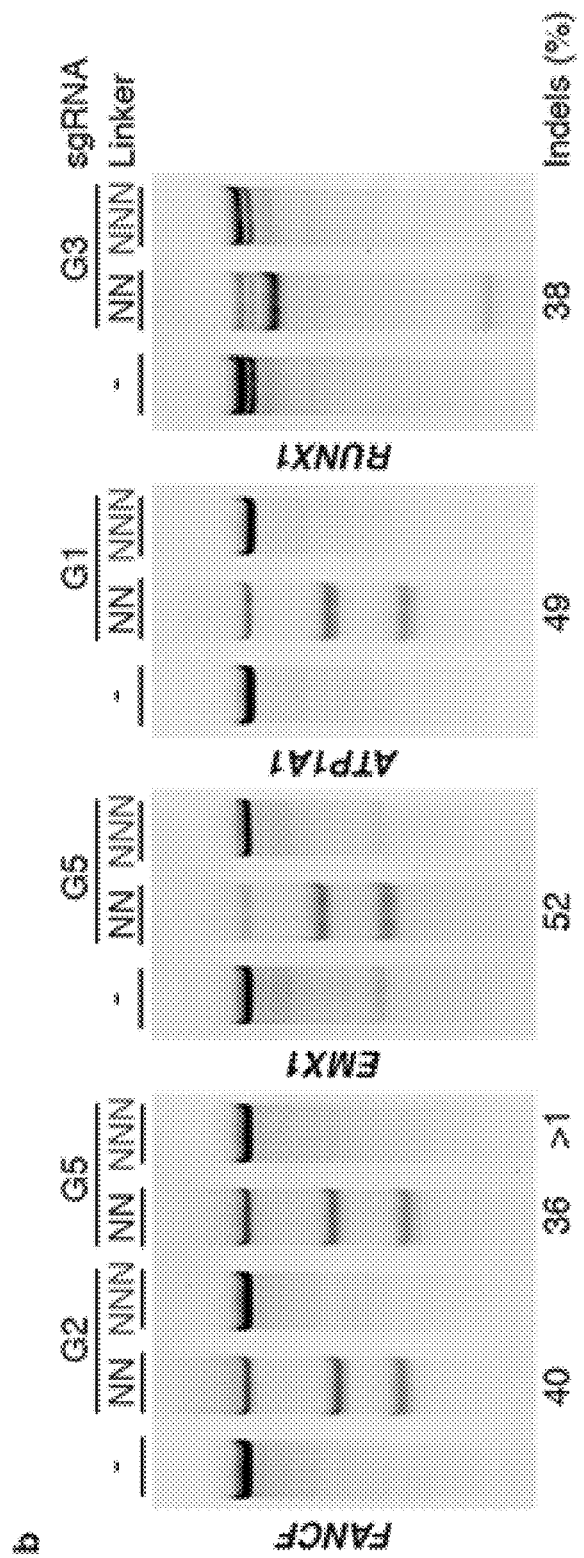

Cas9 orthologs used for rAAV-mediated in vivo genome editing require a more complex PAM than the relatively simple NGG of SpCas9. This restricts the range of accessible targets but may increase specificity by reducing the occurrence of off-target mutagenesis. The consensus PAM for St1Cas9 (LMD-9 and DGCC7710 strains that differ by only 2 aa) has been defined as $N^1N^2A^3G^4A^5A^6$ (W[7]), however sequences closely related to the consensus can be functional in test tubes and in bacterial cells[29, 34, 73-76]. While recognition of an A-rich PAM may ease targeting A/T-rich regions of genomes, we found that St1Cas9 can be targeted to both NNAGAA and NNGGAA PAMs in mammalian cells (FIG. 8). Of note, the presence of an A at position 7 of the PAM correlates with high activity (FIG. 8). While the length of the nonconserved linker ($N^1N^2$) has also been shown to be flexible and an extension from 2 to 3 bases has been shown to be tolerated[31, 77], we failed to reproduce this observation in human cells suggesting a higher stringency of the system in this context (FIG. 8).

Figure 9A:
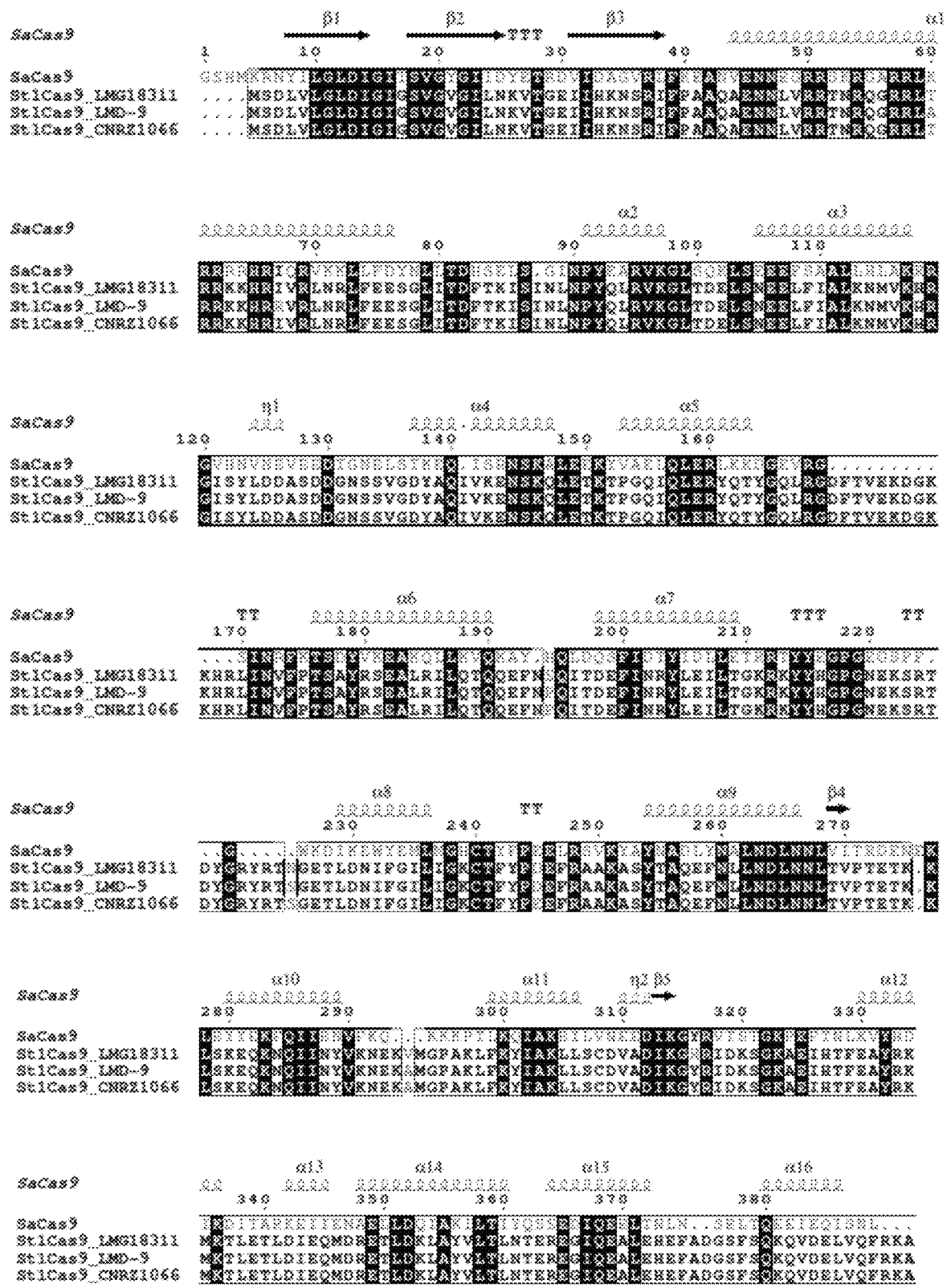
FIG. 9: Amino acid sequence alignment of SaCas9 (SEQ ID NO: 15) with St1Cas9 from different strains (SEQ ID NOs: 16-18 corresponding to St1Cas9_LMD-9, St1Cas9_LMG18311 and St1Cas9_CNRZ1066, respectively). The secondary structure of SaCas95 (5CZZ) is displayed above the sequences, which are numbered according to the residues of SaCas9. Identical residues are highlighted in black. Alignment was performed with Clustal Omega6 and ESPript7.
Figure 9B:
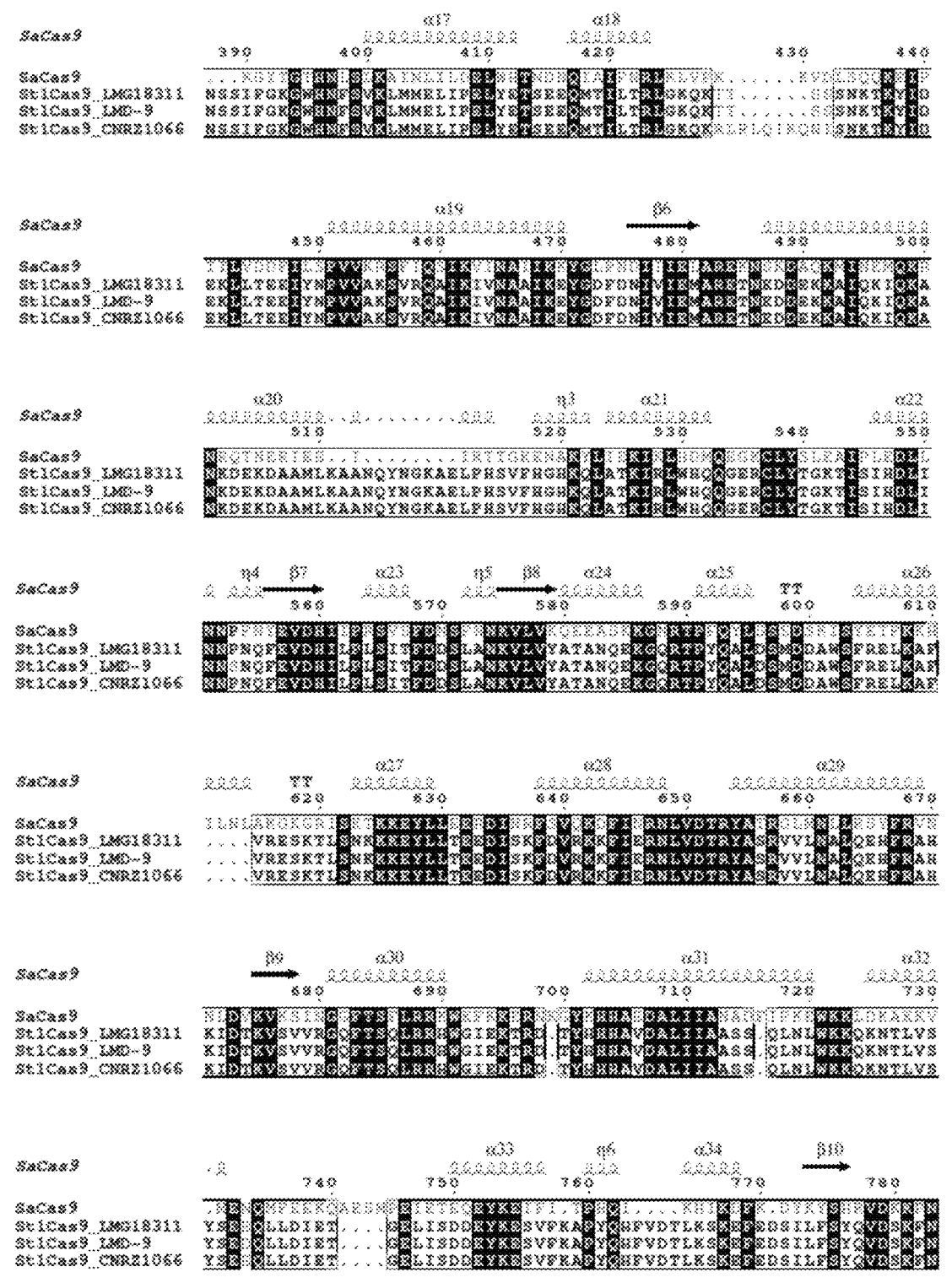
Figure 9C:
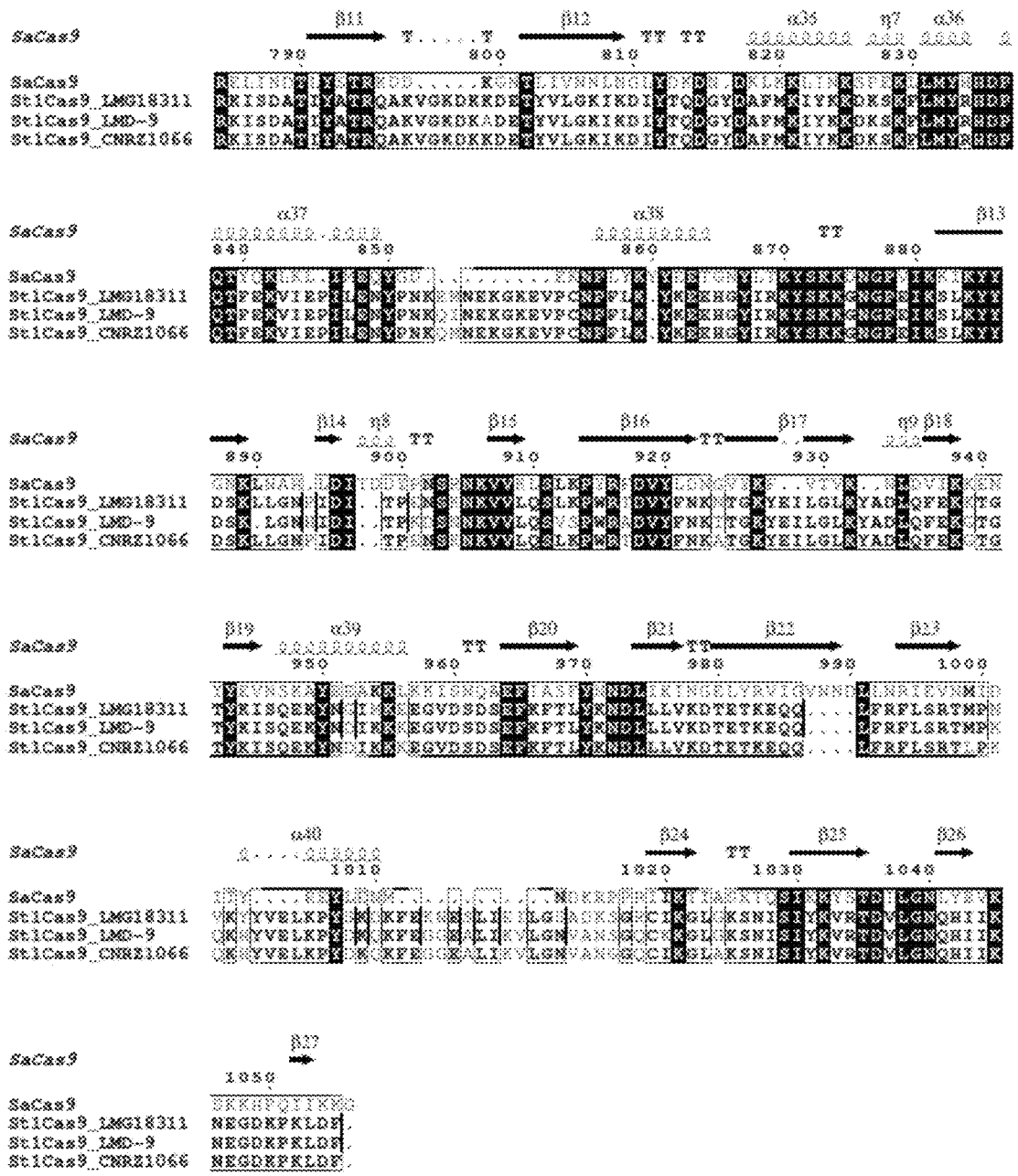
Figure 10A:
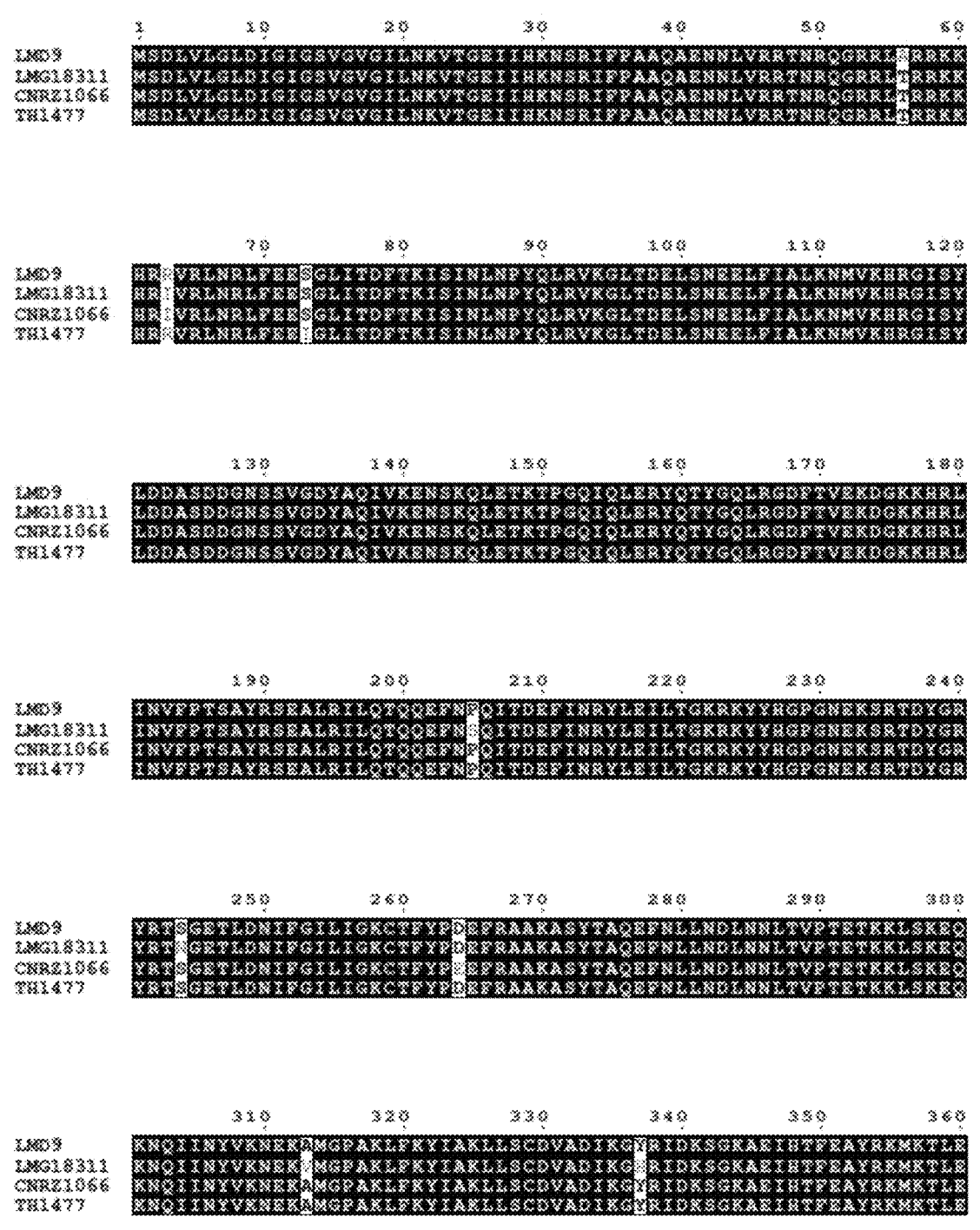
Figure 10B:
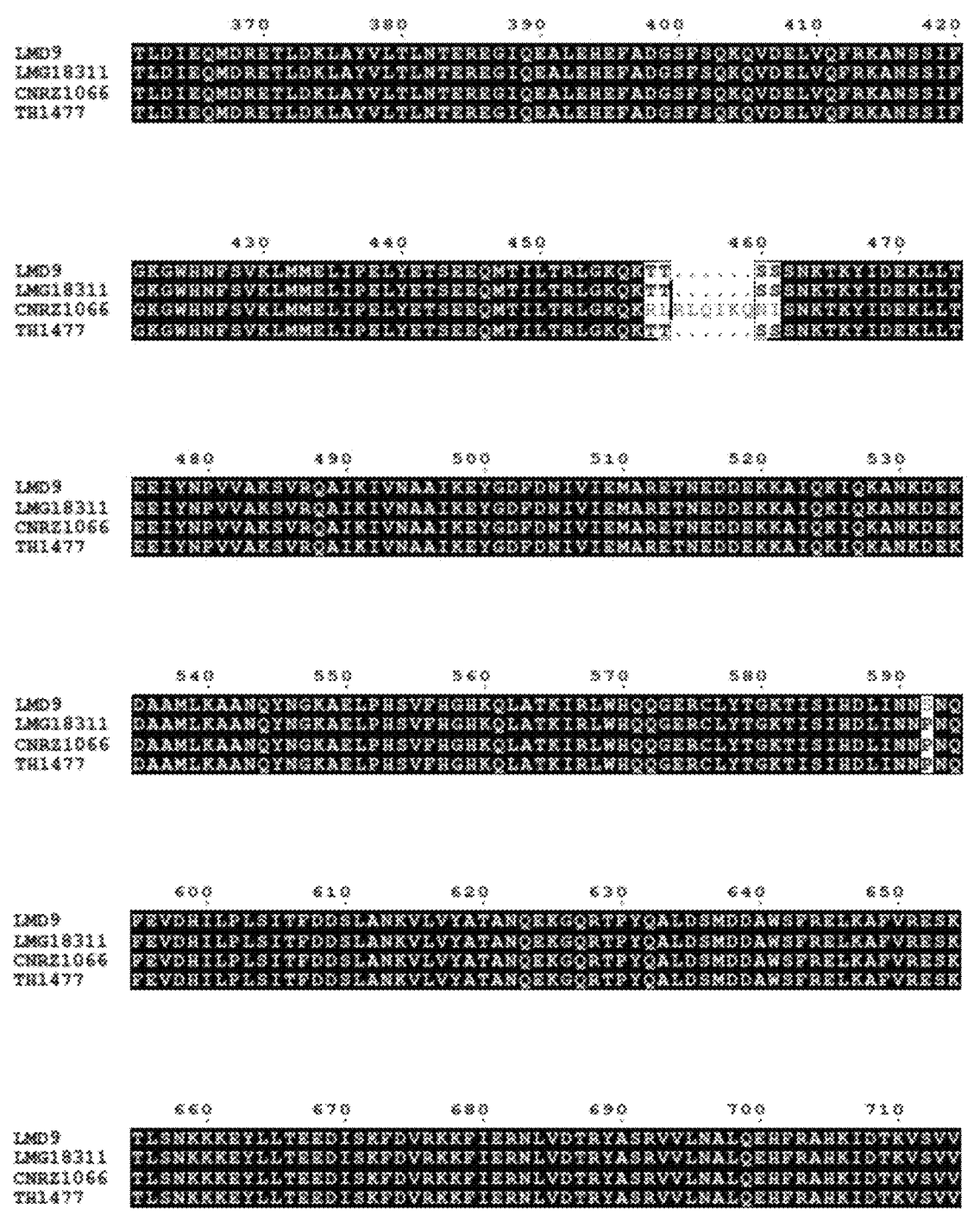
Figure 10C:
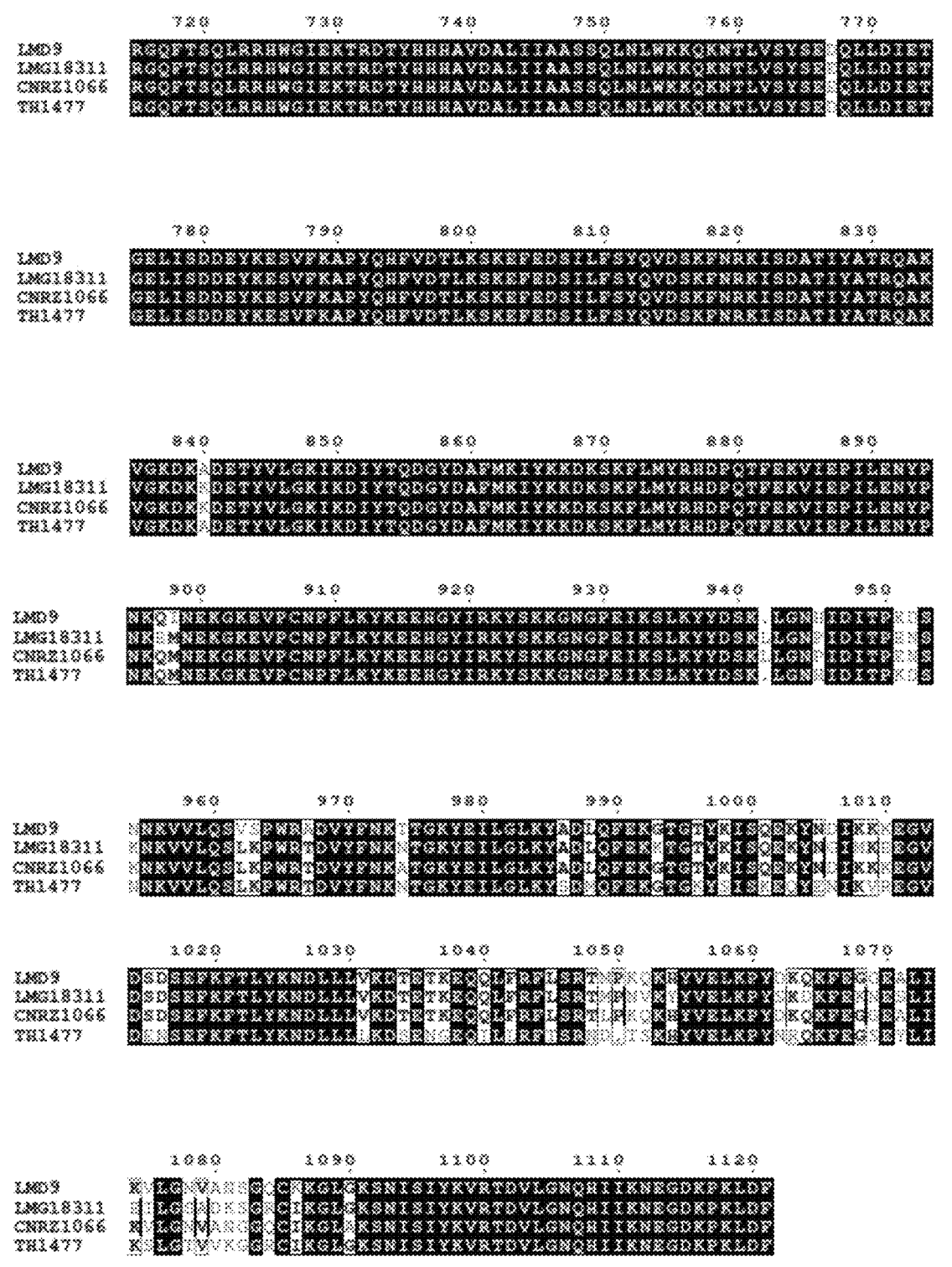

In embodiments, different St1Cas9 PAM sequences may be used, for example, inferred consensus PAM sequences for St1Cas9 from strains CNRZ1066 and LMG13811 are NNACAA(W) and NNGCAA(A), respectively[24, 26]. Notably, LMG13811 CRISPR1 system transplanted in E. coli or reconstituted from purified components can target DNA using the NNGCAAA PAM[77]. At the protein level, the sequence of these three St1Cas9 variants diverges mostly within the C-terminal PAM-interacting (PI) domain (FIGS. 9-10).

Example 5: Engineering St1Cas9 Nucleases with Altered Protospacer Adjacent Motif (PAM) Specificities One constraint for the use of St1Cas9 is its requirement for a longer PAM of the form $N_1N_2A_3G_4A_5A_6W_7$ (where W is A or T) that can restrict targeting. This consensus was initially obtained by examining the sequences flanking CRISPR-Cas9 target sites within bacteriophage genomes. However, sequences closely related to the consensus (NNA-GAAW and NNGGAAW) can be functional in test tubes or when transplanted in E. coli. These differences are believed to emerge from the different stringency imparted by the heterologous systems. Nevertheless, these deviations from the consensus suggest that there is some flexibility in PAM recognition. Thus, it is crucial to define functional PAMs for each Cas9 in their proper context; in our case, human and mouse cells.

Figure 18:
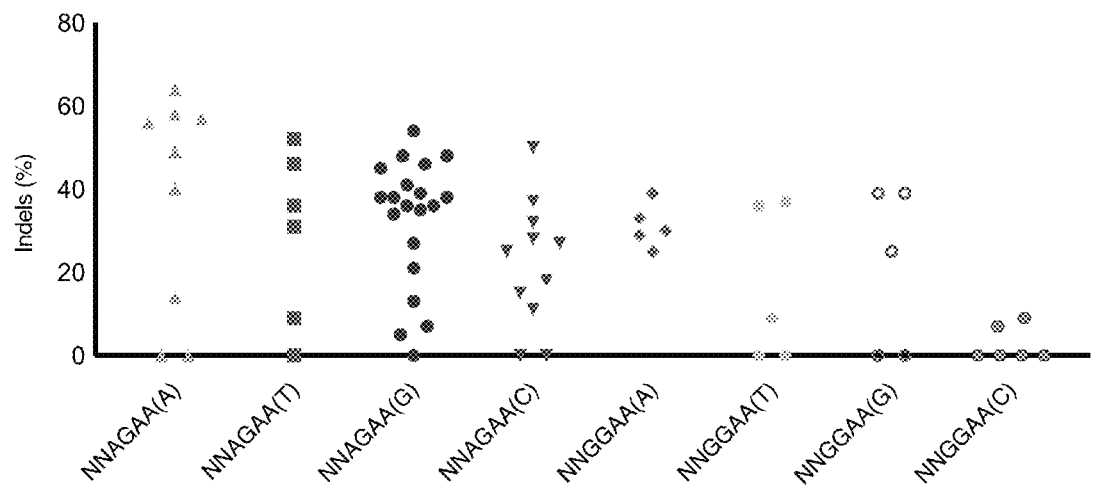
FIG. 18: St1Cas9 LMD-9 is functional at both NNAGAA and NNGGAA PAM sequences in human cells. (a) Results of surveyor assays to determine St1Cas9 activity programmed with various sgRNAs targeting various PAMs. K562 cells were transiently transfected with a single vector (1 µg) driving the expression of St1Cas9 LMD-9 and its sgRNA. Surveyor assays were performed 3 days later to determine the frequency of indels. An expression vector encoding EGFP (−) was used as a negative control.
Figure 19A:
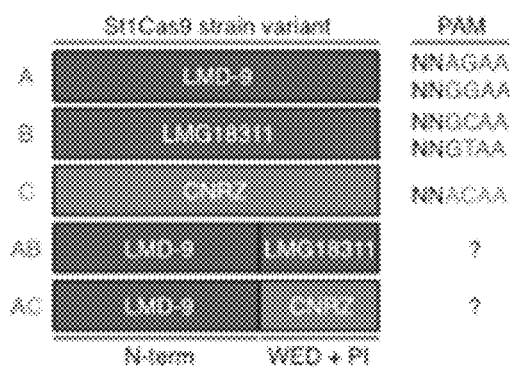
FIG. 19: Rewiring St1Cas9 LMD-9 to target a distinct PAM sequence using variants. (a) Schematic representation of St1Cas9 from the LMD-9 (A), LMG18311 (B), and CNRZ 1066 (C) strains along with their predicted or experimentally determined PAMs. The hybrid protein (AB) containing the N-terminal of St1Cas9 LMD-9 and the C-terminal domain (WED+PI) of St1Cas9 LMG18311 and CNRZ 1066 are also represented. (b-g) Surveyor assays to determine the activity of St1Cas9 variants programmed with sgRNAs targeting different PAM in human cells. K562 cells were transiently transfected with a single vector (1 µg) driving the expression of St1Cas9's and its sgRNA. Surveyor assays were performed 3 days later to determine the frequency of indels, as indicated at the base of each lane. An expression vector encoding EGFP (−) was used as a negative control.
Figures 19B, 19C, 19D:
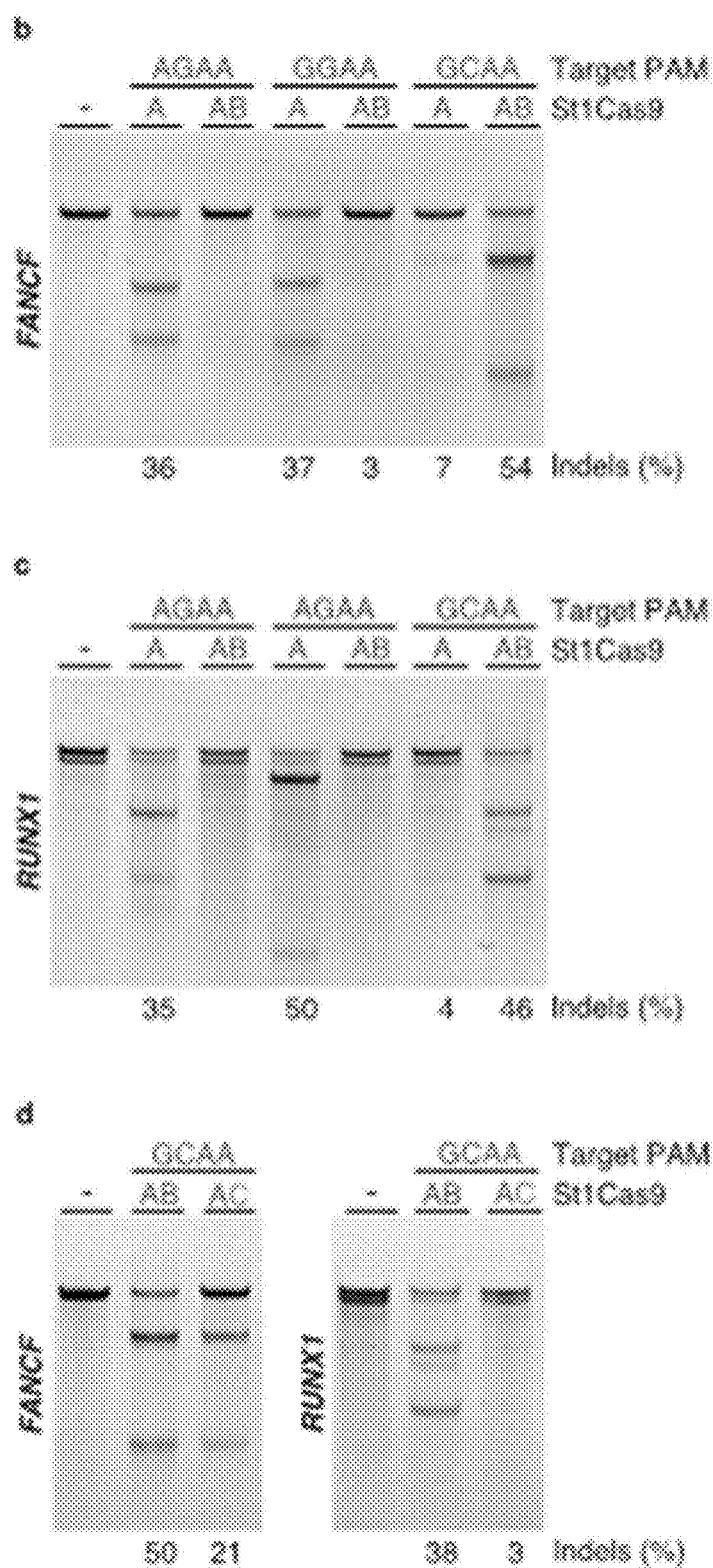
Figure 19E:
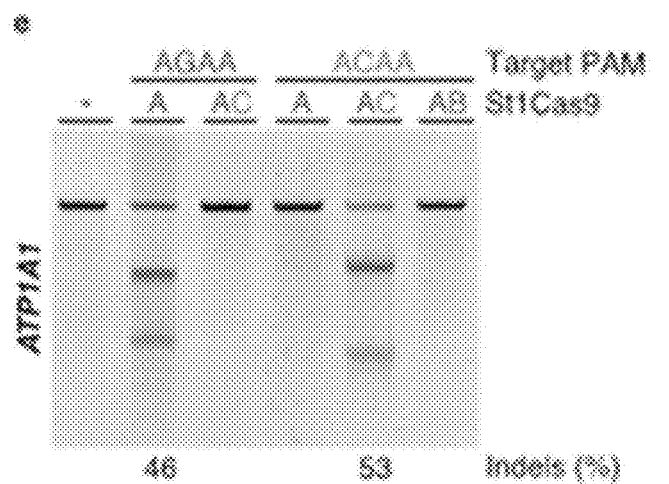
Figure 19F:
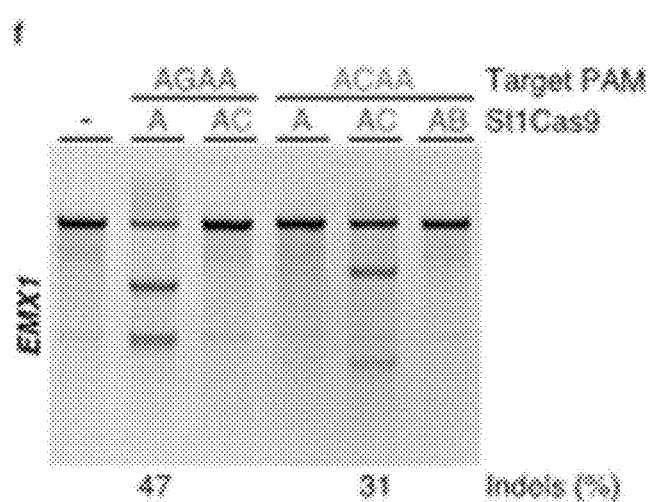
Figure 19G:
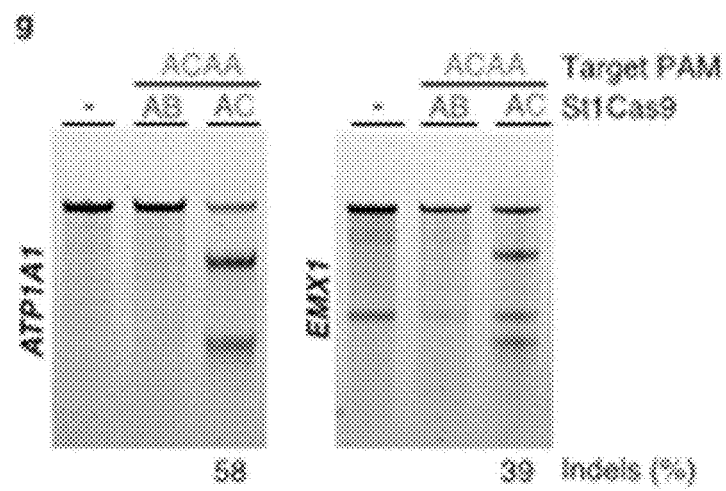

We first codon-optimized St1Cas9 for expression in human cells and appended N- and C-terminal nuclear localization signals (NLS). We show that both $NNAGAAW_7$ and $NNGGAAW_7$ PAM sequences could direct DNA cleavage with equivalent efficacy in cells (FIG. 18). We also observed that substitutions at position 7 are well tolerated. (FIG. 18). Thus, it appears that a functional PAM for St1Cas9 requires a core of four specific base pairs (NNAGAA or NNGGAA). By itself, removing the requirement for a W at position 7, increases the targeting range twofold. Since NNGGAA PAMs behave similarly, this results in an additional twofold expansion. By comparison, SaCas9 requires an NNGRRT (where R is A or G) PAM for cleavage.

We show herein the identification of St1Cas9 enzymes with distinct PAM specificities. The St1Cas9 protein sequence used in nearly all studies so far was derived from the LMD-9 or DGCC7710 strains that differ by only two conservative substitutions. We studied the LMD-9 St1Cas9 as well as St1Cas9 from strains LMG18311, CNRZ1066 and TH1477. As noted above, at the protein level, the sequence of these three St1Cas9 variants diverges mostly within the C-terminal wedge (WED) and PAM-interacting (PI) domains (FIGS. 10 and 35b). Using the structure of SaCas9[28] as a guide, we tested whether swapping the C-terminus of St1Cas9 LMD-9 with the ones from the LMG 18311, CNRZ 1066 and TH1477 could reprogram PAM specificity, and we thus engineered hybrid proteins containing the N-terminal domain of St1Cas9 LMD-9 (REC lobe, HNH and RuvC nuclease domains, and phosphate lock loop;

aa 1-826) and C-terminal domains of St1Cas9 LMG 18311, CNRZ 1066 and TH1477 (WED and PI domains; aa 827-1121) (FIG. 19). While St1Cas9 LMD-9 could only target NNAGAA and NNGGAA PAMs, the hybrid constructs targeted with high efficacy NNACAA and NNGCAA PAMs, respectively (FIG. 19). We observed limited cross reactivity indicating that true reprogramming, as opposed to relaxed specificity was achieved. These data highlight the modularity inherent to Cas9 enzymes, and this strategy may be used to further expand the targeting range of St1Cas9.

Example 6: Engineering St1Cas9 Variants with Expanded Targeting Range

Figure 20A:
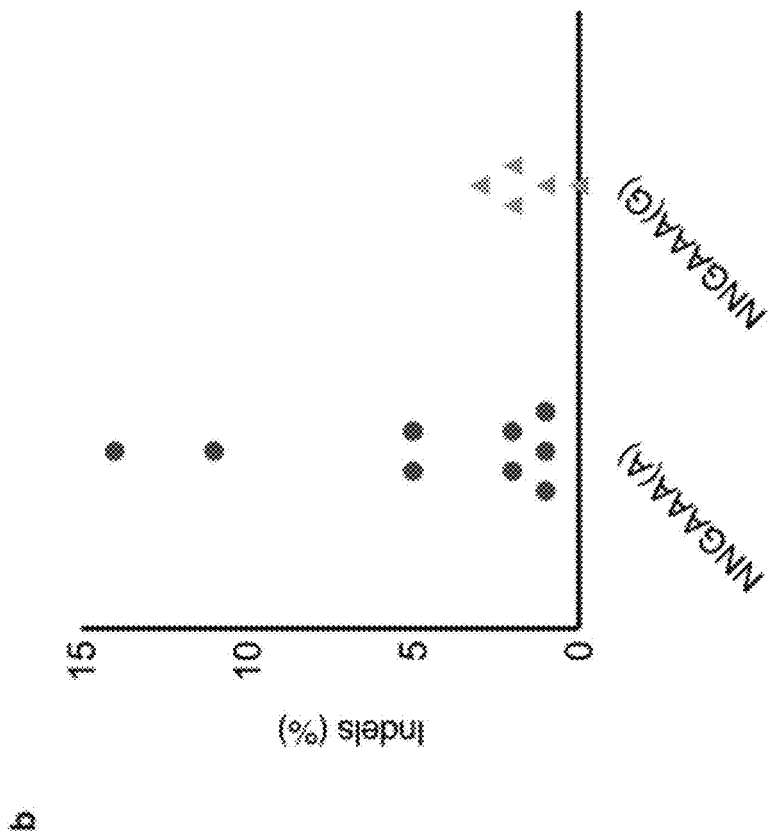
FIG. 20: Rewiring St1Cas9 LMD-9 to target distinct PAM sequences using variants. (a) Predicted PAM specificity for various St1Cas9 variants based on SPAMALOT. (b) Results of TIDE assays to determine St1Cas9 TH1477 activity programmed with various sgRNAs targeting various PAMs. K562 cells were transiently transfected with a single vector (1 µg) driving the expression of St1Cas9 TH1477 and its sgRNA. TIDE assays were performed 3 days later to determine the frequency of indels. An expression vector encoding EGFP (−) was used as a negative control.
Figure 20B:
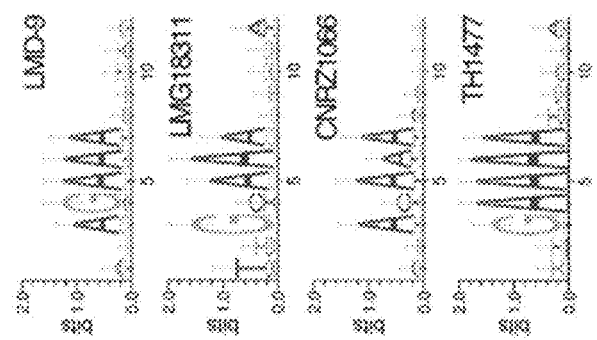

In an effort to identify additional St1Cas9 proteins with novel PAM requirements, we used a recently published bioinformatics pipeline called "Search for PAMs by Alignment Of Targets" (SPAMALOT)[86]. This process identified an additional St1Cas9 represented by strain TH1477 that potentially targets NNGAAA PAMs (FIG. 20a). We generated chimeric fusion proteins with the N-terminus of LMD-9 and the C-terminal domain of TH1477 as we have done for CNRZ1066 and LMG1831. This approach yielded an active St1Cas9 derived from the TH1477 strain that can target NNGAAA PAMs (FIG. 20b).

Example 7: Converting St1Cas9 to a Base Editor

Figure 21:
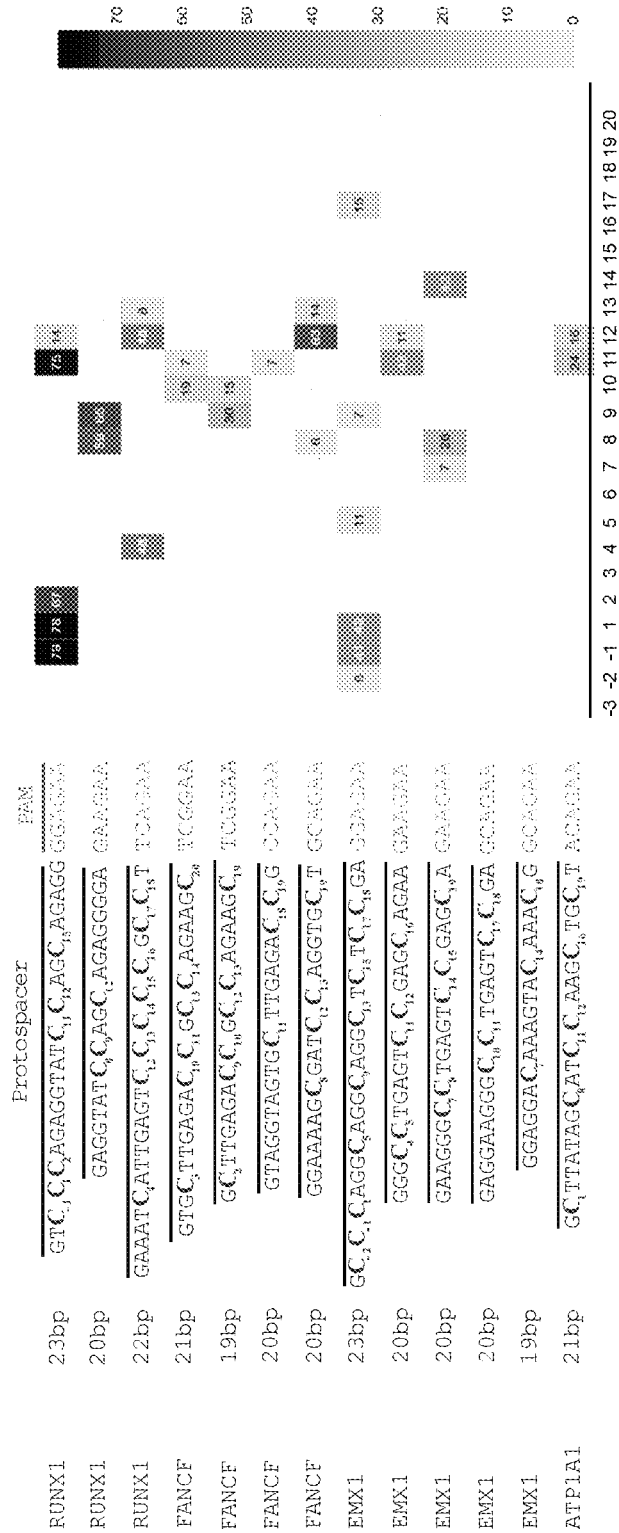
FIG. 21: Converting St1Cas9 LMD-9 to a cytosine base editor (CBE). St1BE4max programmed with sgRNAs targeting NNAGAA and NNGGAA PAMs in human cells. K562 cells were transiently transfected with a single vector (1 µg) driving the expression of St1BE4max LMD-9 and its sgRNA. Quantification of base editing from sanger sequencing reads was performed 3 days later using EditR™ software. Numbers in each box indicate the % of C to T conversions. Protospacer target sequence SEQ ID NOs: 182, 180 and 178 (RUNX1); 172, 171, 169 and 168 (FANCF); 157, 162, 161, 159 and 160 (EMX1); 185 (ATP1A1).

DNA base editors comprise fusions between a catalytically impaired Cas nuclease and a base modification enzyme that operates on single-stranded DNA (ssDNA)[80]. Cytosine base editors (CBEs) convert a C·G base pair into a T·A using the APOBEC1 cytidine deaminase. Fusion of APOBEC1 to the Streptococcus pyogenes D10A mutant (nickase) and two copies of the uracil DNA glycosylase inhibitor (UGI), resulted in the creation of BE4max enzyme. The Staphylococcus aureus Cas9 has also been converted into a base editor to create SaBE4. We have created St1BE4max by exchanging SpCas9 D10A for St1Cas9 D9A (LMD-9) into the original BE4max construct. This created a potent CBE with novel targeting specificity due to the unique PAM of St1Cas9 (FIG. 21). Our data indicate that St1BE4max has a similar activity window to SaBE4. Since the activity window (aka editing window) of base editors is narrow there is a distinct advantage of creating base editors targetable to a broad range of PAM sequences. This is particularly important considering the recent engineering of deaminase domains with even more narrower editing windows, such as APOBEC3A (eA3A), which preferentially deaminates cytidines in specific motifs according to a TCR>TCY>VCN hierarchy[80].

Figures 22A, 22B:
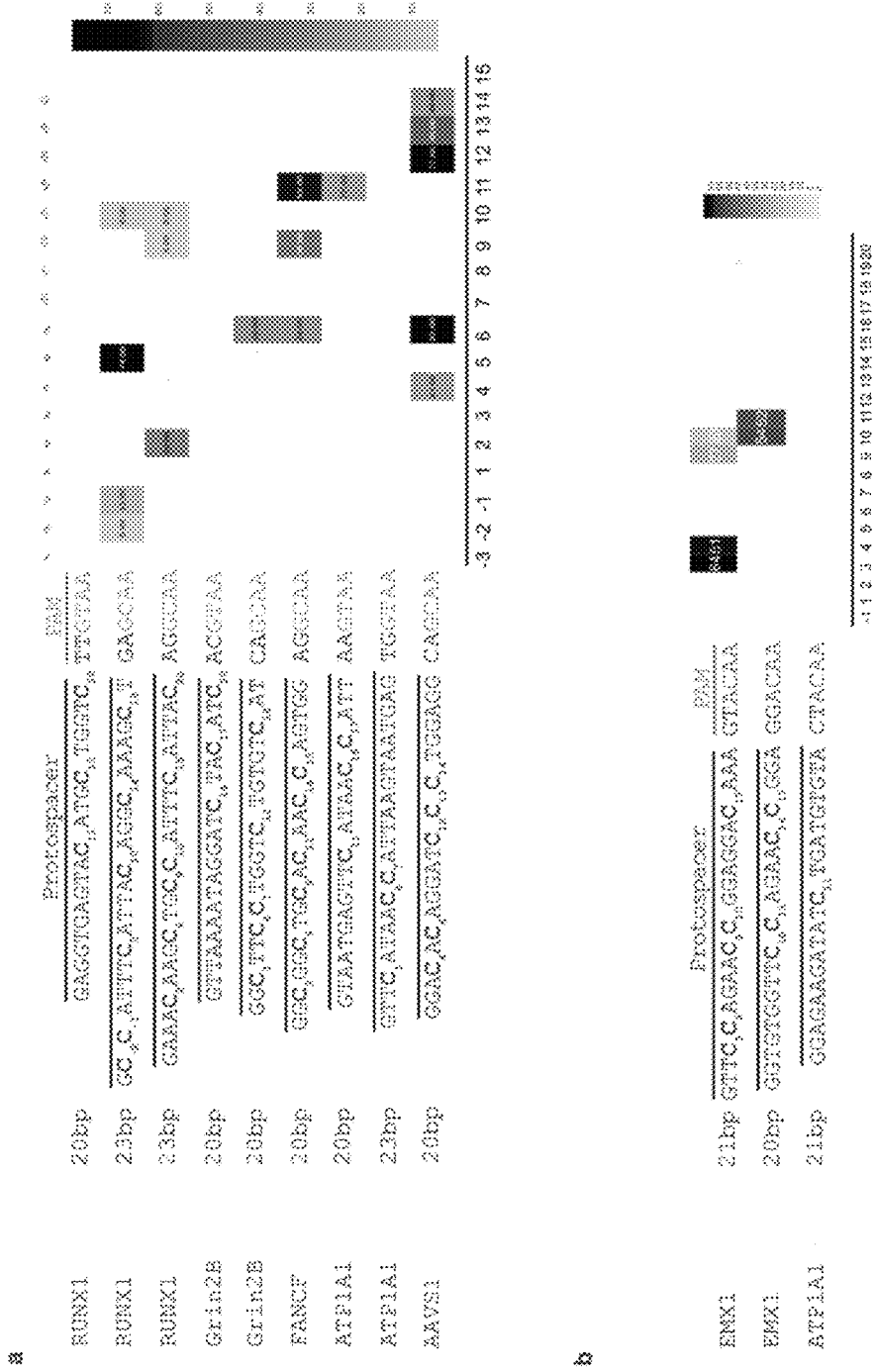
FIG. 22: Rewiring St1BE4max to target distinct PAM sequences using variants. (a-b) St1BE4max LMG 18311 and CNRZ 1066 were programmed with sgRNAs targeting NNGCAA and NNACAA PAMs, respectively. K562 cells were transiently transfected with a single vector (1 µg) driving the expression of St1BE4max variants and its sgRNA. Quantification of base editing from sanger sequencing reads was performed 3 days later using the EditR™ software. Numbers in each box indicate the % of C to T conversions. Protospacer target sequence SEQ ID NOs: 237, 236 and 235 (RUNX1); 258 and 239 (Grin2B); 234 (FANCF); 241 and 240 (ATP1A1, panel a); 238 (AAVS1); 243 and 242 (EMX1); 245 (ATP1A1, panel b).

We then proceeded to demonstrate that the St1Cas9 strain variants that display unique PAM preferences are also functional as CBEs. Specifically, LMD-9/LMG18311 hybrid- and LMD-9/CNRZ1066 hybrid-based St1BE4max are potent base editors at NNGCAA and NNACAA PAMs, respectively (FIG. 22). These data further demonstrate the use of St1Cas9 as a genome editing platform and the value of creating St1Cas9 fusions based on variants.

TABLE 3

St1Cas9 guide (spacer) sequences targeting NNAGAA PAMs (Examples 1-4)

| Gene | ID | bp | 5' | Target Sequence | SEQ ID NO: | PAM | 3' |
|---|---|---|---|---|---|---|---|
| EMX1 | G1 | 22 | ACCTGG | GCCAGGGAGGGAGGGGCACAGA | 70 | TGAGAA | ACTCAG |
|  | G2 | 19 | AGAACC | GGAGGACAAAGTACAAACG | 71 | GCAGAA | GCTGGA |
|  | G3 | 24 | GTTCCA | GAACCGGAGGACAAAGTACAAACG | 72 | GCAGAA | GCTGGA |
|  | G4 | 20 | CTGGAG | GAGGAAGGGCCTGAGTCCGA | 73 | GCAGAA | GAAGAA |
|  | G5 | 20 | GAGGAG | GAAGGGCCTGAGTCCGAGCA | 74 | GAAGAA | GAAGGG |
|  | G6 | 20 | GAGGAA | GGGCCTGAGTCCGAGCAGAA | 75 | GAAGAA | GGGCTC |
|  | G7 | 23 | GGGCCC | GCCCAGGCAGGCAGGCTCTCCGA | 76 | GGAGAA | GGCCAA |
| FANCF | G1 | 20 | AAGCTC | GGAAAAGCGATCCAGGTGCT | 77 | GCAGAA | GGGATT |
|  | G2 | 20 | GCTGAC | GTAGGTAGTGCTTGAGACCG | 78 | CCAGAA | GCTCGG |
| RUNX1 | G1 | 21 | ATTACT | GTACTAATCAGATGGAAGCTCT | 79 | TCAGAA | ATGTTT |
|  | G2 | 22 | GTAAAA | GAAATCATTGAGTCCCCGCCT | 80 | TCAGAA | GTGGGT |
|  | G3 | 20 | GTCCCT | GAGGTATCCAGCAGAGGGGA | 81 | GAAGAA | AGAGAG |
|  | G4 | 23 | TGGGGA | GTCCCAGAGGTATCCAGCAGAGG | 82 | GGAGAA | GAAAGA |
| ATP1A1 | G1 | 20 | TCTGTA | GCAGCTTGGATGCTATAAGC | 83 | CAAGAA | ACAAAG |
| Hpd | G1 | 20 | CTACTT | GGTACCCCACGCAGAAAGCT | 84 | CGAGAA | CGGGGC |
|  | G2 | 20 | TTGTAT | GTTGGGGCCTCGAATCCAGG | 85 | TAAGAA | ACGGCC |
|  | G3 | 20 | TATGGA | GATACCACACACACCCTGGT | 86 | GGAGAA | GATCAA |
|  | G4 | 21 | CAGTTT | GTAGTAAGAAGATGGGGCGGC | 87 | CAAGAA | CTCCGT |
|  | G5 | 21 | GGAGCT | GCATATCCTAGTCGACTATGA | 88 | CGAGAA | AGGCTA |
| Pcsk9 | G1 | 19 | CCAACA | GGTCACTGCTCATCTTCAC | 89 | CAAGAA | GCCAGG |
|  | G2 | 19 | CCAACA | GGGTCACTGCTCATCTTCAC | 90 | CAAGAA | GCCAGG |
|  | G3 | 20 | CCCAAC | GAGGTCACTGCTCATCTTCAC | 91 | CAAGAA | GCCAGG |
|  | G4 | 19 | AATCAC | GCACGACGCCTCCCGCTCCT | 92 | GGAGAA | GCTGGA |
|  | G5 | 20 | CAATCA | GCCACGACGCCTCCCGCTCCT | 93 | GGAGAA | GCTGGA |
|  | G6 | 20 | GGCCTG | GAGACCCATGTCCACTGCCA | 94 | CCAGAA | GGACCA |
| Pck1 | G1 | 20 | GGATAT | GGTGGGAACTCACTACTCGG | 95 | GAAGAA | ATGCTT |
|  | G2 | 20 | ATCCTG | GGCATAACTAACCCCGAAGG | 96 | CAAGAA | GAAATA |
|  | G3 | 20 | ATAATG | GGGCACTGGCTGGCAGGGGT | 97 | GCAGAA | TCTCGA |
|  | G4 | 20 | GCCAGG | GTATTTGCCGAAGTTGTAGCC | 98 | GAAGAA | GGGTCG |

"G" in position 1 of the guide indicates a mismatch to the genome and it is not counted in the size (bp) of the guide.

TABLE 4

St1Cas9 guide target sequences targeting NNGGAA PAMs (Examples 1-4)

| Gene | ID | bp | 5' | Target Sequence | SEQ ID NO: | PAM | 3' |
|---|---|---|---|---|---|---|---|
| EMX1 | G8 | 22 | GACAAA | GTACAAACGGCAGAAGCTGGAG | 99 | GAGGAA | GGGCCT |
| FANCF | G3 | 20 | GCGGAA | GTAGGGCCTTCGCGCACCTC | 100 | ATGGAA | TCCCTT |
|  | G4 | 19 | GGTAGT | GCTTGAGACCGCCAGAAGC | 101 | TCGGAA | AAGCGA |
|  | G5 | 21 | TAGGTA | GTGCTTGAGACCGCCAGAAGC | 102 | TCGGAA | AAGCGA |
|  | G6 | 20 | ACCGAG | GGCCTGGAAGTTCGCTAATC | 103 | CCGGAA | CTGGAC |
| VEGFA | G1 | 20 | GGTGGG | GAGAGGGACACACAGATCTA | 104 | TTGGAA | TCCTGG |
|  | G2 | 20 | GGGCCT | GAGAGCCGTTCCCTCTTTGC | 105 | TAGGAA | TATTGA |
|  | G3 | 20 | CCCGCG | GGGCATTGGCGAGGAGGGAG | 106 | CAGGAA | AGTGAG |
|  | G4 | 19 | CAGCCT | GAAAATTACCCATCCGCCC | 107 | CCGGAA | ACTCTG |
|  | G5 | 23 | TTCACA | GCCTGAAAATTACCCATCCGCCC | 108 | CCGGAA | ACTCTG |

TABLE 5

St1Cas9 guide target sequences targeting PAMs with a NNN linker (Examples 1-4)

| Gene | ID | bp | Target 5' | Target Sequence | SEQ ID NO: | PAM | 3' |
|---|---|---|---|---|---|---|---|
| EMX1 | G5 | 20 | GGAGGA | GGAAGGGCCTGAGTCCGAGC | 109 | AGAAGAA | GAAGGG |
| FANCF | G2 | 19 | GCTGAC | GTAGGTAGTGCTTGAGACC | 110 | GCCAGAA | GCTCGG |
|  | G5 | 20 | TAGGTA | GTGCTTGAGACCGCCAGAAG | 111 | CTCGGAA | AAGCGA |
| ATP1A1 | G1 | 19 | TCTGTA | GCAGCTTGGATGCTATAAG | 112 | CCAAGAA | ACAAAG |
| RUNX1 | G3 | 19 | GTCCCT | GAGGTATCCAGCAGAGGGG | 113 | AGAAGAA | AGAGAG |

TABLE 6

SaCas9 guide (spacer) sequences targeting NNGRRT PAMs (Examples 1-4)

| Gene | ID | bp | Target 5' | Target Sequence | SEQ ID NO: | PAM | 3' |
|---|---|---|---|---|---|---|---|
| EMX1 | G1 | 21 | GGGTGG | GCAACCACAAACCCACGAGGG | 114 | CAGAGT | GCTGCT |
| FANCF | G1 | 21 | GCGGAA | GTAGGGCCTTCGCGCACCTCA | 115 | TGGAAT | CCCTTC |
| RUNX1 | G1 | 23 | CAGCAT | GTACTCACCTCTCATGAAGCACT | 116 | GTGGGT | ACGAAG |
| Hgd | G1 | 20 | CATCCT | GGAGGTCTATGGTGTCCACT | 117 | TTGAGT | TACCTG |
| Hpd | G1 | 20 | AGGTGA | GAGTTTGCTGTGCTGCAGACG | 118 | GTGAGT | GAACAC |

"G" in position 1 of the guide indicates a mismatch to the genome and it is not counted in the size (bp) of the guide.

TABLE 7

SaCas9 and St1Cas9 sgRNAs

| sgRNA | Sequence |
|---|---|
| St1Cas9_v0 | GTTTTTGTACTCTCAAGATTTAAGTAACTGTACAACGAAACTTACACAGTTACTTAAATCTTGCAGAAGCTACAAAGATAAGGCTTCATGCCGAAATCAACACCCTGTCATTTTATGGCAGGGTGTTTT (SEQ ID NO: 119) GUUUUUGUACUCUCAAGAUUUAAGUAACUGUACAACGAAACUUACACAGUUACUUAAAUCUUGCAGAAGCUACAAAGAUAAGGCUUCAUGCCGAAAUCAACACCCUGUCAUUUUAUGGCAGGGUGUUUU (RNA; SEQ ID NO: 120) |
| St1Cas9_v1 | GTCTTTGTACTCTGGTACCAGAAGCTACAAAGATAAGGCTTCATGCCGAAATCAACACCCTGTCATTTTATGGCAGGGTGTTTT (SEQ ID NO: 121) GUCUUUGUACUCUGGUACCAGAAGCUACAAAGAUAAGGCUUCAUGCCGAAAUCAACACCCUGUCAUUUUAUGGCAGGGUGUUUU (RNA; SEQ ID NO: 122) |
| SaCas9 | GTTTTAGTACTCTGGAAACAGAATCTACTAAAACAAGGCAAAATGCCGTGTTTATCTCGTCAACTTGTTGGCGAGAT (SEQ ID NO: 123 GUUUUAGUACUCUGGAAACAGAAUCUACUAAAACAAGGCAAAAUGCCGUGUUUAUCUCGUCAACUUGUUGGCGAGAU (RNA; SEQ ID NO: 124) |

TABLE 8

Sequences for TBG and LP1B promoters

| Promoter | Sequence |
|---|---|
| TBG | GGGCTGGAAGCTACCTTTGACATCATTTCCTCTGCGAATGCATGTATAATTTCTACAGAACCTATTAGAAAGGATCACCCAGCCTCTGCTTTTGTACAACTTTCCCTTAAAAAACTGCCAATTCCACTGCTGTTTGGCCCAATAGTGAGAACTTTTTCCTGCTGCCTCTTGGTGCTTTTGCCTATGGCCCCTATTCTGCCTGCTGAAGACACTCTTGCCAGCATGGACTTAAACCCCTCCAGCTCTGACAATCCTCTTTCTCTTTTGTTTTACATGAAGGGTCTGGCAGCCAAAGCAATCACTCAAAGTTCAAACCTTATCATTTTTGCTTTGTTCCTCTTGGCCTTGGTTTTGTACATCAGCT |

TABLE 8-continued

Sequences for TBG and LP1B promoters

| Promoter | Sequence |
|---|---|
|  | TTGAAAATACCATCCCAGGGTTAATGCTGGGGTTAATTTATAACTAAGAGTGCTCTAGTTTTGCAATACAGGA CATGCTATAAAAATGGAAAGAT (SEQ ID NO: 125) |
| LP1b | CCCTAAAATGGGCAAACATTGCAAGCAGCAAACAGCAAACACACAGCCCTCCCTGCCTGCTGACCTTGGAG CTGGGGCAGAGGTCAGAGACCTCTCTGGGCCCATGCCACCTCCAACATCCACTCGACCCCTTGGAATTTCG GTGGAGAGGAGCAGAGGTTGTCCTGGCGTGGTTTAGGTAGTGTGAGAGGGTGGACACAGGACGCTGTGGT TTCTGAGCCAGGGGGCGACTCAGATCCCAGCCAGTGGACTTAGCCCCTGTTTGCTCCTCCGATAACTGGGG TGACCTTGGTTAATATTCACCAGCAGCCTCCCCCGTTGCCCCTCTGGATCCACTGCTTAAATACGGACGAGG ACAGGGCCCTGTCTCCTCAGCTTCAGGCACCACCACTGACCTGGGACAGTGAATCCGGACTCTAAGGTAAA TATAAAATTTTTAAGTGTATAATGTGTTAAACTACTGATTCTAATTGTTTCTCTCTTTTAGATTCCAACCTTTGG AACTGA (SEQ ID NO: 126) |

TABLE 9

FOR primers and amplicon sizes for Surveyor and TIDE assays.

| Target | Primer | SEQ ID NO: | Size (bp) |
|---|---|---|---|
| EMX1 Forward | CCATCCCCTTCTGTGAATGT | 127 | 639 |
| EMX1 Reverse | GGAGATTGGAGACACGGAGA | 128 |  |
|  |  |  |  |
| FANCF Forward | AGGAACACGGATAAAGACGCTGG | 129 | 492 |
| FANCF Reverse | AGTTGCTGCACCAGGTGGTAACG | 130 |  |
|  |  |  |  |
| RUNX1 Forward | CCAGCACAACTTACTCGCACTTGAC | 131 | 601 |
| RUNX1 Reverse | CATCACCAACCCACAGCCAAGG | 132 |  |
|  |  |  |  |
| VEGFA Forward | GAGAAGGCCAGGGGTCACTCCAG | 133 | 278 |
| VEGFA Reverse | AGCCCGCCGCAATGAAGG | 134 |  |
|  |  |  |  |
| Hpd exon 7 Forward | GCAGGCGCAGTGCCCAAGACAC | 135 | 498 |
| Hpd exon 7 Reverse | CAGCACATGCCCAGGTCACATGG | 136 |  |
|  |  |  |  |
| Hpd exon 8 Forward | GCCATGAGGACAGAAAGAGCATC | 137 | 409 |
| Hpd exon 8 Reverse | GATATTCCAGTCTCCCAGAGAAG | 138 |  |
|  |  |  |  |
| Hpd exon 12 Forward | CTCGCATACTTGAAGGCTGTGCC | 139 | 429 |
| Hpd exon 12 Reverse | GATAGGGACTCTGCTACCTCCTG | 140 |  |
|  |  |  |  |
| Hpd exon 13 Forward | GGCTTTGGTGGTGCAGTAGCCTT | 141 | 402 |
| Hpd exon 13 Reverse | GACCTCACACCATTGGGCTCCAG | 142 |  |
|  |  |  |  |
| Pck1 exon 5 Forward | GATGTGCACCACAAGCTCACTGT | 143 | 567 |
| Pck1 exon 5 Reverse | GAGTTCGGTGCTGTTGTCTAAGA | 144 |  |
|  |  |  |  |
| Pck1 exon 6 Forward | GCTAGTTTGGAAGACAGTCCTAG | 145 | 494 |
| Pck1 exon 6 Reverse | GTCCCTCTCTATCCAGATGATCC | 146 |  |
|  |  |  |  |
| Pck1 exon 8 Forward | GCAACTTAAGGGCTATCAACCCA | 147 | 556 |
| Pck1 exon 8 Reverse | GTCTGGATATAGGAGGGAGATCT | 148 |  |
|  |  |  |  |
| Pck1 exon 10 Forward | GAACACAAGGGTGAGTCACAGTC | 149 | 565 |
| Pck1 exon 10 Reverse | CATCTGGCTGATTCTCTGTTTCA | 150 |  |
|  |  |  |  |
| Pcsk9 exon 2 Forward | GATACGCATGCTACACTGAGATG | 151 | 534 |
| Pcsk9 exon 2 Reverse | CACAGGCAGTAGACAAACCAG | 152 |  |
|  |  |  |  |
| Pcsk9 exon 9 Forward | GCACCCATGAGACAGGTGAGCAG | 153 | 559 |
| Pcsk9 exon 9 Reverse | GCAGAGACAATGGGTGGCTAATA | 154 |  |
|  |  |  |  |
| Pcsk9 exon 10 Forward | GCTGGAAGCTTTATGATGGAGAT | 155 | 599 |
| Pcsk9 exon 10 Reverse | GACACACCTCAGAGCCTTCCCTT | 156 |  |

TABLE 10

LMD-9 St1Cas9 guide target sequences (Examples 5-7)

| Gene | ID | bp | Target Sequene | SEQ ID NO: | PAM | 3' |
|---|---|---|---|---|---|---|
| EMX1 | G1 | 19 | GAGGCAGGCAGGCTCTCCGA | 157 | GGAGAA | GGCCAA |
|  | G1 | 23 | GCCCAGGCAGGCAGGCTCTCCGA | 158 | GGAGAA | GGCCAA |
|  | G2 | 20 | GAGGAAGGGCCTGAGTCCGA | 159 | GCAGAA | GAAGAA |
|  | G3 | 19 | GGAGGACAAAGTACAAACG | 160 | GCAGAA | GCTGGA |
|  | G4 | 20 | GAAGGGCCTGAGTCCGAGCA | 161 | GAAGAA | GAAGGG |
|  | G5 | 20 | GGGCCTGAGTCCGAGCAGAA | 162 | GAAGAA | GGGCTC |
|  | G6 | 19 | GAGGGAGGGAGGGGCACAGA | 163 | TGAGAA | ACTCAG |
|  | G6 | 22 | GCCAGGGAGGGAGGGGCACAGA | 164 | TGAGAA | ACTCAG |
|  | G7 | 19 | GCAAACGGCAGAAGCTGGAG | 165 | GAGGAA | GGGCCT |
|  | G7 | 22 | GTACAAACGGCAGAAGCTGGAG | 166 | GAGGAA | GGGCCT |
|  | G8 | 21 | GTACAAACGGCAGAAGCTGGA | 167 | GGAGGA | AGGGCC |
| FANCF | G1 | 20 | GGAAAAGCGATCCAGGTGCT | 168 | GCAGAA | GGGATT |
|  | G2 | 20 | GTAGGTAGTGCTTGAGACCG | 169 | CCAGAA | GCTCGG |
|  | G4 | 20 | GTAGGGCCTTCGCGCACCTC | 170 | ATGGAA | TCCCTT |
|  | G5 | 19 | GCTTGAGACCGCCAGAAGC | 171 | TCGGAA | AAGCGA |
|  | G5 | 21 | GTGCTTGAGACCGCCAGAAGC | 172 | TCGGAA | AAGCGA |
|  | G6 | 20 | GGCCTGGAAGTTCGCTAATC | 173 | CCGGAA | CTGGAC |
|  | G7 | 20 | GGCGACTCTCTGCGTACTGA | 174 | TTGGAA | CATCCG |
| RUNX1 | G1 | 19 | GCTAATCAGATGGAAGCTCT | 175 | TCAGAA | ATGTTT |
|  | G1 | 21 | GTACTAATCAGATGGAAGCTCT | 176 | TCAGAA | ATGTTT |
|  | G2 | 19 | GATCATTGAGTCCCCCGCCT | 177 | TCAGAA | GTGGGT |
|  | G2 | 22 | GAAATCATTGAGTCCCCCGCCT | 178 | TCAGAA | GTGGGT |
|  | G3 | 19 | GGTTTTCGCTCCGAAGGTA | 179 | AAAGAA | ATCATT |
|  | G4 | 20 | GAGGTATCCAGCAGAGGGGA | 180 | GAAGAA | AGAGAG |
|  | G5 | 19 | GCAGAGGTATCCAGCAGAGG | 181 | GGAGAA | GAAAGA |
|  | G5 | 23 | GTCCCAGAGGTATCCAGCAGAGG | 182 | GGAGAA | GAAAGA |
|  | G7 | 22 | GAATTCCTCTCACAAACAAGAC | 183 | AGGGAA | CTGGCA |
| ATP1A1 | G1 | 20 | GCAGCTTGGATGCTATAAGC | 184 | CAAGAA | ACAAAG |
|  | G2 | 21 | GCTTATAGCATCCAAGCTGCT | 185 | ACAGAA | GAGGAA |
|  | G3 | 19 | GCAAATCCATATGCTGAATT | 186 | ACAGAA | CTCACA |
|  | G3 | 20 | GACAAATCCATATGCTGAATT | 187 | ACAGAA | CTCACA |
|  | G3 | 25 | GTACTACAAATCCATATGCTGAATT | 188 | ACAGAA | CTCACA |
|  | G7 | 20 | GCATCCAAGCTGCTACAGAA | 189 | GAGGAA | CCTCAA |
|  | G8 | 19 | GCATCCAAGCTGCTACAGA | 190 | AGAGGA | ACCTCA |
| VEGF | G2 | 20 | GAGAGGGACACACAGATCTA | 191 | TTGGAA | TCCTGG |
|  | G3 | 20 | GAGAGCCGTTCCCTCTTTGC | 192 | TAGGAA | TATTGA |
|  | G4 | 20 | GGGCATTGGCGAGGAGGGAG | 193 | CAGGAA | AGTGAG |
|  | G5 | 19 | GAAAATTACCCATCCGCCC | 194 | CCGGAA | ACTCTG |
|  | G5 | 23 | GCCTGAAAATTACCCATCCGCCC | 195 | CCGGAA | ACTCTG |
| Hpd | G1 | 20 | GGTACCCCACGCAGAAAGCT | 196 | CGAGAA | CGGGGC |
|  | G2 | 20 | GTTGGGGCCTCGAATCCAGG | 197 | TAAGAA | ACGGCC |
|  | G3 | 20 | GATACCACACACACCCTGGT | 198 | GGAGAA | GATCAA |
|  | G4 | 21 | GTAGTAAGAAGATGGGGCGGC | 199 | CAAGAA | CTCCGT |
|  | G5 | 21 | GCATATCCTAGTCGACTATGA | 200 | CGAGAA | AGGCTA |
| Pcsk9 | G1 | 19 | GGTCACTGCTCATCTTCAC | 201 | CAAGAA | GCCAGG |
|  | G2 | 19 | GGGTCACTGCTCATCTTCAC | 202 | CAAGAA | GCCAGG |
|  | G3 | 20 | GAGGTCACTGCTCATCTTCAC | 203 | CAAGAA | GCCAGG |
|  | G4 | 19 | GCACGACGCCTCCCGCTCCT | 204 | GGAGAA | GCTGGA |
|  | G5 | 20 | GCCACGACGCCTCCCGCTCCT | 205 | GGAGAA | GCTGGA |
|  | G6 | 20 | GAGACCCATGTCCACTGCCA | 206 | CCAGAA | GGACCA |
| Pck1 | G1 | 20 | GGTGGGAACTCACTACTCGG | 207 | GAAGAA | ATGCTT |
|  | G2 | 20 | GGCATAACTAACCCCGAAGG | 208 | CAAGAA | GAAATA |
|  | G3 | 20 | GGGCACTGGCTGGCAGGGGT | 209 | GCAGAA | TCTCGA |
|  | G4 | 20 | GTATTTGCCGAAGTTGTAGCC | 210 | GAAGAA | GGGTCG |
| FANCF B | G1 | 21 | GCAAGCGCTCCCACAGGCTGC | 211 | TGAGAA | ACCTGG |
|  | G2 | 19 | GCCTGTGGGAGCGCTTGCC | 212 | TCAGAA | CAACTT |
|  | G3 | 19 | GCCTTTGTCTCGTCGGCCC | 213 | CAAGAA | GAGTTG |
|  | G4 | 19 | GCAAAGACTTCCGAATTCC | 214 | CCAGAA | GCCAGT |
|  | G5 | 22 | GTCAACGTTTGCACTATGACCT | 215 | TCAGAA | AGGCAT |
|  | G6 | 22 | GCTTTACAGGTCTCCAGGGCAG | 216 | TTAGAA | CTTTAT |
|  | G7 | 22 | GTAATAACACAGCATTGCCTAT | 217 | ACAGAA | CTGAGG |
|  | G8 | 19 | GCTGTGTTATTACTTGAAT | 218 | ATAGAA | TATATA |
|  | G9 | 23 | GACACACGAAGGCATATATTTGG | 219 | TGAGAA | CATTGT |
|  | G10 | 22 | GTCTCGTCGGCCCAAGAAGAG | 220 | TTGGAA | CCCGGC |
|  | G11 | 22 | GACCTTCAGAAAGGCATTTGGG | 221 | TTGGAA | CTGAGT |

TABLE 10-continued

LMD-9 St1Cas9 guide target sequences (Examples 5-7)

| Gene | ID | bp | Target Sequene | SEQ ID NO: | PAM | 3' |
|---|---|---|---|---|---|---|
| AAVS1 | G2 | 20 | GAGGGGACAGATAAAAGTAC | 222 | CCAGAA | CCAGAG |
|  | G4' | 23 | GAAATGGGGGTGTGTCACCAGAT | 223 | AAGGAA | TCTGCC |
|  | G5' | 22 | GTTAGACCCAATATCAGGAGAC | 224 | TAGGAA | GGAGGA |
|  | G6' | 19 | GAGCCACATTAACCGGCCC | 225 | TGGGAA | TATAAG |
|  | G8' | 22 | GACTAGCTGAGCTCTCGGACCC | 226 | CTGGAA | GATGCC |
|  | G9' | 20 | GAAGATGCCATGACAGGGGG | 227 | CTGGAA | GAGCTA |
| CFTR | G1 | 20 | GCTATTTTTATGGGACATTT | 228 | TCAGAA | CTCCAA |
|  | G3 | 20 | GGAGAGTTTGGGGAAAAAG | 229 | GAAGAA | TTCTAT |
|  | G4 | 23 | GTATAGAGTTGATTGGATTGAGA | 230 | ATAGAA | TTCTTC |
|  | G5 | 20 | GCCTTCTCTCTAAAGGCTCA | 231 | TCAGAA | TCCTCT |
|  | G6 | 20 | GCAGTATCGCCTCTCCCTGC | 232 | TCAGAA | TCTGGT |
|  | G7 | 21 | GACTGGAGAGTTTGGGGAAAA | 233 | AAGGAA | GAATTC |

TABLE 11

LMG 18311 St1Cas9 guide target sequences (Examples 5-7)

| Gene | ID | bp | Target Sequene | SEQ ID NO: | PAM | 3' |
|---|---|---|---|---|---|---|
| FANCF | G202 | 20 | GGCGGCTGCACAACCAGTGG | 234 | AGGCAA | GAGGGC |
| RUNX1 | G201 | 23 | GAAACAAGCTGCCATTTCATTAC | 235 | AGGCAA | AGCTGA |
|  | G202 | 23 | GCCATTTCATTACAGGCAAAGCT | 236 | GAGCAA | AAGTAG |
|  | 205 | 20 | GAGGTGAGTACATGCTGGTC | 237 | TTGTAA | TATCTA |
| AAVS1 | G201 | 20 | GGACACAGGATCCCTGGAGG | 238 | CAGCAA | ACATGC |
| Grin2B | G206 | 20 | GGCTTCCTGGTCTGTGTCAT | 239 | CAGCAA | ACACCA |
| ATP1A1 | G202 | 23 | GTTCATAACCATTAAGTAATGAG | 240 | TGGTAA | TTGAGA |
|  | G203 | 20 | GTAATGAGTTCATAACCATT | 241 | AAGTAA | TGAGTG |

TABLE 12

CNRZ 1066 St1Cas9 guide target sequences (Examples 5-7)

| Gene | ID | bp | Target Sequene | SEQ ID NO: | PAM | 3' |
|---|---|---|---|---|---|---|
| EMX1 | G101 | 20 | GGTGTGGTTCCAGAACCGGA | 242 | GGACAA | AGTACA |
|  | G102 | 21 | GTTCCAGAACCGGAGGACAAA | 243 | GTACAA | ACGGCA |
| ATP1A1 | G102 | 21 | GCTTGGATGCTATAAGCCAAG | 243 | AAACAA | AGAATC |
|  | G103 | 21 | GGAGAAGATATCTGATGTGTA | 245 | CTACAA | ATCCAT |
|  | G104 | 20 | GGTAATTGAGAAGAAGTGGG | 246 | AGACAA | AGACGG |

TABLE 13

TH1477 St1Cas9 guide target sequences (Examples 5-7)

| Gene | ID | bp | Target Sequene | SEQ ID NO: | PAM | 3' |
|---|---|---|---|---|---|---|
| FANCF | 303a | 19 | GAGAGTCGCCGTCTCCAAG | 247 | GTGAAA | GCGGAA |
|  | 304 | 20 | GCTTGAGACCGCCAGAAGCT | 248 | CGGAAA | AGCGAT |
|  | 308 | 21 | GCTCTTCGTAGTGGTGCATTT | 249 | AGGAAA | AGACAA |
|  | 309 | 19 | GAATATATAGTTTACAAAA | 250 | ATGAAA | ATTACA |

TABLE 13-continued

TH1477 St1Cas9 guide target sequences (Examples 5-7)

| Gene | ID | bp | Target Sequene | SEQ ID NO: | PAM | 3' |
|---|---|---|---|---|---|---|
| RUNX1 | 302 | 21 | GTCTGAAGCCATCGCTTCCTC | 251 | CTGAAA | ATGCAC |
|  | 304 | 19 | GATTTCTTTTACCTTCGGA | 252 | GCGAAA | ACCAAG |
| Grin2b | 301 | 21 | GTTCAAGGATTTCTGAGGCTT | 253 | TTGAAA | GTTTCA |
|  | 303 | 20 | GTATTTGCTCTGCAGAATGA | 254 | GAGAAA | ATGAAA |
|  | 304 | 20 | GGAGTTGGGTTTGGTGCTCA | 255 | ATGAAA | GGAGAT |
|  | 305 | 20 | GTCGACTCCCTGCAAACACA | 256 | AAGAAA | GAGCAT |
|  | 306 | 21 | GTGGCCATCAAGGATGCCCAC | 257 | GAGAAA | GATGAT |
|  | 307 | 20 | GTTAAAATAGGATCTACATC | 258 | ACGTAA |  |
| AAVS1 | 301 | 23 | GCCACTAGGGACAGGATTGGTGA | 259 | CAGAAA | AGCCCC |

TABLE 14

Sequences described herein

| SEQ ID NO(s): | Description |
|---|---|
| 1 | sgRNA, FIG. 1b (positions 21-103) |
| 2-3 | target nucleic acid sequence, FIG. 1c, sense and antisense; FANCF |
| 4-5 | target nucleic acid sequence, FIG. 3c, sense and antisense |
| 6 | amino acid sequence; FIG. 3c |
| 7-11 | sgRNAs, FIG. 5c, in order shown |
| 12-13 | target nucleic acid sequence, FIG. 6a, sense and antisense |
| 14 | amino acid sequence; FIG. 6a |
| 15 | SaCas9 amino acid sequence, FIG. 9 |
| 16 | St1Cas9_LMD-9 amino acid sequence, FIGS. 9 and 10 |
| 17 | St1Cas9_LMG18311 amino acid sequence, FIGS. 9 and 10 |
| 18 | St1Cas9_CNR71066 amino acid sequence, FIGS. 9 and 10 |
| 19 | St1Cas9 TH1477 amino acid sequence |
| 20-21 | Guide sequence, sense and antisense, FIG. 11 |
| 22 | Full nucleic acid sequence, FIG. 16 |
| 23-24 | SV40 NLS nucleic acid sequences, FIGS. 16, 23a, 23b, 25a, 25b, 27a, 27b |
| 25 | ST1Cas9 nucleic acid sequence (LMD-9), FIG. 16 |
| 26-27 | Linker between NLS and ST1Cas9, nucleic acid sequences, FIGS. 16, 23a, 23b, 25a, 25b, 27a, 27b |
| 28 | Full amino acid sequence, FIG. 17 |
| 29 | SV40 NLS amino acid sequence, FIGS. 17, 24, 26, 28 |
| 30 | ST1Cas9 amino acid sequence (LMD-9), FIG. 17 |
| 31-32 | Linker between NLS and ST1Cas9, amino acid sequences, FIGS. 17, 24, 26, 28 |
| 33 | Full nucleic acid sequence, FIGS. 23a-23b |
| 34 | ST1Cas9 hybrid nucleic acid sequence (LMD-9/LMG18311), FIGS. 23a-23b |
| 35 | Full amino acid sequence, FIG. 24 |
| 36 | ST1Cas9 hybrid amino acid sequence (LMD-9/LMG18311), FIG. 24 |
| 37 | Full nucleic acid sequence, FIGS. 25a-25b |
| 38 | ST1Cas9 hybrid nucleic acid sequence (LMD-9/CNRZ1066), FIGS. 25a-25b |
| 39 | Full amino acid sequence, FIG. 26 |
| 40 | ST1Cas9 hybrid amino acid sequence (LMD-9/CNRZ1066), FIG. 26 |
| 41 | Full nucleic acid sequence, FIGS. 27a-27b |
| 42 | ST1Cas9 hybrid nucleic acid sequence (LMD-9/TH1477), FIGS. 27a-27b |
| 43 | Full amino acid sequence, FIG. 28 |
| 44 | ST1Cas9 hybrid amino acid sequence (LMD-9/TH1477), FIG. 28 |
| 45 | Full nucleic acid sequence, FIGS. 29a-29b |
| 46 | rAPOBEC1 nucleic acid sequence; FIGS. 29a-29b |
| 47 | UGI nucleic acid sequence, FIGS. 29a-29b |
| 48 | 3xHA nucleic acid sequence, FIGS. 29a-29b |
| 49 | Full amino acid sequence, FIG. 30 |
| 50 | rAPOBEC1 amino acid sequence; FIGS. 30, 32, 34 |
| 51 | UGI amino acid sequence, FIGS. 30, 32, 34 |
| 52 | 3xHA amino acid sequence, FIGS. 30, 32, 34 |
| 53 | Full nucleic acid sequence, FIGS. 31a-31b |
| 54 | ST1Cas9 nucleic acid sequence (LMD-9/LMG18311 hybrid), FIGS. 31a-31b |
| 55 | Full nucleic acid sequence, FIG. 32 |
| 56 | ST1Cas9 amino acid sequence (LMD-9/LMG18311 hybrid), FIG. 32 |
| 57 | Full nucleic acid sequence, FIGS. 33a-33b |
| 58 | ST1Cas9 nucleic acid sequence (LMD-9/CNRZ1066 hybrid), FIGS. 33a-33b |
| 59 | Full nucleic acid sequence, FIG. 34 |
| 60 | ST1Cas9 amino acid sequence (LMD-9/CNRZ1066 hybrid), FIG. 34 |
| 61 | Nucleoplasmin NLS amino acid sequence |
| 62-65 | NLS amino acid sequences |
| 66-67 | target nucleic acid sequence, FIG. 1c, sense and antisense; EMX1 |

TABLE 14-continued

Sequences described herein

| SEQ ID NO(s): | Description |
|---|---|
| 68-69 | target nucleic acid sequence, FIG. 1c, sense and antisense; RUNX1 |
| 70-98 | guide target sequences, Table 3 |
| 99-108 | guide target sequences, Table 4 |
| 109-113 | guide target sequences, Table 5 |
| 114-118 | guide target sequences, Table 6 |
| 119-124 | sgRNAs (DNA and RNA sequences), Table 7 |
| 125-126 | TBG and LP1B promoter sequences, Table 8 |
| 127-156 | PCR Primer sequences, Table 9 |
| 157-259 | guide target sequences, Tables 10-13 |
| 260-263 | amino acid sequences of ST1Cas9 C-terminal region (LMD-9, LMG18311, CNRZ1066, and TH1477), FIG. 35 |
| 264-267 | amino acid sequences of ST1Cas9 N-terminal region (LMD-9, LMG18311, CNRZ1066, and TH1477), FIG. 10 |
| 268 | CRISPR nuclease recognition sequence |

While the invention has been described in connection with specific embodiments thereof, it will be understood that the scope of the claims should not be limited by the preferred embodiments set forth in the examples, but should be given the broadest interpretation consistent with the description as a whole. In the claims, the word "comprising" is used as an open-ended term, substantially equivalent to the phrase "including, but not limited to". The singular forms "a", "an" and "the" include corresponding plural references unless the context clearly dictates otherwise.

REFERENCES

1. Komor, A. C., Badran, A. H. & Liu, D. R. CRISPR-Based Technologies for the Manipulation of Eukaryotic Genomes. *Cell* 169, 559 (2017).
2. Jinek, M. et al. A programmable dual-RNA-guided DNA endonuclease in adaptive bacterial immunity. *Science* 337, 816-821 (2012).
3. Koonin, E. V., Makarova, K. S. & Zhang, F. Diversity, classification and evolution of CRISPR-Cas systems. *Curr Opin Microbiol* 37, 67-78 (2017).
4. Shmakov, S. et al. Diversity and evolution of class 2 CRISPR-Cas systems. *Nat Rev Microbiol* 15, 169-182 (2017).
5. Hille, F. et al. The Biology of CRISPR-Cas: Backward and Forward. *Cell* 172, 1239-1259 (2018).
6. Esvelt, K. M. et al. Orthogonal Cas9 proteins for RNA-guided gene regulation and editing. *Nat Methods* 10, 1116-1121 (2013).
7. Ran, F. A. et al. In vivo genome editing using *Staphylococcus aureus* Cas9. *Nature* 520, 186-191 (2015).
8. Chen, F. et al. Targeted activation of diverse CRISPR-Cas systems for mammalian genome editing via proximal CRISPR targeting. *Nat Commun* 8, 14958 (2017).
9. Anderson, E. M. et al. *Lactobacillus gasseri* CRISPR-Cas9 characterization In Vitro reveals a flexible mode of protospacer-adjacent motif recognition. *PLOS One* 13, e0192181 (2018).
10. Zetsche, B. et al. Cpf1 is a single RNA-guided endonuclease of a class 2 CRISPR-Cas system. *Cell* 163, 759-771 (2015).
11. Colella, P., Ronzitti, G. & Mingozzi, F. Emerging Issues in AAV-Mediated In Vivo Gene Therapy. *Mol Ther Methods Clin Dev* 8, 87-104 (2018).
12. Friedland, A. E. et al. Characterization of *Staphylococcus aureus* Cas9: a smaller Cas9 for all-in-one adeno-associated virus delivery and paired nickase applications. *Genome Biol* 16, 257 (2015).
13. Kim, E. et al. In vivo genome editing with a small Cas9 orthologue derived from *Campylobacter jejuni*. *Nat Commun* 8, 14500 (2017).
14. Ibraheim, R. et al. All-in-One Adeno-associated Virus Delivery and Genome Editing by *Neisseria meningitidis* Cas9 in vivo. *bioRxiv* (2018).
15. Mir, A., Edraki, A., Lee, J. & Sontheimer, E. J. Type II-C CRISPR-Cas9 Biology, Mechanism, and Application. *ACS Chem Biol* 13, 357-365 (2018).
16. Anguela, X. M. et al. Robust ZFN-mediated genome editing in adult hemophilic mice. *Blood* 122, 3283-3287 (2013).
17. Li, H. et al. In vivo genome editing restores haemostasis in a mouse model of haemophilia. *Nature* 475, 217-221 (2011).
18. Sharma, R. et al. In vivo genome editing of the albumin locus as a platform for protein replacement therapy. *Blood* 126, 1777-1784 (2015).
19 Nami, F. et al. Strategies for In Vivo Genome Editing in Nondividing Cells. *Trends Biotechnol* (2018).
20. He Z, Proudfoot C, Mileham A, J., McLaren D G, Whitelaw B A, Lillico S G. Highly efficient targeted chromosome deletions using CRISPR/Cas9. *Biotechnology and Bioengineering*. 112 (5): 1060-4 (2015).
21. Byrne S M, Ortiz L, Mali P, Aach J, Church G M. Multi-kilobase homozygous targeted gene replacement in human induced pluripotent stem cells. *Nucleic Acids Res.* 43(3):e21 (2015).
22. Schneller, J. L., Lee, C. M., Bao, G. & Venditti, C. P. Genome editing for inborn errors of metabolism: advancing towards the clinic. *BMC Med* 15, 43 (2017).
23. Lau, C. H. & Suh, Y. In vivo genome editing in animals using AAV-CRISPR system: applications to translational research of human disease. *F1000Res* 6, 2153 (2017).
24. Bolotin, A. et al. Complete sequence and comparative genome analysis of the dairy bacterium *Streptococcus thermophilus*. *Nat Biotechnol* 22, 1554-1558 (2004).
25. Barrangou, R. & Horvath, P. A decade of discovery: CRISPR functions and applications. *Nat Microbiol* 2, 17092 (2017).
26. Bolotin, A., Quinquis, B., Sorokin, A. & Ehrlich, S. D. Clustered regularly interspaced short palindrome repeats (CRISPRs) have spacers of extrachromosomal origin. *Microbiology* 151, 2551-2561 (2005).

27. Barrangou, R. et al. CRISPR provides acquired resistance against viruses in prokaryotes. *Science* 315, 1709-1712 (2007).
28. Horvath, P. et al. Diversity, activity, and evolution of CRISPR loci in *Streptococcus thermophilus*. *J Bacteriol* 190, 1401-1412 (2008).
29. Deveau, H. et al. Phage response to CRISPR-encoded resistance in *Streptococcus thermophilus*. *J Bacteriol* 190, 1390-1400 (2008).
30. Garneau, J. E. et al. The CRISPR/Cas bacterial immune system cleaves bacteriophage and plasmid DNA. *Nature* 468, 67-71 (2010).
31. Briner, A. E. et al. Guide RNA functional modules direct Cas9 activity and orthogonality. *Mol Cell* 56, 333-339 (2014).
32. Hynes, A. P. et al. An anti-CRISPR from a virulent streptococcal phage inhibits *Streptococcus pyogenes* Cas9. *Nat Microbiol* 2, 1374-1380 (2017).
33. Chari, R., Mali, P., Moosburner, M. & Church, G. M. Unraveling CRISPR-Cas9 genome engineering parameters via a library-on-library approach. *Nat Methods* 12, 823-826 (2015).
34. Kleinstiver, B. P. et al. Engineered CRISPR-Cas9 nucleases with altered PAM specificities. *Nature* 523, 481-485 (2015).
35. Agudelo, D. et al. Marker-free coselection for CRISPR-driven genome editing in human cells. *Nat Methods* 14, 615-620 (2017).
36. Dalvai, M. et al. A Scalable Genome-Editing-Based Approach for Mapping Multiprotein Complexes in Human Cells. *Cell Rep* 13, 621-633 (2015).
37. Guschin, D. Y. et al. A rapid and general assay for monitoring endogenous gene modification. *Methods Mol Biol* 649, 247-256 (2010).
38. Brinkman, E. K., Chen, T., Amendola, M. & van Steensel, B. Easy quantitative assessment of genome editing by sequence trace decomposition. *Nucleic Acids Res* 42, e168 (2014).
39. Haeussler, M. et al. Evaluation of off-target and on-target scoring algorithms and integration into the guide RNA selection tool CRISPOR. *Genome Biol* 17, 148 (2016).
40. Tomoeda, K. et al. Mutations in the 4-hydroxyphenylpyruvic acid dioxygenase gene are responsible for tyrosinemia type III and hawkinsinuria. *Mol Genet Metab* 71, 506-510 (2000).
41. Ruetschi, U. et al. Mutations in the 4-hydroxyphenylpyruvate dioxygenase gene (HPD) in patients with tyrosinemia type III. *Hum Genet* 106, 654-662 (2000).
42. Russell, S. et al. Efficacy and safety of voretigene neparvovec (AAV2-hRPE65v2) in patients with RPE65-mediated inherited retinal dystrophy: a randomised, controlled, open-label, phase 3 trial. *Lancet* 390, 849-860 (2017).
43. George, L. A. et al. Hemophilia B Gene Therapy with a High-Specific-Activity Factor IX Variant. *N Engl J Med* 377, 2215-2227 (2017).
44. Nathwani, A. C. et al. Long-term safety and efficacy of factor IX gene therapy in hemophilia B. *N Engl J Med* 371, 1994-2004 (2014).
45. Mckay, T. R. et al. Perinatal gene transfer to the liver. *Curr Pharm Des* 17, 2528-2541 (2011).
46. Wang, L. et al. AAV8-mediated hepatic gene transfer in infant rhesus monkeys (*Macaca mulatta*). *Mol Ther* 19, 2012-2020 (2011).
47. Wang, L., Wang, H., Bell, P., McMenamin, D. & Wilson, J. M. Hepatic gene transfer in neonatal mice by adeno-associated virus serotype 8 vector. *Hum Gene Ther* 23, 533-539 (2012).
48. Yang, Y. et al. A dual AAV system enables the Cas9-mediated correction of a metabolic liver disease in newborn mice. *Nat Biotechnol* 34, 334-338 (2016).
49. Morrow, G. & Tanguay, R. M. Biochemical and Clinical Aspects of Hereditary Tyrosinemia Type 1. *Adv Exp Med Biol* 959, 9-21 (2017).
50. Grompe, M. Fah Knockout Animals as Models for Therapeutic Liver Repopulation. *Adv Exp Med Biol* 959, 215-230 (2017).
51. Endo, F. et al. Complete rescue of lethal albino c14COS mice by null mutation of 4-hydroxyphenylpyruvate dioxygenase and induction of apoptosis of hepatocytes in these mice by in vivo retrieval of the tyrosine catabolic pathway. *J Biol Chem* 272, 24426-24432 (1997).
52. Pankowicz, F. P. et al. Reprogramming metabolic pathways in vivo with CRISPR/Cas9 genome editing to treat hereditary tyrosinaemia. *Nat Commun* 7, 12642 (2016).
53. Nathwani, A. C. et al. Self-complementary adeno-associated virus vectors containing a novel liver-specific human factor IX expression cassette enable highly efficient transduction of murine and nonhuman primate liver. *Blood* 107, 2653-2661 (2006).
54. McIntosh, J. et al. Therapeutic levels of FVIII following a single peripheral vein administration of rAAV vector encoding a novel human factor VIII variant. *Blood* 121, 3335-3344 (2013).
55. Pawluk, A., Davidson, A. R. & Maxwell, K. L. Anti-CRISPR: discovery, mechanism and function. *Nat Rev Microbiol* 16, 12-17 (2018).
56. Shin, J. et al. Disabling Cas9 by an anti-CRISPR DNA mimic. *Sci Adv* 3, e1701620 (2017).
57. Rauch, B. J. et al. Inhibition of CRISPR-Cas9 with Bacteriophage Proteins. *Cell* 168, 150-158 e110 (2017).
58. Rousseau, B. A., Hou, Z., Gramelspacher, M. J. & Zhang, Y. Programmable RNA Cleavage and Recognition by a Natural CRISPR-Cas9 System from *Neisseria meningitidis*. *Mol Cell* 69, 906-914 e904 (2018).
59. Strutt, S. C., Torrez, R. M., Kaya, E., Negrete, O. A. & Doudna, J. A. RNA-dependent RNA targeting by CRISPR-Cas9. *Elife* 7 (2018).
60. Zhang, Y., Rajan, R., Seifert, H. S., Mondragon, A. & Sontheimer, E. J. DNase H Activity of *Neisseria meningitidis* Cas9. *Mol Cell* 60, 242-255 (2015).
61. Stephenson, A. A., Raper, A. T. & Suo, Z. Bidirectional Degradation of DNA Cleavage Products Catalyzed by CRISPR/Cas9. *J Am Chem Soc* 140, 3743-3750 (2018).
62. Ma, E., Harrington, L. B., O'Connell, M. R., Zhou, K. & Doudna, J. A. Single-Stranded DNA Cleavage by Divergent CRISPR-Cas9 Enzymes. *Mol Cell* 60, 398-407 (2015).
63. Dugar, G. et al. CRISPR RNA-Dependent Binding and Cleavage of Endogenous RNAs by the *Campylobacter jejuni* Cas9. *Mol Cell* 69, 893-905 e897 (2018)
64. Chen, J. S. et al. CRISPR-Cas12a target binding unleashes indiscriminate single-stranded DNase activity. *Science* (2018).
65. Boettcher, M. et al. Dual gene activation and knockout screen reveals directional dependencies in genetic networks. *Nat Biotechnol* 36, 170-178 (2018).
66. Fonfara, I. et al. Phylogeny of Cas9 determines functional exchangeability of dual-RNA and Cas9 among orthologous type II CRISPR-Cas systems. *Nucleic Acids Res* 42, 2577-2590 (2014).

67. Goudy, K. S., Annoni, A., Naldini, L. & Roncarolo, M. G. Manipulating Immune Tolerance with Micro-RNA Regulated Gene Therapy. *Frontiers in microbiology* 2, 221 (2011).
68. Charlesworth, C. T. et al. Identification of Pre-Existing Adaptive Immunity to Cas9 Proteins in Humans. *bioRxiv* (2018).
69. Moreno, A. M. et al. Exploring protein orthogonality in immune space: a case study with AAV and Cas9 orthologs. *bioRxiv* (2018).
70. Wagner, D. L. et al. High prevalence of *S. pyogenes* Cas9-specific T cell sensitization within the adult human population-A balanced effector/regulatory T cell response. *bioRxiv* (2018).
71. Chew, W. L. et al. A multifunctional AAV—CRISPR-Cas9 and its host response. *Nat Methods* 13, 868-874 (2016).
72. Muller, M. et al. *Streptococcus thermophilus* CRISPR-Cas9 Systems Enable Specific Editing of the Human Genome. *Mol Ther* 24, 636-644 (2016).
73. Karvelis, T., Gasiunas, G. & Siksnys, V. Methods for decoding Cas9 protospacer adjacent motif (PAM) sequences: A brief overview. *Methods* 121-122, 3-8 (2017).
74. Leenay, R. T. & Beisel, C. L. Deciphering, Communicating, and Engineering the CRISPR PAM. *J Mol Biol* 429, 177-191 (2017).
75. Rock, J. M. et al. Programmable transcriptional repression in mycobacteria using an orthogonal CRISPR interference platform. *Nat Microbiol* 2, 16274 (2017).
76. Makarova, K. et al. Comparative genomics of the lactic acid bacteria. *Proc Natl Acad Sci USA* 103, 15611-15616 (2006).
77. Chen, H., Choi, J. & Bailey, S. Cut site selection by the two nuclease domains of the Cas9 RNA-guided endonuclease. *J Biol Chem* 289, 13284-13294 (2014).
78. Hu, J. H. et al. Evolved Cas9 variants with broad PAM compatibility and high DNA specificity. *Nature* 556, 57-63 (2018).
79. Kleinstiver, B. P. et al. Broadening the targeting range of *Staphylococcus aureus* CRISPR-Cas9 by modifying PAM recognition. *Nat Biotechnol* 33, 1293-1298 (2015).
80. Chatterjee, P., Jakimo, N. & Jacobson, J. M. Divergent PAM Specificity of a Highly-Similar SpCas9 Ortholog. *bioRxiv* (2018).
81. Gray, S. J. et al. Production of recombinant adeno-associated viral vectors and use in in vitro and in vivo administration. *Curr Protoc Neurosci* Chapter 4, Unit 4 17 (2011).
82. Aurnhammer, C. et al. Universal real-time PCR for the detection and quantification of adeno-associated virus serotype 2-derived inverted terminal repeat sequences. *Hum Gene Ther Methods* 23, 18-28 (2012).
83. Grompe, M. et al. Loss of fumarylacetoacetate hydrolase is responsible for the neonatal hepatic dysfunction phenotype of lethal albino mice. *Genes Dev* 7, 2298-2307 (1993).
84. Yardeni, T., Eckhaus, M., Morris, H. D., Huizing, M. & Hoogstraten-Miller, S. Retro-orbital injections in mice. *Lab Anim* (NY) 40, 155-160 (2011).
85. Cyr, D., Giguere, R., Villain, G., Lemieux, B. & Drouin, R. A GC/MS validated method for the nanomolar range determination of succinylacetone in amniotic fluid and plasma: an analytical tool for tyrosinemia type I. *J Chromatogr B Analyt Technol Biomed Life Sci* 832, 24-29 (2006).
86. Chatterjee, P., Jakimo, N. & Jacobson, J. M. Minimal PAM specificity of a highly similar SpCas9 ortholog. Sci Adv 4, eaau0766 (2018).

What is claimed is:

1. An isolated hybrid clustered regularly interspaced short palindromic repeats (CRISPR) nuclease polypeptide comprising guide RNA (gRNA)-binding and nuclease domains from *Streptococcus thermophilus* strain LMD-9, and a protospacer adjacent motif (PAM)-interacting domain from *Streptococcus thermophilus* strain LMG18311, CNRZ1066 or TH1477, wherein the hybrid CRISPR nuclease polypeptide comprises the amino acid sequence of SEQ ID NO: 36, SEQ ID NO: 40 or SEQ ID NO: 44.

2. A nucleic acid comprising a nucleotide sequence encoding the isolated polypeptide of claim 1.

3. A vector comprising the nucleic acid of claim 2.

4. The isolated polypeptide of claim 1, comprising the amino acid sequence of SEQ ID NO: 36.

5. The isolated polypeptide of claim 1, comprising the amino acid sequence of SEQ ID NO: 40.

6. The isolated polypeptide of claim 1, comprising the amino acid sequence of SEQ ID NO: 44.

* * * * *

SEQUENCE LISTING

```
<160> NUMBER OF SEQ ID NOS: 268

<210> SEQ ID NO 1
<211> LENGTH: 84
<212> TYPE: RNA
<213> ORGANISM: Artificial Sequence
<220> FEATURE:
<223> OTHER INFORMATION: Synthetic, engineered or hybrid sequence

<400> SEQUENCE: 1
gucuuuguac ucugguacca gaagcuacaa agauaaggcu ucaugccgaa aucaacaccc        60
ugucauuuua uggcagggug uuuu                                              84

<210> SEQ ID NO 2
<211> LENGTH: 32
<212> TYPE: DNA
<213> ORGANISM: Artificial Sequence
<220> FEATURE:
<223> OTHER INFORMATION: Synthetic, engineered or hybrid sequence

<400> SEQUENCE: 2
gacgtaggta gtgcttgaga ccgccagaag ct                                     32

<210> SEQ ID NO 3
<211> LENGTH: 32
<212> TYPE: DNA
<213> ORGANISM: Artificial Sequence
<220> FEATURE:
<223> OTHER INFORMATION: Synthetic, engineered or hybrid sequence
```

```
<400> SEQUENCE: 3
agcttctggc ggtctcaagc actacctacg tc                                32

<210> SEQ ID NO 4
<211> LENGTH: 46
<212> TYPE: DNA
<213> ORGANISM: Artificial Sequence
<220> FEATURE:
<223> OTHER INFORMATION: Synthetic, engineered or hybrid sequence

<400> SEQUENCE: 4
gcatatccta gtcgactatg acgagaaagg ctacctccta cagatc                 46

<210> SEQ ID NO 5
<211> LENGTH: 46
<212> TYPE: DNA
<213> ORGANISM: Artificial Sequence
<220> FEATURE:
<223> OTHER INFORMATION: Synthetic, engineered or hybrid sequence

<400> SEQUENCE: 5
gatctgtagg aggtagcctt tctcgtcata gtcgactagg atatgc                 46

<210> SEQ ID NO 6
<211> LENGTH: 15
<212> TYPE: PRT
<213> ORGANISM: Artificial Sequence
<220> FEATURE:
<223> OTHER INFORMATION: Synthetic, engineered or hybrid sequence

<400> SEQUENCE: 6

His Ile Leu Val Asp Tyr Asp Glu Lys Gly Tyr Leu Leu Gln Ile
1               5                   10                  15

<210> SEQ ID NO 7
<211> LENGTH: 129
<212> TYPE: RNA
<213> ORGANISM: Artificial Sequence
<220> FEATURE:
<223> OTHER INFORMATION: Synthetic, engineered or hybrid sequence

<400> SEQUENCE: 7
guuuuuguac ucucaagauu uaaguaacug uacaacgaaa cuuacacagu uacuuaaauc  60
uugcagaagc uacaaagaua aggcuucaug ccgaaaucaa cacccuguca uuuuauggca  120
ggguguuuu                                                         129

<210> SEQ ID NO 8
<211> LENGTH: 97
<212> TYPE: RNA
<213> ORGANISM: Artificial Sequence
<220> FEATURE:
<223> OTHER INFORMATION: Synthetic, engineered or hybrid sequence

<400> SEQUENCE: 8
guuuuuguac ucucaagauu caauaaucuu gcagaagcua caaagauaag gcuucaugcc  60
gaaaucaaca cccugucauu uuauggcagg guguuuu                          97

<210> SEQ ID NO 9
<211> LENGTH: 87
<212> TYPE: RNA
<213> ORGANISM: Artificial Sequence
<220> FEATURE:
<223> OTHER INFORMATION: Synthetic, engineered or hybrid sequence
```

<400> SEQUENCE: 9
guuuuuguac ucucagaaau gcagaagcua caaagauaag gcuucaugcc gaaaucaaca      60
cccugucauu uuauggcagg guguuuu                                         87

<210> SEQ ID NO 10
<211> LENGTH: 84
<212> TYPE: RNA
<213> ORGANISM: Artificial Sequence
<220> FEATURE:
<223> OTHER INFORMATION: Synthetic, engineered or hybrid sequence

<400> SEQUENCE: 10
gucuuuguac ucugguacca gaagcuacaa agauaaggcu ucaugccgaa aucaacaccc      60
ugucauuuua uggcagggug uuuu                                            84

<210> SEQ ID NO 11
<211> LENGTH: 80
<212> TYPE: RNA
<213> ORGANISM: Artificial Sequence
<220> FEATURE:
<223> OTHER INFORMATION: Synthetic, engineered or hybrid sequence

<400> SEQUENCE: 11
gucuuuguac ucgaaagaag cuacaaagau aaggcuucau gccgaaauca acacccuguc      60
auuuuauggc agggguguuuu                                                80

<210> SEQ ID NO 12
<211> LENGTH: 46
<212> TYPE: DNA
<213> ORGANISM: Artificial Sequence
<220> FEATURE:
<223> OTHER INFORMATION: Synthetic, engineered or hybrid sequence

<400> SEQUENCE: 12
tggccgtttc ttacctggat tcgaggcccc aacatacaag gatacc                    46

<210> SEQ ID NO 13
<211> LENGTH: 46
<212> TYPE: DNA
<213> ORGANISM: Artificial Sequence
<220> FEATURE:
<223> OTHER INFORMATION: Synthetic, engineered or hybrid sequence

<400> SEQUENCE: 13
ggtatccttg tatgttgggg cctcgaatcc aggtaagaaa cggcca                    46

<210> SEQ ID NO 14
<211> LENGTH: 16
<212> TYPE: PRT
<213> ORGANISM: Artificial Sequence
<220> FEATURE:
<223> OTHER INFORMATION: Synthetic, engineered or hybrid sequence

<400> SEQUENCE: 14

Gly Arg Phe Leu Pro Pro Gly Phe Glu Ala Pro Thr Tyr Lys Asp Thr
1               5                   10                  15

<210> SEQ ID NO 15
<211> LENGTH: 1056
<212> TYPE: PRT
<213> ORGANISM: Artificial Sequence
<220> FEATURE:
<223> OTHER INFORMATION: Synthetic, engineered or hybrid sequence

<400> SEQUENCE: 15

```
Cys Ser Met Met Lys Arg Asn Tyr Ile Leu Gly Leu Asp Ile Gly Ile
1               5                   10                  15

Thr Ser Val Gly Tyr Gly Ile Ile Asp Tyr Glu Thr Arg Asp Val Ile
            20                  25                  30

Asp Ala Gly Val Arg Leu Phe Lys Glu Ala Asn Val Glu Asn Asn Glu
        35                  40                  45

Gly Arg Arg Ser Lys Arg Gly Ala Arg Arg Leu Lys Arg Arg Arg Arg
    50                  55                  60

His Arg Ile Gln Arg Val Lys Lys Leu Leu Phe Asp Tyr Asn Leu Leu
65                  70                  75                  80

Thr Asp His Ser Glu Leu Ser Gly Ile Asn Pro Tyr Glu Ala Arg Val
                85                  90                  95

Lys Gly Leu Ser Gln Lys Leu Ser Glu Glu Phe Ser Ala Ala Leu
            100                 105                 110

Leu His Leu Ala Lys Arg Arg Gly Val His Asn Val Asn Glu Val Glu
        115                 120                 125

Glu Asp Thr Gly Asn Glu Leu Ser Thr Lys Glu Gln Ile Ser Arg Asn
130                 135                 140

Ser Lys Ala Leu Glu Glu Lys Tyr Val Ala Glu Leu Gln Leu Glu Arg
145                 150                 155                 160

Leu Lys Lys Asp Gly Glu Val Arg Gly Ser Ile Asn Arg Phe Lys Thr
                165                 170                 175

Ser Asp Tyr Val Lys Glu Ala Lys Gln Leu Leu Lys Val Gln Lys Ala
            180                 185                 190

Tyr His Gln Leu Asp Gln Ser Phe Ile Asp Thr Tyr Ile Asp Leu Leu
        195                 200                 205

Glu Thr Arg Arg Thr Tyr Tyr Glu Gly Pro Gly Glu Gly Ser Pro Phe
210                 215                 220

Gly Trp Lys Asp Ile Lys Glu Trp Tyr Glu Met Leu Met Gly His Cys
225                 230                 235                 240

Thr Tyr Phe Pro Glu Glu Leu Arg Ser Val Lys Tyr Ala Tyr Asn Ala
                245                 250                 255

Asp Leu Tyr Asn Ala Leu Asn Asp Leu Asn Asn Leu Val Ile Thr Arg
            260                 265                 270

Asp Glu Asn Glu Lys Leu Glu Tyr Tyr Glu Lys Phe Gln Ile Ile Glu
        275                 280                 285

Asn Val Phe Lys Gln Lys Lys Lys Pro Thr Leu Lys Gln Ile Ala Lys
290                 295                 300

Glu Ile Leu Val Asn Glu Glu Asp Ile Lys Gly Tyr Arg Val Thr Ser
305                 310                 315                 320

Thr Gly Lys Pro Glu Phe Thr Asn Leu Lys Val Tyr His Asp Ile Lys
                325                 330                 335

Asp Ile Thr Ala Arg Lys Glu Ile Ile Glu Asn Ala Glu Leu Leu Asp
            340                 345                 350

Gln Ile Ala Lys Ile Leu Thr Ile Tyr Gln Ser Ser Glu Asp Ile Gln
        355                 360                 365

Glu Glu Leu Thr Asn Leu Asn Ser Glu Leu Thr Gln Glu Glu Ile Glu
370                 375                 380

Gln Ile Ser Asn Leu Lys Gly Tyr Thr Gly Thr His Asn Leu Ser Leu
385                 390                 395                 400

Lys Ala Ile Asn Leu Ile Leu Asp Glu Leu Trp His Thr Asn Asp Asn
```

|                    |                    | 405                |                    |                    | 410                |                    |                    | 415                |                    |
|---|---|---|---|---|---|---|---|---|---|

Gln Ile Ala Ile Phe Asn Arg Leu Lys Leu Val Pro Lys Lys Val Asp
                420                 425                 430

Leu Ser Gln Gln Lys Glu Ile Pro Thr Thr Leu Val Asp Asp Phe Ile
            435                 440                 445

Leu Ser Pro Val Val Lys Arg Ser Phe Ile Gln Ser Ile Lys Val Ile
        450                 455                 460

Asn Ala Ile Ile Lys Lys Tyr Gly Leu Pro Asn Asp Ile Ile Ile Glu
465                 470                 475                 480

Leu Ala Arg Glu Lys Asn Ser Lys Asp Ala Gln Lys Met Ile Asn Glu
                485                 490                 495

Met Gln Lys Arg Asn Arg Gln Thr Asn Glu Arg Ile Glu Glu Ile Ile
            500                 505                 510

Arg Thr Thr Gly Lys Glu Asn Ala Lys Tyr Leu Ile Glu Lys Ile Lys
        515                 520                 525

Leu His Asp Met Gln Glu Gly Lys Cys Leu Tyr Ser Leu Glu Ala Ile
    530                 535                 540

Pro Leu Glu Asp Leu Leu Asn Asn Pro Phe Asn Tyr Glu Val Asp His
545                 550                 555                 560

Ile Ile Pro Arg Ser Val Ser Phe Asp Asn Ser Phe Asn Asn Lys Val
                565                 570                 575

Leu Val Lys Gln Glu Glu Asn Ser Lys Lys Gly Asn Arg Thr Pro Phe
            580                 585                 590

Gln Tyr Leu Ser Ser Ser Asp Ser Lys Ile Ser Tyr Glu Thr Phe Lys
        595                 600                 605

Lys His Ile Leu Asn Leu Ala Lys Gly Lys Gly Arg Ile Ser Lys Thr
    610                 615                 620

Lys Lys Glu Tyr Leu Leu Glu Glu Arg Asp Ile Asn Arg Phe Ser Val
625                 630                 635                 640

Gln Lys Asp Phe Ile Asn Arg Asn Leu Val Asp Thr Arg Tyr Ala Thr
                645                 650                 655

Arg Gly Leu Met Asn Leu Leu Arg Ser Tyr Phe Arg Val Asn Asn Leu
            660                 665                 670

Asp Val Lys Val Lys Ser Ile Asn Gly Gly Phe Thr Ser Phe Leu Arg
        675                 680                 685

Arg Lys Trp Lys Phe Lys Lys Glu Arg Asn Lys Gly Tyr Lys His His
    690                 695                 700

Ala Glu Asp Ala Leu Ile Ile Ala Asn Ala Asp Phe Ile Phe Lys Glu
705                 710                 715                 720

Trp Lys Lys Leu Asp Lys Ala Lys Lys Val Met Glu Asn Gln Met Phe
                725                 730                 735

Glu Glu Lys Gln Ala Glu Ser Met Pro Glu Ile Glu Thr Glu Gln Glu
            740                 745                 750

Tyr Lys Glu Ile Phe Ile Thr Pro His Gln Ile Lys His Ile Lys Asp
        755                 760                 765

Phe Lys Asp Tyr Lys Tyr Ser His Arg Val Asp Lys Lys Pro Asn Arg
    770                 775                 780

Glu Leu Ile Asn Asp Thr Leu Tyr Ser Thr Arg Lys Asp Asp Lys Gly
785                 790                 795                 800

Asn Thr Leu Ile Val Asn Asn Leu Asn Gly Leu Tyr Asp Lys Asp Asn
                805                 810                 815

Asp Lys Leu Lys Lys Leu Ile Asn Lys Ser Pro Glu Lys Leu Leu Met
            820                 825                 830

```
Tyr His His Asp Pro Gln Thr Tyr Gln Lys Leu Lys Leu Ile Met Glu
            835                 840                 845

Gln Tyr Gly Asp Glu Lys Asn Pro Leu Tyr Lys Tyr Tyr Glu Glu Thr
850                 855                 860

Gly Asn Tyr Leu Thr Lys Tyr Ser Lys Lys Asp Asn Gly Pro Val Ile
865                 870                 875                 880

Lys Lys Ile Lys Tyr Tyr Gly Asn Lys Leu Asn Ala His Leu Asp Ile
            885                 890                 895

Thr Asp Asp Tyr Pro Asn Ser Arg Asn Lys Val Val Lys Leu Ser Leu
        900                 905                 910

Lys Pro Tyr Arg Phe Asp Val Tyr Leu Asp Asn Gly Val Tyr Lys Phe
            915                 920                 925

Val Thr Val Lys Asn Leu Asp Val Ile Lys Lys Glu Asn Tyr Tyr Glu
        930                 935                 940

Val Asn Ser Lys Cys Tyr Glu Glu Ala Lys Lys Leu Lys Lys Ile Ser
945                 950                 955                 960

Asn Gln Ala Glu Phe Ile Ala Ser Phe Tyr Asn Asn Asp Leu Ile Lys
            965                 970                 975

Ile Asn Gly Glu Leu Tyr Arg Val Ile Gly Val Asn Asn Asp Leu Leu
        980                 985                 990

Asn Arg Ile Glu Val Asn Met Ile Asp Ile Thr Tyr Arg Glu Tyr Leu
            995                1000                1005

Glu Asn Met Asn Asp Lys Arg Pro Pro Arg Ile Ile Lys Thr Ile
1010                1015                1020

Ala Ser Lys Thr Gln Ser Ile Lys Lys Tyr Ser Thr Asp Ile Leu
1025                1030                1035

Gly Asn Leu Tyr Glu Val Lys Ser Lys Lys His Pro Gln Ile Ile
1040                1045                1050

Lys Lys Gly
1055

<210> SEQ ID NO 16
<211> LENGTH: 1121
<212> TYPE: PRT
<213> ORGANISM: Artificial Sequence
<220> FEATURE:
<223> OTHER INFORMATION: Synthetic, engineered or hybrid sequence

<400> SEQUENCE: 16

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Ala Arg Arg Lys His Arg Arg Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
            85                  90                  95

Thr Asp Glu Leu Ser Asn Glu Glu Leu Phe Ile Ala Leu Lys Asn Met
        100                 105                 110

Val Lys His Arg Gly Ile Ser Tyr Leu Asp Asp Ala Ser Asp Asp Gly
    115                 120                 125
```

```
Asn Ser Ser Val Gly Asp Tyr Ala Gln Ile Val Lys Glu Asn Ser Lys
        130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Glu Phe Asn Pro Gln Ile Thr
        195                 200                 205

Asp Glu Phe Ile Asn Arg Tyr Leu Glu Ile Leu Thr Gly Lys Arg Lys
210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
        435                 440                 445

Ile Leu Thr Arg Leu Gly Lys Gln Lys Thr Thr Ser Ser Ser Asn Lys
    450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
        515                 520                 525

Ala Asn Lys Asp Glu Lys Asp Ala Ala Met Leu Lys Ala Ala Asn Gln
    530                 535                 540
```

-continued

```
Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
            565                 570                 575

Leu Tyr Thr Gly Lys Thr Ile Ser Ile His Asp Leu Ile Asn Asn Ser
        580                 585                 590

Asn Gln Phe Glu Val Asp His Ile Leu Pro Leu Ser Ile Thr Phe Asp
    595                 600                 605

Asp Ser Leu Ala Asn Lys Val Leu Val Tyr Ala Thr Ala Asn Gln Glu
610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
            645                 650                 655

Ser Asn Lys Lys Lys Glu Tyr Leu Leu Thr Glu Glu Asp Ile Ser Lys
        660                 665                 670

Phe Asp Val Arg Lys Lys Phe Ile Glu Arg Asn Leu Val Asp Thr Arg
    675                 680                 685

Tyr Ala Ser Arg Val Val Leu Asn Ala Leu Gln Glu His Phe Arg Ala
690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
            725                 730                 735

His His Ala Val Asp Ala Leu Ile Ile Ala Ala Ser Ser Gln Leu Asn
        740                 745                 750

Leu Trp Lys Lys Gln Lys Asn Thr Leu Val Ser Tyr Ser Glu Asp Gln
    755                 760                 765

Leu Leu Asp Ile Glu Thr Gly Glu Leu Ile Ser Asp Asp Glu Tyr Lys
770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
            805                 810                 815

Lys Phe Asn Arg Lys Ile Ser Asp Ala Thr Ile Tyr Ala Thr Arg Gln
        820                 825                 830

Ala Lys Val Gly Lys Asp Lys Ala Asp Glu Thr Tyr Val Leu Gly Lys
    835                 840                 845

Ile Lys Asp Ile Tyr Thr Gln Asp Gly Tyr Asp Ala Phe Met Lys Ile
850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
            885                 890                 895

Gln Ile Asn Glu Lys Gly Lys Glu Val Pro Cys Asn Pro Phe Leu Lys
        900                 905                 910

Tyr Lys Glu Glu His Gly Tyr Ile Arg Lys Tyr Ser Lys Lys Gly Asn
    915                 920                 925

Gly Pro Glu Ile Lys Ser Leu Lys Tyr Tyr Asp Ser Lys Leu Gly Asn
930                 935                 940

His Ile Asp Ile Thr Pro Lys Asp Ser Asn Asn Lys Val Val Leu Gln
945                 950                 955                 960

Ser Val Ser Pro Trp Arg Ala Asp Val Tyr Phe Asn Lys Thr Thr Gly
```

```
                           965                 970                 975
Lys Tyr Glu Ile Leu Gly Leu Lys Tyr Ala Asp Leu Gln Phe Glu Lys
                 980                 985                 990

Gly Thr Gly Thr Tyr Lys Ile Ser Gln Glu Lys Tyr Asn Asp Ile Lys
         995                1000                1005

Lys Lys Glu Gly Val Asp Ser Asp Ser Glu Phe Lys Phe Thr Leu
    1010                1015                1020

Tyr Lys Asn Asp Leu Leu Val Lys Asp Thr Glu Thr Lys Glu
    1025                1030                1035

Gln Gln Leu Phe Arg Phe Leu Ser Arg Thr Met Pro Lys Gln Lys
    1040                1045                1050

His Tyr Val Glu Leu Lys Pro Tyr Asp Lys Gln Lys Phe Glu Gly
    1055                1060                1065

Gly Glu Ala Leu Ile Lys Val Leu Gly Asn Val Ala Asn Ser Gly
    1070                1075                1080

Gln Cys Lys Lys Gly Leu Gly Lys Ser Asn Ile Ser Ile Tyr Lys
    1085                1090                1095

Val Arg Thr Asp Val Leu Gly Asn Gln His Ile Ile Lys Asn Glu
    1100                1105                1110

Gly Asp Lys Pro Lys Leu Asp Phe
    1115                1120
```

<210> SEQ ID NO 17
<211> LENGTH: 1122
<212> TYPE: PRT
<213> ORGANISM: Artificial Sequence
<220> FEATURE:
<223> OTHER INFORMATION: Synthetic, engineered or hybrid sequence

<400> SEQUENCE: 17

```
Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
                20                  25                  30

Arg Ile Phe Pro Ala Ala Gln Ala Glu Asn Asn Leu Val Arg Arg Thr
        35                  40                  45

Asn Arg Gln Gly Arg Arg Leu Thr Arg Arg Lys Lys His Arg Ile Val
    50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Ser Gln Ile Thr
```

```
            195                 200                 205
Asp Glu Phe Ile Asn Arg Tyr Leu Glu Ile Leu Thr Gly Lys Arg Lys
210                 215                 220

Tyr Tyr His Gly Pro Gly Asn Glu Lys Ser Arg Thr Asp Tyr Gly Arg
225                 230                 235                 240

Tyr Arg Thr Asn Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
                275                 280                 285

Val Pro Thr Glu Thr Lys Lys Leu Ser Lys Glu Gln Lys Asn Gln Ile
290                 295                 300

Ile Asn Tyr Val Lys Asn Glu Lys Val Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

His Arg Ile Asp Lys Ser Gly Lys Ala Glu Ile His Thr Phe Glu Ala
                340                 345                 350

Tyr Arg Lys Met Lys Thr Leu Glu Thr Leu Asp Ile Glu Gln Met Asp
                355                 360                 365

Arg Glu Thr Leu Asp Lys Leu Ala Tyr Val Leu Thr Leu Asn Thr Glu
370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
                420                 425                 430

Met Glu Leu Ile Pro Glu Leu Tyr Glu Thr Ser Glu Glu Gln Met Thr
                435                 440                 445

Ile Leu Thr Arg Leu Gly Lys Gln Lys Thr Thr Ser Ser Ser Asn Lys
450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
                500                 505                 510

Glu Thr Asn Glu Asp Asp Glu Lys Lys Ala Ile Gln Lys Ile Gln Lys
                515                 520                 525

Ala Asn Lys Asp Glu Lys Asp Ala Ala Met Leu Lys Ala Ala Asn Gln
                530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Pro
                580                 585                 590

Asn Gln Phe Glu Val Asp His Ile Leu Pro Leu Ser Ile Thr Phe Asp
                595                 600                 605

Asp Ser Leu Ala Asn Lys Val Leu Val Tyr Ala Thr Ala Asn Gln Glu
610                 615                 620
```

-continued

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
            645                 650                 655

Ser Asn Lys Lys Lys Glu Tyr Leu Leu Thr Glu Glu Asp Ile Ser Lys
        660                 665                 670

Phe Asp Val Arg Lys Lys Phe Ile Glu Arg Asn Leu Val Asp Thr Arg
    675                 680                 685

Tyr Ala Ser Arg Val Val Leu Asn Ala Leu Gln Glu His Phe Arg Ala
690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
            725                 730                 735

His His Ala Val Asp Ala Leu Ile Ile Ala Ala Ser Ser Gln Leu Asn
        740                 745                 750

Leu Trp Lys Lys Gln Lys Asn Thr Leu Val Ser Tyr Ser Glu Glu Gln
    755                 760                 765

Leu Leu Asp Ile Glu Thr Gly Glu Leu Ile Ser Asp Asp Glu Tyr Lys
770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
            805                 810                 815

Lys Phe Asn Arg Lys Ile Ser Asp Ala Thr Ile Tyr Ala Thr Arg Gln
        820                 825                 830

Ala Lys Val Gly Lys Asp Lys Asp Glu Thr Tyr Val Leu Gly Lys
    835                 840                 845

Ile Lys Asp Ile Tyr Thr Gln Asp Gly Tyr Asp Ala Phe Met Lys Ile
850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
            885                 890                 895

Glu Met Asn Glu Lys Gly Lys Glu Val Pro Cys Asn Pro Phe Leu Lys
        900                 905                 910

Tyr Lys Glu Glu His Gly Tyr Ile Arg Lys Tyr Ser Lys Lys Gly Asn
    915                 920                 925

Gly Pro Glu Ile Lys Ser Leu Lys Tyr Tyr Asp Ser Lys Leu Leu Gly
930                 935                 940

Asn Pro Ile Asp Ile Thr Pro Glu Asn Ser Lys Asn Lys Val Val Leu
945                 950                 955                 960

Gln Ser Leu Lys Pro Trp Arg Thr Asp Val Tyr Phe Asn Lys Asn Thr
            965                 970                 975

Gly Lys Tyr Glu Ile Leu Gly Leu Lys Tyr Ala Asp Leu Gln Phe Glu
        980                 985                 990

Lys Lys Thr Gly Thr Tyr Lys Ile Ser Gln Glu Lys Tyr Asn Gly Ile
    995                 1000                1005

Met Lys Glu Glu Gly Val Asp Ser Asp Ser Glu Phe Lys Phe Thr
    1010                1015                1020

Leu Tyr Lys Asn Asp Leu Leu Val Lys Asp Thr Glu Thr Lys
    1025                1030                1035

-continued

```
Glu Gln Gln Leu Phe Arg Phe Leu Ser Arg Thr Met Pro Asn Val
    1040                1045                1050
Lys Tyr Tyr Val Glu Leu Lys Pro Tyr Ser Lys Asp Lys Phe Glu
    1055                1060                1065
Lys Asn Glu Ser Leu Ile Glu Ile Leu Gly Ser Ala Asp Lys Ser
    1070                1075                1080
Gly Arg Cys Ile Lys Gly Leu Gly Lys Ser Asn Ile Ser Ile Tyr
    1085                1090                1095
Lys Val Arg Thr Asp Val Leu Gly Asn Gln His Ile Ile Lys Asn
    1100                1105                1110
Glu Gly Asp Lys Pro Lys Leu Asp Phe
    1115                1120
```

<210> SEQ ID NO 18
<211> LENGTH: 1128
<212> TYPE: PRT
<213> ORGANISM: Artificial Sequence
<220> FEATURE:
<223> OTHER INFORMATION: Synthetic, engineered or hybrid sequence

<400> SEQUENCE: 18

```
Met Ser Asp Leu Val Leu Gly Leu Asp Ile Gly Ile Gly Ser Val Gly
1               5                   10                  15
Val Gly Ile Leu Asn Lys Val Thr Gly Glu Ile Ile His Lys Asn Ser
            20                  25                  30
Arg Ile Phe Pro Ala Ala Gln Ala Glu Asn Asn Leu Val Arg Arg Thr
        35                  40                  45
Asn Arg Gln Gly Arg Arg Leu Thr Arg Arg Lys Lys His Arg Ile Val
    50                  55                  60
Arg Leu Asn Arg Leu Phe Glu Glu Ser Gly Leu Ile Thr Asp Phe Thr
65                  70                  75                  80
Lys Ile Ser Ile Asn Leu Asn Pro Tyr Gln Leu Arg Val Lys Gly Leu
                85                  90                  95
Thr Asp Glu Leu Ser Asn Glu Glu Leu Phe Ile Ala Leu Lys Asn Met
            100                 105                 110
Val Lys His Arg Gly Ile Ser Tyr Leu Asp Asp Ala Ser Asp Asp Gly
        115                 120                 125
Asn Ser Ser Val Gly Asp Tyr Ala Gln Ile Val Lys Glu Asn Ser Lys
    130                 135                 140
Gln Leu Glu Thr Lys Thr Pro Gly Gln Ile Gln Leu Glu Arg Tyr Gln
145                 150                 155                 160
Thr Tyr Gly Gln Leu Arg Gly Asp Phe Thr Val Glu Lys Asp Gly Lys
                165                 170                 175
Lys His Arg Leu Ile Asn Val Phe Pro Thr Ser Ala Tyr Arg Ser Glu
            180                 185                 190
Ala Leu Arg Ile Leu Gln Thr Gln Gln Glu Phe Asn Pro Gln Ile Thr
        195                 200                 205
Asp Glu Phe Ile Asn Arg Tyr Leu Glu Ile Leu Thr Gly Lys Arg Lys
    210                 215                 220
Tyr Tyr His Gly Pro Gly Asn Glu Lys Ser Arg Thr Asp Tyr Gly Arg
225                 230                 235                 240
Tyr Arg Thr Ser Gly Glu Thr Leu Asp Asn Ile Phe Gly Ile Leu Ile
                245                 250                 255
Gly Lys Cys Thr Phe Tyr Pro Asp Glu Phe Arg Ala Ala Lys Ala Ser
            260                 265                 270
```

```
Tyr Thr Ala Gln Glu Phe Asn Leu Leu Asn Asp Leu Asn Asn Leu Thr
            275                 280                 285

Val Pro Thr Glu Thr Lys Lys Leu Ser Lys Glu Gln Lys Asn Gln Ile
290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
            355                 360                 365

Arg Glu Thr Leu Asp Lys Leu Ala Tyr Val Leu Thr Leu Asn Thr Glu
370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
                420                 425                 430

Met Glu Leu Ile Pro Glu Leu Tyr Glu Thr Ser Glu Glu Gln Met Thr
            435                 440                 445

Ile Leu Thr Arg Leu Gly Lys Gln Lys Arg Leu Arg Leu Gln Ile Lys
            450                 455                 460

Gln Asn Ile Ser Asn Lys Thr Lys Tyr Ile Asp Glu Lys Leu Leu Thr
465                 470                 475                 480

Glu Glu Ile Tyr Asn Pro Val Val Ala Lys Ser Val Arg Gln Ala Ile
                485                 490                 495

Lys Ile Val Asn Ala Ala Ile Lys Glu Tyr Gly Asp Phe Asp Asn Ile
                500                 505                 510

Val Ile Glu Met Ala Arg Glu Thr Asn Glu Asp Asp Glu Lys Lys Ala
            515                 520                 525

Ile Gln Lys Ile Gln Lys Ala Asn Lys Asp Glu Lys Asp Ala Ala Met
530                 535                 540

Leu Lys Ala Ala Asn Gln Tyr Asn Gly Lys Ala Glu Leu Pro His Ser
545                 550                 555                 560

Val Phe His Gly His Lys Gln Leu Ala Thr Lys Ile Arg Leu Trp His
                565                 570                 575

Gln Gln Gly Glu Arg Cys Leu Tyr Thr Gly Lys Thr Ile Ser Ile His
            580                 585                 590

Asp Leu Ile Asn Asn Pro Asn Gln Phe Glu Val Asp His Ile Leu Pro
            595                 600                 605

Leu Ser Ile Thr Phe Asp Asp Ser Leu Ala Asn Lys Val Leu Val Tyr
610                 615                 620

Ala Thr Ala Asn Gln Glu Lys Gly Gln Arg Thr Pro Tyr Gln Ala Leu
625                 630                 635                 640

Asp Ser Met Asp Asp Ala Trp Ser Phe Arg Glu Leu Lys Ala Phe Val
                645                 650                 655

Arg Glu Ser Lys Thr Leu Ser Asn Lys Lys Glu Tyr Leu Leu Thr
                660                 665                 670

Glu Glu Asp Ile Ser Lys Phe Asp Val Arg Lys Lys Phe Ile Glu Arg
            675                 680                 685

Asn Leu Val Asp Thr Arg Tyr Ala Ser Arg Val Val Leu Asn Ala Leu
```

```
            690                 695                 700
Gln Glu His Phe Arg Ala His Lys Ile Asp Thr Lys Val Ser Val Val
705                 710                 715                 720

Arg Gly Gln Phe Thr Ser Gln Leu Arg Arg His Trp Gly Ile Glu Lys
                725                 730                 735

Thr Arg Asp Thr Tyr His His His Ala Val Asp Ala Leu Ile Ile Ala
                740                 745                 750

Ala Ser Ser Gln Leu Asn Leu Trp Lys Lys Gln Lys Asn Thr Leu Val
                755                 760                 765

Ser Tyr Ser Glu Glu Gln Leu Leu Asp Ile Glu Thr Gly Glu Leu Ile
                770                 775                 780

Ser Asp Asp Glu Tyr Lys Glu Ser Val Phe Lys Ala Pro Tyr Gln His
785                 790                 795                 800

Phe Val Asp Thr Leu Lys Ser Lys Glu Phe Glu Asp Ser Ile Leu Phe
                805                 810                 815

Ser Tyr Gln Val Asp Ser Lys Phe Asn Arg Lys Ile Ser Asp Ala Thr
                820                 825                 830

Ile Tyr Ala Thr Arg Gln Ala Lys Val Gly Lys Asp Lys Lys Asp Glu
                835                 840                 845

Thr Tyr Val Leu Gly Lys Ile Lys Asp Ile Tyr Thr Gln Asp Gly Tyr
                850                 855                 860

Asp Ala Phe Met Lys Ile Tyr Lys Lys Asp Lys Ser Lys Phe Leu Met
865                 870                 875                 880

Tyr Arg His Asp Pro Gln Thr Phe Glu Lys Val Ile Glu Pro Ile Leu
                885                 890                 895

Glu Asn Tyr Pro Asn Lys Gln Met Asn Glu Lys Gly Lys Glu Val Pro
                900                 905                 910

Cys Asn Pro Phe Leu Lys Tyr Lys Glu Glu His Gly Tyr Ile Arg Lys
                915                 920                 925

Tyr Ser Lys Lys Gly Asn Gly Pro Glu Ile Lys Ser Leu Lys Tyr Tyr
                930                 935                 940

Asp Ser Lys Leu Leu Gly Asn Pro Ile Asp Ile Thr Pro Glu Asn Ser
945                 950                 955                 960

Lys Asn Lys Val Val Leu Gln Ser Leu Lys Pro Trp Arg Thr Asp Val
                965                 970                 975

Tyr Phe Asn Lys Ala Thr Gly Lys Tyr Glu Ile Leu Gly Leu Lys Tyr
                980                 985                 990

Ala Asp Leu Gln Phe Glu Lys Gly Thr Gly Thr Tyr Lys Ile Ser Gln
                995                 1000                1005

Glu Lys Tyr Asn Asp Ile Lys Lys Lys Glu Gly Val Asp Ser Asp
                1010                1015                1020

Ser Glu Phe Lys Phe Thr Leu Tyr Lys Asn Asp Leu Leu Leu Val
                1025                1030                1035

Lys Asp Thr Glu Thr Lys Glu Gln Gln Leu Phe Arg Phe Leu Ser
                1040                1045                1050

Arg Thr Leu Pro Lys Gln Lys His Tyr Val Glu Leu Lys Pro Tyr
                1055                1060                1065

Asp Lys Gln Lys Phe Glu Gly Gly Glu Ala Leu Ile Lys Val Leu
                1070                1075                1080

Gly Asn Val Ala Asn Gly Gly Gln Cys Ile Lys Gly Leu Ala Lys
                1085                1090                1095

Ser Asn Ile Ser Ile Tyr Lys Val Arg Thr Asp Val Leu Gly Asn
                1100                1105                1110
```

```
Gln His Ile Ile Lys Asn Glu Gly Asp Lys Pro Lys Leu Asp Phe
    1115                1120               1125
```

```
<210> SEQ ID NO 19
<211> LENGTH: 1120
<212> TYPE: PRT
<213> ORGANISM: Artificial Sequence
<220> FEATURE:
<223> OTHER INFORMATION: Synthetic, engineered or hybrid sequence

<400> SEQUENCE: 19

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
            20                  25                  30

Arg Ile Phe Pro Ala Ala Gln Ala Glu Asn Asn Leu Val Arg Arg Thr
        35                  40                  45

Asn Arg Gln Gly Arg Arg Leu Thr Arg Arg Lys His Arg Arg Val
    50                  55                  60

Arg Leu Asn Arg Leu Phe Glu Glu Ile Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
            100                 105                 110

Val Lys His Arg Gly Ile Ser Tyr Leu Asp Asp Ala Ser Asp Gly
        115                 120                 125

Asn Ser Ser Val Gly Asp Tyr Ala Gln Ile Val Lys Glu Asn Ser Lys
    130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
        275                 280                 285

Val Pro Thr Glu Thr Lys Lys Leu Ser Lys Glu Gln Lys Asn Gln Ile
    290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

Tyr Arg Ile Asp Lys Ser Gly Lys Ala Glu Ile His Thr Phe Glu Ala
            340                 345                 350
```

```
Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
        370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
                420                 425                 430

Met Glu Leu Ile Pro Glu Leu Tyr Glu Thr Ser Glu Gly Gln Met Thr
        435                 440                 445

Ile Leu Thr Arg Leu Gly Lys Gln Lys Thr Thr Ser Ser Ser Asn Lys
        450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
                500                 505                 510

Glu Thr Asn Glu Asp Asp Glu Lys Lys Ala Ile Gln Lys Ile Gln Lys
        515                 520                 525

Ala Asn Lys Asp Glu Lys Asp Ala Ala Met Leu Lys Ala Ala Asn Gln
        530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Pro
                580                 585                 590

Asn Gln Phe Glu Val Asp His Ile Leu Pro Leu Ser Ile Thr Phe Asp
        595                 600                 605

Asp Ser Leu Ala Asn Lys Val Leu Val Tyr Ala Thr Ala Asn Gln Glu
        610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
                660                 665                 670

Phe Asp Val Arg Lys Lys Phe Ile Glu Arg Asn Leu Val Asp Thr Arg
        675                 680                 685

Tyr Ala Ser Arg Val Val Leu Asn Ala Leu Gln Glu His Phe Arg Ala
        690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His His Ala Val Asp Ala Leu Ile Ile Ala Ala Ser Ser Gln Leu Asn
                740                 745                 750

Leu Trp Lys Lys Gln Lys Asn Thr Leu Val Ser Tyr Ser Glu Asp Gln
        755                 760                 765
```

```
Leu Leu Asp Ile Glu Thr Gly Glu Leu Ile Ser Asp Asp Glu Tyr Lys
770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr Ile Tyr Ala Thr Arg Gln
                820                 825                 830

Ala Lys Val Gly Lys Asp Lys Ala Asp Glu Thr Tyr Val Leu Gly Lys
                835                 840                 845

Ile Lys Asp Ile Tyr Thr Gln Asp Gly Tyr Asp Ala Phe Met Lys Ile
850                 855                 860

Tyr Lys Lys Asp Lys Ser Lys Phe Leu Met Tyr Arg His Asp Pro Gln
865                 870                 875                 880

Thr Phe Glu Lys Val Ile Glu Pro Ile Leu Glu Asn Tyr Pro Asn Lys
                885                 890                 895

Gln Met Asn Glu Lys Gly Lys Glu Val Pro Cys Asn Pro Phe Leu Lys
                900                 905                 910

Tyr Lys Glu Glu His Gly Tyr Ile Arg Lys Tyr Ser Lys Lys Gly Asn
                915                 920                 925

Gly Pro Glu Ile Lys Ser Leu Lys Tyr Tyr Asp Ser Lys Leu Gly Asn
930                 935                 940

His Ile Asp Ile Thr Pro Lys Asp Ser Asn Asn Lys Val Val Leu Gln
945                 950                 955                 960

Ser Leu Lys Pro Trp Arg Thr Asp Val Tyr Phe Asn Lys Asn Thr Gly
                965                 970                 975

Lys Tyr Glu Ile Leu Gly Leu Lys Tyr Ser Asp Met Gln Phe Glu Lys
                980                 985                 990

Gly Thr Gly Lys Tyr Ser Ile Ser Lys Glu Gln Tyr Glu Asn Ile Lys
                995                 1000                1005

Val Arg Glu Gly Val Asp Glu Asn Ser Glu Phe Lys Phe Thr Leu
    1010                1015                1020

Tyr Lys Asn Asp Leu Leu Leu Lys Asp Ser Glu Asn Gly Glu
    1025                1030                1035

Gln Ile Leu Leu Arg Phe Thr Ser Arg Asn Asp Thr Ser Lys His
    1040                1045                1050

Tyr Val Glu Leu Lys Pro Tyr Asn Arg Gln Lys Phe Glu Gly Ser
    1055                1060                1065

Glu Tyr Leu Ile Lys Ser Leu Gly Thr Val Val Lys Gly Gly Arg
    1070                1075                1080

Cys Ile Lys Gly Leu Gly Lys Ser Asn Ile Ser Ile Tyr Lys Val
    1085                1090                1095

Arg Thr Asp Val Leu Gly Asn Gln His Ile Ile Lys Asn Glu Gly
    1100                1105                1110

Asp Lys Pro Lys Leu Asp Phe
    1115                1120

<210> SEQ ID NO 20
<211> LENGTH: 24
<212> TYPE: DNA
<213> ORGANISM: Artificial Sequence
<220> FEATURE:
<223> OTHER INFORMATION: Synthetic, engineered or hybrid sequence
<220> FEATURE:
<221> NAME/KEY: misc_feature
<222> LOCATION: (6)..(24)
```

```
<223> OTHER INFORMATION: Each n is independently A, C, G, T, U, unknown,
      or other

<400> SEQUENCE: 20
caccgnnnnn nnnnnnnnnn nnnn                                              24

<210> SEQ ID NO 21
<211> LENGTH: 24
<212> TYPE: DNA
<213> ORGANISM: Artificial Sequence
<220> FEATURE:
<223> OTHER INFORMATION: Synthetic, engineered or hybrid sequence
<220> FEATURE:
<221> NAME/KEY: misc_feature
<222> LOCATION: (5)..(23)
<223> OTHER INFORMATION: Each n is independently A, C, G, T, U, unknown,
      or other

<400> SEQUENCE: 21
agacnnnnnn nnnnnnnnnn nnnc                                              24

<210> SEQ ID NO 22
<211> LENGTH: 3450
<212> TYPE: DNA
<213> ORGANISM: Artificial Sequence
<220> FEATURE:
<223> OTHER INFORMATION: Synthetic, engineered or hybrid sequence

<400> SEQUENCE: 22
atgggcgccc caaagaagaa gcggaaggtc ggtatccacg gagtcccagc agccagcgac        60
ctggtgctgg gcctggacat cggcatcggc agcgtgggcg tgggcatcct gaacaaggtg      120
accggcgaga tcatccacaa gaacagtcgc atcttccctg ctgctcaggc tgagaacaac      180
ctggtgcgcc gcaccaaccg ccagggtcgc cggcttgctc gccgcaagaa gcaccggcgc      240
gtgcgcctga accgctgtt cgaggagagc ggcctgatca ccgacttcac caagatcagc      300
atcaacctga cccctacca gctgcgcgtg aagggcctga ccgacgagct gagcaacgag      360
gagctgttca tcgccctgaa gaacatggtg aagcaccgcg gcatcagcta cctggacgac      420
gccagcgacg acggcaacag cagcgtgggc gactacgccc agatcgtgaa ggagaacagc      480
aagcagctgg agaccaagac ccccggccag atccagctgg agcgctacca gacctacggc      540
cagctgcgcg cgacttcac cgtggagaag gacggcaaga agcaccgcct gatcaacgtg      600
ttccccacca gcgcctaccg cagcgaggcc ctgcgcatcc tgcagaccca gcaggagttc      660
aaccccgaga tcaccgacga gttcatcaac cgctacctgg agatcctgac cggcaagcgc      720
aagtactacc acggccccgg caacgagaag agccgcaccg actacggccg ctaccgcacc      780
agcggcgaga ccctggacaa catcttcggc atcctgatcg gcaagtgcac cttctacccc      840
gacgagttcc gcgccgccaa ggccagctac accgcccagg agttcaatct gctgaacgac      900
ctgaacaacc tgaccgtgcc caccgagacc aagaagctga gcaaggagca gaagaaccag      960
atcatcaact acgtgaagaa cgagaaggct atgggccccg ccaagctgtt caagtacatc     1020
gccaagctgc tgagctgcga cgtggccgac atcaagggct accgcatcga caagagcggc     1080
aaggccgaga tccacacctt cgaggcctac cgcaagatga gaccctgga ccctggac     1140 atcgagcaga tggaccgaga gaccctggac aagctggcct acgtgctgac cctgaacacc     1200
gagcgcgagg gcatccagga ggccctggag cacgagttcg ccgacggcag cttcagccag     1260
aaacaggtgg acgagctggt gcagttccgc aaggccaaca gcagcatctt cggcaagggc     1320
tggcacaact tcagcgtgaa gctgatgatg gagctgatcc ccgagctgta cgagaccagc     1380
```

```
gaggagcaga tgaccatcct gacccgcctg ggcaagcaga agaccaccag cagcagcaac    1440
aagaccaagt acatcgacga gaagctgctg accgaggaga tctacaaccc cgtggtggcc    1500
aagagcgtgc gccaggccat caagatcgtg aacgccgcca tcaaggagta cggcgacttc    1560
gacaacatcg tgatcgagat ggcccgcgag accaacgagg acgacgagaa gaaggccatc    1620
cagaagatcc agaaggccaa caaggacgag aaggacgccg ccatgctgaa ggccgccaac    1680
cagtacaacg gcaaggccga gctgccccac agcgtgttcc acggccacaa gcagctggcc    1740
accaagatcc gcctgtggca ccagcagggc gagcgctgcc tgtacaccgg caagaccatc    1800
agcatccacg acctgatcaa caacagcaac cagttcgagg tggaccacat cctgcccctg    1860
agcatcacct tcgacgacag cctggccaac aaggtgctgg tgtacgccac cgccaaccag    1920
gagaagggcc agcgcacccc ctaccaggcc ctggacagca tggacgacgc ctggagcttc    1980
cgcgagctga aggccttcgt gcgcgagagc aagaccctga gcaacaagaa gaaggagtat    2040
ctgctgaccg aggaggacat cagcaagttc gacgtgcgca agaagttcat cgagcgcaac    2100
ctggtggaca cccgctacgc cagccgcgtg gtgctgaacg ccctgcagga gcacttccgc    2160
gcccacaaga tcgacaccaa ggtgagcgtg gtgcgcggcc agttcaccag ccagctgcgc    2220
cgccactggg gcatcgagaa gacccgcgac acctaccacc accacgccgt ggacgccctg    2280
atcattgcgg cttctagcca gctgaacctg tggaagaagc agaagaacac cctggtgagc    2340
tacagcgagg accagctgct ggacatcgag accggcgagc tgatcagcga cgacgagtac    2400
aaggagagcg tgttcaaggc cccctaccag cacttcgtgg acaccctgaa gagcaaggag    2460
ttcgaggaca gcatcctgtt cagctaccag gtggacagca agttcaaccg caagatcagc    2520
gacgccacca tctacgccac ccgccaggcc aaggtgggca aggacaaggc cgacgagacc    2580
tacgtgctgg gcaagatcaa ggacatctac acccaggacg gctacgacgc cttcatgaag    2640
atctacaaga aggacaagag caagttcctg atgtaccgcc acgaccccca gaccttcgag    2700
aaggtgatcg agcccatcct ggagaactac cccaacaagc agatcaacga gaaaggcaag    2760
gaggtgcccc gcaacccctt cctgaagtac aaggaggagc acggctacat ccgcaagtac    2820
agcaagaagg gcaacggccc cgagatcaag agcctgaagt actacgacag caagctgggc    2880
aaccacatcg acatcacccc caaggacagc aacaacaagg tggtgctgca gagcgtgagc    2940
ccctggcgcg ccgacgtgta cttcaacaag accaccggca gtacgagat cctgggctg     3000 aagtacgccg atctgcagtt tgagaaaggc acaggcacct acaagatcag ccaggagaag    3060
tacaacgaca tcaagaagaa ggagggcgtg gacagcgaca gcgagttcaa gttcaccctg    3120
tacaagaacg accttctgct ggtgaaggac accgagacca aggagcaaca gctgttccgc    3180
ttcctgagcc gcaccatgcc caagcagaag cactacgtgg agctgaagcc ctacgacaag    3240
cagaagttcg agggcggcga ggccctgatc aaggtgctgg gcaacgtggc caacagcggc    3300
cagtgcaaga agggcctggg caagagcaac atcagcatct acaaggtgcg caccgacgtg    3360
ctgggcaacc agcacatcat caagaacgag ggcgacaagc ccaagttgga cttcagcagg    3420 gctgaccccca agaagaagag gaaggtgtga                                    3450
```

<210> SEQ ID NO 23  
<211> LENGTH: 21  
<212> TYPE: DNA  
<213> ORGANISM: Artificial Sequence  
<220> FEATURE:  
<223> OTHER INFORMATION: Synthetic, engineered or hybrid sequence

```
<400> SEQUENCE: 23
ccaaagaaga agcggaaggt c                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 24
cccaagaaga agaggaaggt g                                              21

<210> SEQ ID NO 25
<211> LENGTH: 3360
<212> TYPE: DNA
<213> ORGANISM: Artificial Sequence
<220> FEATURE:
<223> OTHER INFORMATION: Synthetic, engineered or hybrid sequence

<400> SEQUENCE: 25
agcgacctgg tgctgggcct ggacatcggc atcggcagcg tgggcgtggg catcctgaac      60
aaggtgaccg cgagatcat ccacaagaac agtcgcatct ccctgctgc tcaggctgag      120 aacaacctgg tgcgccgcac caaccgccag ggtcgccggc ttgctcgccg caagaagcac     180
cggcgcgtgc gcctgaaccg cctgttcgag gagagcggcc tgatcaccga cttcaccaag     240
atcagcatca acctgaaccc ctaccagctg cgcgtgaagg gcctgaccga cgagctgagc     300
aacgaggagc tgttcatcgc cctgaagaac atggtgaagc accgcggcat cagctacctg     360
gacgacgcca gcgacgacgg caacagcagc gtgggcgact acgcccagat cgtgaaggag     420
aacagcaagc agctggagac caagaccccc ggccagatcc agctggagcg ctaccagacc     480
tacggccagc tgcgcggcga cttcaccgtg gagaaggacg gcaagaagca ccgcctgatc     540
aacgtgttcc ccaccagcgc ctaccgcagc gaggccctgc gcatcctgca gacccagcag     600
gagttcaacc cccagatcac cgacgagttc atcaaccgct acctggagat cctgaccggc     660
aagcgcaagt actaccacgg ccccggcaac gagaagagcc gcaccgacta cggccgctac     720
cgcaccagcg gcgagaccct ggacaacatc ttcggcatcc tgatcggcaa gtgcaccttc     780
taccccgacg agttccgcgc cgccaaggcc agctacaccg cccaggagtt caatctgctg     840
aacgacctga caacctgac cgtgcccacc gagaccaaga gctgagcaa ggagcagaag      900 aaccagatca tcaactacgt gaagaacgag aaggctatgg cccccgccaa gctgttcaag     960
tacatcgcca agctgctgag ctgcgacgtg gccgacatca agggctaccg catcgacaag    1020
agcggcaagg ccgagatcca caccttcgag gcctaccgca agatgaagac cctggagacc    1080
ctggacatcg agcagatgga ccgagagacc ctggacaagc tggcctacgt gctgaccctg    1140
aacaccgagc gcgagggcat ccaggaggcc ctggagcacg agttcgccga cggcagcttc    1200
agccagaaac aggtggacga gctggtgcag ttccgcaagg ccaacagcag catcttcggc    1260
aagggctggc acaacttcag cgtgaagctg atgatggagc tgatccccga gctgtacgag    1320
accagcgagg agcagatgac catcctgacc cgcctgggca gcagaagac caccagcagc    1380 agcaacaaga ccaagtacat cgacgagaag ctgctgaccg aggagatcta caaccccgtg    1440
gtggccaaga gcgtgcgcca ggccatcaag atcgtgaacg ccgccatcaa ggagtacggc    1500
gacttcgaca catcgtgat cgagatggcc cgcgagacca acgaggacga cgagaagaag    1560
gccatccaga agatccagaa ggccaacaag gacgagaagg acgccgccat gctgaaggcc    1620
```

```
gccaaccagt acaacggcaa ggccgagctg ccccacagcg tgttccacgg ccacaagcag    1680
ctggccacca agatccgcct gtggcaccag cagggcgagc gctgcctgta caccggcaag    1740
accatcagca tccacgacct gatcaacaac agcaaccagt tcgaggtgga ccacatcctg    1800
cccctgagca tcaccttcga cgacagcctg gccaacaagg tgctggtgta cgccaccgcc    1860
aaccaggaga agggccagcg cacccccctac caggccctgg acagcatgga cgacgcctgg    1920
agcttccgcg agctgaaggc cttcgtgcgc gagagcaaga ccctgagcaa caagaagaag    1980
gagtatctgc tgaccgagga ggacatcagc aagttcgacg tgcgcaagaa gttcatcgag    2040
cgcaacctgg tggacacccg ctacgccagc cgcgtggtgc tgaacgccct gcaggagcac    2100
ttccgcgccc acaagatcga caccaaggtg agcgtggtgc gcggccagtt caccagccag    2160
ctgcgccgcc actggggcat cgagaagacc cgcgacacct accaccacca cgccgtggac    2220
gccctgatca ttgcggcttc tagccagctg aacctgtgga agaagcagaa gaacaccctg    2280
gtgagctaca gcgaggacca gctgctggac atcgagaccg cgagctgat cagcgacgac    2340 gagtacaagg agagcgtgtt caaggccccc taccagcact tcgtggacac cctgaagagc    2400
aaggagttcg aggacagcat cctgttcagc taccaggtgg acagcaagtt caaccgcaag    2460
atcagcgacg ccaccatcta cgccacccgc caggccaagg tgggcaagga caaggccgac    2520
gagacctacg tgctgggcaa gatcaaggac atctacaccc aggacggcta cgacgccttc    2580
atgaagatct acaagaagga caagagcaag ttcctgatgt accgccacga cccccagacc    2640
ttcgagaagg tgatcgagcc catcctggag aactacccca caagcagat caacgagaaa    2700 ggcaaggagg tgccctgcaa cccccttcctg aagtacaagg aggagcacgg ctacatccgc    2760
aagtacagca agaagggcaa cggccccgag atcaagagcc tgaagtacta cgacagcaag    2820
ctgggcaacc acatcgacat caccccaag gacagcaaca caaggtggt gctgcagagc    2880 gtgagcccct ggcgcgccga cgtgtacttc aacaagacca ccggcaagta cgagatcctg    2940
gggctgaagt acgccgatct gcagtttgag aaaggcacag gcacctacaa gatcagccag    3000
gagaagtaca cgacatcaa gaagaaggag ggcgtggaca gcgacagcga gttcaagttc    3060
accctgtaca agaacgacct tctgctggtg aaggacaccg agaccaagga gcaacagctg    3120
ttccgcttcc tgagccgcac catgcccaag cagaagcact acgtggagct gaagccctac    3180
gacaagcaga agttcgaggg cggcgaggcc ctgatcaagg tgctgggcaa cgtggccaac    3240
agcggccagt gcaagaaggg cctgggcaag agcaacatca gcatctacaa ggtgcgcacc    3300
gacgtgctgg gcaaccagca catcatcaag aacgagggcg acaagcccaa gttggacttc    3360
```

<210> SEQ ID NO 26
<211> LENGTH: 24
<212> TYPE: DNA
<213> ORGANISM: Artificial Sequence
<220> FEATURE:
<223> OTHER INFORMATION: Synthetic, engineered or hybrid sequence

<400> SEQUENCE: 26
ggtatccacg gagtcccagc agcc                                            24

<210> SEQ ID NO 27
<211> LENGTH: 12
<212> TYPE: DNA
<213> ORGANISM: Artificial Sequence
<220> FEATURE:
<223> OTHER INFORMATION: Synthetic, engineered or hybrid sequence

<400> SEQUENCE: 27
agcagggctg ac    12

<210> SEQ ID NO 28
<211> LENGTH: 1149
<212> TYPE: PRT
<213> ORGANISM: Artificial Sequence
<220> FEATURE:
<223> OTHER INFORMATION: Synthetic, engineered or hybrid sequence

<400> SEQUENCE: 28

```
Met Gly Ala Pro Lys Lys Arg Lys Val Gly Ile His Gly Val Pro
1               5                   10                  15

Ala Ala Ser Asp Leu Val Leu Gly Leu Asp Ile Gly Ile Gly Ser Val
            20                  25                  30

Gly Val Gly Ile Leu Asn Lys Val Thr Gly Glu Ile Ile His Lys Asn
                35                  40                  45

Ser Arg Ile Phe Pro Ala Ala Gln Ala Glu Asn Asn Leu Val Arg Arg
        50                  55                  60

Thr Asn Arg Gln Gly Arg Arg Leu Ala Arg Lys Lys His Arg Arg
65                  70                  75                  80

Val Arg Leu Asn Arg Leu Phe Glu Glu Ser Gly Leu Ile Thr Asp Phe
                85                  90                  95

Thr Lys Ile Ser Ile Asn Leu Asn Pro Tyr Gln Leu Arg Val Lys Gly
                100                 105                 110

Leu Thr Asp Glu Leu Ser Asn Glu Glu Leu Phe Ile Ala Leu Lys Asn
            115                 120                 125

Met Val Lys His Arg Gly Ile Ser Tyr Leu Asp Asp Ala Ser Asp Asp
            130                 135                 140

Gly Asn Ser Ser Val Gly Asp Tyr Ala Gln Ile Val Lys Glu Asn Ser
145                 150                 155                 160

Lys Gln Leu Glu Thr Lys Thr Pro Gly Gln Ile Gln Leu Glu Arg Tyr
                165                 170                 175

Gln Thr Tyr Gly Gln Leu Arg Gly Asp Phe Thr Val Glu Lys Asp Gly
            180                 185                 190

Lys Lys His Arg Leu Ile Asn Val Phe Pro Thr Ser Ala Tyr Arg Ser
        195                 200                 205

Glu Ala Leu Arg Ile Leu Gln Thr Gln Gln Glu Phe Asn Pro Gln Ile
    210                 215                 220

Thr Asp Glu Phe Ile Asn Arg Tyr Leu Glu Ile Leu Thr Gly Lys Arg
225                 230                 235                 240

Lys Tyr Tyr His Gly Pro Gly Asn Glu Lys Ser Arg Thr Asp Tyr Gly
                245                 250                 255

Arg Tyr Arg Thr Ser Gly Glu Thr Leu Asp Asn Ile Phe Gly Ile Leu
            260                 265                 270

Ile Gly Lys Cys Thr Phe Tyr Pro Asp Glu Phe Arg Ala Ala Lys Ala
        275                 280                 285

Ser Tyr Thr Ala Gln Glu Phe Asn Leu Leu Asn Asp Leu Asn Asn Leu
    290                 295                 300

Thr Val Pro Thr Glu Thr Lys Lys Leu Ser Lys Glu Gln Lys Asn Gln
305                 310                 315                 320

Ile Ile Asn Tyr Val Lys Asn Glu Lys Ala Met Gly Pro Ala Lys Leu
                325                 330                 335

Phe Lys Tyr Ile Ala Lys Leu Leu Ser Cys Asp Val Ala Asp Ile Lys
            340                 345                 350
```

```
Gly Tyr Arg Ile Asp Lys Ser Gly Lys Ala Glu Ile His Thr Phe Glu
            355                 360                 365

Ala Tyr Arg Lys Met Lys Thr Leu Glu Thr Leu Asp Ile Glu Gln Met
    370                 375                 380

Asp Arg Glu Thr Leu Asp Lys Leu Ala Tyr Val Leu Thr Leu Asn Thr
385                 390                 395                 400

Glu Arg Glu Gly Ile Gln Glu Ala Leu Glu His Glu Phe Ala Asp Gly
                405                 410                 415

Ser Phe Ser Gln Lys Gln Val Asp Glu Leu Val Gln Phe Arg Lys Ala
            420                 425                 430

Asn Ser Ser Ile Phe Gly Lys Gly Trp His Asn Phe Ser Val Lys Leu
            435                 440                 445

Met Met Glu Leu Ile Pro Glu Leu Tyr Glu Thr Ser Glu Glu Gln Met
    450                 455                 460

Thr Ile Leu Thr Arg Leu Gly Lys Gln Lys Thr Thr Ser Ser Ser Asn
465                 470                 475                 480

Lys Thr Lys Tyr Ile Asp Glu Lys Leu Leu Thr Glu Glu Ile Tyr Asn
                485                 490                 495

Pro Val Val Ala Lys Ser Val Arg Gln Ala Ile Lys Ile Val Asn Ala
            500                 505                 510

Ala Ile Lys Glu Tyr Gly Asp Phe Asp Asn Ile Val Ile Glu Met Ala
            515                 520                 525

Arg Glu Thr Asn Glu Asp Asp Glu Lys Lys Ala Ile Gln Lys Ile Gln
            530                 535                 540

Lys Ala Asn Lys Asp Glu Lys Asp Ala Ala Met Leu Lys Ala Ala Asn
545                 550                 555                 560

Gln Tyr Asn Gly Lys Ala Glu Leu Pro His Ser Val Phe His Gly His
                565                 570                 575

Lys Gln Leu Ala Thr Lys Ile Arg Leu Trp His Gln Gly Glu Arg
            580                 585                 590

Cys Leu Tyr Thr Gly Lys Thr Ile Ser Ile His Asp Leu Ile Asn Asn
            595                 600                 605

Ser Asn Gln Phe Glu Val Asp His Ile Leu Pro Leu Ser Ile Thr Phe
    610                 615                 620

Asp Asp Ser Leu Ala Asn Lys Val Leu Val Tyr Ala Thr Ala Asn Gln
625                 630                 635                 640

Glu Lys Gly Gln Arg Thr Pro Tyr Gln Ala Leu Asp Ser Met Asp Asp
                645                 650                 655

Ala Trp Ser Phe Arg Glu Leu Lys Ala Phe Val Arg Glu Ser Lys Thr
            660                 665                 670

Leu Ser Asn Lys Lys Lys Glu Tyr Leu Leu Thr Glu Glu Asp Ile Ser
            675                 680                 685

Lys Phe Asp Val Arg Lys Lys Phe Ile Glu Arg Asn Leu Val Asp Thr
    690                 695                 700

Arg Tyr Ala Ser Arg Val Val Leu Asn Ala Leu Gln Glu His Phe Arg
705                 710                 715                 720

Ala His Lys Ile Asp Thr Lys Val Ser Val Val Arg Gly Gln Phe Thr
                725                 730                 735

Ser Gln Leu Arg Arg His Trp Gly Ile Glu Lys Thr Arg Asp Thr Tyr
            740                 745                 750

His His His Ala Val Asp Ala Leu Ile Ile Ala Ala Ser Ser Gln Leu
            755                 760                 765
```

```
Asn Leu Trp Lys Lys Gln Lys Asn Thr Leu Val Ser Tyr Ser Glu Asp
770                 775                 780

Gln Leu Leu Asp Ile Glu Thr Gly Glu Leu Ile Ser Asp Asp Glu Tyr
785                 790                 795                 800

Lys Glu Ser Val Phe Lys Ala Pro Tyr Gln His Phe Val Asp Thr Leu
                805                 810                 815

Lys Ser Lys Glu Phe Glu Asp Ser Ile Leu Phe Ser Tyr Gln Val Asp
                820                 825                 830

Ser Lys Phe Asn Arg Lys Ile Ser Asp Ala Thr Ile Tyr Ala Thr Arg
                835                 840                 845

Gln Ala Lys Val Gly Lys Asp Lys Ala Asp Glu Thr Tyr Val Leu Gly
850                 855                 860

Lys Ile Lys Asp Ile Tyr Thr Gln Asp Gly Tyr Asp Ala Phe Met Lys
865                 870                 875                 880

Ile Tyr Lys Lys Asp Lys Ser Lys Phe Leu Met Tyr Arg His Asp Pro
                885                 890                 895

Gln Thr Phe Glu Lys Val Ile Glu Pro Ile Leu Glu Asn Tyr Pro Asn
                900                 905                 910

Lys Gln Ile Asn Glu Lys Gly Lys Glu Val Pro Cys Asn Pro Phe Leu
                915                 920                 925

Lys Tyr Lys Glu Glu His Gly Tyr Ile Arg Lys Tyr Ser Lys Lys Gly
                930                 935                 940

Asn Gly Pro Glu Ile Lys Ser Leu Lys Tyr Tyr Asp Ser Lys Leu Gly
945                 950                 955                 960

Asn His Ile Asp Ile Thr Pro Lys Asp Ser Asn Asn Lys Val Val Leu
                965                 970                 975

Gln Ser Val Ser Pro Trp Arg Ala Asp Val Tyr Phe Asn Lys Thr Thr
                980                 985                 990

Gly Lys Tyr Glu Ile Leu Gly Leu Lys Tyr Ala Asp Leu Gln Phe Glu
                995             1000            1005

Lys Gly Thr Gly Thr Tyr Lys Ile Ser Gln Glu Lys Tyr Asn Asp
        1010            1015            1020

Ile Lys Lys Lys Glu Gly Val Asp Ser Asp Ser Glu Phe Lys Phe
        1025            1030            1035

Thr Leu Tyr Lys Asn Asp Leu Leu Leu Val Lys Asp Thr Glu Thr
        1040            1045            1050

Lys Glu Gln Gln Leu Phe Arg Phe Leu Ser Arg Thr Met Pro Lys
        1055            1060            1065

Gln Lys His Tyr Val Glu Leu Lys Pro Tyr Asp Lys Gln Lys Phe
        1070            1075            1080

Glu Gly Gly Glu Ala Leu Ile Lys Val Leu Gly Asn Val Ala Asn
        1085            1090            1095

Ser Gly Gln Cys Lys Lys Gly Leu Gly Lys Ser Asn Ile Ser Ile
        1100            1105            1110

Tyr Lys Val Arg Thr Asp Val Leu Gly Asn Gln His Ile Ile Lys
        1115            1120            1125

Asn Glu Gly Asp Lys Pro Lys Leu Asp Phe Ser Arg Ala Asp Pro
        1130            1135            1140

Lys Lys Lys Arg Lys Val
        1145

<210> SEQ ID NO 29
<211> LENGTH: 7
<212> TYPE: PRT
```

<213> ORGANISM: Artificial Sequence
<220> FEATURE:
<223> OTHER INFORMATION: Synthetic, engineered or hybrid sequence

<400> SEQUENCE: 29

Pro Lys Lys Lys Arg Lys Val
1               5

<210> SEQ ID NO 30
<211> LENGTH: 1120
<212> TYPE: PRT
<213> ORGANISM: Artificial Sequence
<220> FEATURE:
<223> OTHER INFORMATION: Synthetic, engineered or hybrid sequence

<400> SEQUENCE: 30

Ser Asp Leu Val Leu Gly Leu Asp Ile Gly Ile Gly Ser Val Gly Val
1               5                   10                  15

Gly Ile Leu Asn Lys Val Thr Gly Glu Ile Ile His Lys Asn Ser Arg
                20                  25                  30

Ile Phe Pro Ala Ala Gln Ala Glu Asn Asn Leu Val Arg Arg Thr Asn
            35                  40                  45

Arg Gln Gly Arg Arg Leu Ala Arg Arg Lys His Arg Arg Val Arg
        50                  55                  60

Leu Asn Arg Leu Phe Glu Glu Ser Gly Leu Ile Thr Asp Phe Thr Lys
65                  70                  75                  80

Ile Ser Ile Asn Leu Asn Pro Tyr Gln Leu Arg Val Lys Gly Leu Thr
                85                  90                  95

Asp Glu Leu Ser Asn Glu Glu Leu Phe Ile Ala Leu Lys Asn Met Val
            100                 105                 110

Lys His Arg Gly Ile Ser Tyr Leu Asp Asp Ala Ser Asp Asp Gly Asn
        115                 120                 125

Ser Ser Val Gly Asp Tyr Ala Gln Ile Val Lys Glu Asn Ser Lys Gln
    130                 135                 140

Leu Glu Thr Lys Thr Pro Gly Gln Ile Gln Leu Glu Arg Tyr Gln Thr
145                 150                 155                 160

Tyr Gly Gln Leu Arg Gly Asp Phe Thr Val Glu Lys Asp Gly Lys Lys
                165                 170                 175

His Arg Leu Ile Asn Val Phe Pro Thr Ser Ala Tyr Arg Ser Glu Ala
            180                 185                 190

Leu Arg Ile Leu Gln Thr Gln Gln Glu Phe Asn Pro Gln Ile Thr Asp
        195                 200                 205

Glu Phe Ile Asn Arg Tyr Leu Glu Ile Leu Thr Gly Lys Arg Lys Tyr
    210                 215                 220

Tyr His Gly Pro Gly Asn Glu Lys Ser Arg Thr Asp Tyr Gly Arg Tyr
225                 230                 235                 240

Arg Thr Ser Gly Glu Thr Leu Asp Asn Ile Phe Gly Ile Leu Ile Gly
                245                 250                 255

Lys Cys Thr Phe Tyr Pro Asp Glu Phe Arg Ala Ala Lys Ala Ser Tyr
            260                 265                 270

Thr Ala Gln Glu Phe Asn Leu Leu Asn Asp Leu Asn Asn Leu Thr Val
        275                 280                 285

Pro Thr Glu Thr Lys Lys Leu Ser Lys Glu Gln Lys Asn Gln Ile Ile
    290                 295                 300

Asn Tyr Val Lys Asn Glu Lys Ala Met Gly Pro Ala Lys Leu Phe Lys
305                 310                 315                 320

```
Tyr Ile Ala Lys Leu Leu Ser Cys Asp Val Ala Asp Ile Lys Gly Tyr
                325                 330                 335

Arg Ile Asp Lys Ser Gly Lys Ala Glu Ile His Thr Phe Glu Ala Tyr
            340                 345                 350

Arg Lys Met Lys Thr Leu Glu Thr Leu Asp Ile Glu Gln Met Asp Arg
        355                 360                 365

Glu Thr Leu Asp Lys Leu Ala Tyr Val Leu Thr Leu Asn Thr Glu Arg
    370                 375                 380

Glu Gly Ile Gln Glu Ala Leu Glu His Glu Phe Ala Asp Gly Ser Phe
385                 390                 395                 400

Ser Gln Lys Gln Val Asp Glu Leu Val Gln Phe Arg Lys Ala Asn Ser
            405                 410                 415

Ser Ile Phe Gly Lys Gly Trp His Asn Phe Ser Val Lys Leu Met Met
        420                 425                 430

Glu Leu Ile Pro Glu Leu Tyr Glu Thr Ser Glu Glu Gln Met Thr Ile
    435                 440                 445

Leu Thr Arg Leu Gly Lys Gln Lys Thr Thr Ser Ser Asn Lys Thr
    450                 455                 460

Lys Tyr Ile Asp Glu Lys Leu Leu Thr Glu Glu Ile Tyr Asn Pro Val
465                 470                 475                 480

Val Ala Lys Ser Val Arg Gln Ala Ile Lys Ile Val Asn Ala Ala Ile
            485                 490                 495

Lys Glu Tyr Gly Asp Phe Asp Asn Ile Val Ile Glu Met Ala Arg Glu
        500                 505                 510

Thr Asn Glu Asp Asp Glu Lys Lys Ala Ile Gln Lys Ile Gln Lys Ala
    515                 520                 525

Asn Lys Asp Glu Lys Asp Ala Ala Met Leu Lys Ala Ala Asn Gln Tyr
    530                 535                 540

Asn Gly Lys Ala Glu Leu Pro His Ser Val Phe His Gly His Lys Gln
545                 550                 555                 560

Leu Ala Thr Lys Ile Arg Leu Trp His Gln Gln Gly Glu Arg Cys Leu
            565                 570                 575

Tyr Thr Gly Lys Thr Ile Ser Ile His Asp Leu Ile Asn Asn Ser Asn
        580                 585                 590

Gln Phe Glu Val Asp His Ile Leu Pro Leu Ser Ile Thr Phe Asp Asp
    595                 600                 605

Ser Leu Ala Asn Lys Val Leu Val Tyr Ala Thr Ala Asn Gln Glu Lys
    610                 615                 620

Gly Gln Arg Thr Pro Tyr Gln Ala Leu Asp Ser Met Asp Asp Ala Trp
625                 630                 635                 640

Ser Phe Arg Glu Leu Lys Ala Phe Val Arg Glu Ser Lys Thr Leu Ser
            645                 650                 655

Asn Lys Lys Lys Glu Tyr Leu Leu Thr Glu Glu Asp Ile Ser Lys Phe
        660                 665                 670

Asp Val Arg Lys Lys Phe Ile Glu Arg Asn Leu Val Asp Thr Arg Tyr
    675                 680                 685

Ala Ser Arg Val Val Leu Asn Ala Leu Gln Glu His Phe Arg Ala His
    690                 695                 700

Lys Ile Asp Thr Lys Val Ser Val Val Arg Gly Gln Phe Thr Ser Gln
705                 710                 715                 720

Leu Arg Arg His Trp Gly Ile Glu Lys Thr Arg Asp Thr Tyr His His
            725                 730                 735

His Ala Val Asp Ala Leu Ile Ile Ala Ala Ser Ser Gln Leu Asn Leu
```

740                 745                 750
Trp Lys Lys Gln Lys Asn Thr Leu Val Ser Tyr Ser Glu Asp Gln Leu
                755                 760                 765

Leu Asp Ile Glu Thr Gly Glu Leu Ile Ser Asp Asp Glu Tyr Lys Glu
            770                 775                 780

Ser Val Phe Lys Ala Pro Tyr Gln His Phe Val Asp Thr Leu Lys Ser
785                 790                 795                 800

Lys Glu Phe Glu Asp Ser Ile Leu Phe Ser Tyr Gln Val Asp Ser Lys
                805                 810                 815

Phe Asn Arg Lys Ile Ser Asp Ala Thr Ile Tyr Ala Thr Arg Gln Ala
            820                 825                 830

Lys Val Gly Lys Asp Lys Ala Asp Glu Thr Tyr Val Leu Gly Lys Ile
            835                 840                 845

Lys Asp Ile Tyr Thr Gln Asp Gly Tyr Asp Ala Phe Met Lys Ile Tyr
            850                 855                 860

Lys Lys Asp Lys Ser Lys Phe Leu Met Tyr Arg His Asp Pro Gln Thr
865                 870                 875                 880

Phe Glu Lys Val Ile Glu Pro Ile Leu Glu Asn Tyr Pro Asn Lys Gln
                885                 890                 895

Ile Asn Glu Lys Gly Lys Glu Val Pro Cys Asn Pro Phe Leu Lys Tyr
            900                 905                 910

Lys Glu Glu His Gly Tyr Ile Arg Lys Tyr Ser Lys Lys Gly Asn Gly
            915                 920                 925

Pro Glu Ile Lys Ser Leu Lys Tyr Tyr Asp Ser Lys Leu Gly Asn His
            930                 935                 940

Ile Asp Ile Thr Pro Lys Asp Ser Asn Asn Lys Val Val Leu Gln Ser
945                 950                 955                 960

Val Ser Pro Trp Arg Ala Asp Val Tyr Phe Asn Lys Thr Thr Gly Lys
                965                 970                 975

Tyr Glu Ile Leu Gly Leu Lys Tyr Ala Asp Leu Gln Phe Glu Lys Gly
            980                 985                 990

Thr Gly Thr Tyr Lys Ile Ser Gln Glu Lys Tyr Asn Asp Ile Lys Lys
            995                 1000                1005

Lys Glu Gly Val Asp Ser Asp Ser Glu Phe Lys Phe Thr Leu Tyr
        1010                1015                1020

Lys Asn Asp Leu Leu Leu Val Lys Asp Thr Glu Thr Lys Glu Gln
        1025                1030                1035

Gln Leu Phe Arg Phe Leu Ser Arg Thr Met Pro Lys Gln Lys His
        1040                1045                1050

Tyr Val Glu Leu Lys Pro Tyr Asp Lys Gln Lys Phe Glu Gly Gly
        1055                1060                1065

Glu Ala Leu Ile Lys Val Leu Gly Asn Val Ala Asn Ser Gly Gln
        1070                1075                1080

Cys Lys Lys Gly Leu Gly Lys Ser Asn Ile Ser Ile Tyr Lys Val
        1085                1090                1095

Arg Thr Asp Val Leu Gly Asn Gln His Ile Ile Lys Asn Glu Gly
        1100                1105                1110

Asp Lys Pro Lys Leu Asp Phe
        1115                1120

<210> SEQ ID NO 31
<211> LENGTH: 8
<212> TYPE: PRT
<213> ORGANISM: Artificial Sequence

```
<220> FEATURE:
<223> OTHER INFORMATION: Synthetic, engineered or hybrid sequence

<400> SEQUENCE: 31

Gly Ile His Gly Val Pro Ala Ala
1               5

<210> SEQ ID NO 32
<211> LENGTH: 4
<212> TYPE: PRT
<213> ORGANISM: Artificial Sequence
<220> FEATURE:
<223> OTHER INFORMATION: Synthetic, engineered or hybrid sequence

<400> SEQUENCE: 32

Ser Arg Ala Asp
1

<210> SEQ ID NO 33
<211> LENGTH: 3456
<212> TYPE: DNA
<213> ORGANISM: Artificial Sequence
<220> FEATURE:
<223> OTHER INFORMATION: Synthetic, engineered or hybrid sequence

<400> SEQUENCE: 33
atgggcgccc caaagaagaa gcggaaggtc ggtatccacg gagtcccagc agccagcgac      60
ctggtgctgg gcctggacat cggcatcggc agcgtgggcg tgggcatcct gaacaaggtg     120
accggcgaga tcatccacaa gaacagtcgc atcttccctg ctgctcaggc tgagaacaac     180
ctggtgcgcc gcaccaaccg ccagggtcgc cggcttgctc gccgcaagaa gcaccggcgc     240
gtgcgcctga accgcctgtt cgaggagagc ggcctgatca ccgacttcac caagatcagc     300
atcaacctga ccccctacca gctgcgcgtg aagggcctga ccgacgagct gagcaacgag     360
gagctgttca tcgccctgaa gaacatggtg aagcaccgcg gcatcagcta cctggacgac     420
gccagcgacg acggcaacag cagcgtgggc gactacgccc agatcgtgaa ggagaacagc     480
aagcagctgg agaccaagac ccccggccag atccagctgg agcgctacca gacctacgcc     540
cagctgcgcg gcgacttcac cgtggagaag acggcaaga agcaccgcct gatcaacgtg     600
ttccccacca gcgcctaccg cagcgaggcc ctgcgcatcc tgcagaccca gcaggagttc     660
aaccccgaga tcaccgacga gttcatcaac cgctacctgg agatcctgac cggcaagcgc     720
aagtactacc acggccccgg caacgagaag agccgcaccg actacggccg ctaccgcacc     780
agcggcgaga ccctggacaa catcttcggc atcctgatcg gcaagtgcac cttctacccc     840
gacgagttcc gcgccgccaa ggccagctac accgcccagg agttcaatct gctgaacgac     900
ctgaacaacc tgaccgtgcc caccgagacc aagaagctga gcaaggagca agaaaccag     960 atcatcaact acgtgaagaa cgagaaggct atgggccccg ccaagctgtt caagtacatc    1020
gccaagctgc tgagctgcga cgtggccgac atcaagggct accgcatcga caagagcggc    1080
aaggccgaga tccacaccct tcgaggccta ccgcaagatga agaccctgga gaccctggac    1140
atcgagcaga tggaccgaga gaccctggac aagctggcct acgtgctgac cctgaacacc    1200
gagcgcgagg gcatccagga ggccctggag cacgagttcg ccgacggcag cttcagccag    1260
aaacaggtgg acgagctggt gcagttccgc aaggccaaca gcagcatctt cggcaagggc    1320
tggcacaact tcagcgtgaa gctgatgatg gagctgatcc ccgagctgta cgagaccagc    1380
gaggagcaga tgaccatcct gacccgcctg ggcaagcaga agaccaccag cagcagcaac    1440
```

```
aagaccaagt acatcgacga gaagctgctg accgaggaga tctacaaccc cgtggtggcc      1500
aagagcgtgc gccaggccat caagatcgtg aacgccgcca tcaaggagta cggcgacttc      1560
gacaacatcg tgatcgagat ggcccgcgag accaacgagg acgacgagaa gaaggccatc      1620
cagaagatcc agaaggccaa caaggacgag aaggacgccg ccatgctgaa ggccgccaac      1680
cagtacaacg gcaaggccga gctgccccac agcgtgttcc acggccacaa gcagctggcc      1740
accaagatcc gcctgtggca ccagcagggc gagcgctgcc tgtacaccgg caagaccatc      1800
agcatccacg acctgatcaa caacagcaac cagttcgagg tggaccacat cctgcccctg      1860
agcatcacct tcgacgacag cctggccaac aaggtgctgg tgtacgccac cgccaaccag      1920
gagaagggcc agcgcacccc ctaccaggcc ctggacagca tggacgacgc ctggagcttc      1980
cgcgagctga aggccttcgt gcgcgagagc aagaccctga gcaacaagaa gaaggagtat      2040
ctgctgaccg aggaggacat cagcaagttc gacgtgcgca agaagttcat cgagcgcaac      2100
ctggtggaca cccgctacgc cagccgcgtg gtgctgaacg ccctgcagga gcacttccgc      2160
gcccacaaga tcgacaccaa ggtgagcgtg gtgcgcggcc agttcaccag ccagctgcgc      2220
cgccactggg gcatcgagaa gacccgcgac acctaccacc accacgccgt ggacgccctg      2280
atcattgcgg cttctagcca gctgaacctg tggaagaagc agaagaacac cctggtgagc      2340
tacagcgagg agcagctgct ggacatcgag accggcgagc tgatcagcga cgacgagtac      2400
aaggagagcg tgttcaaggc ccccaaccag cacttcgtgg acaccctgaa gagcaaggag      2460
ttcgaggaca gcatcctgtt cagctaccag gtggacagca gttcaaccg caagatcagc      2520 gacgccacca tctacgccac ccgccaggcc aaggtgggca aggacaagaa ggacgagacc      2580
tacgtgctgg gcaagatcaa ggacatctac acccaggacg gctacgacgc cttcatgaag      2640
atctacaaga aggacaagag caagttcctg atgtaccgcc acgaccccca gaccttcgag      2700
aaggtgatcg agcccatcct ggagaactac cccaacaagc agatgaacga gaaaggcaag      2760
gaggtgccct gcaaccccct cctgaagtac aaggaggagc acggctacat ccgcaagtac      2820
agcaagaagg gcaacggccc cgagatcaag agcctgaagt actacgacag caagctgctg      2880
ggcaacccca tcgacatcac ccccgaaaac agcaagaaca aggtggtgct gcagagcctt      2940
aagccctggc gcaccgacgt gtacttcaac aagaacaccg gcaagtacga gatcctgggg      3000
ctgaagtacg ccgatctgca gtttgagaaa aagacaggca cctacaagat cagccaggag      3060
aagtacaacg gcatcatgaa ggaggagggc gtggacagcg acagcgagtt caagttcacc      3120
ctgtacaaga cgaccttcct gctggtgaag gacaccgaga ccaaggagca acagctgttc      3180
cgcttcctga gccgcaccat gcccaacgtg aagtactacg tggagctgaa gcctacagc      3240 aaggacaagt cgagaagaa cgagagcctg atcgagatcc tgggcagcgc cgacaagagc      3300
ggcaggtgca tcaagggcct gggcaagagc aacatcagca tctacaaggt gcgcaccgac      3360
gtgctgggca accagcacat catcaagaac gagggcgaca gcccaagtt ggacttcagc      3420 agggctgacc ccaagaagaa gaggaaggtg ggatcc                               3456
```

<210> SEQ ID NO 34
<211> LENGTH: 3363
<212> TYPE: DNA
<213> ORGANISM: Artificial Sequence
<220> FEATURE:
<223> OTHER INFORMATION: Synthetic, engineered or hybrid sequence

<400> SEQUENCE: 34

```
agcgacctgg tgctgggcct ggacatcggc atcggcagcg tgggcgtggg catcctgaac        60
```

```
aaggtgaccg gcgagatcat ccacaagaac agtcgcatct tccctgctgc tcaggctgag    120
aacaacctgg tgcgccgcac caaccgccag ggtcgccggc ttgctcgccg caagaagcac    180
cggcgcgtgc gcctgaaccg cctgttcgag gagagcggcc tgatcaccga cttcaccaag    240
atcagcatca acctgaaccc ctaccagctg cgcgtgaagg gcctgaccga cgagctgagc    300
aacgaggagc tgttcatcgc cctgaagaac atggtgaagc accgcggcat cagctacctg    360
gacgacgcca gcgacgacgg caacagcagc gtgggcgact acgcccagat cgtgaaggag    420
aacagcaagc agctggagac caagaccccc ggccagatcc agctggagcg ctaccagacc    480 tacgccagc tgcgcggcga cttcaccgtg gagaaggacg gcaagaagca ccgcctgatc     540
aacgtgttcc ccaccagcgc ctaccgcagc gaggccctgc gcatcctgca gacccagcag    600
gagttcaacc cccagatcac cgacgagttc atcaaccgct acctggagat cctgaccggc    660
aagcgcaagt actaccacgg ccccggcaac gagaagagcc gcaccgacta cggccgctac    720
cgcaccagcg gcgagaccct ggacaacatc ttcggcatcc tgatcggcaa gtgcaccttc    780
taccccgacg agttccgcgc cgccaaggcc agctacaccg cccaggagtt caatctgctg    840
aacgacctga caacctgac cgtgcccacc gagaccaaga gctgagcaa ggagcagaag      900 aaccagatca tcaactacgt gaagaacgag aaggctatgg ccccgccaa gctgttcaag     960 tacatcgcca gctgctgag ctgcgacgtg gccgacatca agggctaccg catcgacaag    1020
agcggcaagg ccgagatcca caccttcgag gcctaccgca gatgaagac cctggagacc    1080 ctggacatcg agcagatgga ccgagagacc ctggacaagc tggcctacgt gctgacccctg   1140 aacaccgagc gcgagggcat ccaggaggcc ctggagcacg agttcgccga cggcagcttc    1200
agccagaaac aggtggacga gctggtgcag ttccgcaagg ccaacagcag catcttcggc    1260
aagggctggc acaacttcag cgtgaagctg atgatggagc tgatccccga gctgtacgag    1320
accagcgagg agcagatgac catcctgacc cgcctgggca gcagaagac caccagcagc    1380 agcaacaaga ccaagtacat cgacgagaag ctgctgaccg aggagatcta caaccccgtg    1440
gtggccaaga gcgtgcgcca ggccatcaag atcgtgaacg ccgcatcaa ggagtacggc    1500 gacttcgaca acatcgtgat cgagatggcc cgcgagacca acgaggacga cgagaagaag    1560
gccatccaga agatccagaa ggccaacaag gacgagaagg acgccgccat gctgaaggcc    1620
gccaaccagt acaacggcaa ggccgagctg ccccacagcg tgttccacgg ccacaagcag    1680
ctggccacca agatccgcct gtggcaccag cagggcgagc gctgcctgta caccggcaag    1740
accatcagca tccacgacct gatcaacaac agcaaccagt tcgaggtgga ccacatcctg    1800
cccctgagca tcaccttcga cgacagcctg gccaacaagg tgctggtgta cgccaccgcc    1860
aaccaggaga agggccagcg cacccccta caggccctgg acagcatgga cgacgcctgg    1920
agcttccgcg agctgaaggc cttcgtgcgc gagagcaaga ccctgagcaa caagaagaag    1980
gagtatctgc tgaccgagga ggacatcagc aagttcgacg tgcgcaagaa gttcatcgag    2040
cgcaacctgg tggacacccg ctacgccagc cgcgtggtgc tgaacgccct gcaggagcac    2100
ttccgcgccc acaagatcga caccaaggtg agcgtggtgc gcggccagtt caccagccag    2160
ctgcgccgcc actggggcat cgagaagacc cgcgacacct accaccacca cgccgtggac    2220
gccctgatca ttgcggcttc tagccagctg aacctgtgga gaagcagaa gaacaccctg    2280 gtgagctaca gcgaggagca gctgctggac atcgagaccg gcgagctgat cagcgacgac    2340
gagtacaagg agagcgtgtt caaggccccc taccagcact tcgtggacac cctgaagagc    2400
```

```
aaggagttcg aggacagcat cctgttcagc taccaggtgg acagcaagtt caaccgcaag    2460
atcagcgacg ccaccatcta cgccacccgc caggccaagg tgggcaagga caagaaggac    2520
gagacctacg tgctgggcaa gatcaaggac atctacaccc aggacggcta cgacgccttc    2580
atgaagatct acaagaagga caagagcaag ttcctgatgt accgccacga cccccagacc    2640
ttcgagaagg tgatcgagcc catcctggag aactacccca caagcagat gaacgagaaa    2700 ggcaaggagt gccctgcaa ccccttcctg aagtacaagg aggagcacgg ctacatccgc     2760
aagtacagca agaagggcaa cggccccgag atcaagagcc tgaagtacta cgacagcaag    2820
ctgctgggca ccccatcga catcaccccc gaaaacagca agaacaaggt ggtgctgcag     2880
agccttaagc cctggcgcac cgacgtgtac ttcaacaaga acaccggcaa gtacgagatc    2940
ctggggctga agtacgccga tctgcagttt gagaaaaaga caggcaccta caagatcagc    3000
caggagaagt acaacggcat catgaaggag gagggcgtgg acgcgacag cgagttcaag     3060 ttcaccctgt acaagaacga ccttctgctg gtgaaggaca ccgagaccaa ggagcaacag    3120
ctgttccgct tcctgagccg caccatgccc aacgtgaagt actacgtgga gctgaagccc    3180
tacagcaagg acaagttcga gaagaacgag agcctgatcg agatcctggg cagcgccgac    3240
aagagcggca ggtgcatcaa gggcctgggc aagagcaaca tcagcatcta aaggtgcgc    3300 accgacgtgc tgggcaacca gcacatcatc aagaacgagg gcgacaagcc caagttggac    3360
ttc                                                                 3363

<210> SEQ ID NO 35
<211> LENGTH: 1152
<212> TYPE: PRT
<213> ORGANISM: Artificial Sequence
<220> FEATURE:
<223> OTHER INFORMATION: Synthetic, engineered or hybrid sequence

<400> SEQUENCE: 35

Met Gly Ala Pro Lys Lys Lys Arg Lys Val Gly Ile His Gly Val Pro
1               5                   10                  15

Ala Ala Ser Asp Leu Val Leu Gly Leu Asp Ile Gly Ile Gly Ser Val
            20                  25                  30

Gly Val Gly Ile Leu Asn Lys Val Thr Gly Glu Ile Ile His Lys Asn
        35                  40                  45

Ser Arg Ile Phe Pro Ala Ala Gln Ala Glu Asn Asn Leu Val Arg Arg
    50                  55                  60

Thr Asn Arg Gln Gly Arg Arg Leu Ala Arg Lys Lys His Arg Arg
65                  70                  75                  80

Val Arg Leu Asn Arg Leu Phe Glu Glu Ser Gly Leu Ile Thr Asp Phe
                85                  90                  95

Thr Lys Ile Ser Ile Asn Leu Asn Pro Tyr Gln Leu Arg Val Lys Gly
            100                 105                 110

Leu Thr Asp Glu Leu Ser Asn Glu Glu Leu Phe Ile Ala Leu Lys Asn
        115                 120                 125

Met Val Lys His Arg Gly Ile Ser Tyr Leu Asp Asp Ala Ser Asp Asp
    130                 135                 140

Gly Asn Ser Ser Val Gly Asp Tyr Ala Gln Ile Val Lys Glu Asn Ser
145                 150                 155                 160

Lys Gln Leu Glu Thr Lys Thr Pro Gly Gln Ile Gln Leu Glu Arg Tyr
                165                 170                 175

Gln Thr Tyr Gly Gln Leu Arg Gly Asp Phe Thr Val Glu Lys Asp Gly
            180                 185                 190
```

```
Lys Lys His Arg Leu Ile Asn Val Phe Pro Thr Ser Ala Tyr Arg Ser
        195                 200                 205

Glu Ala Leu Arg Ile Leu Gln Thr Gln Gln Glu Phe Asn Pro Gln Ile
        210                 215                 220

Thr Asp Glu Phe Ile Asn Arg Tyr Leu Glu Ile Leu Thr Gly Lys Arg
225                 230                 235                 240

Lys Tyr Tyr His Gly Pro Gly Asn Glu Lys Ser Arg Thr Asp Tyr Gly
        245                 250                 255

Arg Tyr Arg Thr Ser Gly Glu Thr Leu Asp Asn Ile Phe Gly Ile Leu
        260                 265                 270

Ile Gly Lys Cys Thr Phe Tyr Pro Asp Glu Phe Arg Ala Ala Lys Ala
        275                 280                 285

Ser Tyr Thr Ala Gln Glu Phe Asn Leu Leu Asn Asp Leu Asn Asn Leu
        290                 295                 300

Thr Val Pro Thr Glu Thr Lys Lys Leu Ser Lys Glu Gln Lys Asn Gln
305                 310                 315                 320

Ile Ile Asn Tyr Val Lys Asn Glu Lys Ala Met Gly Pro Ala Lys Leu
                325                 330                 335

Phe Lys Tyr Ile Ala Lys Leu Leu Ser Cys Asp Val Ala Asp Ile Lys
                340                 345                 350

Gly Tyr Arg Ile Asp Lys Ser Gly Lys Ala Glu Ile His Thr Phe Glu
                355                 360                 365

Ala Tyr Arg Lys Met Lys Thr Leu Glu Thr Leu Asp Ile Glu Gln Met
        370                 375                 380

Asp Arg Glu Thr Leu Asp Lys Leu Ala Tyr Val Leu Thr Leu Asn Thr
385                 390                 395                 400

Glu Arg Glu Gly Ile Gln Glu Ala Leu Glu His Glu Phe Ala Asp Gly
                405                 410                 415

Ser Phe Ser Gln Lys Gln Val Asp Glu Leu Val Gln Phe Arg Lys Ala
                420                 425                 430

Asn Ser Ser Ile Phe Gly Lys Gly Trp His Asn Phe Ser Val Lys Leu
        435                 440                 445

Met Met Glu Leu Ile Pro Glu Leu Tyr Glu Thr Ser Glu Glu Gln Met
        450                 455                 460

Thr Ile Leu Thr Arg Leu Gly Lys Gln Lys Thr Thr Ser Ser Ser Asn
465                 470                 475                 480

Lys Thr Lys Tyr Ile Asp Glu Lys Leu Leu Thr Glu Glu Ile Tyr Asn
                485                 490                 495

Pro Val Val Ala Lys Ser Val Arg Gln Ala Ile Lys Ile Val Asn Ala
                500                 505                 510

Ala Ile Lys Glu Tyr Gly Asp Phe Asp Asn Ile Val Ile Glu Met Ala
        515                 520                 525

Arg Glu Thr Asn Glu Asp Asp Glu Lys Lys Ala Ile Gln Lys Ile Gln
        530                 535                 540

Lys Ala Asn Lys Asp Glu Lys Asp Ala Ala Met Leu Lys Ala Ala Asn
545                 550                 555                 560

Gln Tyr Asn Gly Lys Ala Glu Leu Pro His Ser Val Phe His Gly His
                565                 570                 575

Lys Gln Leu Ala Thr Lys Ile Arg Leu Trp His Gln Gly Glu Arg
                580                 585                 590

Cys Leu Tyr Thr Gly Lys Thr Ile Ser Ile His Asp Leu Ile Asn Asn
        595                 600                 605
```

```
Ser Asn Gln Phe Glu Val Asp His Ile Leu Pro Leu Ser Ile Thr Phe
    610                 615                 620

Asp Asp Ser Leu Ala Asn Lys Val Leu Val Tyr Ala Thr Ala Asn Gln
625                 630                 635                 640

Glu Lys Gly Gln Arg Thr Pro Tyr Gln Ala Leu Asp Ser Met Asp Asp
                645                 650                 655

Ala Trp Ser Phe Arg Glu Leu Lys Ala Phe Val Arg Glu Ser Lys Thr
            660                 665                 670

Leu Ser Asn Lys Lys Glu Tyr Leu Leu Thr Glu Asp Ile Ser
        675                 680                 685

Lys Phe Asp Val Arg Lys Phe Ile Glu Arg Asn Leu Val Asp Thr
690                 695                 700

Arg Tyr Ala Ser Arg Val Val Leu Asn Ala Leu Gln Glu His Phe Arg
705                 710                 715                 720

Ala His Lys Ile Asp Thr Lys Val Ser Val Val Arg Gly Gln Phe Thr
                725                 730                 735

Ser Gln Leu Arg Arg His Trp Gly Ile Glu Lys Thr Arg Asp Thr Tyr
            740                 745                 750

His His His Ala Val Asp Ala Leu Ile Ile Ala Ala Ser Ser Gln Leu
        755                 760                 765

Asn Leu Trp Lys Lys Gln Lys Asn Thr Leu Val Ser Tyr Ser Glu Glu
770                 775                 780

Gln Leu Leu Asp Ile Glu Thr Gly Glu Leu Ile Ser Asp Asp Glu Tyr
785                 790                 795                 800

Lys Glu Ser Val Phe Lys Ala Pro Tyr Gln His Phe Val Asp Thr Leu
                805                 810                 815

Lys Ser Lys Glu Phe Glu Asp Ser Ile Leu Phe Ser Tyr Gln Val Asp
            820                 825                 830

Ser Lys Phe Asn Arg Lys Ile Ser Asp Ala Thr Ile Tyr Ala Thr Arg
        835                 840                 845

Gln Ala Lys Val Gly Lys Asp Lys Lys Asp Thr Tyr Val Leu Gly
850                 855                 860

Lys Ile Lys Asp Ile Tyr Thr Gln Asp Gly Tyr Asp Ala Phe Met Lys
865                 870                 875                 880

Ile Tyr Lys Lys Asp Lys Ser Lys Phe Leu Met Tyr Arg His Asp Pro
                885                 890                 895

Gln Thr Phe Glu Lys Val Ile Glu Pro Ile Leu Glu Asn Tyr Pro Asn
            900                 905                 910

Lys Gln Met Asn Glu Lys Gly Lys Glu Val Pro Cys Asn Pro Phe Leu
        915                 920                 925

Lys Tyr Lys Glu Glu His Gly Tyr Ile Arg Lys Tyr Ser Lys Lys Gly
930                 935                 940

Asn Gly Pro Glu Ile Lys Ser Leu Lys Tyr Tyr Asp Ser Lys Leu Leu
945                 950                 955                 960

Gly Asn Pro Ile Asp Ile Thr Pro Glu Asn Ser Lys Asn Lys Val Val
                965                 970                 975

Leu Gln Ser Leu Lys Pro Trp Arg Thr Asp Val Tyr Phe Asn Lys Asn
            980                 985                 990

Thr Gly Lys Tyr Glu Ile Leu Gly Leu Lys Tyr Ala Asp Leu Gln Phe
        995                 1000                1005

Glu Lys Lys Thr Gly Thr Tyr Lys Ile Ser Gln Glu Lys Tyr Asn
    1010                1015                1020

Gly Ile Met Lys Glu Glu Gly Val Asp Ser Asp Ser Glu Phe Lys
```

```
                1025                1030                1035

Phe Thr Leu Tyr Lys Asn Asp Leu Leu Leu Val Lys Asp Thr Glu
        1040                1045                1050

Thr Lys Glu Gln Gln Leu Phe Arg Phe Leu Ser Arg Thr Met Pro
    1055                1060                1065

Asn Val Lys Tyr Tyr Val Glu Leu Lys Pro Tyr Ser Lys Asp Lys
        1070                1075                1080

Phe Glu Lys Asn Glu Ser Leu Ile Glu Ile Leu Gly Ser Ala Asp
        1085                1090                1095

Lys Ser Gly Arg Cys Ile Lys Gly Leu Gly Lys Ser Asn Ile Ser
        1100                1105                1110

Ile Tyr Lys Val Arg Thr Asp Val Leu Gly Asn Gln His Ile Ile
        1115                1120                1125

Lys Asn Glu Gly Asp Lys Pro Lys Leu Asp Phe Ser Arg Ala Asp
        1130                1135                1140

Pro Lys Lys Lys Arg Lys Val Gly Ser
    1145                1150

<210> SEQ ID NO 36
<211> LENGTH: 1121
<212> TYPE: PRT
<213> ORGANISM: Artificial Sequence
<220> FEATURE:
<223> OTHER INFORMATION: Synthetic, engineered or hybrid sequence

<400> SEQUENCE: 36

Ser Asp Leu Val Leu Gly Leu Asp Ile Gly Ile Gly Ser Val Gly
1               5                   10                  15

Gly Ile Leu Asn Lys Val Thr Gly Glu Ile Ile His Lys Asn Ser Arg
            20                  25                  30

Ile Phe Pro Ala Ala Gln Ala Glu Asn Asn Leu Val Arg Arg Thr Asn
        35                  40                  45

Arg Gln Gly Arg Arg Leu Ala Arg Arg Lys Lys His Arg Arg Val Arg
    50                  55                  60

Leu Asn Arg Leu Phe Glu Glu Ser Gly Leu Ile Thr Asp Phe Thr Lys
65                  70                  75                  80

Ile Ser Ile Asn Leu Asn Pro Tyr Gln Leu Arg Val Lys Gly Leu Thr
                85                  90                  95

Asp Glu Leu Ser Asn Glu Glu Leu Phe Ile Ala Leu Lys Asn Met Val
            100                 105                 110

Lys His Arg Gly Ile Ser Tyr Leu Asp Asp Ala Ser Asp Asp Gly Asn
        115                 120                 125

Ser Ser Val Gly Asp Tyr Ala Gln Ile Val Lys Glu Asn Ser Lys Gln
    130                 135                 140

Leu Glu Thr Lys Thr Pro Gly Gln Ile Gln Leu Glu Arg Tyr Gln Thr
145                 150                 155                 160

Tyr Gly Gln Leu Arg Gly Asp Phe Thr Val Glu Lys Asp Gly Lys Lys
                165                 170                 175

His Arg Leu Ile Asn Val Phe Pro Thr Ser Ala Tyr Arg Ser Glu Ala
            180                 185                 190

Leu Arg Ile Leu Gln Thr Gln Gln Glu Phe Asn Pro Gln Ile Thr Asp
        195                 200                 205

Glu Phe Ile Asn Arg Tyr Leu Glu Ile Leu Thr Gly Lys Arg Lys Tyr
        210                 215                 220

Tyr His Gly Pro Gly Asn Glu Lys Ser Arg Thr Asp Tyr Gly Arg Tyr
```

-continued

```
            225                 230                 235                 240
Arg Thr Ser Gly Glu Thr Leu Asp Asn Ile Phe Gly Ile Leu Ile Gly
                245                 250                 255
Lys Cys Thr Phe Tyr Pro Asp Glu Phe Arg Ala Ala Lys Ala Ser Tyr
                260                 265                 270
Thr Ala Gln Glu Phe Asn Leu Leu Asn Asp Leu Asn Asn Leu Thr Val
                275                 280                 285
Pro Thr Glu Thr Lys Lys Leu Ser Lys Glu Gln Lys Asn Gln Ile Ile
                290                 295                 300
Asn Tyr Val Lys Asn Glu Lys Ala Met Gly Pro Ala Lys Leu Phe Lys
305                 310                 315                 320
Tyr Ile Ala Lys Leu Leu Ser Cys Asp Val Ala Asp Ile Lys Gly Tyr
                325                 330                 335
Arg Ile Asp Lys Ser Gly Lys Ala Glu Ile His Thr Phe Glu Ala Tyr
                340                 345                 350
Arg Lys Met Lys Thr Leu Glu Thr Leu Asp Ile Glu Gln Met Asp Arg
                355                 360                 365
Glu Thr Leu Asp Lys Leu Ala Tyr Val Leu Thr Leu Asn Thr Glu Arg
                370                 375                 380
Glu Gly Ile Gln Glu Ala Leu Glu His Glu Phe Ala Asp Gly Ser Phe
385                 390                 395                 400
Ser Gln Lys Gln Val Asp Glu Leu Val Gln Phe Arg Lys Ala Asn Ser
                405                 410                 415
Ser Ile Phe Gly Lys Gly Trp His Asn Phe Ser Val Lys Leu Met Met
                420                 425                 430
Glu Leu Ile Pro Glu Leu Tyr Glu Thr Ser Glu Glu Gln Met Thr Ile
                435                 440                 445
Leu Thr Arg Leu Gly Lys Gln Lys Thr Thr Ser Ser Ser Asn Lys Thr
                450                 455                 460
Lys Tyr Ile Asp Glu Lys Leu Leu Thr Glu Glu Ile Tyr Asn Pro Val
465                 470                 475                 480
Val Ala Lys Ser Val Arg Gln Ala Ile Lys Ile Val Asn Ala Ala Ile
                485                 490                 495
Lys Glu Tyr Gly Asp Phe Asp Asn Ile Val Ile Glu Met Ala Arg Glu
                500                 505                 510
Thr Asn Glu Asp Asp Glu Lys Lys Ala Ile Gln Lys Ile Gln Lys Ala
                515                 520                 525
Asn Lys Asp Glu Lys Asp Ala Ala Met Leu Lys Ala Ala Asn Gln Tyr
                530                 535                 540
Asn Gly Lys Ala Glu Leu Pro His Ser Val Phe His Gly His Lys Gln
545                 550                 555                 560
Leu Ala Thr Lys Ile Arg Leu Trp His Gln Gln Gly Glu Arg Cys Leu
                565                 570                 575
Tyr Thr Gly Lys Thr Ile Ser Ile His Asp Leu Ile Asn Asn Ser Asn
                580                 585                 590
Gln Phe Glu Val Asp His Ile Leu Pro Leu Ser Ile Thr Phe Asp Asp
                595                 600                 605
Ser Leu Ala Asn Lys Val Leu Val Tyr Ala Thr Ala Asn Gln Glu Lys
                610                 615                 620
Gly Gln Arg Thr Pro Tyr Gln Ala Leu Asp Ser Met Asp Asp Ala Trp
625                 630                 635                 640
Ser Phe Arg Glu Leu Lys Ala Phe Val Arg Glu Ser Lys Thr Leu Ser
                645                 650                 655
```

```
Asn Lys Lys Lys Glu Tyr Leu Leu Thr Glu Glu Asp Ile Ser Lys Phe
        660             665             670

Asp Val Arg Lys Lys Phe Ile Glu Arg Asn Leu Val Asp Thr Arg Tyr
        675             680             685

Ala Ser Arg Val Val Leu Asn Ala Leu Gln Glu His Phe Arg Ala His
        690             695             700

Lys Ile Asp Thr Lys Val Ser Val Val Arg Gly Gln Phe Thr Ser Gln
705             710             715             720

Leu Arg Arg His Trp Gly Ile Glu Lys Thr Arg Asp Thr Tyr His His
                725             730             735

His Ala Val Asp Ala Leu Ile Ile Ala Ala Ser Ser Gln Leu Asn Leu
        740             745             750

Trp Lys Lys Gln Lys Asn Thr Leu Val Ser Tyr Ser Glu Glu Gln Leu
        755             760             765

Leu Asp Ile Glu Thr Gly Glu Leu Ile Ser Asp Glu Tyr Lys Glu
        770             775             780

Ser Val Phe Lys Ala Pro Tyr Gln His Phe Val Asp Thr Leu Lys Ser
785             790             795             800

Lys Glu Phe Glu Asp Ser Ile Leu Phe Ser Tyr Gln Val Asp Ser Lys
                805             810             815

Phe Asn Arg Lys Ile Ser Asp Ala Thr Ile Tyr Ala Thr Arg Gln Ala
        820             825             830

Lys Val Gly Lys Asp Lys Lys Asp Glu Thr Tyr Val Leu Gly Lys Ile
        835             840             845

Lys Asp Ile Tyr Thr Gln Asp Gly Tyr Asp Ala Phe Met Lys Ile Tyr
        850             855             860

Lys Lys Asp Lys Ser Lys Phe Leu Met Tyr Arg His Asp Pro Gln Thr
865             870             875             880

Phe Glu Lys Val Ile Glu Pro Ile Leu Glu Asn Tyr Pro Asn Lys Gln
                885             890             895

Met Asn Glu Lys Gly Lys Glu Val Pro Cys Asn Pro Phe Leu Lys Tyr
        900             905             910

Lys Glu Glu His Gly Tyr Ile Arg Lys Tyr Ser Lys Lys Gly Asn Gly
        915             920             925

Pro Glu Ile Lys Ser Leu Lys Tyr Tyr Asp Ser Lys Leu Leu Gly Asn
        930             935             940

Pro Ile Asp Ile Thr Pro Glu Asn Ser Lys Asn Lys Val Val Leu Gln
945             950             955             960

Ser Leu Lys Pro Trp Arg Thr Asp Val Tyr Phe Asn Lys Asn Thr Gly
                965             970             975

Lys Tyr Glu Ile Leu Gly Leu Lys Tyr Ala Asp Leu Gln Phe Glu Lys
        980             985             990

Lys Thr Gly Thr Tyr Lys Ile Ser  Gln Glu Lys Tyr Asn  Gly Ile Met
        995             1000             1005

Lys Glu  Glu Gly Val Asp Ser  Asp Ser Glu Phe Lys  Phe Thr Leu
        1010             1015             1020

Tyr Lys  Asn Asp Leu Leu Leu  Val Lys Asp Thr Glu  Thr Lys Glu
        1025             1030             1035

Gln Gln  Leu Phe Arg Phe Leu  Ser Arg Thr Met Pro  Asn Val Lys
        1040             1045             1050

Tyr Tyr  Val Glu Leu Lys Pro  Tyr Ser Lys Asp Lys  Phe Glu Lys
        1055             1060             1065
```

```
Asn Glu Ser Leu Ile Glu Ile Leu Gly Ser Ala Asp Lys Ser Gly
    1070            1075                1080

Arg Cys Ile Lys Gly Leu Gly Lys Ser Asn Ile Ser Ile Tyr Lys
    1085            1090                1095

Val Arg Thr Asp Val Leu Gly Asn Gln His Ile Ile Lys Asn Glu
    1100            1105                1110

Gly Asp Lys Pro Lys Leu Asp Phe
    1115            1120

<210> SEQ ID NO 37
<211> LENGTH: 3456
<212> TYPE: DNA
<213> ORGANISM: Artificial Sequence
<220> FEATURE:
<223> OTHER INFORMATION: Synthetic, engineered or hybrid sequence

<400> SEQUENCE: 37
```

| | |
|---|---:|
| atgggcgccc caaagaagaa gcggaaggtc ggtatccacg gagtcccagc agccagcgac | 60 |
| ctggtgctgg gcctggacat cggcatcggc agcgtgggcg tgggcatcct gaacaaggtg | 120 |
| accggcgaga tcatccacaa gaacagtcgc atcttccctg ctgctcaggc tgagaacaac | 180 |
| ctggtgcgcc gcaccaaccg ccagggtcgc cggcttgctc gccgcaagaa gcaccggcgc | 240 |
| gtgcgcctga ccgcctgtt cgaggagagc ggcctgatca ccgacttcac caagatcagc | 300 |
| atcaacctga cccctacca gctgcgcgtg aagggcctga ccgacgagct gagcaacgag | 360 |
| gagctgttca tcgccctgaa gaacatggtg aagcaccgcg gcatcagcta cctggacgac | 420 |
| gccagcgacg acggcaacag cagcgtgggc gactacgccc agatcgtgaa ggagaacagc | 480 |
| aagcagctgg agaccaagac ccccggccag atccagctgg agcgctacca gacctacggc | 540 |
| cagctgcgcg gcgacttcac cgtggagaag gacggcaaga gcaccgcct gatcaacgtg | 600 |
| ttccccacca gcgcctaccg cagcgaggcc ctgcgcatcc tgcagaccca gcaggagttc | 660 |
| aacccccaga tcaccgacga gttcatcaac cgctacctgg agatcctgac cggcaagcgc | 720 |
| aagtactacc acggccccgg caacgagaag agccgcaccg actacggccg ctaccgcacc | 780 |
| agcggcgaga ccctggacaa catcttcggc atcctgatcg gcaagtgcac cttctacccc | 840 |
| gacgagttcc gcgccgccaa ggccagctac accgcccagg agttcaatct gctgaacgac | 900 |
| ctgaacaacc tgaccgtgcc caccgagacc aagaagctga gcaaggagca gaagaaccag | 960 |
| atcatcaact acgtgaagaa cgagaaggct atgggccccg ccaagctgtt caagtacatc | 1020 |
| gccaagctgc tgagctgcga cgtggccgac atcaagggct accgcatcga caagagcggc | 1080 |
| aaggccgaga tccacacctt cgaggcctac cgcaagatga gaccctgga ccctggac | 1140 |
| atcgagcaga tggaccgaga gaccctggac aagctggcct acgtgctgac cctgaacacc | 1200 |
| gagcgcgagg gcatccagga ggccctggag cacgagttcg ccgacggcag cttcagccag | 1260 |
| aaacaggtgg acgagctggt gcagttccgc aaggccaaca gcagcatctt cggcaagggc | 1320 |
| tggcacaact tcagcgtgaa gctgatgatg gagctgatcc ccgagctgta cgagaccagc | 1380 |
| gaggagcaga tgaccatcct gacccgcctg ggcaagcaga gaccaccag cagcagcaac | 1440 |
| aagaccaagt acatcgacga gaagctgctg accgaggaga tctacaaccc cgtggtggcc | 1500 |
| aagagcgtgc gccaggccat caagatcgtg aacgccgcca tcaaggagta cggcgacttc | 1560 |
| gacaacatcg tgatcgagat ggcccgcgag accaacgagg acgacgagaa gaaggccatc | 1620 |
| cagaagatcc agaaggccaa caaggacgag aaggacgccg ccatgctgaa ggccgccaac | 1680 |
| cagtacaacg gcaaggccga gctgccccac agcgtgttcc acggccacaa gcagctggcc | 1740 |

```
accaagatcc gcctgtggca ccagcagggc gagcgctgcc tgtacaccgg caagaccatc    1800
agcatccacg acctgatcaa caacagcaac cagttcgagg tggaccacat cctgcccctg    1860
agcatcacct tcgacgacag cctggccaac aaggtgctgg tgtacgccac cgccaaccag    1920
gagaagggcc agcgcacccc ctaccaggcc ctggacagca tggacgacgc ctggagcttc    1980
cgcgagctga aggccttcgt gcgcgagagc aagaccctga gcaacaagaa gaaggagtat    2040
ctgctgaccg aggaggacat cagcaagttc gacgtgcgca agaagttcat cgagcgcaac    2100
ctggtggaca cccgctacgc cagccgcgtg gtgctgaacg ccctgcagga gcacttccgc    2160
gcccacaaga tcgacaccaa ggtgagcgtg gtgcgcggcc agttcaccag ccagctgcgc    2220
cgccactggg gcatcgagaa gacccgcgac acctaccacc accacgccgt ggacgccctg    2280
atcattgcgg cttctagcca gctgaacctg tggaagaagc agaagaacac cctggtgagc    2340
tacagcgagg agcagctgct ggacatcgag accggcgagc tgatcagcga cgacgagtac    2400
aaggagagcg tgttcaaggc cccctaccag cacttcgtgg acaccctgaa gagcaaggag    2460
ttcgaggaca gcatcctgtt cagctaccag gtggacagca gttcaaccg caagatcagc    2520 gacgccacca tctacgccac ccgccaggcc aaggtgggca aggacaagaa ggacgagacc    2580
tacgtgctgg gcaagatcaa ggacatctac acccaggacg gctacgacgc cttcatgaag    2640
atctacaaga aggacaagag caagttcctg atgtaccgcc acgacccca gaccttcgag    2700 aaggtgatcg agcccatcct ggagaactac cccaacaagc agatgaacga gaaaggcaag    2760
gaggtgccct gcaaccccctt cctgaagtac aaggaggagc acggctacat ccgcaagtac    2820
agcaagaagg gcaacggccc cgagatcaag agcctgaagt actacgacag caagctgctg    2880
ggcaacccca tcgacatcac ccccgaaaac agcaagaaca aggtggtgct gcagagcctt    2940
aagccctggc gcaccgacgt gtacttcaac aaggccaccg gcaagtacga gatcctgggg    3000
ctgaagtacg ccgatctgca gtttgagaaa ggcacaggca cctacaagat cagccaggag    3060
aagtacaacg acatcaagaa gaaggagggc gtggacagca cagcgagtt caagttcacc    3120 ctgtacaaga cgaccttct gctggtgaag gacaccgaga ccaaggagca acagctgttc    3180
cgcttcctga gccgcaccct gcccaagcag aagcactacg tggagctgaa gccctacgac    3240
aagcagaagt cgagggcgg cgaggccctg atcaaggtgc tgggcaacgt ggccaacggc    3300
ggccagtgca tcagggcct ggccaagagc aacatcagca tctacaaggt gcgcaccgac    3360
gtgctgggca ccagcacat catcaagaac gagggcgaca gcccaagtt ggacttcagc    3420 agggctgacc ccaagaagaa gaggaaggtg ggatcc                              3456
```

<210> SEQ ID NO 38
<211> LENGTH: 3363
<212> TYPE: DNA
<213> ORGANISM: Artificial Sequence
<220> FEATURE:
<223> OTHER INFORMATION: Synthetic, engineered or hybrid sequence

<400> SEQUENCE: 38

```
agcgacctgg tgctgggcct ggacatcggc atcggcagcg tgggcgtggg catcctgaac      60
aaggtgaccg cgagatcat ccacaagaac agtcgcatct ccctgctgc tcaggctgag     120 aacaacctgg tgcgccgcac caaccgccag ggtcgccggc ttgctcgccg caagaagcac     180
cggcgcgtgc gcctgaaccg cctgttcgag gagagcggcc tgatcaccga cttcaccaag     240
atcagcatca acctgaaccc ctaccagctg cgcgtgaagg gcctgaccga cgagctgagc     300
```

```
aacgaggagc tgttcatcgc cctgaagaac atggtgaagc accgcggcat cagctacctg    360
gacgacgcca gcgacgacgg caacagcagc gtgggcgact acgcccagat cgtgaaggag    420
aacagcaagc agctggagac caagaccccc ggccagatcc agctggagcg ctaccagacc    480 tacgccagc tgcgcggcga cttcaccgtg gagaaggacg gcaagaagca ccgcctgatc    540
aacgtgttcc ccaccagcgc ctaccgcagc gaggccctgc gcatcctgca gacccagcag    600
gagttcaacc cccagatcac cgacgagttc atcaaccgct acctggagat cctgaccggc    660
aagcgcaagt actaccacgg ccccggcaac gagaagagcc gcaccgacta cggccgctac    720
cgcaccagcg gcgagaccct ggacaacatc ttcggcatcc tgatcggcaa gtgcaccttc    780
taccccgacg agttccgcgc cgccaaggcc agctacaccg cccaggagtt caatctgctg    840
aacgacctga caacctgac cgtgcccacc gagaccaaga agctgagcaa ggagcagaag    900
aaccagatca tcaactacgt gaagaacgag aaggctatgg gccccgccaa gctgttcaag    960
tacatcgcca agctgctgag ctgcgacgtg gccgacatca agggctaccg catcgacaag   1020
agcggcaagg ccgagatcca caccttcgag gcctaccgca agatgaagac cctggagacc   1080
ctggacatcg agcagatgga ccgagagacc ctggacaagc tggcctacgt gctgacccetg   1140 aacaccgagc gcgagggcat ccaggaggcc ctggagcacg agttcgccga cggcagcttc   1200
agccagaaac aggtggacga gctggtgcag ttccgcaagg ccaacagcag catcttcggc   1260
aagggctggc acaacttcag cgtgaagctg atgatggagc tgatccccga gctgtacgag   1320
accagcgagg agcagatgac catcctgacc cgcctgggca gcagaagac caccagcagc   1380 agcaacaaga ccaagtacat cgacgagaag ctgctgaccg aggagatcta caaccccgtg   1440
gtggccaaga gcgtgcgcca ggccatcaag atcgtgaacg ccgccatcaa ggagtacggc   1500
gacttcgaca catcgtgat cgagatggcc cgcgagacca acgaggacga cgagaagaag   1560
gccatccaga agatccagaa ggccaacaag gacgagaagg acgccgccat gctgaaggcc   1620
gccaaccagt acaacggcaa ggccgagctg ccccacagcg tgttccacgg ccacaagcag   1680
ctggccacca agatccgcct gtggcaccag cagggcgagc gctgcctgta caccggcaag   1740
accatcagca tccacgacct gatcaacaac agcaaccagt cgaggtgga ccacatcctg   1800 cccctgagca tcaccttcga cgacagcctg gccaacaagg tgctggtgta cgccaccgcc   1860
aaccaggaga agggccagcg cacccctac caggccctgg acagcatgga cgacgcctgg   1920
agcttccgcg agctgaaggc cttcgtgcgc gagagcaaga ccctgagcaa caagaagaag   1980
gagtatctgc tgaccgagga ggacatcagc aagttcgacg tgcgcaagaa gttcatcgag   2040
cgcaacctgg tggacacccg ctacgccagc cgcgtggtgc tgaacgccct gcaggagcac   2100
ttccgcgccc acaagatcga caccaaggtg agcgtggtgc gcggccagtt caccagccag   2160
ctgcgccgcc actggggcat cgagaagacc cgcgacacct accaccacca cgccgtggac   2220
gccctgatca ttgcggcttc tagccagctg aacctgtgga gaagcagaa gaacaccctg   2280 gtgagctaca gcgaggagca gctgctggac atcgagaccg cgagctgat cagcgacgac   2340 gagtacaagg agagcgtgtt caaggccccc taccagcact cgtggacac cctgaagagc   2400 aaggagttcg aggacagcat cctgttcagc taccaggtgg acagcaagtt caaccgcaag   2460
atcagcgacg ccaccatcta cgccacccgc caggccaagg tgggcaagga caagaaggac   2520
gagacctacg tgctgggcaa gatcaaggac atctacaccc aggacggcta cgacgccttc   2580
atgaagatct acaagaagga caagagcaag ttcctgatgt accgccacga cccccagacc   2640
ttcgagaagg tgatcgagcc catcctggag aactacccca caagcagat gaacgagaaa   2700
```

-continued

```
ggcaaggagg tgccctgcaa ccccttcctg aagtacaagg aggagcacgg ctacatccgc    2760
aagtacagca agaagggcaa cggccccgag atcaagagcc tgaagtacta cgacagcaag    2820
ctgctgggca accccatcga catcaccccc gaaaacagca gaacaaggt ggtgctgcag     2880 agccttaagc cctggcgcac cgacgtgtac ttcaacaagg ccaccggcaa gtacgagatc    2940
ctggggctga agtacgccga tctgcagttt gagaaaggca caggcaccta caagatcagc    3000
caggagaagt acaacgacat caagaagaag gagggcgtgg acagcgacag cgagttcaag    3060
ttcaccctgt acaagaacga ccttctgctg gtgaaggaca ccgagaccaa ggagcaacag    3120
ctgttccgct tcctgagccg caccctgccc aagcagaagc actacgtgga gctgaagccc    3180
tacgacaagc agaagttcga gggcggcgag gccctgatca aggtgctggg caacgtggcc    3240
aacggcggcc agtgcatcaa gggcctggcc aagagcaaca tcagcatcta aggtgcgc     3300 accgacgtgc tgggcaacca gcacatcatc aagaacgagg cgacaagcc caagttggac    3360 ttc                                                                  3363
```

<210> SEQ ID NO 39
<211> LENGTH: 1152
<212> TYPE: PRT
<213> ORGANISM: Artificial Sequence
<220> FEATURE:
<223> OTHER INFORMATION: Synthetic, engineered or hybrid sequence

<400> SEQUENCE: 39

```
Met Gly Ala Pro Lys Lys Arg Lys Val Gly Ile His Gly Val Pro
1               5                   10                  15

Ala Ala Ser Asp Leu Val Leu Gly Leu Asp Ile Gly Ile Gly Ser Val
                20                  25                  30

Gly Val Gly Ile Leu Asn Lys Val Thr Gly Glu Ile Ile His Lys Asn
            35                  40                  45

Ser Arg Ile Phe Pro Ala Ala Gln Ala Glu Asn Asn Leu Val Arg Arg
        50                  55                  60

Thr Asn Arg Gln Gly Arg Arg Leu Ala Arg Lys Lys His Arg Arg
65                  70                  75              80

Val Arg Leu Asn Arg Leu Phe Glu Glu Ser Gly Leu Ile Thr Asp Phe
                85                  90                  95

Thr Lys Ile Ser Ile Asn Leu Asn Pro Tyr Gln Leu Arg Val Lys Gly
            100                 105                 110

Leu Thr Asp Glu Leu Ser Asn Glu Glu Leu Phe Ile Ala Leu Lys Asn
        115                 120                 125

Met Val Lys His Arg Gly Ile Ser Tyr Leu Asp Asp Ala Ser Asp Asp
    130                 135                 140

Gly Asn Ser Ser Val Gly Asp Tyr Ala Gln Ile Val Lys Glu Asn Ser
145                 150                 155             160

Lys Gln Leu Glu Thr Lys Thr Pro Gly Gln Ile Gln Leu Glu Arg Tyr
                165                 170                 175

Gln Thr Tyr Gly Gln Leu Arg Gly Asp Phe Thr Val Glu Lys Asp Gly
            180                 185                 190

Lys Lys His Arg Leu Ile Asn Val Phe Pro Thr Ser Ala Tyr Arg Ser
        195                 200                 205

Glu Ala Leu Arg Ile Leu Gln Thr Gln Gln Glu Phe Asn Pro Gln Ile
    210                 215                 220

Thr Asp Glu Phe Ile Asn Arg Tyr Leu Glu Ile Leu Thr Gly Lys Arg
225                 230                 235             240
```

-continued

Lys Tyr Tyr His Gly Pro Gly Asn Glu Lys Ser Arg Thr Asp Tyr Gly
                245                 250                 255

Arg Tyr Arg Thr Ser Gly Glu Thr Leu Asp Asn Ile Phe Gly Ile Leu
            260                 265                 270

Ile Gly Lys Cys Thr Phe Tyr Pro Asp Glu Phe Arg Ala Ala Lys Ala
            275                 280                 285

Ser Tyr Thr Ala Gln Glu Phe Asn Leu Leu Asn Asp Leu Asn Asn Leu
        290                 295                 300

Thr Val Pro Thr Glu Thr Lys Lys Leu Ser Lys Glu Gln Lys Asn Gln
305                 310                 315                 320

Ile Ile Asn Tyr Val Lys Asn Glu Lys Ala Met Gly Pro Ala Lys Leu
                325                 330                 335

Phe Lys Tyr Ile Ala Lys Leu Leu Ser Cys Asp Val Ala Asp Ile Lys
                340                 345                 350

Gly Tyr Arg Ile Asp Lys Ser Gly Lys Ala Glu Ile His Thr Phe Glu
            355                 360                 365

Ala Tyr Arg Lys Met Lys Thr Leu Glu Thr Leu Asp Ile Glu Gln Met
        370                 375                 380

Asp Arg Glu Thr Leu Asp Lys Leu Ala Tyr Val Leu Thr Leu Asn Thr
385                 390                 395                 400

Glu Arg Glu Gly Ile Gln Glu Ala Leu Glu His Glu Phe Ala Asp Gly
                405                 410                 415

Ser Phe Ser Gln Lys Gln Val Asp Glu Leu Val Gln Phe Arg Lys Ala
            420                 425                 430

Asn Ser Ser Ile Phe Gly Lys Gly Trp His Asn Phe Ser Val Lys Leu
            435                 440                 445

Met Met Glu Leu Ile Pro Glu Leu Tyr Glu Thr Ser Glu Glu Gln Met
450                 455                 460

Thr Ile Leu Thr Arg Leu Gly Lys Gln Lys Thr Thr Ser Ser Ser Asn
465                 470                 475                 480

Lys Thr Lys Tyr Ile Asp Glu Lys Leu Leu Thr Glu Glu Ile Tyr Asn
                485                 490                 495

Pro Val Val Ala Lys Ser Val Arg Gln Ala Ile Lys Ile Val Asn Ala
            500                 505                 510

Ala Ile Lys Glu Tyr Gly Asp Phe Asp Asn Ile Val Ile Glu Met Ala
        515                 520                 525

Arg Glu Thr Asn Glu Asp Asp Glu Lys Lys Ala Ile Gln Lys Ile Gln
530                 535                 540

Lys Ala Asn Lys Asp Glu Lys Asp Ala Ala Met Leu Lys Ala Ala Asn
545                 550                 555                 560

Gln Tyr Asn Gly Lys Ala Glu Leu Pro His Ser Val Phe His Gly His
                565                 570                 575

Lys Gln Leu Ala Thr Lys Ile Arg Leu Trp His Gln Gly Glu Arg
                580                 585                 590

Cys Leu Tyr Thr Gly Lys Thr Ile Ser Ile His Asp Leu Ile Asn Asn
        595                 600                 605

Ser Asn Gln Phe Glu Val Asp His Ile Leu Pro Leu Ser Ile Thr Phe
610                 615                 620

Asp Asp Ser Leu Ala Asn Lys Val Leu Val Tyr Ala Thr Ala Asn Gln
625                 630                 635                 640

Glu Lys Gly Gln Arg Thr Pro Tyr Gln Ala Leu Asp Ser Met Asp Asp
                645                 650                 655

-continued

```
Ala Trp Ser Phe Arg Glu Leu Lys Ala Phe Val Arg Glu Ser Lys Thr
            660                 665                 670

Leu Ser Asn Lys Lys Glu Tyr Leu Leu Thr Glu Glu Asp Ile Ser
        675                 680                 685

Lys Phe Asp Val Arg Lys Phe Ile Glu Arg Asn Leu Val Asp Thr
    690                 695                 700

Arg Tyr Ala Ser Arg Val Val Leu Asn Ala Leu Gln Glu His Phe Arg
705                 710                 715                 720

Ala His Lys Ile Asp Thr Lys Val Ser Val Arg Gly Gln Phe Thr
            725                 730                 735

Ser Gln Leu Arg Arg His Trp Gly Ile Glu Lys Thr Arg Asp Thr Tyr
        740                 745                 750

His His His Ala Val Asp Ala Leu Ile Ile Ala Ala Ser Ser Gln Leu
    755                 760                 765

Asn Leu Trp Lys Lys Gln Lys Asn Thr Leu Val Ser Tyr Ser Glu Glu
        770                 775                 780

Gln Leu Leu Asp Ile Glu Thr Gly Glu Leu Ile Ser Asp Asp Glu Tyr
785                 790                 795                 800

Lys Glu Ser Val Phe Lys Ala Pro Tyr Gln His Phe Val Asp Thr Leu
            805                 810                 815

Lys Ser Lys Glu Phe Glu Asp Ser Ile Leu Phe Ser Tyr Gln Val Asp
        820                 825                 830

Ser Lys Phe Asn Arg Lys Ile Ser Asp Ala Thr Ile Tyr Ala Thr Arg
    835                 840                 845

Gln Ala Lys Val Gly Lys Asp Lys Lys Asp Glu Thr Tyr Val Leu Gly
        850                 855                 860

Lys Ile Lys Asp Ile Tyr Thr Gln Asp Gly Tyr Asp Ala Phe Met Lys
865                 870                 875                 880

Ile Tyr Lys Lys Asp Lys Ser Lys Phe Leu Met Tyr Arg His Asp Pro
            885                 890                 895

Gln Thr Phe Glu Lys Val Ile Glu Pro Ile Leu Glu Asn Tyr Pro Asn
        900                 905                 910

Lys Gln Met Asn Glu Lys Gly Lys Glu Val Pro Cys Asn Pro Phe Leu
    915                 920                 925

Lys Tyr Lys Glu Glu His Gly Tyr Ile Arg Lys Tyr Ser Lys Lys Gly
        930                 935                 940

Asn Gly Pro Glu Ile Lys Ser Leu Lys Tyr Tyr Asp Ser Lys Leu Leu
945                 950                 955                 960

Gly Asn Pro Ile Asp Ile Thr Pro Glu Asn Ser Lys Asn Lys Val Val
            965                 970                 975

Leu Gln Ser Leu Lys Pro Trp Arg Thr Asp Val Tyr Phe Asn Lys Ala
        980                 985                 990

Thr Gly Lys Tyr Glu Ile Leu Gly Leu Lys Tyr Ala Asp Leu Gln Phe
    995                 1000                 1005

Glu Lys Gly Thr Gly Thr Tyr Lys Ile Ser Gln Glu Lys Tyr Asn
    1010                 1015                 1020

Asp Ile Lys Lys Lys Glu Gly Val Asp Ser Asp Ser Glu Phe Lys
    1025                 1030                 1035

Phe Thr Leu Tyr Lys Asn Asp Leu Leu Leu Val Lys Asp Thr Glu
    1040                 1045                 1050

Thr Lys Glu Gln Gln Leu Phe Arg Phe Leu Ser Arg Thr Leu Pro
    1055                 1060                 1065

Lys Gln Lys His Tyr Val Glu Leu Lys Pro Tyr Asp Lys Gln Lys
```

```
                    1070                1075                1080

Phe Glu Gly Gly Glu Ala Leu Ile Lys Val Leu Gly Asn Val Ala
    1085                1090                1095

Asn Gly Gly Gln Cys Ile Lys Gly Leu Ala Lys Ser Asn Ile Ser
    1100                1105                1110

Ile Tyr Lys Val Arg Thr Asp Val Leu Gly Asn Gln His Ile Ile
    1115                1120                1125

Lys Asn Glu Gly Asp Lys Pro Lys Leu Asp Phe Ser Arg Ala Asp
    1130                1135                1140

Pro Lys Lys Lys Arg Lys Val Gly Ser
    1145                1150

<210> SEQ ID NO 40
<211> LENGTH: 1121
<212> TYPE: PRT
<213> ORGANISM: Artificial Sequence
<220> FEATURE:
<223> OTHER INFORMATION: Synthetic, engineered or hybrid sequence

<400> SEQUENCE: 40

Ser Asp Leu Val Leu Gly Leu Asp Ile Gly Ile Gly Ser Val Gly Val
1               5                   10                  15

Gly Ile Leu Asn Lys Val Thr Gly Glu Ile Ile His Lys Asn Ser Arg
                20                  25                  30

Ile Phe Pro Ala Ala Gln Ala Glu Asn Asn Leu Val Arg Arg Thr Asn
            35                  40                  45

Arg Gln Gly Arg Arg Leu Ala Arg Arg Lys Lys His Arg Arg Val Arg
        50                  55                  60

Leu Asn Arg Leu Phe Glu Glu Ser Gly Leu Ile Thr Asp Phe Thr Lys
65                  70                  75                  80

Ile Ser Ile Asn Leu Asn Pro Tyr Gln Leu Arg Val Lys Gly Leu Thr
                85                  90                  95

Asp Glu Leu Ser Asn Glu Glu Leu Phe Ile Ala Leu Lys Asn Met Val
            100                 105                 110

Lys His Arg Gly Ile Ser Tyr Leu Asp Asp Ala Ser Asp Asp Gly Asn
        115                 120                 125

Ser Ser Val Gly Asp Tyr Ala Gln Ile Val Lys Glu Asn Ser Lys Gln
    130                 135                 140

Leu Glu Thr Lys Thr Pro Gly Gln Ile Gln Leu Glu Arg Tyr Gln Thr
145                 150                 155                 160

Tyr Gly Gln Leu Arg Gly Asp Phe Thr Val Glu Lys Asp Gly Lys Lys
                165                 170                 175

His Arg Leu Ile Asn Val Phe Pro Thr Ser Ala Tyr Arg Ser Glu Ala
            180                 185                 190

Leu Arg Ile Leu Gln Thr Gln Gln Glu Phe Asn Pro Gln Ile Thr Asp
        195                 200                 205

Glu Phe Ile Asn Arg Tyr Leu Glu Ile Leu Thr Gly Lys Arg Lys Tyr
    210                 215                 220

Tyr His Gly Pro Gly Asn Glu Lys Ser Arg Thr Asp Tyr Gly Arg Tyr
225                 230                 235                 240

Arg Thr Ser Gly Glu Thr Leu Asp Asn Ile Phe Gly Ile Leu Ile Gly
                245                 250                 255

Lys Cys Thr Phe Tyr Pro Asp Glu Phe Arg Ala Ala Lys Ala Ser Tyr
            260                 265                 270

Thr Ala Gln Glu Phe Asn Leu Leu Asn Asp Leu Asn Asn Leu Thr Val
```

-continued

```
            275                 280                 285
Pro Thr Glu Thr Lys Lys Leu Ser Lys Glu Gln Lys Asn Gln Ile Ile
290                 295                 300
Asn Tyr Val Lys Asn Glu Lys Ala Met Gly Pro Ala Lys Leu Phe Lys
305                 310                 315                 320
Tyr Ile Ala Lys Leu Leu Ser Cys Asp Val Ala Asp Ile Lys Gly Tyr
            325                 330                 335
Arg Ile Asp Lys Ser Gly Lys Ala Glu Ile His Thr Phe Glu Ala Tyr
            340                 345                 350
Arg Lys Met Lys Thr Leu Glu Thr Leu Asp Ile Glu Gln Met Asp Arg
            355                 360                 365
Glu Thr Leu Asp Lys Leu Ala Tyr Val Leu Thr Leu Asn Thr Glu Arg
            370                 375                 380
Glu Gly Ile Gln Glu Ala Leu Glu His Glu Phe Ala Asp Gly Ser Phe
385                 390                 395                 400
Ser Gln Lys Gln Val Asp Glu Leu Val Gln Phe Arg Lys Ala Asn Ser
            405                 410                 415
Ser Ile Phe Gly Lys Gly Trp His Asn Phe Ser Val Lys Leu Met Met
            420                 425                 430
Glu Leu Ile Pro Glu Leu Tyr Glu Thr Ser Glu Gln Met Thr Ile
            435                 440                 445
Leu Thr Arg Leu Gly Lys Gln Lys Thr Thr Ser Ser Asn Lys Thr
450                 455                 460
Lys Tyr Ile Asp Glu Lys Leu Leu Thr Glu Glu Ile Tyr Asn Pro Val
465                 470                 475                 480
Val Ala Lys Ser Val Arg Gln Ala Ile Lys Ile Val Asn Ala Ile
            485                 490                 495
Lys Glu Tyr Gly Asp Phe Asp Asn Ile Val Ile Glu Met Ala Arg Glu
            500                 505                 510
Thr Asn Glu Asp Asp Glu Lys Lys Ala Ile Gln Lys Ile Gln Lys Ala
            515                 520                 525
Asn Lys Asp Glu Lys Asp Ala Ala Met Leu Lys Ala Ala Asn Gln Tyr
530                 535                 540
Asn Gly Lys Ala Glu Leu Pro His Ser Val Phe His Gly His Lys Gln
545                 550                 555                 560
Leu Ala Thr Lys Ile Arg Leu Trp His Gln Gln Gly Glu Arg Cys Leu
            565                 570                 575
Tyr Thr Gly Lys Thr Ile Ser Ile His Asp Leu Ile Asn Asn Ser Asn
            580                 585                 590
Gln Phe Glu Val Asp His Ile Leu Pro Leu Ser Ile Thr Phe Asp Asp
            595                 600                 605
Ser Leu Ala Asn Lys Val Leu Val Tyr Ala Thr Ala Asn Gln Glu Lys
            610                 615                 620
Gly Gln Arg Thr Pro Tyr Gln Ala Leu Asp Ser Met Asp Asp Ala Trp
625                 630                 635                 640
Ser Phe Arg Glu Leu Lys Ala Phe Val Arg Glu Ser Lys Thr Leu Ser
            645                 650                 655
Asn Lys Lys Lys Glu Tyr Leu Leu Thr Glu Glu Asp Ile Ser Lys Phe
            660                 665                 670
Asp Val Arg Lys Lys Phe Ile Glu Arg Asn Leu Val Asp Thr Arg Tyr
            675                 680                 685
Ala Ser Arg Val Val Leu Asn Ala Leu Gln Glu His Phe Arg Ala His
            690                 695                 700
```

```
Lys Ile Asp Thr Lys Val Ser Val Val Arg Gly Gln Phe Thr Ser Gln
705                 710                 715                 720

Leu Arg Arg His Trp Gly Ile Glu Lys Thr Arg Asp Thr Tyr His His
            725                 730                 735

His Ala Val Asp Ala Leu Ile Ile Ala Ala Ser Ser Gln Leu Asn Leu
        740                 745                 750

Trp Lys Lys Gln Lys Asn Thr Leu Val Ser Tyr Ser Glu Glu Gln Leu
            755                 760                 765

Leu Asp Ile Glu Thr Gly Glu Leu Ile Ser Asp Glu Tyr Lys Glu
770                 775                 780

Ser Val Phe Lys Ala Pro Tyr Gln His Phe Val Asp Thr Leu Lys Ser
785                 790                 795                 800

Lys Glu Phe Glu Asp Ser Ile Leu Phe Ser Tyr Gln Val Asp Ser Lys
                805                 810                 815

Phe Asn Arg Lys Ile Ser Asp Ala Thr Ile Tyr Ala Thr Arg Gln Ala
            820                 825                 830

Lys Val Gly Lys Asp Lys Lys Asp Glu Thr Tyr Val Leu Gly Lys Ile
        835                 840                 845

Lys Asp Ile Tyr Thr Gln Asp Gly Tyr Asp Ala Phe Met Lys Ile Tyr
850                 855                 860

Lys Lys Asp Lys Ser Lys Phe Leu Met Tyr Arg His Asp Pro Gln Thr
865                 870                 875                 880

Phe Glu Lys Val Ile Glu Pro Ile Leu Glu Asn Tyr Pro Asn Lys Gln
                885                 890                 895

Met Asn Glu Lys Gly Lys Glu Val Pro Cys Asn Pro Phe Leu Lys Tyr
            900                 905                 910

Lys Glu Glu His Gly Tyr Ile Arg Lys Tyr Ser Lys Lys Gly Asn Gly
        915                 920                 925

Pro Glu Ile Lys Ser Leu Lys Tyr Tyr Asp Ser Lys Leu Leu Gly Asn
    930                 935                 940

Pro Ile Asp Ile Thr Pro Glu Asn Ser Lys Asn Lys Val Val Leu Gln
945                 950                 955                 960

Ser Leu Lys Pro Trp Arg Thr Asp Val Tyr Phe Asn Lys Ala Thr Gly
                965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser Gln Glu Lys Tyr Asn Asp Ile Lys
        995                 1000                1005

Lys Lys Glu Gly Val Asp Ser Asp Ser Glu Phe Lys Phe Thr Leu
    1010                1015                1020

Tyr Lys Asn Asp Leu Leu Val Lys Asp Thr Glu Thr Lys Glu
    1025                1030                1035

Gln Gln Leu Phe Arg Phe Leu Ser Arg Thr Leu Pro Lys Gln Lys
    1040                1045                1050

His Tyr Val Glu Leu Lys Pro Tyr Asp Lys Gln Lys Phe Glu Gly
    1055                1060                1065

Gly Glu Ala Leu Ile Lys Val Leu Gly Asn Val Ala Asn Gly Gly
    1070                1075                1080

Gln Cys Ile Lys Gly Leu Ala Lys Ser Asn Ile Ser Ile Tyr Lys
    1085                1090                1095

Val Arg Thr Asp Val Leu Gly Asn Gln His Ile Ile Lys Asn Glu
    1100                1105                1110
```

Gly Asp Lys Pro Lys Leu Asp Phe
   1115                1120

<210> SEQ ID NO 41
<211> LENGTH: 3450
<212> TYPE: DNA
<213> ORGANISM: Artificial Sequence
<220> FEATURE:
<223> OTHER INFORMATION: Synthetic, engineered or hybrid sequence

<400> SEQUENCE: 41

| | |
|---|---|
| atgggcgccc caaagaagaa gcggaaggtc ggtatccacg gagtcccagc agccagcgac | 60 |
| ctggtgctgg gcctggacat cggcatcggc agcgtgggcg tgggcatcct gaacaaggtg | 120 |
| accggcgaga tcatccacaa gaacagtcgc atcttccctg ctgctcaggc tgagaacaac | 180 |
| ctggtgcgcc gcaccaaccg ccagggtcgc cggcttgctc gccgcaagaa gcaccggcgc | 240 |
| gtgcgcctga accgctgttc gaggagagc ggcctgatca ccgacttcac caagatcagc | 300 |
| atcaacctga ccccctacca gctgcgcgtg aagggcctga ccgacgagct gagcaacgag | 360 |
| gagctgttca tcgccctgaa gaacatggtg aagcaccgcg gcatcagcta cctggacgac | 420 |
| gccagcgacg acggcaacag cagcgtgggc gactacgccc agatcgtgaa ggagaacagc | 480 |
| aagcagctgg agaccaagac ccccggccag atccagctgg agcgctacca gacctacggc | 540 |
| cagctgcgcg gcgacttcac cgtggagaag gacggcaaga agcaccgcct gatcaacgtg | 600 |
| ttccccacca gcgcctaccg cagcgaggcc ctgcgcatcc tgcagaccca gcaggagttc | 660 |
| aaccccaga tcaccgacga gttcatcaac cgctacctgg agatcctgac cggcaagcgc | 720 |
| aagtactacc acggccccgg caacgagaag agccgcaccg actacggccg ctaccgcacc | 780 |
| agcggcgaga ccctggacaa catcttcggc atcctgatcg gcaagtgcac cttctacccc | 840 |
| gacgagttcc gcgccgccaa ggccagctac accgcccagg agttcaatct gctgaacgac | 900 |
| ctgaacaacc tgaccgtgcc caccgagacc aagaagctga gcaaggagca agaagaaccag | 960 |
| atcatcaact acgtgaagaa cgagaaggct atgggccccg ccaagctgtt caagtacatc | 1020 |
| gccaagctgc tgagctgcga cgtggccgac atcaagggct accgcatcga caagagcggc | 1080 |
| aaggccgaga tccacaccct tcgaggccta cgcaagatga gaccctgga cccctggac | 1140 |
| atcgagcaga tggaccgaga gaccctggac aagctggcct acgtgctgac cctgaacacc | 1200 |
| gagcgcgagg gcatccagga ggccctggag cacgagttcg ccgacggcag cttcagccag | 1260 |
| aaacaggtgg acgagctggt gcagttccgc aaggccaaca gcagcatctt cggcaagggc | 1320 |
| tggcacaact tcagcgtgaa gctgatgatg gagctgatcc ccgagctgta cgagaccagc | 1380 |
| gaggagcaga tgaccatcct gacccgcctg ggcaagcaga agaccaccag cagcagcaac | 1440 |
| aagaccaagt acatcgacga agctgctgc accgaggaga tctacaaccc cgtggtggcc | 1500 |
| aagagcgtgc gccaggccat caagatcgtg aacgccgcca tcaaggagta cggcgacttc | 1560 |
| gacaacatcg tgatcgagat ggcccgcgag accaacgagg acgacgagaa gaaggccatc | 1620 |
| cagaagatcc agaaggccaa caaggacgag aaggacgccg ccatgctgaa ggccgccaac | 1680 |
| cagtacaacg gcaaggccga gctgccccac agcgtgttcc acggccacaa gcagctggcc | 1740 |
| accaagatcc gcctgtggca ccagcagggc gagcgctgcc tgtacaccgg caagaccatc | 1800 |
| agcatccacg acctgatcaa caacagcaac cagttcgagg tggaccacat cctgcccctg | 1860 |
| agcatcacct tcgacgacag cctggccaac aaggtgctgg tgtacgccac cgccaaccag | 1920 |
| gagaagggcc agcgcacccc ctaccaggcc ctggacagca tggacgacgc ctggagcttc | 1980 |

| | |
|---|---|
| cgcgagctga aggccttcgt gcgcgagagc aagaccctga gcaacaagaa gaaggagtat | 2040 |
| ctgctgaccg aggaggacat cagcaagttc gacgtgcgca agaagttcat cgagcgcaac | 2100 |
| ctggtggaca cccgctacgc cagccgcgtg gtgctgaacg ccctgcagga gcacttccgc | 2160 |
| gcccacaaga tcgacaccaa ggtgagcgtg gtgcgcggcc agttcaccag ccagctgcgc | 2220 |
| cgccactggg gcatcgagaa gacccgcgac acctaccacc accacgccgt ggacgccctg | 2280 |
| atcattgcgg cttctagcca gctgaacctg tggaagaagc agaagaacac cctggtgagc | 2340 |
| tacagcgagg accagctgct ggacatcgag accggcgagc tgatcagcga cgacgagtac | 2400 |
| aaggagagcg tgttcaaggc cccctaccag cacttcgtgg acaccctgaa gagcaaggag | 2460 |
| ttcgaggaca gcatcctgtt cagctaccag gtggacagca agttcaaccg caagatcagc | 2520 |
| gacgccacca tctacgccac ccgccaggcc aaggtgggca aggacaaggc cgacgagacc | 2580 |
| tacgtgctgg gcaagatcaa ggacatctac acccaggacg gctacgacgc cttcatgaag | 2640 |
| atctacaaga aggacaagag caagttcctg atgtaccgcc acgaccccca gaccttcgag | 2700 |
| aaggtgatcg agcccatcct ggagaactac cccaacaagc agatcaacga gaaaggcaag | 2760 |
| gaggtgccct gcaaccccct cctgaagtac aaggaggagc acggctacat ccgcaagtac | 2820 |
| agcaagaagg gcaacggccc cgagatcaag agcctgaagt actacgacag caagctgggc | 2880 |
| aaccacatcg acatcacccc caaggacagc aacaacaagg tggtgctgca gagcgtgagc | 2940 |
| ccctggcgcg ccgacgtgta cttcaacaag aacaccggca gtacgagat cctggggctg | 3000 |
| aagtacagcg atatgcagtt tgagaaaggc acaggcaagt acagcatcag caaggagcag | 3060 |
| tacgagaaca tcaaggtgcg cgagggcgtg gacgagaaca gcgagttcaa gttcaccctg | 3120 |
| tacaagaacg accttctgct gctgaaggac agcgagaacg gcgagcaaat cctgctgcgc | 3180 |
| ttcaccagcc gcaacgacac cagcaagcac tacgtgagc tgaagcccta caaccgccag | 3240 |
| aagttcgagg gcagcgagta cctgatcaag agcctgggca ccgtggtgaa gggcggcagg | 3300 |
| tgcatcaagg gcctgggcaa gagcaacatc agcatctaca aggtgcgcac cgacgtgctg | 3360 |
| ggcaaccagc acatcatcaa gaacgagggc gacaagccca gttggactt cagcagggct | 3420 |
| gaccccaaga agaagaggaa ggtgggatcc | 3450 |

<210> SEQ ID NO 42
<211> LENGTH: 3357
<212> TYPE: DNA
<213> ORGANISM: Artificial Sequence
<220> FEATURE:
<223> OTHER INFORMATION: Synthetic, engineered or hybrid sequence

<400> SEQUENCE: 42

| | |
|---|---|
| agcgacctgg tgctgggcct ggacatcggc atcggcagcg tgggcgtggg catcctgaac | 60 |
| aaggtgaccg gcgagatcat ccacaagaac agtcgcatct tccctgctgc tcaggctgag | 120 |
| aacaacctgg tgcgccgcac caaccgccag ggtcgccggc ttgctcgccg caagaagcac | 180 |
| cggcgcgtgc gcctgaaccg cctgttcgag gagagcggcc tgatcaccga cttcaccaag | 240 |
| atcagcatca acctgaaccc ctaccagctg cgcgtgaagg gcctgaccga cgagctgagc | 300 |
| aacgaggagc tgttcatcgc cctgaagaac atggtgaagc accgcggcat cagctacctg | 360 |
| gacgacgcca gcgacgacgg caacagcagc gtgggcgact acgcccagat cgtgaaggag | 420 |
| aacagcaagc agctggagac caagaccccc ggccagatcc agctggagcg ctaccagacc | 480 |
| tacgccagc tgcgcggcga cttcaccgtg gagaaggacg gcaagaagca ccgcctgatc | 540 |
| aacgtgttcc ccaccagcgc ctaccgcagc gaggccctgc gcatcctgca gacccagcag | 600 |

-continued

```
gagttcaacc cccagatcac cgacgagttc atcaaccgct acctggagat cctgaccggc    660
aagcgcaagt actaccacgg ccccggcaac gagaagagcc gcaccgacta cggccgctac    720
cgcaccagcg gcgagaccct ggacaacatc ttcggcatcc tgatcggcaa gtgcaccttc    780
taccccgacg agttccgcgc cgccaaggcc agctacaccg cccaggagtt caatctgctg    840
aacgacctga caacctgacc gtgcccaccc gagaccaaga agctgagcaa ggagcagaag    900
aaccagatca tcaactacgt gaagaacgag aaggctatgg ccccgccaa gctgttcaag     960 tacatcgcca agctgctgag ctgcgacgtg ccgacatca agggctaccg catcgacaag    1020
agcggcaagg ccgagatcca caccttcgag gcctaccgca agatgaagac cctggagacc    1080
ctggacatcg agcagatgga ccgagagacc ctggacaagc tggcctacgt gctgaccctg    1140
aacaccgagc gcgagggcat ccaggaggcc ctggagcacg agttcgccga cggcagcttc    1200
agccagaaac aggtggacga gctggtgcag ttccgcaagg ccaacagcag catcttcggc    1260
aagggctggc acaacttcag cgtgaagctg atgatggagc tgatccccga gctgtacgag    1320
accagcgagg agcagatgac catcctgacc cgcctgggca gcagaagac caccagcagc    1380 agcaacaaga ccaagtacat cgacgagaag ctgctgaccg aggagatcta aaccccgtg    1440 gtggccaaga gcgtgcgcca ggccatcaag atcgtgaacg ccgccatcaa ggagtacggc    1500
gacttcgaca acatcgtgat cgagatggcc cgcgagacca acgaggacga cgagaagaag    1560
gccatccaga agatccagaa ggccaacaag gacgagaagg acgccgccat gctgaaggcc    1620
gccaaccagt acaacggcaa ggccgagctg ccccacagcg tgttccacgg ccacaagcag    1680
ctggccacca agatccgcct gtggcaccag cagggcgagc gctgcctgta caccggcaag    1740
accatcagca tccacgacct gatcaacaac agcaaccagt cgaggtgga ccacatcctg     1800 cccctgagca tcaccttcga cgacagcctg gccaacaagg tgctggtgta cgccaccgcc    1860
aaccaggaga agggccagcg cacccccctac caggccctgg acagcatgga cgacgcctgg    1920
agcttccgcg agctgaaggc cttcgtgcgc gagagcaaga ccctgagcaa caagaagaag    1980
gagtatctgc tgaccgagga ggacatcagc aagttcgacg tgcgcaagaa gttcatcgag    2040
cgcaacctgg tggacacccg ctacgccagc cgcgtggtgc tgaacgccct gcaggagcac    2100
ttccgcgccc acaagatcga caccaaggtg agcgtggtgc gcggccagtt caccagccag    2160
ctgcgccgcc actggggcat cgagaagacc cgcgacacct accaccacca cgccgtggac    2220
gccctgatca ttgcggcttc tagccagctg aacctgtgga agaagcagaa gaacaccctg    2280
gtgagctaca gcgaggacca gctgctggac atcgagaccg cgagctgat cagcgacgac    2340 gagtacaagg agagcgtgtt caaggccccc taccagcact tcgtggacac cctgaagagc    2400
aaggagttcg aggacagcat cctgttcagc taccaggtgg acagcaagtt caaccgcaag    2460
atcagcgacg ccaccatcta cgccacccgc caggccaagg tgggcaagga caaggccgac    2520
gagacctacg tgctgggcaa gatcaaggac atctacaccc aggacggcta cgacgccttc    2580
atgaagatct acaagaagga caagagcaag ttcctgatgt accgccacga cccccagacc    2640
ttcgagaagg tgatcgagcc catcctggag aactacccca caagcagat caacgagaaa    2700 ggcaaggagg tgcctgcaa cccttcctg aagtacaagg aggagcacgg ctacatccgc      2760
aagtacagca agaagggcaa cggccccgag atcaagagcc tgaagtacta cgacagcaag    2820
ctgggcaacc acatcgacat caccccaag gacagcaaca caaggtggt gctgcagagc     2880 gtgagcccct ggcgcgccga cgtgtacttc aacaagaaca ccggcaagta cgagatcctg    2940
```

```
gggctgaagt acagcgatat gcagtttgag aaaggcacag gcaagtacag catcagcaag    3000
gagcagtacg agaacatcaa ggtgcgcgag ggcgtggacg agaacagcga gttcaagttc    3060
accctgtaca agaacgacct tctgctgctg aaggacagcg agaacggcga gcaaatcctg    3120
ctgcgcttca ccagccgcaa cgacaccagc aagcactacg tggagctgaa gccctacaac    3180
cgccagaagt tcgagggcag cgagtacctg atcaagagcc tgggcaccgt ggtgaagggc    3240
ggcaggtgca tcaagggcct gggcaagagc aacatcagca tctacaaggt gcgcaccgac    3300
gtgctgggca accagcacat catcaagaac gagggcgaca agcccaagtt ggacttc       3357
```

<210> SEQ ID NO 43
<211> LENGTH: 1150
<212> TYPE: PRT
<213> ORGANISM: Artificial Sequence
<220> FEATURE:
<223> OTHER INFORMATION: Synthetic, engineered or hybrid sequence

<400> SEQUENCE: 43

```
Met Gly Ala Pro Lys Lys Arg Lys Val Gly Ile His Gly Val Pro
1               5                   10                  15

Ala Ala Ser Asp Leu Val Leu Gly Leu Asp Ile Gly Ile Gly Ser Val
            20                  25                  30

Gly Val Gly Ile Leu Asn Lys Val Thr Gly Glu Ile Ile His Lys Asn
        35                  40                  45

Ser Arg Ile Phe Pro Ala Ala Gln Ala Glu Asn Asn Leu Val Arg Arg
    50                  55                  60

Thr Asn Arg Gln Gly Arg Arg Leu Ala Arg Lys Lys His Arg Arg
65                  70                  75                  80

Val Arg Leu Asn Arg Leu Phe Glu Glu Ser Gly Leu Ile Thr Asp Phe
                85                  90                  95

Thr Lys Ile Ser Ile Asn Leu Asn Pro Tyr Gln Leu Arg Val Lys Gly
            100                 105                 110

Leu Thr Asp Glu Leu Ser Asn Glu Glu Leu Phe Ile Ala Leu Lys Asn
        115                 120                 125

Met Val Lys His Arg Gly Ile Ser Tyr Leu Asp Asp Ala Ser Asp Asp
    130                 135                 140

Gly Asn Ser Ser Val Gly Asp Tyr Ala Gln Ile Val Lys Glu Asn Ser
145                 150                 155                 160

Lys Gln Leu Glu Thr Lys Thr Pro Gly Gln Ile Gln Leu Glu Arg Tyr
                165                 170                 175

Gln Thr Tyr Gly Gln Leu Arg Gly Asp Phe Thr Val Glu Lys Asp Gly
            180                 185                 190

Lys Lys His Arg Leu Ile Asn Val Phe Pro Thr Ser Ala Tyr Arg Ser
        195                 200                 205

Glu Ala Leu Arg Ile Leu Gln Thr Gln Gln Glu Phe Asn Pro Gln Ile
    210                 215                 220

Thr Asp Glu Phe Ile Asn Arg Tyr Leu Glu Ile Leu Thr Gly Lys Arg
225                 230                 235                 240

Lys Tyr Tyr His Gly Pro Gly Asn Glu Lys Ser Arg Thr Asp Tyr Gly
                245                 250                 255

Arg Tyr Arg Thr Ser Gly Glu Thr Leu Asp Asn Ile Phe Gly Ile Leu
            260                 265                 270

Ile Gly Lys Cys Thr Phe Tyr Pro Asp Glu Phe Arg Ala Ala Lys Ala
        275                 280                 285

Ser Tyr Thr Ala Gln Glu Phe Asn Leu Leu Asn Asp Leu Asn Asn Leu
```

```
                 290                 295                 300
Thr Val Pro Thr Glu Thr Lys Lys Leu Ser Lys Glu Gln Lys Asn Gln
305                 310                 315                 320

Ile Ile Asn Tyr Val Lys Asn Glu Lys Ala Met Gly Pro Ala Lys Leu
                325                 330                 335

Phe Lys Tyr Ile Ala Lys Leu Leu Ser Cys Asp Val Ala Asp Ile Lys
                340                 345                 350

Gly Tyr Arg Ile Asp Lys Ser Gly Lys Ala Glu Ile His Thr Phe Glu
                355                 360                 365

Ala Tyr Arg Lys Met Lys Thr Leu Glu Thr Leu Asp Ile Glu Gln Met
                370                 375                 380

Asp Arg Glu Thr Leu Asp Lys Leu Ala Tyr Val Leu Thr Leu Asn Thr
385                 390                 395                 400

Glu Arg Glu Gly Ile Gln Glu Ala Leu Glu His Glu Phe Ala Asp Gly
                405                 410                 415

Ser Phe Ser Gln Lys Gln Val Asp Glu Leu Val Gln Phe Arg Lys Ala
                420                 425                 430

Asn Ser Ser Ile Phe Gly Lys Gly Trp His Asn Phe Ser Val Lys Leu
                435                 440                 445

Met Met Glu Leu Ile Pro Glu Leu Tyr Glu Thr Ser Glu Glu Gln Met
                450                 455                 460

Thr Ile Leu Thr Arg Leu Gly Lys Gln Lys Thr Thr Ser Ser Ser Asn
465                 470                 475                 480

Lys Thr Lys Tyr Ile Asp Glu Lys Leu Leu Thr Glu Glu Ile Tyr Asn
                485                 490                 495

Pro Val Val Ala Lys Ser Val Arg Gln Ala Ile Lys Ile Val Asn Ala
                500                 505                 510

Ala Ile Lys Glu Tyr Gly Asp Phe Asp Asn Ile Val Ile Glu Met Ala
                515                 520                 525

Arg Glu Thr Asn Glu Asp Asp Glu Lys Lys Ala Ile Gln Lys Ile Gln
                530                 535                 540

Lys Ala Asn Lys Asp Glu Lys Asp Ala Ala Met Leu Lys Ala Ala Asn
545                 550                 555                 560

Gln Tyr Asn Gly Lys Ala Glu Leu Pro His Ser Val Phe His Gly His
                565                 570                 575

Lys Gln Leu Ala Thr Lys Ile Arg Leu Trp His Gln Gly Glu Arg
                580                 585                 590

Cys Leu Tyr Thr Gly Lys Thr Ile Ser Ile His Asp Leu Ile Asn Asn
                595                 600                 605

Ser Asn Gln Phe Glu Val Asp His Ile Leu Pro Leu Ser Ile Thr Phe
610                 615                 620

Asp Asp Ser Leu Ala Asn Lys Val Leu Val Tyr Ala Thr Ala Asn Gln
625                 630                 635                 640

Glu Lys Gly Gln Arg Thr Pro Tyr Gln Ala Leu Asp Ser Met Asp Asp
                645                 650                 655

Ala Trp Ser Phe Arg Glu Leu Lys Ala Phe Val Arg Glu Ser Lys Thr
                660                 665                 670

Leu Ser Asn Lys Lys Lys Glu Tyr Leu Leu Thr Glu Glu Asp Ile Ser
                675                 680                 685

Lys Phe Asp Val Arg Lys Lys Phe Ile Glu Arg Asn Leu Val Asp Thr
                690                 695                 700

Arg Tyr Ala Ser Arg Val Val Leu Asn Ala Leu Gln Glu His Phe Arg
705                 710                 715                 720
```

```
Ala His Lys Ile Asp Thr Lys Val Ser Val Arg Gly Gln Phe Thr
                725                 730                 735

Ser Gln Leu Arg Arg His Trp Gly Ile Glu Lys Thr Arg Asp Thr Tyr
            740                 745                 750

His His His Ala Val Asp Ala Leu Ile Ile Ala Ala Ser Ser Gln Leu
        755                 760                 765

Asn Leu Trp Lys Lys Gln Lys Asn Thr Leu Val Ser Tyr Ser Glu Asp
770                 775                 780

Gln Leu Leu Asp Ile Glu Thr Gly Glu Leu Ile Ser Asp Asp Glu Tyr
785                 790                 795                 800

Lys Glu Ser Val Phe Lys Ala Pro Tyr Gln His Phe Val Asp Thr Leu
                805                 810                 815

Lys Ser Lys Glu Phe Glu Asp Ser Ile Leu Phe Ser Tyr Gln Val Asp
            820                 825                 830

Ser Lys Phe Asn Arg Lys Ile Ser Asp Ala Thr Ile Tyr Ala Thr Arg
        835                 840                 845

Gln Ala Lys Val Gly Lys Asp Lys Ala Asp Glu Thr Tyr Val Leu Gly
    850                 855                 860

Lys Ile Lys Asp Ile Tyr Thr Gln Asp Gly Tyr Asp Ala Phe Met Lys
865                 870                 875                 880

Ile Tyr Lys Lys Asp Lys Ser Lys Phe Leu Met Tyr Arg His Asp Pro
                885                 890                 895

Gln Thr Phe Glu Lys Val Ile Glu Pro Ile Leu Glu Asn Tyr Pro Asn
            900                 905                 910

Lys Gln Ile Asn Glu Lys Gly Lys Glu Val Pro Cys Asn Pro Phe Leu
        915                 920                 925

Lys Tyr Lys Glu Glu His Gly Tyr Ile Arg Lys Tyr Ser Lys Lys Gly
    930                 935                 940

Asn Gly Pro Glu Ile Lys Ser Leu Lys Tyr Tyr Asp Ser Lys Leu Gly
945                 950                 955                 960

Asn His Ile Asp Ile Thr Pro Lys Asp Ser Asn Asn Lys Val Val Leu
                965                 970                 975

Gln Ser Val Ser Pro Trp Arg Ala Asp Val Tyr Phe Asn Lys Asn Thr
            980                 985                 990

Gly Lys Tyr Glu Ile Leu Gly Leu Lys Tyr Ser Asp Met Gln Phe Glu
        995                 1000                1005

Lys Gly Thr Gly Lys Tyr Ser Ile Ser Lys Glu Gln Tyr Glu Asn
    1010                1015                1020

Ile Lys Val Arg Glu Gly Val Asp Glu Asn Ser Glu Phe Lys Phe
    1025                1030                1035

Thr Leu Tyr Lys Asn Asp Leu Leu Leu Leu Lys Asp Ser Glu Asn
    1040                1045                1050

Gly Glu Gln Ile Leu Leu Arg Phe Thr Ser Arg Asn Asp Thr Ser
    1055                1060                1065

Lys His Tyr Val Glu Leu Lys Pro Tyr Asn Arg Gln Lys Phe Glu
    1070                1075                1080

Gly Ser Glu Tyr Leu Ile Lys Ser Leu Gly Thr Val Val Lys Gly
    1085                1090                1095

Gly Arg Cys Ile Lys Gly Leu Gly Lys Ser Asn Ile Ser Ile Tyr
    1100                1105                1110

Lys Val Arg Thr Asp Val Leu Gly Asn Gln His Ile Ile Lys Asn
    1115                1120                1125
```

-continued

```
Glu Gly Asp Lys Pro Lys Leu Asp Phe Ser Arg Ala Asp Pro Lys
    1130                1135                1140

Lys Lys Arg Lys Val Gly Ser
    1145                1150

<210> SEQ ID NO 44
<211> LENGTH: 1119
<212> TYPE: PRT
<213> ORGANISM: Artificial Sequence
<220> FEATURE:
<223> OTHER INFORMATION: Synthetic, engineered or hybrid sequence

<400> SEQUENCE: 44

Ser Asp Leu Val Leu Gly Leu Asp Ile Gly Ile Gly Ser Val Gly Val
1               5                   10                  15

Gly Ile Leu Asn Lys Val Thr Gly Glu Ile Ile His Lys Asn Ser Arg
            20                  25                  30

Ile Phe Pro Ala Ala Gln Ala Glu Asn Asn Leu Val Arg Arg Thr Asn
        35                  40                  45

Arg Gln Gly Arg Arg Leu Ala Arg Arg Lys Lys His Arg Arg Val Arg
    50                  55                  60

Leu Asn Arg Leu Phe Glu Glu Ser Gly Leu Ile Thr Asp Phe Thr Lys
65                  70                  75                  80

Ile Ser Ile Asn Leu Asn Pro Tyr Gln Leu Arg Val Lys Gly Leu Thr
                85                  90                  95

Asp Glu Leu Ser Asn Glu Glu Leu Phe Ile Ala Leu Lys Asn Met Val
            100                 105                 110

Lys His Arg Gly Ile Ser Tyr Leu Asp Asp Ala Ser Asp Gly Asn
        115                 120                 125

Ser Ser Val Gly Asp Tyr Ala Gln Ile Val Lys Glu Asn Ser Lys Gln
    130                 135                 140

Leu Glu Thr Lys Thr Pro Gly Gln Ile Gln Leu Glu Arg Tyr Gln Thr
145                 150                 155                 160

Tyr Gly Gln Leu Arg Gly Asp Phe Thr Val Glu Lys Asp Gly Lys Lys
                165                 170                 175

His Arg Leu Ile Asn Val Phe Pro Thr Ser Ala Tyr Arg Ser Glu Ala
            180                 185                 190

Leu Arg Ile Leu Gln Thr Gln Gln Glu Phe Asn Pro Gln Ile Thr Asp
        195                 200                 205

Glu Phe Ile Asn Arg Tyr Leu Glu Ile Leu Thr Gly Lys Arg Lys Tyr
    210                 215                 220

Tyr His Gly Pro Gly Asn Glu Lys Ser Arg Thr Asp Tyr Gly Arg Tyr
225                 230                 235                 240

Arg Thr Ser Gly Glu Thr Leu Asp Asn Ile Phe Gly Ile Leu Ile Gly
                245                 250                 255

Lys Cys Thr Phe Tyr Pro Asp Glu Phe Arg Ala Ala Lys Ala Ser Tyr
            260                 265                 270

Thr Ala Gln Glu Phe Asn Leu Leu Asn Asp Leu Asn Asn Leu Thr Val
        275                 280                 285

Pro Thr Glu Thr Lys Lys Leu Ser Lys Glu Gln Lys Asn Gln Ile Ile
    290                 295                 300

Asn Tyr Val Lys Asn Glu Lys Ala Met Gly Pro Ala Lys Leu Phe Lys
305                 310                 315                 320

Tyr Ile Ala Lys Leu Leu Ser Cys Asp Val Ala Asp Ile Lys Gly Tyr
                325                 330                 335
```

-continued

Arg Ile Asp Lys Ser Gly Lys Ala Glu Ile His Thr Phe Glu Ala Tyr
            340                 345                 350

Arg Lys Met Lys Thr Leu Glu Thr Leu Asp Ile Glu Gln Met Asp Arg
            355                 360                 365

Glu Thr Leu Asp Lys Leu Ala Tyr Val Leu Thr Leu Asn Thr Glu Arg
    370                 375                 380

Glu Gly Ile Gln Glu Ala Leu Glu His Glu Phe Ala Asp Gly Ser Phe
385                 390                 395                 400

Ser Gln Lys Gln Val Asp Glu Leu Val Gln Phe Arg Lys Ala Asn Ser
                405                 410                 415

Ser Ile Phe Gly Lys Gly Trp His Asn Phe Ser Val Lys Leu Met Met
            420                 425                 430

Glu Leu Ile Pro Glu Leu Tyr Glu Thr Ser Glu Glu Gln Met Thr Ile
            435                 440                 445

Leu Thr Arg Leu Gly Lys Gln Lys Thr Thr Ser Ser Asn Lys Thr
    450                 455                 460

Lys Tyr Ile Asp Glu Lys Leu Leu Thr Glu Glu Ile Tyr Asn Pro Val
465                 470                 475                 480

Val Ala Lys Ser Val Arg Gln Ala Ile Lys Ile Val Asn Ala Ala Ile
                485                 490                 495

Lys Glu Tyr Gly Asp Phe Asp Asn Ile Val Ile Glu Met Ala Arg Glu
            500                 505                 510

Thr Asn Glu Asp Asp Glu Lys Lys Ala Ile Gln Lys Ile Gln Lys Ala
            515                 520                 525

Asn Lys Asp Glu Lys Asp Ala Ala Met Leu Lys Ala Ala Asn Gln Tyr
    530                 535                 540

Asn Gly Lys Ala Glu Leu Pro His Ser Val Phe His Gly His Lys Gln
545                 550                 555                 560

Leu Ala Thr Lys Ile Arg Leu Trp His Gln Gln Gly Glu Arg Cys Leu
                565                 570                 575

Tyr Thr Gly Lys Thr Ile Ser Ile His Asp Leu Ile Asn Asn Ser Asn
            580                 585                 590

Gln Phe Glu Val Asp His Ile Leu Pro Leu Ser Ile Thr Phe Asp Asp
            595                 600                 605

Ser Leu Ala Asn Lys Val Leu Val Tyr Ala Thr Ala Asn Gln Glu Lys
    610                 615                 620

Gly Gln Arg Thr Pro Tyr Gln Ala Leu Asp Ser Met Asp Asp Ala Trp
625                 630                 635                 640

Ser Phe Arg Glu Leu Lys Ala Phe Val Arg Glu Ser Lys Thr Leu Ser
                645                 650                 655

Asn Lys Lys Lys Glu Tyr Leu Leu Thr Glu Glu Asp Ile Ser Lys Phe
            660                 665                 670

Asp Val Arg Lys Lys Phe Ile Glu Arg Asn Leu Val Asp Thr Arg Tyr
    675                 680                 685

Ala Ser Arg Val Val Leu Asn Ala Leu Gln Glu His Phe Arg Ala His
    690                 695                 700

Lys Ile Asp Thr Lys Val Ser Val Val Arg Gly Gln Phe Thr Ser Gln
705                 710                 715                 720

Leu Arg Arg His Trp Gly Ile Glu Lys Thr Arg Asp Thr Tyr His His
                725                 730                 735

His Ala Val Asp Ala Leu Ile Ile Ala Ala Ser Ser Gln Leu Asn Leu
            740                 745                 750

Trp Lys Lys Gln Lys Asn Thr Leu Val Ser Tyr Ser Glu Asp Gln Leu

```
                755                 760                 765
Leu Asp Ile Glu Thr Gly Glu Leu Ile Ser Asp Asp Glu Tyr Lys Glu
770                 775                 780
Ser Val Phe Lys Ala Pro Tyr Gln His Phe Val Asp Thr Leu Lys Ser
785                 790                 795                 800
Lys Glu Phe Glu Asp Ser Ile Leu Phe Ser Tyr Gln Val Asp Ser Lys
                805                 810                 815
Phe Asn Arg Lys Ile Ser Asp Ala Thr Ile Tyr Ala Thr Arg Gln Ala
        820                 825                 830
Lys Val Gly Lys Asp Lys Ala Asp Glu Thr Tyr Val Leu Gly Lys Ile
            835                 840                 845
Lys Asp Ile Tyr Thr Gln Asp Gly Tyr Asp Ala Phe Met Lys Ile Tyr
850                 855                 860
Lys Lys Asp Lys Ser Lys Phe Leu Met Tyr Arg His Asp Pro Gln Thr
865                 870                 875                 880
Phe Glu Lys Val Ile Glu Pro Ile Leu Glu Asn Tyr Pro Asn Lys Gln
                885                 890                 895
Ile Asn Glu Lys Gly Lys Glu Val Pro Cys Asn Pro Phe Leu Lys Tyr
        900                 905                 910
Lys Glu Glu His Gly Tyr Ile Arg Lys Tyr Ser Lys Lys Gly Asn Gly
            915                 920                 925
Pro Glu Ile Lys Ser Leu Lys Tyr Tyr Asp Ser Lys Leu Gly Asn His
930                 935                 940
Ile Asp Ile Thr Pro Lys Asp Ser Asn Asn Lys Val Val Leu Gln Ser
945                 950                 955                 960
Val Ser Pro Trp Arg Ala Asp Val Tyr Phe Asn Lys Asn Thr Gly Lys
                965                 970                 975
Tyr Glu Ile Leu Gly Leu Lys Tyr Ser Asp Met Gln Phe Glu Lys Gly
        980                 985                 990
Thr Gly Lys Tyr Ser Ile Ser Lys  Glu Gln Tyr Glu Asn  Ile Lys Val
            995                 1000                1005
Arg Glu  Gly Val Asp Glu Asn  Ser Glu Phe Lys Phe  Thr Leu Tyr
        1010                1015                1020
Lys Asn  Asp Leu Leu Leu Leu  Lys Asp Ser Glu Asn  Gly Glu Gln
        1025                1030                1035
Ile Leu  Leu Arg Phe Thr Ser  Arg Asn Asp Thr Ser  Lys His Tyr
        1040                1045                1050
Val Glu  Leu Lys Pro Tyr Asn  Arg Gln Lys Phe Glu  Gly Ser Glu
        1055                1060                1065
Tyr Leu  Ile Lys Ser Leu Gly  Thr Val Val Lys Gly  Gly Arg Cys
        1070                1075                1080
Ile Lys  Gly Leu Gly Lys Ser  Asn Ile Ser Ile Tyr  Lys Val Arg
        1085                1090                1095
Thr Asp  Val Leu Gly Asn Gln  His Ile Ile Lys Asn  Glu Gly Asp
        1100                1105                1110
Lys Pro  Lys Leu Asp Phe
        1115

<210> SEQ ID NO 45
<211> LENGTH: 4944
<212> TYPE: DNA
<213> ORGANISM: Artificial Sequence
<220> FEATURE:
<223> OTHER INFORMATION: Synthetic, engineered or hybrid sequence
```

```
<400> SEQUENCE: 45
atgaaacgga cagccgacgg aagcgagttc gagtcaccaa agaagaagcg gaaagtctcc      60
tcagagactg ggcctgtcgc cgtcgatcca accctgcgcc gccggattga acctcacgag     120
tttgaagtgt tctttgaccc ccgggagctg agaaaggaga catgcctgct gtacgagatc     180
aactggggag gcaggcactc catctggagg cacacctctc agaacacaaa taagcacgtg     240
gaggtgaact tcatcgagaa gtttaccaca gagcggtact tctgcccaa taccagatgt      300 agcatcacat ggtttctgag ctggtcccct tgcggagagt gtagcagggc catcaccgag     360
ttcctgtcca gatatccaca cgtgacactg tttatctaca cgccaggct gtatcaccac      420 gcagacccaa ggaataggca gggcctgcgc gatctgatca gctccggcgt gaccatccag     480
atcatgacag agcaggagtc cggctactgc tggcggaact cgtgaatta ttctcctagc      540 aacgaggccc actggcctag gtacccacac ctgtgggtgc cctgtacgt gctggagctg      600 tattgcatca tcctgggcct gccccttgt ctgaatatcc tgcggagaaa gcagccccag      660
ctgaccttct ttacaatcgc cctgcagtct tgtcactatc agaggctgcc acccacatc      720 ctgtgggcca caggcctgaa gtctggagga tctagcggag ctcctctgg cagcgagaca      780 ccaggaacaa gcgagtcagc aacaccgag agcagtggcg gcagcagcgg cggcagcagc      840
gacctggtgc tgggcctggc tatcggcatc ggcagcgtgg gcgtgggcat cctgaacaag     900
gtgaccggcg agatcatcca caagaacagt cgcatcttcc ctgctgctca ggctgagaac     960
aacctggtgc gccgcaccaa cgccagggt cgccggcttg ctcgccgcaa gaagcaccgg     1020
cgcgtgcgcc tgaaccgcct gttcgaggag agcggcctga tcaccgactt caccaagatc     1080
agcatcaacc tgaaccccta ccagctgcgc gtgaagggcc tgaccgacga gctgagcaac     1140
gaggagctgt tcatcgccct gaagaacatg gtgaagcacc gcggcatcag ctacctggac     1200
gacgccagcg acgacggcaa cagcagcgtg ggcgactacg cccagatcgt gaaggagaac     1260
agcaagcagc tggagaccaa gacccccggc cagatccagc tggagcgcta ccagacctac     1320
ggccagctgc gcggcgactt caccgtggag aaggacggca agaagcaccg cctgatcaac     1380
gtgttcccca ccagcgccta ccgcagcgag gccctgcgca tcctgcagac ccagcaggag     1440 ttcaacccc agatcaccga cgagttcatc aaccgctacc tggagatcct gaccggcaag     1500
cgcaagtact accacggccc cggcaacgag aagagccgca ccgactacgg ccgctaccgc     1560
accagcggcg agaccctgga caacatcttc ggcatcctga tcggcaagtg caccttctac     1620
cccgacgagt tccgcgccgc caaggccagc tacaccgccc aggagttcaa tctgctgaac     1680
gacctgaaca acctgaccgt gcccaccgag accaagaagc tgagcaagga gcagaagaac     1740
cagatcatca actacgtgaa gaacgagaag gctatgggcc ccgccaagct gttcaagtac     1800
atcgccaagc tgctgagctg cgacgtggcc gacatcaagg gctaccgcat cgacaagagc     1860
ggcaaggccg agatccacac cttcgaggcc taccgcaaga tgaagaccct ggagaccctg     1920
gacatcgagc agatggaccg agagaccctg gacaagctgg cctacgtgct gacccctgaac    1980 accgagcgcg agggcatcca ggaggccctg gagcacgagt cgccgacgg cagcttcagc     2040 cagaaacagg tggacgagct ggtgcagttc cgcaaggcca acagcagcat cttcggcaag     2100
ggctggcaca acttcagcgt gaagctgatg atggagctga tccccgagct gtacgagacc     2160
agcgaggagc agatgaccat cctgacccgc ctgggcaagc agaagaccac cagcagcagc     2220
aacaagacca agtacatcga cgagaagctg ctgaccgagg agatctacaa ccccgtggtg     2280
gccaagagcg tgcgccaggc catcaagatc gtgaacgccg ccatcaagga gtacggcgac     2340
```

-continued

```
ttcgacaaca tcgtgatcga gatggcccgc gagaccaacg aggacgacga gaagaaggcc    2400
atccagaaga tccagaaggc caacaaggac gagaaggacg ccgccatgct gaaggccgcc    2460
aaccagtaca acggcaaggc cgagctgccc cacagcgtgt tccacggcca caagcagctg    2520
gccaccaaga tccgcctgtg gcaccagcag ggcgagcgct gcctgtacac cggcaagacc    2580
atcagcatcc acgacctgat caacaacagc aaccagttcg aggtggacca catcctgccc    2640
ctgagcatca ccttcgacga cagcctggcc aacaaggtgc tggtgtacgc caccgccaac    2700
caggagaagg gccagcgcac cccctaccag gccctggaca gcatggacga cgcctggagc    2760
ttccgcgagc tgaaggcctt cgtgcgcgag agcaagaccc tgagcaacaa gaagaaggag    2820
tatctgctga ccgaggagga catcagcaag ttcgacgtgc gcaagaagtt catcgagcgc    2880
aacctggtgg acacccgcta cgccagccgc gtggtgctga cgccctgca ggagcacttc     2940 cgcgcccaca agatcgacac caaggtgagc gtggtgcgcg ccagttcac cagccagctg     3000 cgccgccact ggggcatcga gaagacccgc gacacctacc accaccacgc cgtggacgcc    3060
ctgatcattg cggcttctag ccagctgaac ctgtggaaga gcagaagaa caccctggtg     3120 agctacagcg aggaccagct gctggacatc gagaccggcg agctgatcag cgacgacgag    3180
tacaaggaga gcgtgttcaa ggcccctac cagcacttcg tggacaccct gaagagcaag     3240
gagttcgagg acagcatcct gttcagctac caggtggaca gcaagttcaa ccgcaagatc    3300
agcgacgcca ccatctacgc cacccgccag gccaaggtgg gcaaggacaa ggccgacgag    3360
acctacgtgc tgggcaagat caaggacatc tacacccagg acggctacga cgccttcatg    3420
aagatctaca agaaggacaa gagcaagttc ctgatgtacc gccacgaccc ccagaccttc    3480
gagaaggtga tcgagcccat cctggagaac taccccaaca gcagatcaa cgagaaaggc     3540 aaggaggtgc cctgcaaccc cttcctgaag tacaaggagg agcacggcta catccgcaag    3600
tacagcaaga agggcaacgg ccccgagatc aagagcctga gtactacga cagcaagctg     3660 ggcaaccaca tcgacatcac ccccaaggac agcaacaaca aggtggtgct gcagagcgtg    3720 agccctggc gcgccgacgt gtacttcaac aagaccaccg caagtacga gatcctgggg     3780 ctgaagtacg ccgatctgca gtttgagaaa ggcacaggca cctacaagat cagccaggag    3840
aagtacaacg acatcaagaa gaaggagggc gtggacagcg acagcgagtt caagttcacc    3900
ctgtacaaga acgccttct gctggtgaag gacaccgaga ccaaggagca acagctgttc     3960
cgcttcctga gccgcaccat gcccaagcag aagcactacg tggagctgaa gcccctacgac    4020 aagcagaagt tcgagggcgg cgaggccctg atcaaggtgc tgggcaacgt ggccaacagc    4080
ggccagtgca gaagggcct gggcaagagc aacatcagca tctacaaggt gcgcaccgac    4140
gtgctgggca ccagcacat catcaagaac gagggcgaca gcccaagtt ggacttcagc     4200 agggctgacc ccaagaagaa gaggaaggtg ggatctagcg gcgggagcgg cgggagcggg    4260
gggagcacta atctgagcga catcattgag aaggagactg ggaaacagct ggtcattcag    4320
gagtccatcc tgatgctgcc tgaggaggtg gaggaagtga tcggcaacaa gccagagtct    4380
gacatcctgg tgcacaccgc ctacgacgag tccacagatg agaatgtgat gctgctgacc    4440
tctgacgccc ccgagtataa gccttgggcc ctggtcatcc aggattctaa cggcgagaat    4500
aagatcaaga tgctgagcgg aggatccgga ggatctggag gcagcaccaa cctgtctgac    4560
atcatcgaga aggagacagg caagcagctg gtcatccagg agagcatcct gatgctgccc    4620
gaagaagtcg aagaagtgat cggaaacaag cctgagagcg atatcctggt ccataccgcc    4680
```

```
tacgacgaga gtaccgacga aaatgtgatg ctgctgacat ccgacgcccc agagtataag    4740
ccctgggctc tggtcatcca ggattccaac ggagagaaca aaatcaaaat gctgtctggc    4800
ggctcaaaaa gaaccgccga cggcagcgaa ttcgagccca agaagaagag gaaagtcgga    4860
tcctacccat acgatgttcc agattacgct tatccctacg acgtgcctga ttatgcatac    4920
ccatatgatg tccccgacta tgcc                                           4944

<210> SEQ ID NO 46
<211> LENGTH: 684
<212> TYPE: DNA
<213> ORGANISM: Artificial Sequence
<220> FEATURE:
<223> OTHER INFORMATION: Synthetic, engineered or hybrid sequence

<400> SEQUENCE: 46
tcctcagaga ctgggcctgt cgccgtcgat ccaaccctgc gccgccggat tgaacctcac     60
gagtttgaag tgttctttga ccccggggag ctgagaaagg agacatgcct gctgtacgag    120
atcaactggg gaggcaggca ctccatctgg aggcacacct ctcagaacac aaataagcac    180
gtggaggtga acttcatcga gaagtttacc acagagcggt acttctgccc caataccaga    240
tgtagcatca catggtttct gagctggtcc ccttgcggag agtgtagcag gccatcacc     300 gagttcctgt ccagatatcc acacgtgaca ctgtttatct acatcgccag gctgtatcac    360
cacgcagacc caaggaatag gcagggcctg cgcgatctga tcagctccgg cgtgaccatc    420
cagatcatga cagagcagga gtccggctac tgctggcgga acttcgtgaa ttattctcct    480
agcaacgagg cccactggcc taggtaccca cacctgtggg tgcgcctgta cgtgctggag    540
ctgtattgca tcatcctggg cctgcccct tgtctgaata tcctgcggag aaagcagccc    600
cagctgacct tctttacaat cgccctgcag tcttgtcact atcagaggct gccaccccac    660
atcctgtggg ccacaggcct gaag                                           684

<210> SEQ ID NO 47
<211> LENGTH: 249
<212> TYPE: DNA
<213> ORGANISM: Artificial Sequence
<220> FEATURE:
<223> OTHER INFORMATION: Synthetic, engineered or hybrid sequence

<400> SEQUENCE: 47
actaatctga gcgacatcat tgagaaggag actgggaaac agctggtcat tcaggagtcc     60
atcctgatgc tgcctgagga ggtggaggaa gtgatcggca acaagccaga gtctgacatc    120
ctggtgcaca ccgcctacga cgagtccaca gatgagaatg tgatgctgct gacctctgac    180
gcccccgagt ataagccttg ggccctggtc atccaggatt ctaacggcga gaataagatc    240
aagatgctg                                                           249

<210> SEQ ID NO 48
<211> LENGTH: 81
<212> TYPE: DNA
<213> ORGANISM: Artificial Sequence
<220> FEATURE:
<223> OTHER INFORMATION: Synthetic, engineered or hybrid sequence

<400> SEQUENCE: 48
tacccatacg atgttccaga ttacgcttat ccctacgacg tgcctgatta tgcataccca     60
tatgatgtcc ccgactatgc c                                              81
```

-continued

```
<210> SEQ ID NO 49
<211> LENGTH: 1648
<212> TYPE: PRT
<213> ORGANISM: Artificial Sequence
<220> FEATURE:
<223> OTHER INFORMATION: Synthetic, engineered or hybrid sequence

<400> SEQUENCE: 49
```

| | | | | | | | | | | | | | | | |
|---|---|---|---|---|---|---|---|---|---|---|---|---|---|---|---|
| Met | Lys | Arg | Thr | Ala | Asp | Gly | Ser | Glu | Phe | Glu | Ser | Pro | Lys | Lys | Lys |
| 1 | | | | 5 | | | | | 10 | | | | | 15 | |
| Arg | Lys | Val | Ser | Ser | Glu | Thr | Gly | Pro | Val | Ala | Val | Asp | Pro | Thr | Leu |
| | | | 20 | | | | | 25 | | | | | 30 | | |
| Arg | Arg | Arg | Ile | Glu | Pro | His | Glu | Phe | Glu | Val | Phe | Phe | Asp | Pro | Arg |
| | | 35 | | | | | 40 | | | | | 45 | | | |
| Glu | Leu | Arg | Lys | Glu | Thr | Cys | Leu | Leu | Tyr | Glu | Ile | Asn | Trp | Gly | Gly |
| 50 | | | | | 55 | | | | | 60 | | | | | |
| Arg | His | Ser | Ile | Trp | Arg | His | Thr | Ser | Gln | Asn | Thr | Asn | Lys | His | Val |
| 65 | | | | | 70 | | | | | 75 | | | | | 80 |
| Glu | Val | Asn | Phe | Ile | Glu | Lys | Phe | Thr | Thr | Glu | Arg | Tyr | Phe | Cys | Pro |
| | | | | 85 | | | | | 90 | | | | | 95 | |
| Asn | Thr | Arg | Cys | Ser | Ile | Thr | Trp | Phe | Leu | Ser | Trp | Ser | Pro | Cys | Gly |
| | | | 100 | | | | | 105 | | | | | 110 | | |
| Glu | Cys | Ser | Arg | Ala | Ile | Thr | Glu | Phe | Leu | Ser | Arg | Tyr | Pro | His | Val |
| | | | 115 | | | | | 120 | | | | | 125 | | |
| Thr | Leu | Phe | Ile | Tyr | Ile | Ala | Arg | Leu | Tyr | His | His | Ala | Asp | Pro | Arg |
| | | 130 | | | | | 135 | | | | | 140 | | | |
| Asn | Arg | Gln | Gly | Leu | Arg | Asp | Leu | Ile | Ser | Ser | Gly | Val | Thr | Ile | Gln |
| 145 | | | | | 150 | | | | | 155 | | | | | 160 |
| Ile | Met | Thr | Glu | Gln | Glu | Ser | Gly | Tyr | Cys | Trp | Arg | Asn | Phe | Val | Asn |
| | | | | 165 | | | | | 170 | | | | | 175 | |
| Tyr | Ser | Pro | Ser | Asn | Glu | Ala | His | Trp | Pro | Arg | Tyr | Pro | His | Leu | Trp |
| | | | 180 | | | | | 185 | | | | | 190 | | |
| Val | Arg | Leu | Tyr | Val | Leu | Glu | Leu | Tyr | Cys | Ile | Ile | Leu | Gly | Leu | Pro |
| | | | 195 | | | | | 200 | | | | | 205 | | |
| Pro | Cys | Leu | Asn | Ile | Leu | Arg | Arg | Lys | Gln | Pro | Gln | Leu | Thr | Phe | Phe |
| | 210 | | | | | 215 | | | | | 220 | | | | |
| Thr | Ile | Ala | Leu | Gln | Ser | Cys | His | Tyr | Gln | Arg | Leu | Pro | Pro | His | Ile |
| 225 | | | | | 230 | | | | | 235 | | | | | 240 |
| Leu | Trp | Ala | Thr | Gly | Leu | Lys | Ser | Gly | Gly | Ser | Gly | Gly | Ser | Gly | Ser |
| | | | | 245 | | | | | 250 | | | | | 255 | |
| Gly | Ser | Glu | Thr | Pro | Gly | Thr | Ser | Glu | Ser | Ala | Thr | Pro | Glu | Ser | Ser |
| | | | 260 | | | | | 265 | | | | | 270 | | |
| Gly | Gly | Ser | Ser | Gly | Gly | Ser | Ser | Asp | Leu | Val | Leu | Gly | Leu | Ala | Ile |
| | | | 275 | | | | | 280 | | | | | 285 | | |
| Gly | Ile | Gly | Ser | Val | Gly | Val | Gly | Ile | Leu | Asn | Lys | Val | Thr | Gly | Glu |
| | | 290 | | | | | 295 | | | | | 300 | | | |
| Ile | Ile | His | Lys | Asn | Ser | Arg | Ile | Phe | Pro | Ala | Ala | Gln | Ala | Glu | Asn |
| 305 | | | | | 310 | | | | | 315 | | | | | 320 |
| Asn | Leu | Val | Arg | Arg | Thr | Asn | Arg | Gln | Gly | Arg | Arg | Leu | Ala | Arg | Arg |
| | | | | 325 | | | | | 330 | | | | | 335 | |
| Lys | Lys | His | Arg | Arg | Val | Arg | Leu | Asn | Arg | Leu | Phe | Glu | Glu | Ser | Gly |
| | | | 340 | | | | | 345 | | | | | 350 | | |
| Leu | Ile | Thr | Asp | Phe | Thr | Lys | Ile | Ser | Ile | Asn | Leu | Asn | Pro | Tyr | Gln |
| | | | 355 | | | | | 360 | | | | | 365 | | |
| Leu | Arg | Val | Lys | Gly | Leu | Thr | Asp | Glu | Leu | Ser | Asn | Glu | Glu | Leu | Phe |

```
             370                 375                 380
Ile Ala Leu Lys Asn Met Val Lys His Arg Gly Ile Ser Tyr Leu Asp
385                 390                 395                 400

Asp Ala Ser Asp Gly Asn Ser Ser Val Gly Asp Tyr Ala Gln Ile
                405                 410                 415

Val Lys Glu Asn Ser Lys Gln Leu Glu Thr Lys Thr Pro Gly Gln Ile
                420                 425                 430

Gln Leu Glu Arg Tyr Gln Thr Tyr Gly Gln Leu Arg Gly Asp Phe Thr
                435                 440                 445

Val Glu Lys Asp Gly Lys Lys His Arg Leu Ile Asn Val Phe Pro Thr
            450                 455                 460

Ser Ala Tyr Arg Ser Glu Ala Leu Arg Ile Leu Gln Thr Gln Gln Glu
465                 470                 475                 480

Phe Asn Pro Gln Ile Thr Asp Glu Phe Ile Asn Arg Tyr Leu Glu Ile
                485                 490                 495

Leu Thr Gly Lys Arg Lys Tyr Tyr His Gly Pro Gly Asn Glu Lys Ser
                500                 505                 510

Arg Thr Asp Tyr Gly Arg Tyr Arg Thr Ser Gly Glu Thr Leu Asp Asn
            515                 520                 525

Ile Phe Gly Ile Leu Ile Gly Lys Cys Thr Phe Tyr Pro Asp Glu Phe
            530                 535                 540

Arg Ala Ala Lys Ala Ser Tyr Thr Ala Gln Glu Phe Asn Leu Leu Asn
545                 550                 555                 560

Asp Leu Asn Asn Leu Thr Val Pro Thr Glu Thr Lys Lys Leu Ser Lys
                565                 570                 575

Glu Gln Lys Asn Gln Ile Ile Asn Tyr Val Lys Asn Glu Lys Ala Met
                580                 585                 590

Gly Pro Ala Lys Leu Phe Lys Tyr Ile Ala Lys Leu Leu Ser Cys Asp
            595                 600                 605

Val Ala Asp Ile Lys Gly Tyr Arg Ile Asp Lys Ser Gly Lys Ala Glu
            610                 615                 620

Ile His Thr Phe Glu Ala Tyr Arg Lys Met Lys Thr Leu Glu Thr Leu
625                 630                 635                 640

Asp Ile Glu Gln Met Asp Arg Glu Thr Leu Asp Lys Leu Ala Tyr Val
                645                 650                 655

Leu Thr Leu Asn Thr Glu Arg Glu Gly Ile Gln Glu Ala Leu Glu His
                660                 665                 670

Glu Phe Ala Asp Gly Ser Phe Ser Gln Lys Gln Val Asp Glu Leu Val
            675                 680                 685

Gln Phe Arg Lys Ala Asn Ser Ser Ile Phe Gly Lys Gly Trp His Asn
690                 695                 700

Phe Ser Val Lys Leu Met Met Glu Leu Ile Pro Glu Leu Tyr Glu Thr
705                 710                 715                 720

Ser Glu Glu Gln Met Thr Ile Leu Thr Arg Leu Gly Lys Gln Lys Thr
                725                 730                 735

Thr Ser Ser Ser Asn Lys Thr Lys Tyr Ile Asp Glu Lys Leu Leu Thr
                740                 745                 750

Glu Glu Ile Tyr Asn Pro Val Val Ala Lys Ser Val Arg Gln Ala Ile
            755                 760                 765

Lys Ile Val Asn Ala Ala Ile Lys Glu Tyr Gly Asp Phe Asp Asn Ile
            770                 775                 780

Val Ile Glu Met Ala Arg Glu Thr Asn Glu Asp Asp Glu Lys Lys Ala
785                 790                 795                 800
```

```
Ile Gln Lys Ile Gln Lys Ala Asn Lys Asp Glu Lys Asp Ala Ala Met
            805                 810                 815

Leu Lys Ala Ala Asn Gln Tyr Asn Gly Lys Ala Glu Leu Pro His Ser
            820                 825                 830

Val Phe His Gly His Lys Gln Leu Ala Thr Lys Ile Arg Leu Trp His
            835                 840                 845

Gln Gln Gly Glu Arg Cys Leu Tyr Thr Gly Lys Thr Ile Ser Ile His
            850                 855                 860

Asp Leu Ile Asn Asn Ser Asn Gln Phe Glu Val Asp His Ile Leu Pro
865                 870                 875                 880

Leu Ser Ile Thr Phe Asp Asp Ser Leu Ala Asn Lys Val Leu Val Tyr
            885                 890                 895

Ala Thr Ala Asn Gln Glu Lys Gly Gln Arg Thr Pro Tyr Gln Ala Leu
            900                 905                 910

Asp Ser Met Asp Asp Ala Trp Ser Phe Arg Glu Leu Lys Ala Phe Val
            915                 920                 925

Arg Glu Ser Lys Thr Leu Ser Asn Lys Lys Glu Tyr Leu Leu Thr
            930                 935                 940

Glu Glu Asp Ile Ser Lys Phe Asp Val Arg Lys Lys Phe Ile Glu Arg
945                 950                 955                 960

Asn Leu Val Asp Thr Arg Tyr Ala Ser Arg Val Val Leu Asn Ala Leu
            965                 970                 975

Gln Glu His Phe Arg Ala His Lys Ile Asp Thr Lys Val Ser Val Val
            980                 985                 990

Arg Gly Gln Phe Thr Ser Gln Leu Arg Arg His Trp Gly Ile Glu Lys
            995                 1000                1005

Thr Arg Asp Thr Tyr His His His Ala Val Asp Ala Leu Ile Ile
    1010                1015                1020

Ala Ala Ser Ser Gln Leu Asn Leu Trp Lys Lys Gln Lys Asn Thr
    1025                1030                1035

Leu Val Ser Tyr Ser Glu Asp Gln Leu Leu Asp Ile Glu Thr Gly
    1040                1045                1050

Glu Leu Ile Ser Asp Asp Glu Tyr Lys Glu Ser Val Phe Lys Ala
    1055                1060                1065

Pro Tyr Gln His Phe Val Asp Thr Leu Lys Ser Lys Glu Phe Glu
    1070                1075                1080

Asp Ser Ile Leu Phe Ser Tyr Gln Val Asp Ser Lys Phe Asn Arg
    1085                1090                1095

Lys Ile Ser Asp Ala Thr Ile Tyr Ala Thr Arg Gln Ala Lys Val
    1100                1105                1110

Gly Lys Asp Lys Ala Asp Glu Thr Tyr Val Leu Gly Lys Ile Lys
    1115                1120                1125

Asp Ile Tyr Thr Gln Asp Gly Tyr Asp Ala Phe Met Lys Ile Tyr
    1130                1135                1140

Lys Lys Asp Lys Ser Lys Phe Leu Met Tyr Arg His Asp Pro Gln
    1145                1150                1155

Thr Phe Glu Lys Val Ile Glu Pro Ile Leu Glu Asn Tyr Pro Asn
    1160                1165                1170

Lys Gln Ile Asn Glu Lys Gly Lys Glu Val Pro Cys Asn Pro Phe
    1175                1180                1185

Leu Lys Tyr Lys Glu Glu His Gly Tyr Ile Arg Lys Tyr Ser Lys
    1190                1195                1200
```

```
Lys Gly Asn Gly Pro Glu Ile Lys Ser Leu Lys Tyr Tyr Asp Ser
    1205                1210                1215

Lys Leu Gly Asn His Ile Asp Ile Thr Pro Lys Asp Ser Asn Asn
    1220                1225                1230

Lys Val Val Leu Gln Ser Val Ser Pro Trp Arg Ala Asp Val Tyr
    1235                1240                1245

Phe Asn Lys Thr Thr Gly Lys Tyr Glu Ile Leu Gly Leu Lys Tyr
    1250                1255                1260

Ala Asp Leu Gln Phe Glu Lys Gly Thr Gly Thr Tyr Lys Ile Ser
    1265                1270                1275

Gln Glu Lys Tyr Asn Asp Ile Lys Lys Lys Glu Gly Val Asp Ser
    1280                1285                1290

Asp Ser Glu Phe Lys Phe Thr Leu Tyr Lys Asn Asp Leu Leu Leu
    1295                1300                1305

Val Lys Asp Thr Glu Thr Lys Glu Gln Gln Leu Phe Arg Phe Leu
    1310                1315                1320

Ser Arg Thr Met Pro Lys Gln Lys His Tyr Val Glu Leu Lys Pro
    1325                1330                1335

Tyr Asp Lys Gln Lys Phe Glu Gly Gly Glu Ala Leu Ile Lys Val
    1340                1345                1350

Leu Gly Asn Val Ala Asn Ser Gly Gln Cys Lys Lys Gly Leu Gly
    1355                1360                1365

Lys Ser Asn Ile Ser Ile Tyr Lys Val Arg Thr Asp Val Leu Gly
    1370                1375                1380

Asn Gln His Ile Ile Lys Asn Glu Gly Asp Lys Pro Lys Leu Asp
    1385                1390                1395

Phe Ser Arg Ala Asp Pro Lys Lys Lys Arg Lys Val Gly Ser Ser
    1400                1405                1410

Gly Gly Ser Gly Gly Ser Gly Gly Ser Thr Asn Leu Ser Asp Ile
    1415                1420                1425

Ile Glu Lys Glu Thr Gly Lys Gln Leu Val Ile Gln Glu Ser Ile
    1430                1435                1440

Leu Met Leu Pro Glu Glu Val Glu Glu Val Ile Gly Asn Lys Pro
    1445                1450                1455

Glu Ser Asp Ile Leu Val His Thr Ala Tyr Asp Glu Ser Thr Asp
    1460                1465                1470

Glu Asn Val Met Leu Leu Thr Ser Asp Ala Pro Glu Tyr Lys Pro
    1475                1480                1485

Trp Ala Leu Val Ile Gln Asp Ser Asn Gly Glu Asn Lys Ile Lys
    1490                1495                1500

Met Leu Ser Gly Gly Ser Gly Gly Ser Gly Gly Ser Thr Asn Leu
    1505                1510                1515

Ser Asp Ile Ile Glu Lys Glu Thr Gly Lys Gln Leu Val Ile Gln
    1520                1525                1530

Glu Ser Ile Leu Met Leu Pro Glu Glu Val Glu Glu Val Ile Gly
    1535                1540                1545

Asn Lys Pro Glu Ser Asp Ile Leu Val His Thr Ala Tyr Asp Glu
    1550                1555                1560

Ser Thr Asp Glu Asn Val Met Leu Leu Thr Ser Asp Ala Pro Glu
    1565                1570                1575

Tyr Lys Pro Trp Ala Leu Val Ile Gln Asp Ser Asn Gly Glu Asn
    1580                1585                1590

Lys Ile Lys Met Leu Ser Gly Gly Ser Lys Arg Thr Ala Asp Gly
```

```
                  1595                1600                1605

Ser Glu  Phe Glu Pro Lys  Lys  Arg Lys Val Gly  Ser Tyr Pro
        1610                1615                1620

Tyr Asp  Val Pro Asp Tyr  Ala  Tyr Pro Tyr Asp  Val Pro Asp Tyr
    1625                1630                1635

Ala Tyr  Pro Tyr Asp Val Pro  Asp Tyr Ala
    1640                1645

<210> SEQ ID NO 50
<211> LENGTH: 228
<212> TYPE: PRT
<213> ORGANISM: Artificial Sequence
<220> FEATURE:
<223> OTHER INFORMATION: Synthetic, engineered or hybrid sequence

<400> SEQUENCE: 50

Ser Ser Glu Thr Gly Pro Val Ala Val Asp Pro Thr Leu Arg Arg Arg
1                5                  10                  15

Ile Glu Pro His Glu Phe Glu Val Phe Phe Asp Pro Arg Glu Leu Arg
                20                  25                  30

Lys Glu Thr Cys Leu Leu Tyr Glu Ile Asn Trp Gly Gly Arg His Ser
            35                  40                  45

Ile Trp Arg His Thr Ser Gln Asn Thr Asn Lys His Val Glu Val Asn
        50                  55                  60

Phe Ile Glu Lys Phe Thr Thr Glu Arg Tyr Phe Cys Pro Asn Thr Arg
65                  70                  75                  80

Cys Ser Ile Thr Trp Phe Leu Ser Trp Ser Pro Cys Gly Glu Cys Ser
                85                  90                  95

Arg Ala Ile Thr Glu Phe Leu Ser Arg Tyr Pro His Val Thr Leu Phe
                100                 105                 110

Ile Tyr Ile Ala Arg Leu Tyr His His Ala Asp Pro Arg Asn Arg Gln
            115                 120                 125

Gly Leu Arg Asp Leu Ile Ser Ser Gly Val Thr Ile Gln Ile Met Thr
        130                 135                 140

Glu Gln Glu Ser Gly Tyr Cys Trp Arg Asn Phe Val Asn Tyr Ser Pro
145                 150                 155                 160

Ser Asn Glu Ala His Trp Pro Arg Tyr Pro His Leu Trp Val Arg Leu
                165                 170                 175

Tyr Val Leu Glu Leu Tyr Cys Ile Ile Leu Gly Leu Pro Pro Cys Leu
                180                 185                 190

Asn Ile Leu Arg Arg Lys Gln Pro Gln Leu Thr Phe Phe Thr Ile Ala
            195                 200                 205

Leu Gln Ser Cys His Tyr Gln Arg Leu Pro Pro His Ile Leu Trp Ala
        210                 215                 220

Thr Gly Leu Lys
225

<210> SEQ ID NO 51
<211> LENGTH: 83
<212> TYPE: PRT
<213> ORGANISM: Artificial Sequence
<220> FEATURE:
<223> OTHER INFORMATION: Synthetic, engineered or hybrid sequence

<400> SEQUENCE: 51

Thr Asn Leu Ser Asp Ile Ile Glu Lys Glu Thr Gly Lys Gln Leu Val
1                5                  10                  15
```

```
Ile Gln Glu Ser Ile Leu Met Leu Pro Glu Glu Val Glu Val Ile
           20                  25                  30

Gly Asn Lys Pro Glu Ser Asp Ile Leu Val His Thr Ala Tyr Asp Glu
        35                  40                  45

Ser Thr Asp Glu Asn Val Met Leu Leu Thr Ser Asp Ala Pro Glu Tyr
    50                  55                  60

Lys Pro Trp Ala Leu Val Ile Gln Asp Ser Asn Gly Glu Asn Lys Ile
65                  70                  75                  80

Lys Met Leu

<210> SEQ ID NO 52
<211> LENGTH: 27
<212> TYPE: PRT
<213> ORGANISM: Artificial Sequence
<220> FEATURE:
<223> OTHER INFORMATION: Synthetic, engineered or hybrid sequence

<400> SEQUENCE: 52

Tyr Pro Tyr Asp Val Pro Asp Tyr Ala Tyr Pro Tyr Asp Val Pro Asp
1               5                   10                  15

Tyr Ala Tyr Pro Tyr Asp Val Pro Asp Tyr Ala
            20                  25

<210> SEQ ID NO 53
<211> LENGTH: 4947
<212> TYPE: DNA
<213> ORGANISM: Artificial Sequence
<220> FEATURE:
<223> OTHER INFORMATION: Synthetic, engineered or hybrid sequence

<400> SEQUENCE: 53
```

| | |
|---|---:|
| atgaaacgga cagccgacgg aagcgagttc gagtcaccaa agaagaagcg gaaagtctcc | 60 |
| tcagagactg ggcctgtcgc cgtcgatcca accctgcgcc gccggattga acctcacgag | 120 |
| tttgaagtgt tctttgaccc ccgggagctg agaaaggaga catgcctgct gtacgagatc | 180 |
| aactggggag gcaggcactc catctggagg cacacctctc agaacacaaa taagcacgtg | 240 |
| gaggtgaact tcatcgagaa gtttaccaca gagcggtact tctgccccaa taccagatgt | 300 |
| agcatcacat ggtttctgag ctggtcccct tgcggagagt gtagcagggc catcaccgag | 360 |
| ttcctgtcca gatatccaca cgtgacactg tttatctaca cgccaggct gtatcaccac | 420 |
| gcagacccaa ggaataggca gggcctgcgc gatctgatca gctccggcgt gaccatccag | 480 |
| atcatgacag agcaggagtc cggctactgc tggcggaact cgtgaatta ttctcctagc | 540 |
| aacgaggccc actggcctag gtacccacac ctgtgggtgc cctgtacgt gctggagctg | 600 |
| tattgcatca tcctgggcct gccccttgt ctgaatatcc tgcggagaaa gcagccccag | 660 |
| ctgaccttct ttacaatcgc cctgcagtct tgtcactatc agaggctgcc accccacatc | 720 |
| ctgtgggcca caggcctgaa gtctggagga tctagcggag ctcctctgg cagcgagaca | 780 |
| ccaggaacaa gcgagtcagc aacaccagag agcagtggcg gcagcagcgg cggcagcagc | 840 |
| gacctggtgc tgggcctggc tatcggcatc ggcagcgtgg gcgtgggcat cctgaacaag | 900 |
| gtgaccggcg agatcatcca caagaacagt cgcatcttcc tgctgctca ggctgagaac | 960 |
| aacctggtgc gccgcaccaa ccgccagggt cgccggcttg ctcgccgcaa gaagcaccgg | 1020 |
| cgcgtgcgcc tgaaccgcct gttcgaggag agcggcctga tcaccgactt caccaagatc | 1080 |
| agcatcaacc tgaaccccta ccagctgcgc gtgaagggcc tgaccgacga gctgagcaac | 1140 |
| gaggagctgt tcatcgccct gaagaacatg gtgaagcacc gcggcatcag ctacctggac | 1200 |

```
gacgccagcg acgacggcaa cagcagcgtg ggcgactacg cccagatcgt gaaggagaac    1260
agcaagcagc tggagaccaa gacccccggc cagatccagc tggagcgcta ccagacctac    1320
ggccagctgc gcggcgactt caccgtggag aaggacggca agaagcaccg cctgatcaac    1380
gtgttcccca ccagcgccta ccgcagcgag gccctgcgca tcctgcagac ccagcaggag    1440
ttcaaccccc agatcaccga cgagttcatc aaccgctacc tggagatcct gaccggcaag    1500
cgcaagtact accacggccc cggcaacgag aagagccgca ccgactacgg ccgctaccgc    1560
accagcggcg agaccctgga caacatcttc ggcatcctga tcggcaagtg caccttctac    1620
cccgacgagt tccgcgccgc caaggccagc tacaccgccc aggagttcaa tctgctgaac    1680
gacctgaaca acctgaccgt gcccaccgag accaagaagc tgagcaagga gcagaagaac    1740
cagatcatca actacgtgaa gaacgagaag gctatgggcc ccgccaagct gttcaagtac    1800
atcgccaagc tgctgagctg cgacgtggcc gacatcaagg gctaccgcat cgacaagagc    1860
ggcaaggccg agatccacac cttcgaggcc taccgcaaga tgaagaccct ggagaccctg    1920
gacatcgagc agatggaccg agagaccctg gacaagctgg cctacgtgct gaccctgaac    1980
accgagcgcg agggcatcca ggaggccctg gagcacgagt cgccgacgg cagcttcagc    2040 cagaaacagg tggacgagct ggtgcagttc cgcaaggcca acagcagcat cttcggcaag    2100
ggctggcaca acttcagcgt gaagctgatg atggagctga tccccgagct gtacgagacc    2160
agcgaggagc agatgaccat cctgacccgc ctgggcaagc agaagaccac cagcagcagc    2220
aacaagacca agtacatcga cgagaagctg ctgaccgagg agatctacaa ccccgtggtg    2280
gccaagagcg tgcgccaggc catcaagatc gtgaacgccg ccatcaagga gtacggcgac    2340
ttcgacaaca tcgtgatcga gatggccgc gagaccaacg aggacgacga gaagaaggcc    2400
atccagaaga tccagaaggc caacaaggac gagaaggacg ccgccatgct gaaggccgcc    2460
aaccagtaca acggcaaggc cgagctgccc cacagcgtgt tccacggcca caagcagctg    2520
gccaccaaga tccgcctgtg caccagcag ggcgagcgct gcctgtacac cggcaagacc    2580
atcagcatcc acgacctgat caacaacagc aaccagttcg aggtggacca catcctgccc    2640
ctgagcatca ccttcgacga cagcctggcc aacaaggtgt ggtgtacgc caccgccaac    2700 caggagaagg gccagcgcac cccctaccag gccctggaca gcatggacga cgcctggagc    2760
ttccgcgagc tgaaggcctt cgtgcgcgag agcaagaccc tgagcaacaa gaagaaggag    2820
tatctgctga ccgaggagga catcagcaag ttcgacgtgc gcaagaagtt catcgagcgc    2880
aacctggtgg acacccgcta cgccagccgc gtggtgctga cgccctgca ggagcacttc    2940 cgcgcccaca agatcgacac caaggtgagc gtggtgcgcg ccagttcac cagccagctg    3000 cgccgccact ggggcatcga aagacccgc gacacctacc accaccacgc cgtggacgcc    3060
ctgatcattg cggcttctag ccagctgaac ctgtggaaga gcagaagaa caccctggtg    3120 agctacagcg aggagcagct gctggacatc gagaccggcg agctgatcag cgacgacgag    3180
tacaaggaga gcgtgttcaa ggccccctac cagcacttcg tggacaccct gaagagcaag    3240
gagttcgagg acagcatcct gttcagctac caggtggaca gcaagttcaa ccgcaagatc    3300
agcgacgcca ccatctacgc cacccgccag gccaaggtgg gcaaggacaa gaaggacgag    3360
acctacgtgc tgggcaagat caaggacatc tacacccagg acggctacga cgccttcatg    3420
aagatctaca gaaggacaa gagcaagttc ctgatgtacc gccacgaccc ccagaccttc    3480
gagaaggtga tcgagcccat cctggagaac taccccaaca gcagatgaa cgagaaaggc    3540
```

| | |
|---|---:|
| aaggaggtgc cctgcaaccc cttcctgaag tacaaggagg agcacggcta catccgcaag | 3600 |
| tacagcaaga agggcaacgg ccccgagatc aagagcctga agtactacga cagcaagctg | 3660 |
| ctgggcaacc ccatcgacat caccccccgaa aacagcaaga acaaggtggt gctgcagagc | 3720 |
| cttaagccct ggcgcaccga cgtgtacttc aacaagaaca ccggcaagta cgagatcctg | 3780 |
| gggctgaagt acgccgatct gcagtttgag aaaaagacag gcacctacaa gatcagccag | 3840 |
| gagaagtaca acggcatcat gaaggaggag ggcgtggaca cgacagcga gttcaagttc | 3900 |
| accctgtaca agaacgacct tctgctggtg aaggacaccg agaccaagga gcaacagctg | 3960 |
| ttccgcttcc tgagccgcac catgcccaac gtgaagtact acgtggagct gaagccctac | 4020 |
| agcaaggaca agttcgagaa gaacgagagc ctgatcgaga tcctgggcag cgccgacaag | 4080 |
| agcggcaggt gcatcaaggg cctgggcaag agcaacatca gcatctacaa ggtgcgcacc | 4140 |
| gacgtgctgg gcaaccagca catcatcaag aacgagggcg acaagcccaa gttggacttc | 4200 |
| agcagggctg acccccaagaa gaagaggaag gtgggatcta gcggcgggag cggcgggagc | 4260 |
| ggggggagca ctaatctgag cgacatcatt gagaaggaga ctgggaaaca gctggtcatt | 4320 |
| caggagtcca tcctgatgct gcctgaggag gtggaggaag tgatcggcaa caagccagag | 4380 |
| tctgacatcc tggtgcacac cgcctacgac gagtccacag atgagaatgt gatgctgctg | 4440 |
| acctctgacg cccccgagta taagccttgg gccctggtca tccaggattc taacggcgag | 4500 |
| aataagatca agatgctgag cggaggatcc ggaggatctg gaggcagcac caacctgtct | 4560 |
| gacatcatcg agaaggagac aggcaagcag ctggtcatcc aggagagcat cctgatgctg | 4620 |
| cccgaagaag tcgaagaagt gatcggaaac aagcctgaga gcgatatcct ggtccatacc | 4680 |
| gcctacgacg agagtaccga cgaaaatgtg atgctgctga catccgacgc cccagagtat | 4740 |
| aagccctggg ctctggtcat ccaggattcc aacggagaga caaaatcaa aatgctgtct | 4800 |
| ggcggctcaa aagaaccgc cgacggcagc gaattcgagc ccaagaagaa gaggaaagtc | 4860 |
| ggatcctacc catacgatgt tccagattac gcttatccct acgacgtgcc tgattatgca | 4920 |
| tacccatatg atgtccccga ctatgcc | 4947 |

<210> SEQ ID NO 54
<211> LENGTH: 3363
<212> TYPE: DNA
<213> ORGANISM: Artificial Sequence
<220> FEATURE:
<223> OTHER INFORMATION: Synthetic, engineered or hybrid sequence

<400> SEQUENCE: 54

| | |
|---|---:|
| agcgacctgg tgctgggcct ggctatcggc atcggcagcg tgggcgtggg catcctgaac | 60 |
| aaggtgaccg gcgagatcat ccacaagaac agtcgcatct ccctgctgc tcaggctgag | 120 |
| aacaacctgg tgcgccgcac caaccgccag ggtcgccggc ttgctcgccg caagaagcac | 180 |
| cggcgcgtgc gcctgaaccg cctgttcgag gagagcggcc tgatcaccga cttcaccaag | 240 |
| atcagcatca acctgaaccc ctaccagctg cgcgtgaagg gcctgaccga cgagctgagc | 300 |
| aacgaggagc tgttcatcgc cctgaagaac atggtgaagc accgcggcat cagctacctg | 360 |
| gacgacgcca gcgacgacgg caacagcagc gtgggcgact acgcccagat cgtgaaggag | 420 |
| aacagcaagc agctggagac caagacccccc ggccagatcc agctggagcg ctaccagacc | 480 |
| tacggccagc tgcgcggcga cttcaccgtg gagaaggacg gcaagaagca ccgcctgatc | 540 |
| aacgtgttcc ccaccagcgc ctaccgcagc gaggccctgc gcatcctgca gacccagcag | 600 |
| gagttcaacc cccagatcac cgacgagttc atcaaccgct acctggagat cctgaccggc | 660 |

-continued

```
aagcgcaagt actaccacgg ccccggcaac gagaagagcc gcaccgacta cggccgctac      720
cgcaccagcg gcgagaccct ggacaacatc ttcggcatcc tgatcggcaa gtgcaccttc      780
taccccgacg agttccgcgc cgccaaggcc agctacaccg cccaggagtt caatctgctg      840
aacgacctga acaacctgac cgtgcccacc gagaccaaga agctgagcaa ggagcagaag      900
aaccagatca tcaactacgt gaagaacgag aaggctatgg ccccgccaa gctgttcaag       960 tacatcgcca agctgctgag ctgcgacgtg gccgacatca agggctaccg catcgacaag     1020
agcggcaagg ccgagatcca caccttcgag gcctaccgca agatgaagac cctggagacc     1080
ctggacatcg agcagatgga ccgagagacc ctggacaagc tggcctacgt gctgaccctg     1140
aacaccgagc gcgagggcat ccaggaggcc ctggagcacg agttcgccga cggcagcttc     1200
agccagaaac aggtggacga gctggtgcag ttccgcaagg ccaacagcag catcttcggc     1260
aagggctggc acaacttcag cgtgaagctg atgatggagc tgatccccga gctgtacgag     1320
accagcgagg agcagatgac catcctgacc cgcctgggca agcagaagac caccagcagc     1380
agcaacaaga ccaagtacat cgacgagaag ctgctgaccg aggagatcta caaccccgtg     1440
gtggccaaga gcgtgcgcca ggccatcaag atcgtgaacg ccgccatcaa ggagtacggc     1500
gacttcgaca acatcgtgat cgagatggcc cgcgagaaca cgaggacga cgagaagaag      1560 gccatccaga agatccagaa ggccaacaag gacgagaagg acgccgccat gctgaaggcc     1620
gccaaccagt acaacggcaa ggccgagctg ccccacagcg tgttccacgg ccacaagcag     1680
ctggccacca gatccgcct gtggcaccag cagggcgagc gctgcctgta caccggcaag      1740
accatcagca tccacgacct gatcaacaac agcaaccagt tcgaggtgga ccacatcctg     1800
cccctgagca tcaccttcga cgacagcctg gccaacaagg tgctggtgta cgccaccgcc     1860
aaccaggaga agggccagcg cacccccta caggccctgg acagcatgga cgacgcctgg      1920
agcttccgcg agctgaaggc cttcgtgcgc gagagcaaga ccctgagcaa caagaagaag     1980
gagtatctgc tgaccgagga ggacatcagc aagttcgacg tgcgcaagaa gttcatcgag     2040
cgcaacctgg tggacacccg ctacgccagc cgcgtggtgc tgaacgccct gcaggagcac     2100
ttccgcgccc acaagatcga caccaaggtg agcgtggtgc gcggcagtt caccagccag      2160 ctgcgccgcc actggggcat cgagaagacc cgcgacacct accaccacca cgccgtggac     2220
gccctgatca ttgcggcttc tagccagctg aacctgtgga gaagcagaa gaacaccctg      2280 gtgagctaca gcgaggagca gctgctggac atcgagaccg gcgagctgat cagcgacgac     2340
gagtacaagg agagcgtgtt caaggccccc taccagcact cgtggacac cctgaagagc      2400 aaggagttcg aggacagcat cctgttcagc taccaggtgg acagcaagtt caaccgcaag     2460
atcagcgacg ccaccatcta cgccaccgc caggccaagg tgggcaagga caagaaggac      2520
gagacctacg tgctgggcaa gatcaaggac atctacaccc aggacggcta cgacgccttc     2580
atgaagatct acaagaagga caagagcaag ttcctgatgt accgccacga ccccagacc      2640 ttcgagaagg tgatcgagcc catcctggag aactacccca caagcagat gaacgagaaa      2700 ggcaaggagg tgccctgcaa ccccttcctg aagtacaagg aggagcacgg ctacatccgc     2760
aagtacagca gaagggcaa cggccccgag atcaagagcc tgaagtacta cgacagcaag     2820
ctgctgggca accccatcga catcacccc gaaaacagca gaacaaggt ggtgctgcag       2880 agccttaagc cctggcgcac cgacgtgtac ttcaacaaga acaccggcaa gtacgagatc     2940
ctggggctga agtacgccga tctgcagttt gagaaaaaga caggcaccta caagatcagc     3000
```

```
caggagaagt acaacggcat catgaaggag gagggcgtgg acagcgacag cgagttcaag    3060
ttcaccctgt acaagaacga ccttctgctg gtgaaggaca ccgagaccaa ggagcaacag    3120
ctgttccgct tcctgagccg caccatgccc aacgtgaagt actacgtgga gctgaagccc    3180
tacagcaagg acaagttcga gaagaacgag agcctgatcg agatcctggg cagcgccgac    3240
aagagcggca ggtgcatcaa gggcctgggc aagagcaaca tcagcatcta caaggtgcgc    3300
accgacgtgc tgggcaacca gcacatcatc aagaacgagg gcgacaagcc caagttggac    3360
ttc                                                                  3363
```

<210> SEQ ID NO 55
<211> LENGTH: 1649
<212> TYPE: PRT
<213> ORGANISM: Artificial Sequence
<220> FEATURE:
<223> OTHER INFORMATION: Synthetic, engineered or hybrid sequence

<400> SEQUENCE: 55

```
Met Lys Arg Thr Ala Asp Gly Ser Glu Phe Glu Ser Pro Lys Lys
1               5                   10                  15

Arg Lys Val Ser Ser Glu Thr Gly Pro Val Ala Val Asp Pro Thr Leu
                20                  25                  30

Arg Arg Arg Ile Glu Pro His Glu Phe Glu Val Phe Phe Asp Pro Arg
        35                  40                  45

Glu Leu Arg Lys Glu Thr Cys Leu Leu Tyr Glu Ile Asn Trp Gly Gly
    50                  55                  60

Arg His Ser Ile Trp Arg His Thr Ser Gln Asn Thr Asn Lys His Val
65                  70                  75                  80

Glu Val Asn Phe Ile Glu Lys Phe Thr Thr Glu Arg Tyr Phe Cys Pro
                85                  90                  95

Asn Thr Arg Cys Ser Ile Thr Trp Phe Leu Ser Trp Ser Pro Cys Gly
            100                 105                 110

Glu Cys Ser Arg Ala Ile Thr Glu Phe Leu Ser Arg Tyr Pro His Val
        115                 120                 125

Thr Leu Phe Ile Tyr Ile Ala Arg Leu Tyr His His Ala Asp Pro Arg
    130                 135                 140

Asn Arg Gln Gly Leu Arg Asp Leu Ile Ser Ser Gly Val Thr Ile Gln
145                 150                 155                 160

Ile Met Thr Glu Gln Glu Ser Gly Tyr Cys Trp Arg Asn Phe Val Asn
                165                 170                 175

Tyr Ser Pro Ser Asn Glu Ala His Trp Pro Arg Tyr Pro His Leu Trp
            180                 185                 190

Val Arg Leu Tyr Val Leu Glu Leu Tyr Cys Ile Ile Leu Gly Leu Pro
        195                 200                 205

Pro Cys Leu Asn Ile Leu Arg Arg Lys Gln Pro Gln Leu Thr Phe Phe
    210                 215                 220

Thr Ile Ala Leu Gln Ser Cys His Tyr Gln Arg Leu Pro Pro His Ile
225                 230                 235                 240

Leu Trp Ala Thr Gly Leu Lys Ser Gly Gly Ser Gly Gly Ser Ser
                245                 250                 255

Gly Ser Glu Thr Pro Gly Thr Ser Glu Ser Ala Thr Pro Glu Ser Ser
            260                 265                 270

Gly Gly Ser Ser Gly Gly Ser Ser Asp Leu Val Leu Gly Leu Ala Ile
        275                 280                 285

Gly Ile Gly Ser Val Gly Val Gly Ile Leu Asn Lys Val Thr Gly Glu
```

```
            290                 295                 300
Ile Ile His Lys Asn Ser Arg Ile Phe Pro Ala Ala Gln Ala Glu Asn
305                 310                 315                 320

Asn Leu Val Arg Arg Thr Asn Arg Gln Gly Arg Leu Ala Arg Arg
            325                 330                 335

Lys Lys His Arg Arg Val Arg Leu Asn Arg Leu Phe Glu Glu Ser Gly
            340                 345                 350

Leu Ile Thr Asp Phe Thr Lys Ile Ser Ile Asn Leu Asn Pro Tyr Gln
            355                 360                 365

Leu Arg Val Lys Gly Leu Thr Asp Glu Leu Ser Asn Glu Glu Leu Phe
            370                 375                 380

Ile Ala Leu Lys Asn Met Val Lys His Arg Gly Ile Ser Tyr Leu Asp
385                 390                 395                 400

Asp Ala Ser Asp Asp Gly Asn Ser Ser Val Gly Asp Tyr Ala Gln Ile
                    405                 410                 415

Val Lys Glu Asn Ser Lys Gln Leu Glu Thr Lys Thr Pro Gly Gln Ile
            420                 425                 430

Gln Leu Glu Arg Tyr Gln Thr Tyr Gly Gln Leu Arg Gly Asp Phe Thr
            435                 440                 445

Val Glu Lys Asp Gly Lys Lys His Arg Leu Ile Asn Val Phe Pro Thr
450                 455                 460

Ser Ala Tyr Arg Ser Glu Ala Leu Arg Ile Leu Gln Thr Gln Gln Glu
465                 470                 475                 480

Phe Asn Pro Gln Ile Thr Asp Glu Phe Ile Asn Arg Tyr Leu Glu Ile
                    485                 490                 495

Leu Thr Gly Lys Arg Lys Tyr Tyr His Gly Pro Gly Asn Glu Lys Ser
            500                 505                 510

Arg Thr Asp Tyr Gly Arg Tyr Arg Thr Ser Gly Glu Thr Leu Asp Asn
            515                 520                 525

Ile Phe Gly Ile Leu Ile Gly Lys Cys Thr Phe Tyr Pro Asp Glu Phe
            530                 535                 540

Arg Ala Ala Lys Ala Ser Tyr Thr Ala Gln Glu Phe Asn Leu Leu Asn
545                 550                 555                 560

Asp Leu Asn Asn Leu Thr Val Pro Thr Glu Thr Lys Lys Leu Ser Lys
                    565                 570                 575

Glu Gln Lys Asn Gln Ile Ile Asn Tyr Val Lys Asn Glu Lys Ala Met
            580                 585                 590

Gly Pro Ala Lys Leu Phe Lys Tyr Ile Ala Lys Leu Leu Ser Cys Asp
            595                 600                 605

Val Ala Asp Ile Lys Gly Tyr Arg Ile Asp Lys Ser Gly Lys Ala Glu
610                 615                 620

Ile His Thr Phe Glu Ala Tyr Arg Lys Met Lys Thr Leu Glu Thr Leu
625                 630                 635                 640

Asp Ile Glu Gln Met Asp Arg Glu Thr Leu Asp Lys Leu Ala Tyr Val
                    645                 650                 655

Leu Thr Leu Asn Thr Glu Arg Glu Gly Ile Gln Glu Ala Leu Glu His
            660                 665                 670

Glu Phe Ala Asp Gly Ser Phe Ser Gln Lys Gln Val Asp Glu Leu Val
            675                 680                 685

Gln Phe Arg Lys Ala Asn Ser Ser Ile Phe Gly Lys Gly Trp His Asn
            690                 695                 700

Phe Ser Val Lys Leu Met Met Glu Leu Ile Pro Glu Leu Tyr Glu Thr
705                 710                 715                 720
```

```
Ser Glu Glu Gln Met Thr Ile Leu Thr Arg Leu Gly Lys Gln Lys Thr
                725                 730                 735

Thr Ser Ser Ser Asn Lys Thr Lys Tyr Ile Asp Glu Lys Leu Leu Thr
            740                 745                 750

Glu Glu Ile Tyr Asn Pro Val Val Ala Lys Ser Val Arg Gln Ala Ile
        755                 760                 765

Lys Ile Val Asn Ala Ala Ile Lys Glu Tyr Gly Asp Phe Asp Asn Ile
    770                 775                 780

Val Ile Glu Met Ala Arg Glu Thr Asn Glu Asp Asp Glu Lys Lys Ala
785                 790                 795                 800

Ile Gln Lys Ile Gln Lys Ala Asn Lys Asp Glu Lys Asp Ala Ala Met
                805                 810                 815

Leu Lys Ala Ala Asn Gln Tyr Asn Gly Lys Ala Glu Leu Pro His Ser
            820                 825                 830

Val Phe His Gly His Lys Gln Leu Ala Thr Lys Ile Arg Leu Trp His
        835                 840                 845

Gln Gln Gly Glu Arg Cys Leu Tyr Thr Gly Lys Thr Ile Ser Ile His
    850                 855                 860

Asp Leu Ile Asn Asn Ser Asn Gln Phe Glu Val Asp His Ile Leu Pro
865                 870                 875                 880

Leu Ser Ile Thr Phe Asp Asp Ser Leu Ala Asn Lys Val Leu Val Tyr
                885                 890                 895

Ala Thr Ala Asn Gln Glu Lys Gly Gln Arg Thr Pro Tyr Gln Ala Leu
            900                 905                 910

Asp Ser Met Asp Asp Ala Trp Ser Phe Arg Glu Leu Lys Ala Phe Val
        915                 920                 925

Arg Glu Ser Lys Thr Leu Ser Asn Lys Lys Glu Tyr Leu Leu Thr
    930                 935                 940

Glu Glu Asp Ile Ser Lys Phe Asp Val Arg Lys Lys Phe Ile Glu Arg
945                 950                 955                 960

Asn Leu Val Asp Thr Arg Tyr Ala Ser Arg Val Val Leu Asn Ala Leu
                965                 970                 975

Gln Glu His Phe Arg Ala His Lys Ile Asp Thr Lys Val Ser Val Val
            980                 985                 990

Arg Gly Gln Phe Thr Ser Gln Leu Arg Arg His Trp Gly Ile Glu Lys
        995                 1000                1005

Thr Arg Asp Thr Tyr His His Ala Val Asp Ala Leu Ile Ile
    1010                1015                1020

Ala Ala Ser Ser Gln Leu Asn Leu Trp Lys Lys Gln Lys Asn Thr
    1025                1030                1035

Leu Val Ser Tyr Ser Glu Glu Gln Leu Leu Asp Ile Glu Thr Gly
    1040                1045                1050

Glu Leu Ile Ser Asp Asp Glu Tyr Lys Glu Ser Val Phe Lys Ala
    1055                1060                1065

Pro Tyr Gln His Phe Val Asp Thr Leu Lys Ser Lys Glu Phe Glu
    1070                1075                1080

Asp Ser Ile Leu Phe Ser Tyr Gln Val Asp Ser Lys Phe Asn Arg
    1085                1090                1095

Lys Ile Ser Asp Ala Thr Ile Tyr Ala Thr Arg Gln Ala Lys Val
    1100                1105                1110

Gly Lys Asp Lys Lys Asp Glu Thr Tyr Val Leu Gly Lys Ile Lys
    1115                1120                1125
```

```
Asp Ile Tyr Thr Gln Asp Gly Tyr Asp Ala Phe Met Lys Ile Tyr
1130                1135                1140

Lys Lys Asp Lys Ser Lys Phe Leu Met Tyr Arg His Asp Pro Gln
1145                1150                1155

Thr Phe Glu Lys Val Ile Glu Pro Ile Leu Glu Asn Tyr Pro Asn
1160                1165                1170

Lys Gln Met Asn Glu Lys Gly Lys Glu Val Pro Cys Asn Pro Phe
1175                1180                1185

Leu Lys Tyr Lys Glu Glu His Gly Tyr Ile Arg Lys Tyr Ser Lys
1190                1195                1200

Lys Gly Asn Gly Pro Glu Ile Lys Ser Leu Lys Tyr Tyr Asp Ser
1205                1210                1215

Lys Leu Leu Gly Asn Pro Ile Asp Ile Thr Pro Glu Asn Ser Lys
1220                1225                1230

Asn Lys Val Val Leu Gln Ser Leu Lys Pro Trp Arg Thr Asp Val
1235                1240                1245

Tyr Phe Asn Lys Asn Thr Gly Lys Tyr Glu Ile Leu Gly Leu Lys
1250                1255                1260

Tyr Ala Asp Leu Gln Phe Glu Lys Lys Thr Gly Thr Tyr Lys Ile
1265                1270                1275

Ser Gln Glu Lys Tyr Asn Gly Ile Met Lys Glu Glu Gly Val Asp
1280                1285                1290

Ser Asp Ser Glu Phe Lys Phe Thr Leu Tyr Lys Asn Asp Leu Leu
1295                1300                1305

Leu Val Lys Asp Thr Glu Thr Lys Glu Gln Gln Leu Phe Arg Phe
1310                1315                1320

Leu Ser Arg Thr Met Pro Asn Val Lys Tyr Tyr Val Glu Leu Lys
1325                1330                1335

Pro Tyr Ser Lys Asp Lys Phe Glu Lys Asn Glu Ser Leu Ile Glu
1340                1345                1350

Ile Leu Gly Ser Ala Asp Lys Ser Gly Arg Cys Ile Lys Gly Leu
1355                1360                1365

Gly Lys Ser Asn Ile Ser Ile Tyr Lys Val Arg Thr Asp Val Leu
1370                1375                1380

Gly Asn Gln His Ile Ile Lys Asn Glu Gly Asp Lys Pro Lys Leu
1385                1390                1395

Asp Phe Ser Arg Ala Asp Pro Lys Lys Lys Arg Lys Val Gly Ser
1400                1405                1410

Ser Gly Gly Ser Gly Gly Ser Gly Gly Ser Thr Asn Leu Ser Asp
1415                1420                1425

Ile Ile Glu Lys Glu Thr Gly Lys Gln Leu Val Ile Gln Glu Ser
1430                1435                1440

Ile Leu Met Leu Pro Glu Glu Val Glu Glu Val Ile Gly Asn Lys
1445                1450                1455

Pro Glu Ser Asp Ile Leu Val His Thr Ala Tyr Asp Glu Ser Thr
1460                1465                1470

Asp Glu Asn Val Met Leu Leu Thr Ser Asp Ala Pro Glu Tyr Lys
1475                1480                1485

Pro Trp Ala Leu Val Ile Gln Asp Ser Asn Gly Glu Asn Lys Ile
1490                1495                1500

Lys Met Leu Ser Gly Gly Ser Gly Gly Ser Gly Gly Ser Thr Asn
1505                1510                1515

Leu Ser Asp Ile Ile Glu Lys Glu Thr Gly Lys Gln Leu Val Ile
```

```
          1520                1525                1530

Gln Glu Ser Ile Leu Met Leu Pro Glu Glu Val Glu Glu Val Ile
        1535                1540                1545

Gly Asn Lys Pro Glu Ser Asp Ile Leu Val His Thr Ala Tyr Asp
        1550                1555                1560

Glu Ser Thr Asp Glu Asn Val Met Leu Leu Thr Ser Asp Ala Pro
        1565                1570                1575

Glu Tyr Lys Pro Trp Ala Leu Val Ile Gln Asp Ser Asn Gly Glu
        1580                1585                1590

Asn Lys Ile Lys Met Leu Ser Gly Gly Ser Lys Arg Thr Ala Asp
        1595                1600                1605

Gly Ser Glu Phe Glu Pro Lys Lys Lys Arg Lys Val Gly Ser Tyr
        1610                1615                1620

Pro Tyr Asp Val Pro Asp Tyr Ala Tyr Pro Tyr Asp Val Pro Asp
        1625                1630                1635

Tyr Ala Tyr Pro Tyr Asp Val Pro Asp Tyr Ala
        1640                1645

<210> SEQ ID NO 56
<211> LENGTH: 1121
<212> TYPE: PRT
<213> ORGANISM: Artificial Sequence
<220> FEATURE:
<223> OTHER INFORMATION: Synthetic, engineered or hybrid sequence

<400> SEQUENCE: 56

Ser Asp Leu Val Leu Gly Leu Ala Ile Gly Ile Gly Ser Val Gly Val
1               5                   10                  15

Gly Ile Leu Asn Lys Val Thr Gly Glu Ile Ile His Lys Asn Ser Arg
            20                  25                  30

Ile Phe Pro Ala Ala Gln Ala Glu Asn Asn Leu Val Arg Arg Thr Asn
        35                  40                  45

Arg Gln Gly Arg Arg Leu Ala Arg Arg Lys Lys His Arg Arg Val Arg
    50                  55                  60

Leu Asn Arg Leu Phe Glu Glu Ser Gly Leu Ile Thr Asp Phe Thr Lys
65                  70                  75                  80

Ile Ser Ile Asn Leu Asn Pro Tyr Gln Leu Arg Val Lys Gly Leu Thr
                85                  90                  95

Asp Glu Leu Ser Asn Glu Glu Leu Phe Ile Ala Leu Lys Asn Met Val
            100                 105                 110

Lys His Arg Gly Ile Ser Tyr Leu Asp Asp Ala Ser Asp Asp Gly Asn
        115                 120                 125

Ser Ser Val Gly Asp Tyr Ala Gln Ile Val Lys Glu Asn Ser Lys Gln
    130                 135                 140

Leu Glu Thr Lys Thr Pro Gly Gln Ile Gln Leu Glu Arg Tyr Gln Thr
145                 150                 155                 160

Tyr Gly Gln Leu Arg Gly Asp Phe Thr Val Glu Lys Asp Gly Lys Lys
                165                 170                 175

His Arg Leu Ile Asn Val Phe Pro Thr Ser Ala Tyr Arg Ser Glu Ala
            180                 185                 190

Leu Arg Ile Leu Gln Thr Gln Gln Glu Phe Asn Pro Gln Ile Thr Asp
        195                 200                 205

Glu Phe Ile Asn Arg Tyr Leu Glu Ile Leu Thr Gly Lys Arg Lys Tyr
    210                 215                 220

Tyr His Gly Pro Gly Asn Glu Lys Ser Arg Thr Asp Tyr Gly Arg Tyr
```

```
            225                 230                 235                 240
Arg Thr Ser Gly Glu Thr Leu Asp Asn Ile Phe Gly Ile Leu Ile Gly
                245                 250                 255
Lys Cys Thr Phe Tyr Pro Asp Glu Phe Arg Ala Ala Lys Ala Ser Tyr
                260                 265                 270
Thr Ala Gln Glu Phe Asn Leu Leu Asn Asp Leu Asn Asn Leu Thr Val
                275                 280                 285
Pro Thr Glu Thr Lys Lys Leu Ser Lys Glu Gln Lys Asn Gln Ile Ile
                290                 295                 300
Asn Tyr Val Lys Asn Glu Lys Ala Met Gly Pro Ala Lys Leu Phe Lys
305                 310                 315                 320
Tyr Ile Ala Lys Leu Leu Ser Cys Asp Val Ala Asp Ile Lys Gly Tyr
                325                 330                 335
Arg Ile Asp Lys Ser Gly Lys Ala Glu Ile His Thr Phe Glu Ala Tyr
                340                 345                 350
Arg Lys Met Lys Thr Leu Glu Thr Leu Asp Ile Glu Gln Met Asp Arg
                355                 360                 365
Glu Thr Leu Asp Lys Leu Ala Tyr Val Leu Thr Leu Asn Thr Glu Arg
                370                 375                 380
Glu Gly Ile Gln Glu Ala Leu Glu His Glu Phe Ala Asp Gly Ser Phe
385                 390                 395                 400
Ser Gln Lys Gln Val Asp Glu Leu Val Gln Phe Arg Lys Ala Asn Ser
                405                 410                 415
Ser Ile Phe Gly Lys Gly Trp His Asn Phe Ser Val Lys Leu Met Met
                420                 425                 430
Glu Leu Ile Pro Glu Leu Tyr Glu Thr Ser Glu Glu Gln Met Thr Ile
                435                 440                 445
Leu Thr Arg Leu Gly Lys Gln Lys Thr Thr Ser Ser Asn Lys Thr
                450                 455                 460
Lys Tyr Ile Asp Glu Lys Leu Leu Thr Glu Glu Ile Tyr Asn Pro Val
465                 470                 475                 480
Val Ala Lys Ser Val Arg Gln Ala Ile Lys Ile Val Asn Ala Ala Ile
                485                 490                 495
Lys Glu Tyr Gly Asp Phe Asp Asn Ile Val Ile Glu Met Ala Arg Glu
                500                 505                 510
Thr Asn Glu Asp Asp Glu Lys Lys Ala Ile Gln Lys Ile Gln Lys Ala
                515                 520                 525
Asn Lys Asp Glu Lys Asp Ala Ala Met Leu Lys Ala Ala Asn Gln Tyr
                530                 535                 540
Asn Gly Lys Ala Glu Leu Pro His Ser Val Phe His Gly His Lys Gln
545                 550                 555                 560
Leu Ala Thr Lys Ile Arg Leu Trp His Gln Gln Gly Glu Arg Cys Leu
                565                 570                 575
Tyr Thr Gly Lys Thr Ile Ser Ile His Asp Leu Ile Asn Asn Ser Asn
                580                 585                 590
Gln Phe Glu Val Asp His Ile Leu Pro Leu Ser Ile Thr Phe Asp Asp
                595                 600                 605
Ser Leu Ala Asn Lys Val Leu Val Tyr Ala Thr Ala Asn Gln Glu Lys
                610                 615                 620
Gly Gln Arg Thr Pro Tyr Gln Ala Leu Asp Ser Met Asp Asp Ala Trp
625                 630                 635                 640
Ser Phe Arg Glu Leu Lys Ala Phe Val Arg Glu Ser Lys Thr Leu Ser
                645                 650                 655
```

-continued

Asn Lys Lys Lys Glu Tyr Leu Leu Thr Glu Glu Asp Ile Ser Lys Phe
            660                 665                 670

Asp Val Arg Lys Lys Phe Ile Glu Arg Asn Leu Val Asp Thr Arg Tyr
            675                 680                 685

Ala Ser Arg Val Val Leu Asn Ala Leu Gln Glu His Phe Arg Ala His
            690                 695                 700

Lys Ile Asp Thr Lys Val Ser Val Val Arg Gly Gln Phe Thr Ser Gln
705                 710                 715                 720

Leu Arg Arg His Trp Gly Ile Glu Lys Thr Arg Asp Thr Tyr His His
                    725                 730                 735

His Ala Val Asp Ala Leu Ile Ile Ala Ala Ser Ser Gln Leu Asn Leu
            740                 745                 750

Trp Lys Lys Gln Lys Asn Thr Leu Val Ser Tyr Ser Glu Glu Gln Leu
            755                 760                 765

Leu Asp Ile Glu Thr Gly Glu Leu Ile Ser Asp Glu Tyr Lys Glu
            770                 775                 780

Ser Val Phe Lys Ala Pro Tyr Gln His Phe Val Asp Thr Leu Lys Ser
785                 790                 795                 800

Lys Glu Phe Glu Asp Ser Ile Leu Phe Ser Tyr Gln Val Asp Ser Lys
                    805                 810                 815

Phe Asn Arg Lys Ile Ser Asp Ala Thr Ile Tyr Ala Thr Arg Gln Ala
            820                 825                 830

Lys Val Gly Lys Asp Lys Lys Asp Glu Thr Tyr Val Leu Gly Lys Ile
            835                 840                 845

Lys Asp Ile Tyr Thr Gln Asp Gly Tyr Asp Ala Phe Met Lys Ile Tyr
            850                 855                 860

Lys Lys Asp Lys Ser Lys Phe Leu Met Tyr Arg His Asp Pro Gln Thr
865                 870                 875                 880

Phe Glu Lys Val Ile Glu Pro Ile Leu Glu Asn Tyr Pro Asn Lys Gln
                    885                 890                 895

Met Asn Glu Lys Gly Lys Glu Val Pro Cys Asn Pro Phe Leu Lys Tyr
            900                 905                 910

Lys Glu Glu His Gly Tyr Ile Arg Lys Tyr Ser Lys Lys Gly Asn Gly
            915                 920                 925

Pro Glu Ile Lys Ser Leu Lys Tyr Tyr Asp Ser Lys Leu Leu Gly Asn
930                 935                 940

Pro Ile Asp Ile Thr Pro Glu Asn Ser Lys Asn Lys Val Val Leu Gln
945                 950                 955                 960

Ser Leu Lys Pro Trp Arg Thr Asp Val Tyr Phe Asn Lys Asn Thr Gly
                    965                 970                 975

Lys Tyr Glu Ile Leu Gly Leu Lys Tyr Ala Asp Leu Gln Phe Glu Lys
            980                 985                 990

Lys Thr Gly Thr Tyr Lys Ile Ser Gln Glu Lys Tyr Asn Gly Ile Met
            995                 1000                1005

Lys Glu Glu Gly Val Asp Ser Asp Ser Glu Phe Lys Phe Thr Leu
            1010                1015                1020

Tyr Lys Asn Asp Leu Leu Leu Val Lys Asp Thr Glu Thr Lys Glu
            1025                1030                1035

Gln Gln Leu Phe Arg Phe Leu Ser Arg Thr Met Pro Asn Val Lys
            1040                1045                1050

Tyr Tyr Val Glu Leu Lys Pro Tyr Ser Lys Asp Lys Phe Glu Lys
            1055                1060                1065

-continued

```
Asn Glu Ser Leu Ile Glu Ile Leu Gly Ser Ala Asp Lys Ser Gly
    1070            1075                1080

Arg Cys Ile Lys Gly Leu Gly Lys Ser Asn Ile Ser Ile Tyr Lys
    1085            1090                1095

Val Arg Thr Asp Val Leu Gly Asn Gln His Ile Ile Lys Asn Glu
    1100            1105                1110

Gly Asp Lys Pro Lys Leu Asp Phe
    1115            1120
```

<210> SEQ ID NO 57
<211> LENGTH: 4947
<212> TYPE: DNA
<213> ORGANISM: Artificial Sequence
<220> FEATURE:
<223> OTHER INFORMATION: Synthetic, engineered or hybrid sequence

<400> SEQUENCE: 57

| | |
|---|---:|
| atgaaacgga cagccgacgg aagcgagttc gagtcaccaa agaagaagcg gaaagtctcc | 60 |
| tcagagactg ggcctgtcgc cgtcgatcca accctgcgcc gccggattga acctcacgag | 120 |
| tttgaagtgt tctttgaccc ccgggagctg agaaaggaga catgcctgct gtacgagatc | 180 |
| aactggggag gcaggcactc catctggagg cacacctctc agaacacaaa taagcacgtg | 240 |
| gaggtgaact tcatcgagaa gtttaccaca gagcggtact tctgccccaa taccagatgt | 300 |
| agcatcacat ggtttctgag ctggtcccct tgccgagagt gtagcagggc catcaccgag | 360 |
| ttcctgtcca gatatcccac cgtgacactg tttatctaca tcgccaggct gtatcaccac | 420 |
| gcagacccaa ggataggca gggcctgcgc gatctgatca gctccggcgt gaccatccag | 480 |
| atcatgacag agcaggagtc cggctactgc tggcggaact tcgtgaatta ttctcctagc | 540 |
| aacgaggccc actggcctag gtacccacac ctgtgggtgc cctgtacgt gctggagctg | 600 |
| tattgcatca tcctgggcct gccccccttgt ctgaatatcc tgcggagaaa gcagccccag | 660 |
| ctgaccttct ttacaatcgc cctgcagtct tgtcactatc agaggctgcc accccacatc | 720 |
| ctgtgggcca caggcctgaa gtctggagga tctagcggag gctcctctgg cagcgagaca | 780 |
| ccaggaacaa gcgagtcagc aacaccagag agcagtggcg gcagcagcgg cggcagcagc | 840 |
| gacctggtgc tgggcctggc tatcggcatc ggcagcgtgg gcgtgggcat cctgaacaag | 900 |
| gtgaccggcg agatcatcca caagaacagt cgcatcttcc ctgctgctca ggctgagaac | 960 |
| aacctggtgc gccgcaccaa ccgccagggt cgccggcttg ctcgccgcaa gaagcaccgg | 1020 |
| cgcgtgcgcc tgaaccgcct gttcgaggag agcggcctga tcaccgactt caccaagatc | 1080 |
| agcatcaacc tgaaccccta ccagctgcgc gtgaagggcc tgaccgacga gctgagcaac | 1140 |
| gaggagctgt tcatcgccct gaagaacatg gtgaagcacc gcggcatcag ctacctggac | 1200 |
| gacgccagcg acgacggcaa cagcagcgtg ggcgactacg cccagatcgt gaaggagaac | 1260 |
| agcaagcagc tggagaccaa gacccccggc cagatccagc tggagcgcta ccagacctac | 1320 |
| ggccagctgc gcggcgactt caccgtggag aaggacggca gaagcaccg cctgatcaac | 1380 |
| gtgttcccca ccagcgccta ccgcagcgag gccctgcgca tcctgcagac cagcaggag | 1440 |
| ttcaacccccc agatcaccga cgagttcatc aaccgctacc tggagatcct gaccggcaag | 1500 |
| cgcaagtact accacggccc cggcaacgag aagagccgca ccgactacgg ccgctaccgc | 1560 |
| accagcggcg agaccctgga caacatcttc ggcatcctga tcggcaagtg caccttctac | 1620 |
| cccgacgagt ccgcgccgc caaggccagc tacaccgccc aggagttcaa tctgctgaac | 1680 |
| gacctgaaca acctgaccgt gcccaccgag accaagaagc tgagcaagga gcagaagaac | 1740 |

```
cagatcatca actacgtgaa gaacgagaag gctatgggcc ccgccaagct gttcaagtac    1800
atcgccaagc tgctgagctg cgacgtggcc gacatcaagg gctaccgcat cgacaagagc    1860
ggcaaggccg agatccacac cttcgaggcc taccgcaaga tgaagaccct ggagaccctg    1920
gacatcgagc agatggaccg agagaccctg gacaagctgg cctacgtgct gacccctgaa    1980
accgagcgcg agggcatcca ggaggccctg gagcacgagt cgccgacgg cagcttcagc     2040 cagaaacagg tggacgagct ggtgcagttc cgcaaggcca acagcagcat cttcggcaag    2100
ggctggcaca acttcagcgt gaagctgatg atggagctga tccccgagct gtacgagacc    2160
agcgaggagc agatgaccat cctgacccgc ctgggcaagc agaagaccac cagcagcagc    2220
aacaagacca agtacatcga cgagaagctg ctgaccgagg agatctacaa ccccgtggtg    2280
gccaagagcg tgcgccaggc catcaagatc gtgaacgccg ccatcaagga gtacggcgac    2340
ttcgacaaca tcgtgatcga gatggcccgc gagaccaacg aggacgacga gaagaaggcc    2400
atccagaaga tccagaaggc caacaaggac gagaaggacg ccgccatgct gaaggccgcc    2460
aaccagtaca acggcaaggc cgagctgccc cacagcgtgt tccacggcca caagcagctg    2520
gccaccaaga tccgcctgtg gcaccagcag ggcgagcgct gcctgtacac cggcaagacc    2580
atcagcatcc acgacctgat caacaacagc aaccagttcg aggtggacca catcctgccc    2640
ctgagcatca ccttcgacga cagcctggcc aacaaggtgc tggtgtacgc caccgccaac    2700
caggagaagg gccagcgcac ccctaccag gccctggaca gcatggacga cgcctggagc    2760
ttccgcgagc tgaaggcctt cgtgcgcgag agcaagaccc tgagcaacaa gaagaaggag    2820
tatctgctga ccgaggagga catcagcaag ttcgacgtgc gcaagaagtt catcgagcgc    2880
aacctggtgg acacccgcta cgccagccgc gtggtgctga cgccctgca ggagcacttc    2940 cgcgcccaca agatcgacac caaggtgagc gtggtgcgcg ccagttcac cagccagctg    3000 cgccgccact ggggcatcga aagacccgc gacacctacc accaccacgc cgtggacgcc    3060
ctgatcattg cggcttctag ccagctgaac ctgtggaaga agcagaagaa caccctggtg    3120
agctacagcg aggagcagct gctggacatc gagaccggcg agctgatcag cgacgacgag    3180
tacaaggaga gcgtgttcaa ggccccctac cagcacttcg tggacaccct gaagagcaag    3240
gagttcgagg acagcatcct gttcagctac caggtggaca gcaagttcaa ccgcaagatc    3300
agcgacgcca ccatctacgc cacccgccag gccaaggtgg gcaaggacaa gaaggacgag    3360
acctacgtgc tgggcaagat caaggacatc tacacccagg acggctacga cgccttcatg    3420
aagatctaca gaaggacaa gagcaagttc ctgatgtacc gccacgaccc ccagaccttc    3480
gagaaggtga tcgagcccat cctggagaac taccccaaca gcagatgaa cgagaaggc     3540 aaggaggtgc cctgcaaccc cttcctgaag tacaaggagg agcacggcta catccgcaag    3600
tacagcaaga agggcaacgg ccccgagatc aagagcctga gtactacga cagcaagctg    3660 ctgggcaacc ccatcgacat caccccgaa acagcaaga acaaggtggt gctgcagagc    3720
cttaagccct ggcgcaccga cgtgtacttc aacaaggcca ccggcaagta cgagatcctg    3780
gggctgaagt acgccgatct gcagtttgag aaaggcacag gcacctacaa gatcagccag    3840
gagaagtaca cgacatcaa gaagaaggag ggcgtggaca cgcgacagcga gttcaagttc    3900 accctgtaca agaacgacct tctgctggtg aaggacaccg agaccaagga gcaacagctg    3960
ttccgcttcc tgagccgcac cctgcccaag cagaagcact acgtggagct gaagccctac    4020
gacaagcaga agttcgaggg cggcgaggcc ctgatcaagg tgctgggcaa cgtggccaac    4080
```

```
ggcggccagt gcatcaaggg cctggccaag agcaacatca gcatctacaa ggtgcgcacc    4140
gacgtgctgg gcaaccagca catcatcaag aacgagggcg acaagcccaa gttggacttc    4200
agcagggctg accccaagaa gaagaggaag gtgggatcta gcggcgggag cggcgggagc    4260 gggggagca  ctaatctgag cgacatcatt gagaaggaga ctgggaaaca gctggtcatt     4320
caggagtcca tcctgatgct gcctgaggag gtggaggaag tgatcggcaa caagccagag    4380
tctgacatcc tggtgcacac cgcctacgac gagtccacag atgagaatgt gatgctgctg    4440
acctctgacg cccccgagta taagccttgg gccctggtca tccaggattc taacggcgag    4500
aataagatca agatgctgag cggaggatcc ggaggatctg gaggcagcac caacctgtct    4560
gacatcatcg agaaggagac aggcaagcag ctggtcatcc aggagagcat cctgatgctg    4620
cccgaagaag tcgaagaagt gatcggaaac aagcctgaga gcgatatcct ggtccatacc    4680
gcctacgacg agagtaccga cgaaaatgtg atgctgctga catccgacgc cccagagtat    4740
aagccctggg ctctggtcat ccaggattcc aacggagaga acaaaatcaa aatgctgtct    4800
ggcggctcaa aaagaaccgc cgacggcagc gaattcgagc ccaagaagaa gaggaaagtc    4860
ggatcctacc catacgatgt tccagattac gcttatccct acgacgtgcc tgattatgca    4920
tacccatatg atgtccccga ctatgcc                                        4947
```

<210> SEQ ID NO 58
<211> LENGTH: 3363
<212> TYPE: DNA
<213> ORGANISM: Artificial Sequence
<220> FEATURE:
<223> OTHER INFORMATION: Synthetic, engineered or hybrid sequence

<400> SEQUENCE: 58

```
agcgacctgg tgctgggcct ggctatcggc atcggcagcg tgggcgtggg catcctgaac      60
aaggtgaccg gcgagatcat ccacaagaac agtcgcatct ccctgctgc  tcaggctgag    120 aacaacctgt gcgccgcac  caaccgccag ggtcgccggc ttgctcgccg caagaagcac    180
cggcgcgtgc gcctgaaccg cctgttcgag gagagcggcc tgatcaccga cttcaccaag    240
atcagcatca acctgaaccc ctaccagctg cgcgtgaagg gcctgaccga cgagctgagc    300
aacgaggagc tgttcatcgc cctgaagaac atggtgaagc accgcggcat cagctacctg    360
gacgacgcca cgacgacgg  caacagcagc gtgggcgact acgcccagat cgtgaaggag    420
aacagcaagc agctggagac caagaccccc ggccagatcc agctggagcg ctaccagacc    480 tacgccagc  tgcgcggcga cttcaccgtg gagaaggacg gcaagaagca ccgcctgatc    540
aacgtgttcc ccaccagcgc ctaccgcagc gaggccctgc gcatcctgca gacccagcag    600
gagttcaacc ccagatcac  cgacgagttc atcaaccgct acctggagat cctgaccggc    660
aagcgcaagt actaccacgg ccccggcaac gagaagagcc gcaccgacta cggccgctac    720
cgcaccagcg gcgagaccct ggacaacatc ttcggcatcc tgatcggcaa gtgcaccttc    780
taccccgacg agttccgcgc cgccaaggcc agctacaccg cccaggagtt caatctgctg    840
aacgacctga acaacctgac cgtgcccacc gagaccaaga agctgagcaa ggagcagaag    900
aaccagatca tcaactacgt gaagaacgag aaggctatgg cccccgccaa gctgttcaag    960
tacatcgcca agctgctgag ctgcgacgtg gccgacatca agggctaccg catcgacaag   1020
agcggcaagg ccgagatcca caccttcgag gcctaccgca agatgaagac cctggagacc   1080
ctggacatcg agcagatgga ccgagagacc ctggacaagt ggcctacgt  gctgaccctg   1140 aacaccgagc gcgagggcat ccaggaggcc ctggagcacg agttcgccga cggcagcttc   1200
```

```
agccagaaac aggtggacga gctggtgcag ttccgcaagg ccaacagcag catcttcggc    1260
aagggctggc acaacttcag cgtgaagctg atgatggagc tgatccccga gctgtacgag    1320
accagcgagg agcagatgac catcctgacc cgcctgggca agcagaagac caccagcagc    1380
agcaacaaga ccaagtacat cgacgagaag ctgctgaccg aggagatcta caaccccgtg    1440
gtggccaaga gcgtgcgcca ggccatcaag atcgtgaacg ccgccatcaa ggagtacggc    1500
gacttcgaca catcgtgat cgagatggcc cgcgagacca cgaggacga cgagaagaag    1560 gccatccaga agatccagaa ggccaacaag gacgagaagg acgccgccat gctgaaggcc    1620
gccaaccagt acaacggcaa ggccgagctg ccccacagcg tgttccacgg ccacaagcag    1680
ctggccacca agatccgcct gtggcaccag cagggcgagc gctgcctgta caccggcaag    1740
accatcagca tccacgacct gatcaacaac agcaaccagt cgaggtgga ccacatcctg    1800 cccctgagca tcaccttcga cgacagcctg gccaacaagg tgctggtgta cgccaccgcc    1860
aaccaggaga agggccagcg cacccccctac caggccctgg acagcatgga cgacgcctgg    1920
agcttccgcg agctgaaggc cttcgtgcgc gagagcaaga ccctgagcaa caagaagaag    1980
gagtatctgc tgaccgagga ggacatcagc aagttcgacg tgcgcaagaa gttcatcgag    2040
cgcaacctgg tggacacccg ctacgccagc cgcgtggtgc tgaacgccct gcaggagcac    2100
ttccgcgccc acaagatcga caccaaggtg agcgtggtgc gcggcagtt caccagccag    2160 ctgcgccgcc actggggcat cgagaagacc cgcgacacct accaccacca cgccgtggac    2220
gccctgatca ttgcggcttc tagccagctg aacctgtgga gaagcagaa gaacaccctg    2280 gtgagctaca gcgaggagca gctgctggac atcgagaccg cgagctgat cagcgacgac    2340 gagtacaagg agagcgtgtt caaggccccc taccagcact cgtggacac cctgaagagc    2400 aaggagttcg aggacagcat cctgttcagc taccaggtgg acagcaagtt caaccgcaag    2460
atcagcgacg ccaccatcta cgccaccgc caggccaagg tgggcaagga caagaaggac    2520
gagacctacg tgctgggcaa gatcaaggac atctacaccc aggacggcta cgacgccttc    2580
atgaagatct acaagaagga caagagcaag ttcctgatgt accgccacga ccccagacc    2640 ttcgagaagg tgatcgagcc catcctggag aactacccca caagcagat gaacgagaaa    2700 ggcaaggagg tgccctgcaa ccccttcctg aagtacaagg aggagcacgg ctacatccgc    2760
aagtacagca gaaagggcaa cggcccgag atcaagagcc tgaagtacta cgacagcaag    2820
ctgctgggca accccatcga catcaccccc gaaaacagca gaacaaggt ggtgctgcag    2880 agccttaagc cctggcgcac cgacgtgtac ttcaacaagg ccaccggcaa gtacgagatc    2940
ctggggctga gtacgccga tctgcagttt gagaaaggca caggcaccta caagatcagc    3000
caggagaagt acaacgacat caagaagaag gagggcgtgg acagcgacag cgagttcaag    3060
ttcaccctgt acaagaacga ccttctgctg gtgaaggaca ccgagaccaa ggagcaacag    3120
ctgttccgct tcctgagccg cacccgccc aagcagaagc actacgtgga gctgaagccc    3180
tacgacaagc agaagttcga gggcggcgag gccctgatca aggtgctggg caacgtggcc    3240
aacggcggcc agtgcatcaa gggcctggcc aagagcaaca tcagcatcta aaggtgcgc    3300 accgacgtgc tgggcaacca gcacatcatc aagaacgagg cgacaagcc caagttggac    3360 ttc                                                                  3363
```

<210> SEQ ID NO 59
<211> LENGTH: 1649
<212> TYPE: PRT

<213> ORGANISM: Artificial Sequence
<220> FEATURE:
<223> OTHER INFORMATION: Synthetic, engineered or hybrid sequence

<400> SEQUENCE: 59

```
Met Lys Arg Thr Ala Asp Gly Ser Glu Phe Glu Ser Pro Lys Lys Lys
1               5                   10                  15

Arg Lys Val Ser Ser Glu Thr Gly Pro Val Ala Val Asp Pro Thr Leu
            20                  25                  30

Arg Arg Arg Ile Glu Pro His Glu Phe Glu Val Phe Phe Asp Pro Arg
        35                  40                  45

Glu Leu Arg Lys Glu Thr Cys Leu Leu Tyr Glu Ile Asn Trp Gly Gly
    50                  55                  60

Arg His Ser Ile Trp Arg His Thr Ser Gln Asn Thr Asn Lys His Val
65                  70                  75                  80

Glu Val Asn Phe Ile Glu Lys Phe Thr Thr Glu Arg Tyr Phe Cys Pro
                85                  90                  95

Asn Thr Arg Cys Ser Ile Thr Trp Phe Leu Ser Trp Ser Pro Cys Gly
            100                 105                 110

Glu Cys Ser Arg Ala Ile Thr Glu Phe Leu Ser Arg Tyr Pro His Val
        115                 120                 125

Thr Leu Phe Ile Tyr Ile Ala Arg Leu Tyr His His Ala Asp Pro Arg
    130                 135                 140

Asn Arg Gln Gly Leu Arg Asp Leu Ile Ser Ser Gly Val Thr Ile Gln
145                 150                 155                 160

Ile Met Thr Glu Gln Glu Ser Gly Tyr Cys Trp Arg Asn Phe Val Asn
                165                 170                 175

Tyr Ser Pro Ser Asn Glu Ala His Trp Pro Arg Tyr Pro His Leu Trp
            180                 185                 190

Val Arg Leu Tyr Val Leu Glu Leu Tyr Cys Ile Ile Leu Gly Leu Pro
        195                 200                 205

Pro Cys Leu Asn Ile Leu Arg Arg Lys Gln Pro Gln Leu Thr Phe Phe
    210                 215                 220

Thr Ile Ala Leu Gln Ser Cys His Tyr Gln Arg Leu Pro Pro His Ile
225                 230                 235                 240

Leu Trp Ala Thr Gly Leu Lys Ser Gly Gly Ser Gly Gly Ser Ser
                245                 250                 255

Gly Ser Glu Thr Pro Gly Thr Ser Glu Ser Ala Thr Pro Glu Ser Ser
            260                 265                 270

Gly Gly Ser Ser Gly Gly Ser Ser Asp Leu Val Leu Gly Leu Ala Ile
        275                 280                 285

Gly Ile Gly Ser Val Gly Val Gly Ile Leu Asn Lys Val Thr Gly Glu
    290                 295                 300

Ile Ile His Lys Asn Ser Arg Ile Phe Pro Ala Ala Gln Ala Glu Asn
305                 310                 315                 320

Asn Leu Val Arg Arg Thr Asn Arg Gln Gly Arg Arg Leu Ala Arg Arg
                325                 330                 335

Lys Lys His Arg Arg Val Arg Leu Asn Arg Leu Phe Glu Glu Ser Gly
            340                 345                 350

Leu Ile Thr Asp Phe Thr Lys Ile Ser Ile Asn Leu Asn Pro Tyr Gln
        355                 360                 365

Leu Arg Val Lys Gly Leu Thr Asp Glu Leu Ser Asn Glu Glu Leu Phe
    370                 375                 380

Ile Ala Leu Lys Asn Met Val Lys His Arg Gly Ile Ser Tyr Leu Asp
```

-continued

```
385                 390                 395                 400
Asp Ala Ser Asp Asp Gly Asn Ser Ser Val Gly Asp Tyr Ala Gln Ile
                405                 410                 415
Val Lys Glu Asn Ser Lys Gln Leu Glu Thr Lys Thr Pro Gly Gln Ile
                420                 425                 430
Gln Leu Glu Arg Tyr Gln Thr Tyr Gly Gln Leu Arg Gly Asp Phe Thr
                435                 440                 445
Val Glu Lys Asp Gly Lys Lys His Arg Leu Ile Asn Val Phe Pro Thr
        450                 455                 460
Ser Ala Tyr Arg Ser Glu Ala Leu Arg Ile Leu Gln Thr Gln Gln Glu
465                 470                 475                 480
Phe Asn Pro Gln Ile Thr Asp Glu Phe Ile Asn Arg Tyr Leu Glu Ile
                485                 490                 495
Leu Thr Gly Lys Arg Lys Tyr Tyr His Gly Pro Gly Asn Glu Lys Ser
                500                 505                 510
Arg Thr Asp Tyr Gly Arg Tyr Arg Thr Ser Gly Glu Thr Leu Asp Asn
                515                 520                 525
Ile Phe Gly Ile Leu Ile Gly Lys Cys Thr Phe Tyr Pro Asp Glu Phe
                530                 535                 540
Arg Ala Ala Lys Ala Ser Tyr Thr Ala Gln Glu Phe Asn Leu Leu Asn
545                 550                 555                 560
Asp Leu Asn Asn Leu Thr Val Pro Thr Glu Thr Lys Lys Leu Ser Lys
                565                 570                 575
Glu Gln Lys Asn Gln Ile Ile Asn Tyr Val Lys Asn Glu Lys Ala Met
                580                 585                 590
Gly Pro Ala Lys Leu Phe Lys Tyr Ile Ala Lys Leu Leu Ser Cys Asp
                595                 600                 605
Val Ala Asp Ile Lys Gly Tyr Arg Ile Asp Lys Ser Gly Lys Ala Glu
                610                 615                 620
Ile His Thr Phe Glu Ala Tyr Arg Lys Met Lys Thr Leu Glu Thr Leu
625                 630                 635                 640
Asp Ile Glu Gln Met Asp Arg Glu Thr Leu Asp Lys Leu Ala Tyr Val
                645                 650                 655
Leu Thr Leu Asn Thr Glu Arg Glu Gly Ile Gln Glu Ala Leu Glu His
                660                 665                 670
Glu Phe Ala Asp Gly Ser Phe Ser Gln Lys Gln Val Asp Glu Leu Val
                675                 680                 685
Gln Phe Arg Lys Ala Asn Ser Ser Ile Phe Gly Lys Gly Trp His Asn
                690                 695                 700
Phe Ser Val Lys Leu Met Met Glu Leu Ile Pro Glu Leu Tyr Glu Thr
705                 710                 715                 720
Ser Glu Glu Gln Met Thr Ile Leu Thr Arg Leu Gly Lys Gln Lys Thr
                725                 730                 735
Thr Ser Ser Ser Asn Lys Thr Lys Tyr Ile Asp Glu Lys Leu Leu Thr
                740                 745                 750
Glu Glu Ile Tyr Asn Pro Val Val Ala Lys Ser Val Arg Gln Ala Ile
                755                 760                 765
Lys Ile Val Asn Ala Ala Ile Lys Glu Tyr Gly Asp Phe Asp Asn Ile
                770                 775                 780
Val Ile Glu Met Ala Arg Glu Thr Asn Glu Asp Asp Glu Lys Lys Ala
785                 790                 795                 800
Ile Gln Lys Ile Gln Lys Ala Asn Lys Asp Glu Lys Asp Ala Ala Met
                805                 810                 815
```

```
Leu Lys Ala Ala Asn Gln Tyr Asn Gly Lys Ala Glu Leu Pro His Ser
            820                 825                 830

Val Phe His Gly His Lys Gln Leu Ala Thr Lys Ile Arg Leu Trp His
            835                 840                 845

Gln Gln Gly Glu Arg Cys Leu Tyr Thr Gly Lys Thr Ile Ser Ile His
        850                 855                 860

Asp Leu Ile Asn Asn Ser Asn Gln Phe Glu Val Asp His Ile Leu Pro
865                 870                 875                 880

Leu Ser Ile Thr Phe Asp Asp Ser Leu Ala Asn Lys Val Leu Val Tyr
                885                 890                 895

Ala Thr Ala Asn Gln Glu Lys Gly Gln Arg Thr Pro Tyr Gln Ala Leu
            900                 905                 910

Asp Ser Met Asp Asp Ala Trp Ser Phe Arg Glu Leu Lys Ala Phe Val
            915                 920                 925

Arg Glu Ser Lys Thr Leu Ser Asn Lys Lys Glu Tyr Leu Leu Thr
            930                 935                 940

Glu Glu Asp Ile Ser Lys Phe Asp Val Arg Lys Lys Phe Ile Glu Arg
945                 950                 955                 960

Asn Leu Val Asp Thr Arg Tyr Ala Ser Arg Val Val Leu Asn Ala Leu
                965                 970                 975

Gln Glu His Phe Arg Ala His Lys Ile Asp Thr Lys Val Ser Val Val
            980                 985                 990

Arg Gly Gln Phe Thr Ser Gln Leu Arg Arg His Trp Gly Ile Glu Lys
            995                 1000                1005

Thr Arg Asp Thr Tyr His His His Ala Val Asp Ala Leu Ile Ile
    1010                1015                1020

Ala Ala Ser Ser Gln Leu Asn Leu Trp Lys Lys Gln Lys Asn Thr
    1025                1030                1035

Leu Val Ser Tyr Ser Glu Glu Gln Leu Leu Asp Ile Glu Thr Gly
    1040                1045                1050

Glu Leu Ile Ser Asp Asp Glu Tyr Lys Glu Ser Val Phe Lys Ala
    1055                1060                1065

Pro Tyr Gln His Phe Val Asp Thr Leu Lys Ser Lys Glu Phe Glu
    1070                1075                1080

Asp Ser Ile Leu Phe Ser Tyr Gln Val Asp Ser Lys Phe Asn Arg
    1085                1090                1095

Lys Ile Ser Asp Ala Thr Ile Tyr Ala Thr Arg Gln Ala Lys Val
    1100                1105                1110

Gly Lys Asp Lys Lys Asp Glu Thr Tyr Val Leu Gly Lys Ile Lys
    1115                1120                1125

Asp Ile Tyr Thr Gln Asp Gly Tyr Asp Ala Phe Met Lys Ile Tyr
    1130                1135                1140

Lys Lys Asp Lys Ser Lys Phe Leu Met Tyr Arg His Asp Pro Gln
    1145                1150                1155

Thr Phe Glu Lys Val Ile Glu Pro Ile Leu Glu Asn Tyr Pro Asn
    1160                1165                1170

Lys Gln Met Asn Glu Lys Gly Lys Glu Val Pro Cys Asn Pro Phe
    1175                1180                1185

Leu Lys Tyr Lys Glu Glu His Gly Tyr Ile Arg Lys Tyr Ser Lys
    1190                1195                1200

Lys Gly Asn Gly Pro Glu Ile Lys Ser Leu Lys Tyr Tyr Asp Ser
    1205                1210                1215
```

```
Lys Leu Leu Gly Asn Pro Ile Asp Ile Thr Pro Glu Asn Ser Lys
    1220                1225                1230

Asn Lys Val Val Leu Gln Ser Leu Lys Pro Trp Arg Thr Asp Val
    1235                1240                1245

Tyr Phe Asn Lys Ala Thr Gly Lys Tyr Glu Ile Leu Gly Leu Lys
    1250                1255                1260

Tyr Ala Asp Leu Gln Phe Glu Lys Gly Thr Gly Thr Tyr Lys Ile
    1265                1270                1275

Ser Gln Glu Lys Tyr Asn Asp Ile Lys Lys Lys Glu Gly Val Asp
    1280                1285                1290

Ser Asp Ser Glu Phe Lys Phe Thr Leu Tyr Lys Asn Asp Leu Leu
    1295                1300                1305

Leu Val Lys Asp Thr Glu Thr Lys Glu Gln Gln Leu Phe Arg Phe
    1310                1315                1320

Leu Ser Arg Thr Leu Pro Lys Gln Lys His Tyr Val Glu Leu Lys
    1325                1330                1335

Pro Tyr Asp Lys Gln Lys Phe Glu Gly Gly Glu Ala Leu Ile Lys
    1340                1345                1350

Val Leu Gly Asn Val Ala Asn Gly Gly Gln Cys Ile Lys Gly Leu
    1355                1360                1365

Ala Lys Ser Asn Ile Ser Ile Tyr Lys Val Arg Thr Asp Val Leu
    1370                1375                1380

Gly Asn Gln His Ile Ile Lys Asn Glu Gly Asp Lys Pro Lys Leu
    1385                1390                1395

Asp Phe Ser Arg Ala Asp Pro Lys Lys Lys Arg Lys Val Gly Ser
    1400                1405                1410

Ser Gly Gly Ser Gly Gly Ser Gly Gly Ser Thr Asn Leu Ser Asp
    1415                1420                1425

Ile Ile Glu Lys Glu Thr Gly Lys Gln Leu Val Ile Gln Glu Ser
    1430                1435                1440

Ile Leu Met Leu Pro Glu Val Glu Glu Val Ile Gly Asn Lys
    1445                1450                1455

Pro Glu Ser Asp Ile Leu Val His Thr Ala Tyr Asp Glu Ser Thr
    1460                1465                1470

Asp Glu Asn Val Met Leu Leu Thr Ser Asp Ala Pro Glu Tyr Lys
    1475                1480                1485

Pro Trp Ala Leu Val Ile Gln Asp Ser Asn Gly Glu Asn Lys Ile
    1490                1495                1500

Lys Met Leu Ser Gly Gly Ser Gly Gly Ser Gly Gly Ser Thr Asn
    1505                1510                1515

Leu Ser Asp Ile Ile Glu Lys Glu Thr Gly Lys Gln Leu Val Ile
    1520                1525                1530

Gln Glu Ser Ile Leu Met Leu Pro Glu Glu Val Glu Glu Val Ile
    1535                1540                1545

Gly Asn Lys Pro Glu Ser Asp Ile Leu Val His Thr Ala Tyr Asp
    1550                1555                1560

Glu Ser Thr Asp Glu Asn Val Met Leu Leu Thr Ser Asp Ala Pro
    1565                1570                1575

Glu Tyr Lys Pro Trp Ala Leu Val Ile Gln Asp Ser Asn Gly Glu
    1580                1585                1590

Asn Lys Ile Lys Met Leu Ser Gly Gly Ser Lys Arg Thr Ala Asp
    1595                1600                1605

Gly Ser Glu Phe Glu Pro Lys Lys Lys Arg Lys Val Gly Ser Tyr
```

```
              1610              1615              1620
Pro Tyr Asp Val Pro Asp Tyr Ala Tyr Pro Tyr Asp Val Pro Asp
        1625              1630              1635

Tyr Ala Tyr Pro Tyr Asp Val Pro Asp Tyr Ala
        1640              1645

<210> SEQ ID NO 60
<211> LENGTH: 1121
<212> TYPE: PRT
<213> ORGANISM: Artificial Sequence
<220> FEATURE:
<223> OTHER INFORMATION: Synthetic, engineered or hybrid sequence

<400> SEQUENCE: 60

Ser Asp Leu Val Leu Gly Leu Ala Ile Gly Ile Gly Ser Val Gly Val
1               5                   10                  15

Gly Ile Leu Asn Lys Val Thr Gly Glu Ile Ile His Lys Asn Ser Arg
            20                  25                  30

Ile Phe Pro Ala Ala Gln Ala Glu Asn Asn Leu Val Arg Arg Thr Asn
        35                  40                  45

Arg Gln Gly Arg Arg Leu Ala Arg Arg Lys His Arg Arg Val Arg
    50                  55                  60

Leu Asn Arg Leu Phe Glu Glu Ser Gly Leu Ile Thr Asp Phe Thr Lys
65                  70                  75                  80

Ile Ser Ile Asn Leu Asn Pro Tyr Gln Leu Arg Val Lys Gly Leu Thr
                85                  90                  95

Asp Glu Leu Ser Asn Glu Glu Leu Phe Ile Ala Leu Lys Asn Met Val
            100                 105                 110

Lys His Arg Gly Ile Ser Tyr Leu Asp Asp Ala Ser Asp Asp Gly Asn
        115                 120                 125

Ser Ser Val Gly Asp Tyr Ala Gln Ile Val Lys Glu Asn Ser Lys Gln
    130                 135                 140

Leu Glu Thr Lys Thr Pro Gly Gln Ile Gln Leu Glu Arg Tyr Gln Thr
145                 150                 155                 160

Tyr Gly Gln Leu Arg Gly Asp Phe Thr Val Glu Lys Asp Gly Lys Lys
                165                 170                 175

His Arg Leu Ile Asn Val Phe Pro Thr Ser Ala Tyr Arg Ser Glu Ala
            180                 185                 190

Leu Arg Ile Leu Gln Thr Gln Gln Glu Phe Asn Pro Gln Ile Thr Asp
        195                 200                 205

Glu Phe Ile Asn Arg Tyr Leu Glu Ile Leu Thr Gly Lys Arg Lys Tyr
    210                 215                 220

Tyr His Gly Pro Gly Asn Glu Lys Ser Arg Thr Asp Tyr Gly Arg Tyr
225                 230                 235                 240

Arg Thr Ser Gly Glu Thr Leu Asp Asn Ile Phe Gly Ile Leu Ile Gly
                245                 250                 255

Lys Cys Thr Phe Tyr Pro Asp Glu Phe Arg Ala Ala Lys Ala Ser Tyr
            260                 265                 270

Thr Ala Gln Glu Phe Asn Leu Leu Asn Asp Leu Asn Asn Leu Thr Val
        275                 280                 285

Pro Thr Glu Thr Lys Lys Leu Ser Lys Glu Gln Lys Asn Gln Ile Ile
    290                 295                 300

Asn Tyr Val Lys Asn Glu Lys Ala Met Gly Pro Ala Lys Leu Phe Lys
305                 310                 315                 320

Tyr Ile Ala Lys Leu Leu Ser Cys Asp Val Ala Asp Ile Lys Gly Tyr
```

-continued

```
            325                 330                 335
Arg Ile Asp Lys Ser Gly Lys Ala Glu Ile His Thr Phe Glu Ala Tyr
            340                 345                 350
Arg Lys Met Lys Thr Leu Glu Thr Leu Asp Ile Glu Gln Met Asp Arg
            355                 360                 365
Glu Thr Leu Asp Lys Leu Ala Tyr Val Leu Thr Leu Asn Thr Glu Arg
            370                 375                 380
Glu Gly Ile Gln Glu Ala Leu Glu His Glu Phe Ala Asp Gly Ser Phe
385                 390                 395                 400
Ser Gln Lys Gln Val Asp Glu Leu Val Gln Phe Arg Lys Ala Asn Ser
            405                 410                 415
Ser Ile Phe Gly Lys Gly Trp His Asn Phe Ser Val Lys Leu Met Met
            420                 425                 430
Glu Leu Ile Pro Glu Leu Tyr Glu Thr Ser Glu Glu Gln Met Thr Ile
            435                 440                 445
Leu Thr Arg Leu Gly Lys Gln Lys Thr Thr Ser Ser Ser Asn Lys Thr
            450                 455                 460
Lys Tyr Ile Asp Glu Lys Leu Leu Thr Glu Glu Ile Tyr Asn Pro Val
465                 470                 475                 480
Val Ala Lys Ser Val Arg Gln Ala Ile Lys Ile Val Asn Ala Ala Ile
            485                 490                 495
Lys Glu Tyr Gly Asp Phe Asp Asn Ile Val Ile Glu Met Ala Arg Glu
            500                 505                 510
Thr Asn Glu Asp Asp Glu Lys Lys Ala Ile Gln Lys Ile Gln Lys Ala
            515                 520                 525
Asn Lys Asp Glu Lys Asp Ala Ala Met Leu Lys Ala Ala Asn Gln Tyr
            530                 535                 540
Asn Gly Lys Ala Glu Leu Pro His Ser Val Phe His Gly His Lys Gln
545                 550                 555                 560
Leu Ala Thr Lys Ile Arg Leu Trp His Gln Gln Gly Glu Arg Cys Leu
            565                 570                 575
Tyr Thr Gly Lys Thr Ile Ser Ile His Asp Leu Ile Asn Asn Ser Asn
            580                 585                 590
Gln Phe Glu Val Asp His Ile Leu Pro Leu Ser Ile Thr Phe Asp Asp
            595                 600                 605
Ser Leu Ala Asn Lys Val Leu Val Tyr Ala Thr Ala Asn Gln Glu Lys
            610                 615                 620
Gly Gln Arg Thr Pro Tyr Gln Ala Leu Asp Ser Met Asp Asp Ala Trp
625                 630                 635                 640
Ser Phe Arg Glu Leu Lys Ala Phe Val Arg Glu Ser Lys Thr Leu Ser
            645                 650                 655
Asn Lys Lys Lys Glu Tyr Leu Leu Thr Glu Glu Asp Ile Ser Lys Phe
            660                 665                 670
Asp Val Arg Lys Lys Phe Ile Glu Arg Asn Leu Val Asp Thr Arg Tyr
            675                 680                 685
Ala Ser Arg Val Val Leu Asn Ala Leu Gln Glu His Phe Arg Ala His
            690                 695                 700
Lys Ile Asp Thr Lys Val Ser Val Val Arg Gly Gln Phe Thr Ser Gln
705                 710                 715                 720
Leu Arg Arg His Trp Gly Ile Glu Lys Thr Arg Asp Thr Tyr His His
            725                 730                 735
His Ala Val Asp Ala Leu Ile Ile Ala Ala Ser Ser Gln Leu Asn Leu
            740                 745                 750
```

Trp Lys Lys Gln Lys Asn Thr Leu Val Ser Tyr Ser Glu Glu Gln Leu
    755                 760                 765

Leu Asp Ile Glu Thr Gly Glu Leu Ile Ser Asp Asp Glu Tyr Lys Glu
    770                 775                 780

Ser Val Phe Lys Ala Pro Tyr Gln His Phe Val Asp Thr Leu Lys Ser
785                 790                 795                 800

Lys Glu Phe Glu Asp Ser Ile Leu Phe Ser Tyr Gln Val Asp Ser Lys
                805                 810                 815

Phe Asn Arg Lys Ile Ser Asp Ala Thr Ile Tyr Ala Thr Arg Gln Ala
            820                 825                 830

Lys Val Gly Lys Asp Lys Lys Asp Glu Thr Tyr Val Leu Gly Lys Ile
        835                 840                 845

Lys Asp Ile Tyr Thr Gln Asp Gly Tyr Asp Ala Phe Met Lys Ile Tyr
    850                 855                 860

Lys Lys Asp Lys Ser Lys Phe Leu Met Tyr Arg His Asp Pro Gln Thr
865                 870                 875                 880

Phe Glu Lys Val Ile Glu Pro Ile Leu Glu Asn Tyr Pro Asn Lys Gln
                885                 890                 895

Met Asn Glu Lys Gly Lys Glu Val Pro Cys Asn Pro Phe Leu Lys Tyr
            900                 905                 910

Lys Glu Glu His Gly Tyr Ile Arg Lys Tyr Ser Lys Lys Gly Asn Gly
        915                 920                 925

Pro Glu Ile Lys Ser Leu Lys Tyr Tyr Asp Ser Lys Leu Leu Gly Asn
    930                 935                 940

Pro Ile Asp Ile Thr Pro Glu Asn Ser Lys Asn Lys Val Val Leu Gln
945                 950                 955                 960

Ser Leu Lys Pro Trp Arg Thr Asp Val Tyr Phe Asn Lys Ala Thr Gly
                965                 970                 975

Lys Tyr Glu Ile Leu Gly Leu Lys Tyr Ala Asp Leu Gln Phe Glu Lys
            980                 985                 990

Gly Thr Gly Thr Tyr Lys Ile Ser Gln Glu Lys Tyr Asn Asp Ile Lys
        995                 1000                1005

Lys Lys Glu Gly Val Asp Ser Asp Ser Glu Phe Lys Phe Thr Leu
    1010                1015                1020

Tyr Lys Asn Asp Leu Leu Leu Val Lys Asp Thr Glu Thr Lys Glu
    1025                1030                1035

Gln Gln Leu Phe Arg Phe Leu Ser Arg Thr Leu Pro Lys Gln Lys
    1040                1045                1050

His Tyr Val Glu Leu Lys Pro Tyr Asp Lys Gln Lys Phe Glu Gly
    1055                1060                1065

Gly Glu Ala Leu Ile Lys Val Leu Gly Asn Val Ala Asn Gly Gly
    1070                1075                1080

Gln Cys Ile Lys Gly Leu Ala Lys Ser Asn Ile Ser Ile Tyr Lys
    1085                1090                1095

Val Arg Thr Asp Val Leu Gly Asn Gln His Ile Ile Lys Asn Glu
    1100                1105                1110

Gly Asp Lys Pro Lys Leu Asp Phe
    1115                1120

<210> SEQ ID NO 61
<211> LENGTH: 16
<212> TYPE: PRT
<213> ORGANISM: Artificial Sequence
<220> FEATURE:

<223> OTHER INFORMATION: Synthetic, engineered or hybrid sequence

<400> SEQUENCE: 61

Lys Arg Pro Ala Ala Thr Lys Lys Ala Gly Gln Ala Lys Lys Lys Lys
1               5                   10                  15

<210> SEQ ID NO 62
<211> LENGTH: 11
<212> TYPE: PRT
<213> ORGANISM: Artificial Sequence
<220> FEATURE:
<223> OTHER INFORMATION: Synthetic, engineered or hybrid sequence

<400> SEQUENCE: 62

Ser Pro Lys Lys Lys Arg Lys Val Glu Ala Ser
1               5                   10

<210> SEQ ID NO 63
<211> LENGTH: 6
<212> TYPE: PRT
<213> ORGANISM: Artificial Sequence
<220> FEATURE:
<223> OTHER INFORMATION: Synthetic, engineered or hybrid sequence

<400> SEQUENCE: 63

Lys Lys Lys Arg Lys Val
1               5

<210> SEQ ID NO 64
<211> LENGTH: 18
<212> TYPE: PRT
<213> ORGANISM: Artificial Sequence
<220> FEATURE:
<223> OTHER INFORMATION: Synthetic, engineered or hybrid sequence

<400> SEQUENCE: 64

Ser Pro Lys Lys Lys Arg Lys Val Glu Ala Ser Pro Lys Lys Lys Arg
1               5                   10                  15

Lys Val

<210> SEQ ID NO 65
<211> LENGTH: 5
<212> TYPE: PRT
<213> ORGANISM: Artificial Sequence
<220> FEATURE:
<223> OTHER INFORMATION: Synthetic, engineered or hybrid sequence

<400> SEQUENCE: 65

Lys Lys Lys Arg Lys
1               5

<210> SEQ ID NO 66
<211> LENGTH: 32
<212> TYPE: DNA
<213> ORGANISM: Artificial Sequence
<220> FEATURE:
<223> OTHER INFORMATION: Synthetic, engineered or hybrid sequence

<400> SEQUENCE: 66
gaggaagggc ctgagtccga gcagaagaag aa                                    32

<210> SEQ ID NO 67
<211> LENGTH: 32
<212> TYPE: DNA
<213> ORGANISM: Artificial Sequence
<220> FEATURE:

```
<223> OTHER INFORMATION: Synthetic, engineered or hybrid sequence

<400> SEQUENCE: 67
ttcttcttct gctcggactc aggcccttcc tc                                32

<210> SEQ ID NO 68
<211> LENGTH: 32
<212> TYPE: DNA
<213> ORGANISM: Artificial Sequence
<220> FEATURE:
<223> OTHER INFORMATION: Synthetic, engineered or hybrid sequence

<400> SEQUENCE: 68
ccagaggtat ccagcagagg ggagaagaaa ga                                32

<210> SEQ ID NO 69
<211> LENGTH: 32
<212> TYPE: DNA
<213> ORGANISM: Artificial Sequence
<220> FEATURE:
<223> OTHER INFORMATION: Synthetic, engineered or hybrid sequence

<400> SEQUENCE: 69
tctttcttct cccctctgct ggatacctct gg                                32

<210> SEQ ID NO 70
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 70
gccagggagg gagggcaca ga                                            22

<210> SEQ ID NO 71
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 71
ggaggacaaa gtacaaacg                                               19

<210> SEQ ID NO 72
<211> LENGTH: 24
<212> TYPE: DNA
<213> ORGANISM: Artificial Sequence
<220> FEATURE:
<223> OTHER INFORMATION: Synthetic, engineered or hybrid sequence

<400> SEQUENCE: 72
gaaccggagg acaaagtaca aacg                                         24

<210> SEQ ID NO 73
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 73
gaggaagggc ctgagtccga                                              20
```

-continued

```
<210> SEQ ID NO 74
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 74
gaagggcctg agtccgagca                                                   20

<210> SEQ ID NO 75
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 75
gggcctgagt ccgagcagaa                                                   20

<210> SEQ ID NO 76
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 76
gcccaggcag gcaggctctc cga                                               23

<210> SEQ ID NO 77
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 77
ggaaaagcga tccaggtgct                                                   20

<210> SEQ ID NO 78
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 78
gtaggtagtg cttgagaccg                                                   20

<210> SEQ ID NO 79
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 79
gtactaatca gatggaagct ct                                                22

<210> SEQ ID NO 80
<211> LENGTH: 22
<212> TYPE: DNA
<213> ORGANISM: Artificial Sequence
<220> FEATURE:
<223> OTHER INFORMATION: Synthetic, engineered or hybrid sequence
```

```
<400> SEQUENCE: 80
gaaatcattg agtcccccgc ct                                              22

<210> SEQ ID NO 81
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 81
gaggtatcca gcagagggga                                                 20

<210> SEQ ID NO 82
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 82
gtcccagagg tatccagcag agg                                             23

<210> SEQ ID NO 83
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 83
gcagcttgga tgctataagc                                                 20

<210> SEQ ID NO 84
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 84
ggtaccccac gcagaaagct                                                 20

<210> SEQ ID NO 85
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 85
gttggggcct cgaatccagg                                                 20

<210> SEQ ID NO 86
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 86
gataccacac acaccctggt                                                 20

<210> SEQ ID NO 87
<211> LENGTH: 21
```

```
<212> TYPE: DNA
<213> ORGANISM: Artificial Sequence
<220> FEATURE:
<223> OTHER INFORMATION: Synthetic, engineered or hybrid sequence

<400> SEQUENCE: 87
gtagtaagaa gatggggcgg c                                              21

<210> SEQ ID NO 88
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 88
gcatatccta gtcgactatg a                                              21

<210> SEQ ID NO 89
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 89
ggtcactgct catcttcac                                                 19

<210> SEQ ID NO 90
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 90
gggtcactgc tcatcttcac                                                20

<210> SEQ ID NO 91
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 91
gaggtcactg ctcatcttca c                                              21

<210> SEQ ID NO 92
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 92
gcacgacgcc tcccgctcct                                                20

<210> SEQ ID NO 93
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 93
```

```
gccacgacgc ctcccgctcc t                                              21
```

<210> SEQ ID NO 94
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 94

```
gagacccatg tccactgcca                                                20
```

<210> SEQ ID NO 95
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 95

```
ggtgggaact cactactcgg                                                20
```

<210> SEQ ID NO 96
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 96

```
ggcataacta accccgaagg                                                20
```

<210> SEQ ID NO 97
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 97

```
gggcactggc tggcaggggt                                                20
```

<210> SEQ ID NO 98
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 98

```
gtatttgccg aagttgtagc c                                              21
```

<210> SEQ ID NO 99
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 99

```
gtacaaacgg cagaagctgg ag                                             22
```

<210> SEQ ID NO 100
<211> LENGTH: 20
<212> TYPE: DNA
<213> ORGANISM: Artificial Sequence

```
<220> FEATURE:
<223> OTHER INFORMATION: Synthetic, engineered or hybrid sequence

<400> SEQUENCE: 100
gtagggcctt cgcgcacctc                                                    20

<210> SEQ ID NO 101
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 101
gcttgagacc gccagaagc                                                     19

<210> SEQ ID NO 102
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 102
gtgcttgaga ccgccagaag c                                                  21

<210> SEQ ID NO 103
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 103
ggcctggaag ttcgctaatc                                                    20

<210> SEQ ID NO 104
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 104
gagagggaca cacagatcta                                                    20

<210> SEQ ID NO 105
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 105
gagagccgtt ccctctttgc                                                    20

<210> SEQ ID NO 106
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 106
gggcattggc gaggagggag                                                    20
```

```
<210> SEQ ID NO 107
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 107
gaaaattacc catccgccc                                                    19

<210> SEQ ID NO 108
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 108
gcctgaaaat tacccatccg ccc                                               23

<210> SEQ ID NO 109
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 109
ggaagggcct gagtccgagc                                                   20

<210> SEQ ID NO 110
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 110
gtaggtagtg cttgagacc                                                    19

<210> SEQ ID NO 111
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 111
gtgcttgaga ccgccagaag                                                   20

<210> SEQ ID NO 112
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 112
gcagcttgga tgctataag                                                    19

<210> SEQ ID NO 113
<211> LENGTH: 19
<212> TYPE: DNA
<213> ORGANISM: Artificial Sequence
<220> FEATURE:
<223> OTHER INFORMATION: Synthetic, engineered or hybrid sequence
```

```
<400> SEQUENCE: 113
gaggtatcca gcagagggg                                             19

<210> SEQ ID NO 114
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 114
gcaaccacaa acccacgagg g                                          21

<210> SEQ ID NO 115
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 115
gtagggcctt cgcgcacctc a                                          21

<210> SEQ ID NO 116
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 116
gtactcacct ctcatgaagc act                                        23

<210> SEQ ID NO 117
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 117
ggaggtctat ggtgtccact                                            20

<210> SEQ ID NO 118
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 118
gagtttgctg tgctgcagac g                                          21

<210> SEQ ID NO 119
<211> LENGTH: 129
<212> TYPE: DNA
<213> ORGANISM: Artificial Sequence
<220> FEATURE:
<223> OTHER INFORMATION: Synthetic, engineered or hybrid sequence

<400> SEQUENCE: 119
gtttttgtac tctcaagatt taagtaactg tacaacgaaa cttacacagt tacttaaatc    60
ttgcagaagc tacaaagata aggcttcatg ccgaaatcaa caccctgtca ttttatggca   120
```

```
gggtgtttt                                                                  129

<210> SEQ ID NO 120
<211> LENGTH: 129
<212> TYPE: RNA
<213> ORGANISM: Artificial Sequence
<220> FEATURE:
<223> OTHER INFORMATION: Synthetic, engineered or hybrid sequence

<400> SEQUENCE: 120
guuuuuguac ucucaagauu uaaguaacug uacaacgaaa cuuacacagu uacuuaaauc         60
uugcagaagc uacaaagaua aggcuucaug ccgaaaucaa cacccuguca uuuuauggca        120
ggguguuuu                                                                  129

<210> SEQ ID NO 121
<211> LENGTH: 84
<212> TYPE: DNA
<213> ORGANISM: Artificial Sequence
<220> FEATURE:
<223> OTHER INFORMATION: Synthetic, engineered or hybrid sequence

<400> SEQUENCE: 121
gtctttgtac tctggtacca gaagctacaa agataaggct tcatgccgaa atcaacaccc         60
tgtcatttta tggcagggtg tttt                                                 84

<210> SEQ ID NO 122
<211> LENGTH: 84
<212> TYPE: RNA
<213> ORGANISM: Artificial Sequence
<220> FEATURE:
<223> OTHER INFORMATION: Synthetic, engineered or hybrid sequence

<400> SEQUENCE: 122
gucuuuguac ucugguacca gaagcuacaa agauaaggcu ucaugccgaa aucaacaccc         60
ugucauuuua uggcagggug uuuu                                                 84

<210> SEQ ID NO 123
<211> LENGTH: 77
<212> TYPE: DNA
<213> ORGANISM: Artificial Sequence
<220> FEATURE:
<223> OTHER INFORMATION: Synthetic, engineered or hybrid sequence

<400> SEQUENCE: 123
gttttagtac tctggaaaca gaatctacta aacaaggca aaatgccgtg tttatctcgt          60
caacttgttg gcgagat                                                         77

<210> SEQ ID NO 124
<211> LENGTH: 77
<212> TYPE: RNA
<213> ORGANISM: Artificial Sequence
<220> FEATURE:
<223> OTHER INFORMATION: Synthetic, engineered or hybrid sequence

<400> SEQUENCE: 124
guuuuaguac ucuggaaaca gaaucuacua aacaaggca aaaugccgug uuuaucucgu          60
caacuuguug gcgagau                                                         77

<210> SEQ ID NO 125
<211> LENGTH: 460
<212> TYPE: DNA
<213> ORGANISM: Artificial Sequence
```

<220> FEATURE:
<223> OTHER INFORMATION: Synthetic, engineered or hybrid sequence

<400> SEQUENCE: 125

```
gggctggaag ctacctttga catcatttcc tctgcgaatg catgtataat ttctacagaa      60
cctattagaa aggatcaccc agcctctgct tttgtacaac tttcccttaa aaaactgcca     120
attccactgc tgtttggccc aatagtgaga acttttttcct gctgcctctt ggtgcttttg    180
cctatggccc ctattctgcc tgctgaagac actcttgcca gcatggactt aaaccccctcc   240
agctctgaca atcctctttc tcttttgttt tacatgaagg gtctggcagc caaagcaatc    300
actcaaagtt caaaccttat cattttttgc tttgttcctc ttggccttgg ttttgtacat    360
cagctttgaa ataccatcc cagggttaat gctggggtta atttataact aagagtgctc     420
tagttttgca atacaggaca tgctataaaa atggaaagat                            460
```

<210> SEQ ID NO 126
<211> LENGTH: 507
<212> TYPE: DNA
<213> ORGANISM: Artificial Sequence
<220> FEATURE:
<223> OTHER INFORMATION: Synthetic, engineered or hybrid sequence

<400> SEQUENCE: 126

```
ccctaaaatg ggcaaacatt gcaagcagca aacagcaaac acacagccct ccctgcctgc      60
tgaccttgga gctggggcag aggtcagaga cctctctggg cccatgccac ctccaacatc     120
cactcgaccc cttggaattt cggtggagag gagcagaggt tgtcctggcg tggtttaggt     180
agtgtgagag ggtggacaca ggacgctgtg gtttctgagc caggggggcga ctcagatccc   240
agccagtgga cttagcccct gtttgctcct ccgataactg gggtgacctt ggttaatatt    300
caccagcagc ctcccccgtt gccctctctgg atccactgct taaatacgga cgaggacagg   360
gccctgtctc ctcagcttca ggcaccacca ctgacctggg acagtgaatc cggactctaa    420
ggtaaatata aaattttttaa gtgtataatg tgttaaacta ctgattctaa ttgtttctct   480
ctttagatt ccaacctttg gaactga                                           507
```

<210> SEQ ID NO 127
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 127

```
ccatccccctt ctgtgaatgt                                                  20
```

<210> SEQ ID NO 128
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 128

```
ggagattgga gacacggaga                                                   20
```

<210> SEQ ID NO 129
<211> LENGTH: 23
<212> TYPE: DNA
<213> ORGANISM: Artificial Sequence
<220> FEATURE:

<223> OTHER INFORMATION: Synthetic, engineered or hybrid sequence

<400> SEQUENCE: 129
aggaacacgg ataaagacgc tgg                                            23

<210> SEQ ID NO 130
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 130
agttgctgca ccaggtggta acg                                            23

<210> SEQ ID NO 131
<211> LENGTH: 25
<212> TYPE: DNA
<213> ORGANISM: Artificial Sequence
<220> FEATURE:
<223> OTHER INFORMATION: Synthetic, engineered or hybrid sequence

<400> SEQUENCE: 131
ccagcacaac ttactcgcac ttgac                                          25

<210> SEQ ID NO 132
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 132
catcaccaac ccacagccaa gg                                             22

<210> SEQ ID NO 133
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 133
gagaaggcca ggggtcactc cag                                            23

<210> SEQ ID NO 134
<211> LENGTH: 18
<212> TYPE: DNA
<213> ORGANISM: Artificial Sequence
<220> FEATURE:
<223> OTHER INFORMATION: Synthetic, engineered or hybrid sequence

<400> SEQUENCE: 134
agcccgccgc aatgaagg                                                  18

<210> SEQ ID NO 135
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 135
gcaggcgcag tgcccaagac ac                                             22

```
<210> SEQ ID NO 136
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 136
cagcacatgc ccaggtcaca tgg                                          23

<210> SEQ ID NO 137
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 137
gccatgagga cagaaagagc atc                                          23

<210> SEQ ID NO 138
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 138
gatattccag tctcccagag aag                                          23

<210> SEQ ID NO 139
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 139
ctcgcatact tgaaggctgt gcc                                          23

<210> SEQ ID NO 140
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 140
gatagggact ctgctacctc ctg                                          23

<210> SEQ ID NO 141
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 141
ggctttggtg gtgcagtagc ctt                                          23

<210> SEQ ID NO 142
<211> LENGTH: 23
<212> TYPE: DNA
<213> ORGANISM: Artificial Sequence
<220> FEATURE:
<223> OTHER INFORMATION: Synthetic, engineered or hybrid sequence
```

```
<400> SEQUENCE: 142
gacctcacac cattgggctc cag                                          23

<210> SEQ ID NO 143
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 143
gatgtgcacc acaagctcac tgt                                          23

<210> SEQ ID NO 144
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 144
gagttcggtg ctgttgtcta aga                                          23

<210> SEQ ID NO 145
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 145
gctagtttgg aagacagtcc tag                                          23

<210> SEQ ID NO 146
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 146
gtccctctct atccagatga tcc                                          23

<210> SEQ ID NO 147
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 147
gcaacttaag ggctatcaac cca                                          23

<210> SEQ ID NO 148
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 148
gtctggatat aggagggaga tct                                          23

<210> SEQ ID NO 149
<211> LENGTH: 23
```

```
<212> TYPE: DNA
<213> ORGANISM: Artificial Sequence
<220> FEATURE:
<223> OTHER INFORMATION: Synthetic, engineered or hybrid sequence

<400> SEQUENCE: 149
gaacacaagg gtgagtcaca gtc                                            23

<210> SEQ ID NO 150
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 150
catctggctg attctctgtt tca                                            23

<210> SEQ ID NO 151
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 151
gatacgcatg ctacactgag atg                                            23

<210> SEQ ID NO 152
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 152
cacaggcagt agacaaacca g                                              21

<210> SEQ ID NO 153
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 153
gcacccatga gacaggtgag cag                                            23

<210> SEQ ID NO 154
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 154
gcagagacaa tgggtggcta ata                                            23

<210> SEQ ID NO 155
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 155
```

```
gctggaagct ttatgatgga gat                                                    23

<210> SEQ ID NO 156
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 156
gacacacctc agagccttcc ctt                                                    23

<210> SEQ ID NO 157
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 157
gaggcaggca ggctctccga                                                        20

<210> SEQ ID NO 158
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 158
gcccaggcag gcaggctctc cga                                                    23

<210> SEQ ID NO 159
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 159
gaggaagggc ctgagtccga                                                        20

<210> SEQ ID NO 160
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 160
ggaggacaaa gtacaaacg                                                         19

<210> SEQ ID NO 161
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 161
gaagggcctg agtccgagca                                                        20

<210> SEQ ID NO 162
<211> LENGTH: 20
<212> TYPE: DNA
<213> ORGANISM: Artificial Sequence
```

```
<220> FEATURE:
<223> OTHER INFORMATION: Synthetic, engineered or hybrid sequence

<400> SEQUENCE: 162
gggcctgagt ccgagcagaa                                                   20

<210> SEQ ID NO 163
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 163
gagggaggga ggggcacaga                                                   20

<210> SEQ ID NO 164
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 164
gccagggagg gaggggcaca ga                                                22

<210> SEQ ID NO 165
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 165
gcaaacggca gaagctggag                                                   20

<210> SEQ ID NO 166
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 166
gtacaaacgg cagaagctgg ag                                                22

<210> SEQ ID NO 167
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 167
gtacaaacgg cagaagctgg a                                                 21

<210> SEQ ID NO 168
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 168
ggaaaagcga tccaggtgct                                                   20
```

<210> SEQ ID NO 169
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 169
gtaggtagtg cttgagaccg                                                   20

<210> SEQ ID NO 170
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 170
gtagggcctt cgcgcacctc                                                   20

<210> SEQ ID NO 171
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 171
gcttgagacc gccagaagc                                                    19

<210> SEQ ID NO 172
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 172
gtgcttgaga ccgccagaag c                                                 21

<210> SEQ ID NO 173
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 173
ggcctggaag ttcgctaatc                                                   20

<210> SEQ ID NO 174
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 174
ggcgactctc tgcgtactga                                                   20

<210> SEQ ID NO 175
<211> LENGTH: 20
<212> TYPE: DNA
<213> ORGANISM: Artificial Sequence
<220> FEATURE:
<223> OTHER INFORMATION: Synthetic, engineered or hybrid sequence

```
<400> SEQUENCE: 175
gctaatcaga tggaagctct                                              20

<210> SEQ ID NO 176
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 176
gtactaatca gatggaagct ct                                           22

<210> SEQ ID NO 177
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 177
gatcattgag tcccccgcct                                              20

<210> SEQ ID NO 178
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 178
gaaatcattg agtcccccgc ct                                           22

<210> SEQ ID NO 179
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 179
ggttttcgct ccgaaggta                                               19

<210> SEQ ID NO 180
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 180
gaggtatcca gcagagggga                                              20

<210> SEQ ID NO 181
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 181
gcagaggtat ccagcagagg                                              20

<210> SEQ ID NO 182
```

```
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 182
gtcccagagg tatccagcag agg                                              23

<210> SEQ ID NO 183
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 183
gaattcctct cacaaacaag ac                                               22

<210> SEQ ID NO 184
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 184
gcagcttgga tgctataagc                                                  20

<210> SEQ ID NO 185
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 185
gcttatagca tccaagctgc t                                                21

<210> SEQ ID NO 186
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 186
gcaaatccat atgctgaatt                                                  20

<210> SEQ ID NO 187
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 187
gacaaatcca tatgctgaat t                                                21

<210> SEQ ID NO 188
<211> LENGTH: 25
<212> TYPE: DNA
<213> ORGANISM: Artificial Sequence
<220> FEATURE:
<223> OTHER INFORMATION: Synthetic, engineered or hybrid sequence

<400> SEQUENCE: 188
```

```
gtactacaaa tccatatgct gaatt                                          25

<210> SEQ ID NO 189
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 189
gcatccaagc tgctacagaa                                                20

<210> SEQ ID NO 190
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 190
gcatccaagc tgctacaga                                                 19

<210> SEQ ID NO 191
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 191
gagagggaca cacagatcta                                                20

<210> SEQ ID NO 192
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 192
gagagccgtt ccctctttgc                                                20

<210> SEQ ID NO 193
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 193
gggcattggc gaggagggag                                                20

<210> SEQ ID NO 194
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 194
gaaaattacc catccgccc                                                 19

<210> SEQ ID NO 195
<211> LENGTH: 23
<212> TYPE: DNA
```

```
<213> ORGANISM: Artificial Sequence
<220> FEATURE:
<223> OTHER INFORMATION: Synthetic, engineered or hybrid sequence

<400> SEQUENCE: 195
gcctgaaaat tacccatccg ccc                                          23

<210> SEQ ID NO 196
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 196
ggtaccccac gcagaaagct                                              20

<210> SEQ ID NO 197
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 197
gttggggcct cgaatccagg                                              20

<210> SEQ ID NO 198
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 198
gataccacac acaccctggt                                              20

<210> SEQ ID NO 199
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 199
gtagtaagaa gatggggcgg c                                            21

<210> SEQ ID NO 200
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 200
gcatatccta gtcgactatg a                                            21

<210> SEQ ID NO 201
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 201
ggtcactgct catcttcac                                               19
```

<210> SEQ ID NO 202
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 202
gggtcactgc tcatcttcac                                        20

<210> SEQ ID NO 203
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 203
gaggtcactg ctcatcttca c                                      21

<210> SEQ ID NO 204
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 204
gcacgacgcc tcccgctcct                                        20

<210> SEQ ID NO 205
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 205
gccacgacgc ctcccgctcc t                                      21

<210> SEQ ID NO 206
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 206
gagacccatg tccactgcca                                        20

<210> SEQ ID NO 207
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 207
ggtgggaact cactactcgg                                        20

<210> SEQ ID NO 208
<211> LENGTH: 20
<212> TYPE: DNA
<213> ORGANISM: Artificial Sequence
<220> FEATURE:

<223> OTHER INFORMATION: Synthetic, engineered or hybrid sequence

<400> SEQUENCE: 208
ggcataacta accccgaagg                                                      20

<210> SEQ ID NO 209
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 209
gggcactggc tggcaggggt                                                      20

<210> SEQ ID NO 210
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 210
gtatttgccg aagttgtagc c                                                    21

<210> SEQ ID NO 211
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 211
gcaagcgctc ccacaggctg c                                                    21

<210> SEQ ID NO 212
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 212
gcctgtggga gcgcttgcc                                                       19

<210> SEQ ID NO 213
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 213
gcctttgtct cgtcggccc                                                       19

<210> SEQ ID NO 214
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 214
gcaaagactt ccgaattcc                                                       19

-continued

```
<210> SEQ ID NO 215
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 215
gtcaacgttt gcactatgac ct                                              22

<210> SEQ ID NO 216
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 216
gctttacagg tctccagggc ag                                              22

<210> SEQ ID NO 217
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 217
gtaataacac agcattgcct at                                              22

<210> SEQ ID NO 218
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 218
gctgtgttat tacttgaat                                                  19

<210> SEQ ID NO 219
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 219
gacacacgaa ggcatatatt tgg                                             23

<210> SEQ ID NO 220
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 220
gtctcgtcgg ccccaagaag ag                                              22

<210> SEQ ID NO 221
<211> LENGTH: 22
<212> TYPE: DNA
<213> ORGANISM: Artificial Sequence
<220> FEATURE:
<223> OTHER INFORMATION: Synthetic, engineered or hybrid sequence
```

```
<400> SEQUENCE: 221
gaccttcaga aaggcatttg gg                                          22

<210> SEQ ID NO 222
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 222
gaggggacag ataaaagtac                                             20

<210> SEQ ID NO 223
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 223
gaaatggggg tgtgtcacca gat                                         23

<210> SEQ ID NO 224
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 224
gttagaccca atatcaggag ac                                          22

<210> SEQ ID NO 225
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 225
gagccacatt aaccggccc                                              19

<210> SEQ ID NO 226
<211> LENGTH: 22
<212> TYPE: DNA
<213> ORGANISM: Artificial Sequence
<220> FEATURE:
<223> OTHER INFORMATION: Synthetic, engineered or hybrid sequence

<400> SEQUENCE: 226
gactagctga gctctcggac cc                                          22

<210> SEQ ID NO 227
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 227
gaagatgcca tgacaggggg                                             20

<210> SEQ ID NO 228
<211> LENGTH: 20
```

```
<212> TYPE: DNA
<213> ORGANISM: Artificial Sequence
<220> FEATURE:
<223> OTHER INFORMATION: Synthetic, engineered or hybrid sequence

<400> SEQUENCE: 228
gctattttta tgggacattt                                              20

<210> SEQ ID NO 229
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 229
ggagagtttg gggaaaaaag                                              20

<210> SEQ ID NO 230
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 230
gtatagagtt gattggattg aga                                          23

<210> SEQ ID NO 231
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 231
gccttctctc taaaggctca                                              20

<210> SEQ ID NO 232
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 232
gcagtatcgc ctctccctgc                                              20

<210> SEQ ID NO 233
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 233
gactggagag tttggggaaa a                                            21

<210> SEQ ID NO 234
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 234
```
ggcggctgca caaccagtgg                                          20

<210> SEQ ID NO 235
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 235
gaaacaagct gccatttcat tac                                      23

<210> SEQ ID NO 236
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 236
gccatttcat tacaggcaaa gct                                      23

<210> SEQ ID NO 237
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 237
gaggtgagta catgctggtc                                          20

<210> SEQ ID NO 238
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 238
ggacacagga tccctggagg                                          20

<210> SEQ ID NO 239
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 239
ggcttcctgg tctgtgtcat                                          20

<210> SEQ ID NO 240
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 240
gttcataacc attaagtaat gag                                      23

<210> SEQ ID NO 241
<211> LENGTH: 20
<212> TYPE: DNA
<213> ORGANISM: Artificial Sequence

```
<220> FEATURE:
<223> OTHER INFORMATION: Synthetic, engineered or hybrid sequence

<400> SEQUENCE: 241
gtaatgagtt cataaccatt                                               20

<210> SEQ ID NO 242
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 242
ggtgtggttc cagaaccgga                                               20

<210> SEQ ID NO 243
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 243
gttccagaac cggaggacaa a                                             21

<210> SEQ ID NO 244
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 244
gcttggatgc tataagccaa g                                             21

<210> SEQ ID NO 245
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 245
ggagaagata tctgatgtgt a                                             21

<210> SEQ ID NO 246
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 246
ggtaattgag aagaagtggg                                               20

<210> SEQ ID NO 247
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 247
gagagtcgcc gtctccaag                                                19
```

<210> SEQ ID NO 248
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 248
gcttgagacc gccagaagct                                              20

<210> SEQ ID NO 249
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 249
gctcttcgta gtggtgcatt t                                            21

<210> SEQ ID NO 250
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 250
gaatatatag tttacaaaa                                               19

<210> SEQ ID NO 251
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 251
gtctgaagcc atcgcttcct c                                            21

<210> SEQ ID NO 252
<211> LENGTH: 19
<212> TYPE: DNA
<213> ORGANISM: Artificial Sequence
<220> FEATURE:
<223> OTHER INFORMATION: Synthetic, engineered or hybrid sequence

<400> SEQUENCE: 252
gatttctttt accttcgga                                               19

<210> SEQ ID NO 253
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 253
gttcaaggat ttctgaggct t                                            21

<210> SEQ ID NO 254
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 254
gtatttgctc tgcagaatga                                        20

<210> SEQ ID NO 255
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 255
ggagttgggt ttggtgctca                                        20

<210> SEQ ID NO 256
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 256
gtcgactccc tgcaaacaca                                        20

<210> SEQ ID NO 257
<211> LENGTH: 21
<212> TYPE: DNA
<213> ORGANISM: Artificial Sequence
<220> FEATURE:
<223> OTHER INFORMATION: Synthetic, engineered or hybrid sequence

<400> SEQUENCE: 257
gtggccatca aggatgccca c                                      21

<210> SEQ ID NO 258
<211> LENGTH: 20
<212> TYPE: DNA
<213> ORGANISM: Artificial Sequence
<220> FEATURE:
<223> OTHER INFORMATION: Synthetic, engineered or hybrid sequence

<400> SEQUENCE: 258
gttaaaatag gatctacatc                                        20

<210> SEQ ID NO 259
<211> LENGTH: 23
<212> TYPE: DNA
<213> ORGANISM: Artificial Sequence
<220> FEATURE:
<223> OTHER INFORMATION: Synthetic, engineered or hybrid sequence

<400> SEQUENCE: 259
gccactaggg acaggattgg tga                                    23

<210> SEQ ID NO 260
<211> LENGTH: 295
<212> TYPE: PRT
<213> ORGANISM: Artificial Sequence
<220> FEATURE:
<223> OTHER INFORMATION: Synthetic, engineered or hybrid sequence

<400> SEQUENCE: 260

Ile Tyr Ala Thr Arg Gln Ala Lys Val Gly Lys Asp Lys Ala Asp Glu
1               5                   10                  15

Thr Tyr Val Leu Gly Lys Ile Lys Asp Ile Tyr Thr Gln Asp Gly Tyr

```
            20                  25                  30
Asp Ala Phe Met Lys Ile Tyr Lys Asp Lys Ser Lys Phe Leu Met
            35                  40                  45

Tyr Arg His Asp Pro Gln Thr Phe Glu Lys Val Ile Glu Pro Ile Leu
50                      55                  60

Glu Asn Tyr Pro Asn Lys Gln Ile Asn Glu Lys Gly Lys Glu Val Pro
65                  70                  75                  80

Cys Asn Pro Phe Leu Lys Tyr Lys Glu Glu His Gly Tyr Ile Arg Lys
                    85                  90                  95

Tyr Ser Lys Lys Gly Asn Gly Pro Glu Ile Lys Ser Leu Lys Tyr Tyr
                100                 105                 110

Asp Ser Lys Leu Gly Asn His Ile Asp Ile Thr Pro Lys Asp Ser Asn
                115                 120                 125

Asn Lys Val Val Leu Gln Ser Val Ser Pro Trp Arg Ala Asp Val Tyr
                130                 135                 140

Phe Asn Lys Thr Thr Gly Lys Tyr Glu Ile Leu Gly Leu Lys Tyr Ala
145                 150                 155                 160

Asp Leu Gln Phe Glu Lys Gly Thr Gly Thr Tyr Lys Ile Ser Gln Glu
                165                 170                 175

Lys Tyr Asn Asp Ile Lys Lys Lys Glu Gly Val Asp Ser Asp Ser Glu
                180                 185                 190

Phe Lys Phe Thr Leu Tyr Lys Asn Asp Leu Leu Val Lys Asp Thr
                195                 200                 205

Glu Thr Lys Glu Gln Gln Leu Phe Arg Phe Leu Ser Arg Thr Met Pro
                210                 215                 220

Lys Gln Lys His Tyr Val Glu Leu Lys Pro Tyr Asp Lys Gln Lys Phe
225                 230                 235                 240

Glu Gly Gly Glu Ala Leu Ile Lys Val Leu Gly Asn Val Ala Asn Ser
                245                 250                 255

Gly Gln Cys Lys Lys Gly Leu Gly Lys Ser Asn Ile Ser Ile Tyr Lys
                260                 265                 270

Val Arg Thr Asp Val Leu Gly Asn Gln His Ile Ile Lys Asn Glu Gly
                275                 280                 285

Asp Lys Pro Lys Leu Asp Phe
                290                 295

<210> SEQ ID NO 261
<211> LENGTH: 296
<212> TYPE: PRT
<213> ORGANISM: Artificial Sequence
<220> FEATURE:
<223> OTHER INFORMATION: Synthetic, engineered or hybrid sequence

<400> SEQUENCE: 261

Ile Tyr Ala Thr Arg Gln Ala Lys Val Gly Lys Asp Lys Lys Asp Glu
1               5                   10                  15

Thr Tyr Val Leu Gly Lys Ile Lys Asp Ile Tyr Thr Gln Asp Gly Tyr
                20                  25                  30

Asp Ala Phe Met Lys Ile Tyr Lys Lys Asp Lys Ser Lys Phe Leu Met
            35                  40                  45

Tyr Arg His Asp Pro Gln Thr Phe Glu Lys Val Ile Glu Pro Ile Leu
50                  55                  60

Glu Asn Tyr Pro Asn Lys Glu Met Asn Glu Lys Gly Lys Glu Val Pro
65                  70                  75                  80

Cys Asn Pro Phe Leu Lys Tyr Lys Glu Glu His Gly Tyr Ile Arg Lys
```

```
                    85                  90                  95
Tyr Ser Lys Lys Gly Asn Gly Pro Glu Ile Lys Ser Leu Lys Tyr Tyr
                100                 105                 110
Asp Ser Lys Leu Leu Gly Asn Pro Ile Asp Ile Thr Pro Glu Asn Ser
                115                 120                 125
Lys Asn Lys Val Val Leu Gln Ser Leu Lys Pro Trp Arg Thr Asp Val
            130                 135                 140
Tyr Phe Asn Lys Asn Thr Gly Lys Tyr Glu Ile Leu Gly Leu Lys Tyr
145                 150                 155                 160
Ala Asp Leu Gln Phe Glu Lys Lys Thr Gly Thr Tyr Lys Ile Ser Gln
                165                 170                 175
Glu Lys Tyr Asn Gly Ile Met Lys Glu Gly Val Asp Ser Asp Ser
                180                 185                 190
Glu Phe Lys Phe Thr Leu Tyr Lys Asn Asp Leu Leu Val Lys Asp
                195                 200                 205
Thr Glu Thr Lys Glu Gln Gln Leu Phe Arg Phe Leu Ser Arg Thr Met
            210                 215                 220
Pro Asn Val Lys Tyr Tyr Val Glu Leu Lys Pro Tyr Ser Lys Asp Lys
225                 230                 235                 240
Phe Glu Lys Asn Glu Ser Leu Ile Glu Ile Leu Gly Ser Ala Asp Lys
                245                 250                 255
Ser Gly Arg Cys Ile Lys Gly Leu Gly Lys Ser Asn Ile Ser Ile Tyr
                260                 265                 270
Lys Val Arg Thr Asp Val Leu Gly Asn Gln His Ile Ile Lys Asn Glu
                275                 280                 285
Gly Asp Lys Pro Lys Leu Asp Phe
            290                 295

<210> SEQ ID NO 262
<211> LENGTH: 296
<212> TYPE: PRT
<213> ORGANISM: Artificial Sequence
<220> FEATURE:
<223> OTHER INFORMATION: Synthetic, engineered or hybrid sequence

<400> SEQUENCE: 262

Ile Tyr Ala Thr Arg Gln Ala Lys Val Gly Lys Asp Lys Lys Asp Glu
1               5                   10                  15
Thr Tyr Val Leu Gly Lys Ile Lys Asp Ile Tyr Thr Gln Asp Gly Tyr
                20                  25                  30
Asp Ala Phe Met Lys Ile Tyr Lys Lys Asp Lys Ser Lys Phe Leu Met
                35                  40                  45
Tyr Arg His Asp Pro Gln Thr Phe Glu Lys Val Ile Glu Pro Ile Leu
            50                  55                  60
Glu Asn Tyr Pro Asn Lys Gln Met Asn Glu Lys Gly Lys Glu Val Pro
65                  70                  75                  80
Cys Asn Pro Phe Leu Lys Tyr Lys Glu Glu His Gly Tyr Ile Arg Lys
                85                  90                  95
Tyr Ser Lys Lys Gly Asn Gly Pro Glu Ile Lys Ser Leu Lys Tyr Tyr
                100                 105                 110
Asp Ser Lys Leu Leu Gly Asn Pro Ile Asp Ile Thr Pro Glu Asn Ser
                115                 120                 125
Lys Asn Lys Val Val Leu Gln Ser Leu Lys Pro Trp Arg Thr Asp Val
            130                 135                 140
Tyr Phe Asn Lys Ala Thr Gly Lys Tyr Glu Ile Leu Gly Leu Lys Tyr
```

```
                145                 150                 155                 160
Ala Asp Leu Gln Phe Glu Lys Gly Thr Gly Thr Tyr Lys Ile Ser Gln
                    165                 170                 175

Glu Lys Tyr Asn Asp Ile Lys Lys Glu Gly Val Asp Ser Asp Ser
                180                 185                 190

Glu Phe Lys Phe Thr Leu Tyr Lys Asn Asp Leu Leu Leu Val Lys Asp
                    195                 200                 205

Thr Glu Thr Lys Glu Gln Gln Leu Phe Arg Phe Leu Ser Arg Thr Leu
    210                 215                 220

Pro Lys Gln Lys His Tyr Val Glu Leu Lys Pro Tyr Asp Lys Gln Lys
225                 230                 235                 240

Phe Glu Gly Gly Glu Ala Leu Ile Lys Val Leu Gly Asn Val Ala Asn
                    245                 250                 255

Gly Gly Gln Cys Ile Lys Gly Leu Ala Lys Ser Asn Ile Ser Ile Tyr
                260                 265                 270

Lys Val Arg Thr Asp Val Leu Gly Asn Gln His Ile Ile Lys Asn Glu
                275                 280                 285

Gly Asp Lys Pro Lys Leu Asp Phe
            290                 295

<210> SEQ ID NO 263
<211> LENGTH: 294
<212> TYPE: PRT
<213> ORGANISM: Artificial Sequence
<220> FEATURE:
<223> OTHER INFORMATION: Synthetic, engineered or hybrid sequence

<400> SEQUENCE: 263

Ile Tyr Ala Thr Arg Gln Ala Lys Val Gly Lys Asp Lys Ala Asp Glu
1               5                   10                  15

Thr Tyr Val Leu Gly Lys Ile Lys Asp Ile Tyr Thr Gln Asp Gly Tyr
                20                  25                  30

Asp Ala Phe Met Lys Ile Tyr Lys Lys Asp Lys Ser Lys Phe Leu Met
            35                  40                  45

Tyr Arg His Asp Pro Gln Thr Phe Glu Lys Val Ile Glu Pro Ile Leu
    50                  55                  60

Glu Asn Tyr Pro Asn Lys Gln Met Asn Glu Lys Gly Lys Glu Val Pro
65                  70                  75                  80

Cys Asn Pro Phe Leu Lys Tyr Lys Glu Glu His Gly Tyr Ile Arg Lys
                85                  90                  95

Tyr Ser Lys Lys Gly Asn Gly Pro Glu Ile Lys Ser Leu Lys Tyr Tyr
                100                 105                 110

Asp Ser Lys Leu Gly Asn His Ile Asp Ile Thr Pro Lys Asp Ser Asn
            115                 120                 125

Asn Lys Val Val Leu Gln Ser Leu Lys Pro Trp Arg Thr Asp Val Tyr
        130                 135                 140

Phe Asn Lys Asn Thr Gly Lys Tyr Glu Ile Leu Gly Leu Lys Tyr Ser
145                 150                 155                 160

Asp Met Gln Phe Glu Lys Gly Thr Gly Lys Tyr Ser Ile Ser Lys Glu
                    165                 170                 175

Gln Tyr Glu Asn Ile Lys Val Arg Glu Gly Val Asp Glu Asn Ser Glu
                180                 185                 190

Phe Lys Phe Thr Leu Tyr Lys Asn Asp Leu Leu Leu Lys Asp Ser
                    195                 200                 205

Glu Asn Gly Glu Gln Ile Leu Leu Arg Phe Thr Ser Arg Asn Asp Thr
```

```
                    210                 215                 220

Ser Lys His Tyr Val Glu Leu Lys Pro Tyr Asn Arg Gln Lys Phe Glu
225                 230                 235                 240

Gly Ser Glu Tyr Leu Ile Lys Ser Leu Gly Thr Val Val Lys Gly Gly
                    245                 250                 255

Arg Cys Ile Lys Gly Leu Gly Lys Ser Asn Ile Ser Ile Tyr Lys Val
                    260                 265                 270

Arg Thr Asp Val Leu Gly Asn Gln His Ile Ile Lys Asn Glu Gly Asp
                275                 280                 285

Lys Pro Lys Leu Asp Phe
            290

<210> SEQ ID NO 264
<211> LENGTH: 826
<212> TYPE: PRT
<213> ORGANISM: Streptococcus thermophilus

<400> SEQUENCE: 264

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
                20                  25                  30

Arg Ile Phe Pro Ala Ala Gln Ala Glu Asn Asn Leu Val Arg Arg Thr
            35                  40                  45

Asn Arg Gln Gly Arg Arg Leu Ala Arg Arg Lys His Arg Arg Val
50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
                100                 105                 110

Val Lys His Arg Gly Ile Ser Tyr Leu Asp Asp Ala Ser Asp Asp Gly
            115                 120                 125

Asn Ser Ser Val Gly Asp Tyr Ala Gln Ile Val Lys Glu Asn Ser Lys
            130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Pro Gln Ile Thr
            195                 200                 205

Asp Glu Phe Ile Asn Arg Tyr Leu Glu Ile Leu Thr Gly Lys Arg Lys
        210                 215                 220

Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
                245                 250                 255

Gly Lys Cys Thr Phe Tyr Pro Asp Glu Phe Arg Ala Ala Lys Ala Ser
            260                 265                 270

Tyr Thr Ala Gln Glu Phe Asn Leu Leu Asn Asp Leu Asn Asn Leu Thr
            275                 280                 285
```

```
Val Pro Thr Glu Thr Lys Lys Leu Ser Lys Glu Gln Lys Asn Gln Ile
290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
            325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
        355                 360                 365

Arg Glu Thr Leu Asp Lys Leu Ala Tyr Val Leu Thr Leu Asn Thr Glu
    370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
            405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
    435                 440                 445

Ile Leu Thr Arg Leu Gly Lys Gln Lys Thr Thr Ser Ser Asn Lys
    450                 455                 460

Thr Lys Tyr Ile Asp Glu Lys Leu Leu Thr Glu Ile Tyr Asn Pro
465                 470                 475                 480

Val Val Ala Lys Ser Val Arg Gln Ala Ile Lys Ile Val Asn Ala Ala
            485                 490                 495

Ile Lys Glu Tyr Gly Asp Phe Asp Asn Ile Val Ile Glu Met Ala Arg
            500                 505                 510

Glu Thr Asn Glu Asp Asp Glu Lys Lys Ala Ile Gln Lys Ile Gln Lys
    515                 520                 525

Ala Asn Lys Asp Glu Lys Asp Ala Ala Met Leu Lys Ala Ala Asn Gln
    530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
            565                 570                 575

Leu Tyr Thr Gly Lys Thr Ile Ser Ile His Asp Leu Ile Asn Asn Ser
            580                 585                 590

Asn Gln Phe Glu Val Asp His Ile Leu Pro Leu Ser Ile Thr Phe Asp
        595                 600                 605

Asp Ser Leu Ala Asn Lys Val Leu Val Tyr Ala Thr Ala Asn Gln Glu
    610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
            645                 650                 655

Ser Asn Lys Lys Lys Glu Tyr Leu Leu Thr Glu Glu Asp Ile Ser Lys
            660                 665                 670

Phe Asp Val Arg Lys Lys Phe Ile Glu Arg Asn Leu Val Asp Thr Arg
            675                 680                 685

Tyr Ala Ser Arg Val Val Leu Asn Ala Leu Gln Glu His Phe Arg Ala
    690                 695                 700

His Lys Ile Asp Thr Lys Val Ser Val Val Arg Gly Gln Phe Thr Ser
```

```
                705                 710                 715                 720
Gln Leu Arg Arg His Trp Gly Ile Glu Lys Thr Arg Asp Thr Tyr His
                    725                 730                 735

His His Ala Val Asp Ala Leu Ile Ile Ala Ala Ser Ser Gln Leu Asn
                740                 745                 750

Leu Trp Lys Gln Lys Asn Thr Leu Val Ser Tyr Ser Glu Asp Gln
                755                 760                 765

Leu Leu Asp Ile Glu Thr Gly Glu Leu Ile Ser Asp Asp Glu Tyr Lys
                770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                    805                 810                 815

Lys Phe Asn Arg Lys Ile Ser Asp Ala Thr
                820                 825

<210> SEQ ID NO 265
<211> LENGTH: 826
<212> TYPE: PRT
<213> ORGANISM: Streptococcus thermophilus

<400> SEQUENCE: 265

Met Ser Asp Leu Val Leu Gly Leu Asp Ile Gly Ile Gly Ser Val Gly
1               5                   10                  15

Val Gly Ile Leu Asn Lys Val Thr Gly Glu Ile Ile His Lys Asn Ser
                20                  25                  30

Arg Ile Phe Pro Ala Ala Gln Ala Glu Asn Asn Leu Val Arg Arg Thr
            35                  40                  45

Asn Arg Gln Gly Arg Arg Leu Thr Arg Arg Lys Lys His Arg Ile Val
        50                  55                  60

Arg Leu Asn Arg Leu Phe Glu Glu Ser Gly Leu Ile Thr Asp Phe Thr
65                  70                  75                  80

Lys Ile Ser Ile Asn Leu Asn Pro Tyr Gln Leu Arg Val Lys Gly Leu
                85                  90                  95

Thr Asp Glu Leu Ser Asn Glu Glu Leu Phe Ile Ala Leu Lys Asn Met
                100                 105                 110

Val Lys His Arg Gly Ile Ser Tyr Leu Asp Asp Ala Ser Asp Asp Gly
            115                 120                 125

Asn Ser Ser Val Gly Asp Tyr Ala Gln Ile Val Lys Glu Asn Ser Lys
        130                 135                 140

Gln Leu Glu Thr Lys Thr Pro Gly Gln Ile Gln Leu Glu Arg Tyr Gln
145                 150                 155                 160

Thr Tyr Gly Gln Leu Arg Gly Asp Phe Thr Val Glu Lys Asp Gly Lys
                165                 170                 175

Lys His Arg Leu Ile Asn Val Phe Pro Thr Ser Ala Tyr Arg Ser Glu
            180                 185                 190

Ala Leu Arg Ile Leu Gln Thr Gln Gln Glu Phe Asn Ser Gln Ile Thr
        195                 200                 205

Asp Glu Phe Ile Asn Arg Tyr Leu Glu Ile Leu Thr Gly Lys Arg Lys
    210                 215                 220

Tyr Tyr His Gly Pro Gly Asn Glu Lys Ser Arg Thr Asp Tyr Gly Arg
225                 230                 235                 240

Tyr Arg Thr Asn Gly Glu Thr Leu Asp Asn Ile Phe Gly Ile Leu Ile
                245                 250                 255
```

```
Gly Lys Cys Thr Phe Tyr Pro Asp Glu Phe Arg Ala Ala Lys Ala Ser
                260                 265                 270

Tyr Thr Ala Gln Glu Phe Asn Leu Leu Asn Asp Leu Asn Asn Leu Thr
            275                 280                 285

Val Pro Thr Glu Thr Lys Lys Leu Ser Lys Glu Gln Lys Asn Gln Ile
        290                 295                 300

Ile Asn Tyr Val Lys Asn Glu Lys Val Met Gly Pro Ala Lys Leu Phe
305                 310                 315                 320

Lys Tyr Ile Ala Lys Leu Leu Ser Cys Asp Val Ala Asp Ile Lys Gly
                325                 330                 335

His Arg Ile Asp Lys Ser Gly Lys Ala Glu Ile His Thr Phe Glu Ala
                340                 345                 350

Tyr Arg Lys Met Lys Thr Leu Glu Thr Leu Asp Ile Glu Gln Met Asp
            355                 360                 365

Arg Glu Thr Leu Asp Lys Leu Ala Tyr Val Leu Thr Leu Asn Thr Glu
        370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
                405                 410                 415

Ser Ser Ile Phe Gly Lys Gly Trp His Asn Phe Ser Val Lys Leu Met
                420                 425                 430

Met Glu Leu Ile Pro Glu Leu Tyr Glu Thr Ser Glu Glu Gln Met Thr
            435                 440                 445

Ile Leu Thr Arg Leu Gly Lys Gln Lys Thr Thr Ser Ser Ser Asn Lys
        450                 455                 460

Thr Lys Tyr Ile Asp Glu Lys Leu Leu Thr Glu Glu Ile Tyr Asn Pro
465                 470                 475                 480

Val Val Ala Lys Ser Val Arg Gln Ala Ile Lys Ile Val Asn Ala Ala
                485                 490                 495

Ile Lys Glu Tyr Gly Asp Phe Asp Asn Ile Val Ile Glu Met Ala Arg
                500                 505                 510

Glu Thr Asn Glu Asp Asp Glu Lys Lys Ala Ile Gln Lys Ile Gln Lys
            515                 520                 525

Ala Asn Lys Asp Glu Lys Asp Ala Ala Met Leu Lys Ala Ala Asn Gln
        530                 535                 540

Tyr Asn Gly Lys Ala Glu Leu Pro His Ser Val Phe His Gly His Lys
545                 550                 555                 560

Gln Leu Ala Thr Lys Ile Arg Leu Trp His Gln Gln Gly Glu Arg Cys
                565                 570                 575

Leu Tyr Thr Gly Lys Thr Ile Ser Ile His Asp Leu Ile Asn Asn Pro
            580                 585                 590

Asn Gln Phe Glu Val Asp His Ile Leu Pro Leu Ser Ile Thr Phe Asp
        595                 600                 605

Asp Ser Leu Ala Asn Lys Val Leu Val Tyr Ala Thr Ala Asn Gln Glu
610                 615                 620

Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                645                 650                 655

Ser Asn Lys Lys Lys Glu Tyr Leu Leu Thr Glu Glu Asp Ile Ser Lys
            660                 665                 670

Phe Asp Val Arg Lys Lys Phe Ile Glu Arg Asn Leu Val Asp Thr Arg
```

```
                675                 680                 685
Tyr Ala Ser Arg Val Val Leu Asn Ala Leu Gln Glu His Phe Arg Ala
            690                 695                 700
His Lys Ile Asp Thr Lys Val Ser Val Val Arg Gly Gln Phe Thr Ser
705                 710                 715                 720
Gln Leu Arg Arg His Trp Gly Ile Glu Lys Thr Arg Asp Thr Tyr His
                725                 730                 735
His His Ala Val Asp Ala Leu Ile Ile Ala Ala Ser Ser Gln Leu Asn
            740                 745                 750
Leu Trp Lys Lys Gln Lys Asn Thr Leu Val Ser Tyr Ser Glu Glu Gln
                755                 760                 765
Leu Leu Asp Ile Glu Thr Gly Glu Leu Ile Ser Asp Asp Glu Tyr Lys
            770                 775                 780
Glu Ser Val Phe Lys Ala Pro Tyr Gln His Phe Val Asp Thr Leu Lys
785                 790                 795                 800
Ser Lys Glu Phe Glu Asp Ser Ile Leu Phe Ser Tyr Gln Val Asp Ser
                805                 810                 815
Lys Phe Asn Arg Lys Ile Ser Asp Ala Thr
            820                 825

<210> SEQ ID NO 266
<211> LENGTH: 832
<212> TYPE: PRT
<213> ORGANISM: Streptococcus thermophilus

<400> SEQUENCE: 266

Met Ser Asp Leu Val Leu Gly Leu Asp Ile Gly Ile Gly Ser Val Gly
1               5                   10                  15
Val Gly Ile Leu Asn Lys Val Thr Gly Glu Ile Ile His Lys Asn Ser
                20                  25                  30
Arg Ile Phe Pro Ala Ala Gln Ala Glu Asn Asn Leu Val Arg Arg Thr
            35                  40                  45
Asn Arg Gln Gly Arg Arg Leu Thr Arg Arg Lys His Arg Ile Val
50                  55                  60
Arg Leu Asn Arg Leu Phe Glu Glu Ser Gly Leu Ile Thr Asp Phe Thr
65                  70                  75                  80
Lys Ile Ser Ile Asn Leu Asn Pro Tyr Gln Leu Arg Val Lys Gly Leu
                85                  90                  95
Thr Asp Glu Leu Ser Asn Glu Glu Leu Phe Ile Ala Leu Lys Asn Met
            100                 105                 110
Val Lys His Arg Gly Ile Ser Tyr Leu Asp Asp Ala Ser Asp Asp Gly
        115                 120                 125
Asn Ser Ser Val Gly Asp Tyr Ala Gln Ile Val Lys Glu Asn Ser Lys
130                 135                 140
Gln Leu Glu Thr Lys Thr Pro Gly Gln Ile Gln Leu Glu Arg Tyr Gln
145                 150                 155                 160
Thr Tyr Gly Gln Leu Arg Gly Asp Phe Thr Val Glu Lys Asp Gly Lys
                165                 170                 175
Lys His Arg Leu Ile Asn Val Phe Pro Thr Ser Ala Tyr Arg Ser Glu
            180                 185                 190
Ala Leu Arg Ile Leu Gln Thr Gln Gln Glu Phe Asn Pro Gln Ile Thr
        195                 200                 205
Asp Glu Phe Ile Asn Arg Tyr Leu Glu Ile Leu Thr Gly Lys Arg Lys
    210                 215                 220
```

```
Tyr Tyr His Gly Pro Gly Asn Glu Lys Ser Arg Thr Asp Tyr Gly Arg
225                 230                 235                 240

Tyr Arg Thr Ser Gly Glu Thr Leu Asp Asn Ile Phe Gly Ile Leu Ile
            245                 250                 255

Gly Lys Cys Thr Phe Tyr Pro Glu Glu Phe Arg Ala Ala Lys Ala Ser
            260                 265                 270

Tyr Thr Ala Gln Glu Phe Asn Leu Leu Asn Asp Leu Asn Asn Leu Thr
            275                 280                 285

Val Pro Thr Glu Thr Lys Lys Leu Ser Lys Glu Gln Lys Asn Gln Ile
290                 295                 300

Ile Asn Tyr Val Lys Asn Glu Lys Ala Met Gly Pro Ala Lys Leu Phe
305                 310                 315                 320

Lys Tyr Ile Ala Lys Leu Leu Ser Cys Asp Val Ala Asp Ile Lys Gly
            325                 330                 335

Tyr Arg Ile Asp Lys Ser Gly Lys Ala Glu Ile His Thr Phe Glu Ala
            340                 345                 350

Tyr Arg Lys Met Lys Thr Leu Glu Thr Leu Asp Ile Glu Gln Met Asp
            355                 360                 365

Arg Glu Thr Leu Asp Lys Leu Ala Tyr Val Leu Thr Leu Asn Thr Glu
370                 375                 380

Arg Glu Gly Ile Gln Glu Ala Leu Glu His Glu Phe Ala Asp Gly Ser
385                 390                 395                 400

Phe Ser Gln Lys Gln Val Asp Glu Leu Val Gln Phe Arg Lys Ala Asn
            405                 410                 415

Ser Ser Ile Phe Gly Lys Gly Trp His Asn Phe Ser Val Lys Leu Met
            420                 425                 430

Met Glu Leu Ile Pro Glu Leu Tyr Glu Thr Ser Glu Glu Gln Met Thr
            435                 440                 445

Ile Leu Thr Arg Leu Gly Lys Gln Lys Arg Leu Arg Leu Gln Ile Lys
450                 455                 460

Gln Asn Ile Ser Asn Lys Thr Lys Tyr Ile Asp Glu Lys Leu Leu Thr
465                 470                 475                 480

Glu Glu Ile Tyr Asn Pro Val Val Ala Lys Ser Val Arg Gln Ala Ile
            485                 490                 495

Lys Ile Val Asn Ala Ala Ile Lys Glu Tyr Gly Asp Phe Asp Asn Ile
            500                 505                 510

Val Ile Glu Met Ala Arg Glu Thr Asn Glu Asp Asp Glu Lys Lys Ala
            515                 520                 525

Ile Gln Lys Ile Gln Lys Ala Asn Lys Asp Glu Lys Asp Ala Ala Met
530                 535                 540

Leu Lys Ala Ala Asn Gln Tyr Asn Gly Lys Ala Glu Leu Pro His Ser
545                 550                 555                 560

Val Phe His Gly His Lys Gln Leu Ala Thr Lys Ile Arg Leu Trp His
            565                 570                 575

Gln Gln Gly Glu Arg Cys Leu Tyr Thr Gly Lys Thr Ile Ser Ile His
            580                 585                 590

Asp Leu Ile Asn Asn Pro Asn Gln Phe Glu Val Asp His Ile Leu Pro
            595                 600                 605

Leu Ser Ile Thr Phe Asp Asp Ser Leu Ala Asn Lys Val Leu Val Tyr
            610                 615                 620

Ala Thr Ala Asn Gln Glu Lys Gly Gln Arg Thr Pro Tyr Gln Ala Leu
625                 630                 635                 640

Asp Ser Met Asp Asp Ala Trp Ser Phe Arg Glu Leu Lys Ala Phe Val
```

-continued

```
            645                 650                 655
Arg Glu Ser Lys Thr Leu Ser Asn Lys Lys Glu Tyr Leu Leu Thr
                660                 665                 670
Glu Glu Asp Ile Ser Lys Phe Asp Val Arg Lys Lys Phe Ile Glu Arg
            675                 680                 685
Asn Leu Val Asp Thr Arg Tyr Ala Ser Arg Val Val Leu Asn Ala Leu
            690                 695                 700
Gln Glu His Phe Arg Ala His Lys Ile Asp Thr Lys Val Ser Val Val
705                 710                 715                 720
Arg Gly Gln Phe Thr Ser Gln Leu Arg Arg His Trp Gly Ile Glu Lys
                725                 730                 735
Thr Arg Asp Thr Tyr His His His Ala Val Asp Ala Leu Ile Ile Ala
                740                 745                 750
Ala Ser Ser Gln Leu Asn Leu Trp Lys Lys Gln Lys Asn Thr Leu Val
                755                 760                 765
Ser Tyr Ser Glu Glu Gln Leu Leu Asp Ile Glu Thr Gly Glu Leu Ile
            770                 775                 780
Ser Asp Asp Glu Tyr Lys Glu Ser Val Phe Lys Ala Pro Tyr Gln His
785                 790                 795                 800
Phe Val Asp Thr Leu Lys Ser Lys Glu Phe Glu Asp Ser Ile Leu Phe
                805                 810                 815
Ser Tyr Gln Val Asp Ser Lys Phe Asn Arg Lys Ile Ser Asp Ala Thr
                820                 825                 830

<210> SEQ ID NO 267
<211> LENGTH: 826
<212> TYPE: PRT
<213> ORGANISM: Streptococcus thermophilus

<400> SEQUENCE: 267

Met Ser Asp Leu Val Leu Gly Leu Asp Ile Gly Ile Gly Ser Val Gly
1               5                   10                  15
Val Gly Ile Leu Asn Lys Val Thr Gly Glu Ile Ile His Lys Asn Ser
                20                  25                  30
Arg Ile Phe Pro Ala Ala Gln Ala Glu Asn Asn Leu Val Arg Arg Thr
            35                  40                  45
Asn Arg Gln Gly Arg Arg Leu Thr Arg Arg Lys Lys His Arg Arg Val
        50                  55                  60
Arg Leu Asn Arg Leu Phe Glu Glu Ile Gly Leu Ile Thr Asp Phe Thr
65                  70                  75                  80
Lys Ile Ser Ile Asn Leu Asn Pro Tyr Gln Leu Arg Val Lys Gly Leu
                85                  90                  95
Thr Asp Glu Leu Ser Asn Glu Glu Leu Phe Ile Ala Leu Lys Asn Met
            100                 105                 110
Val Lys His Arg Gly Ile Ser Tyr Leu Asp Asp Ala Ser Asp Asp Gly
            115                 120                 125
Asn Ser Ser Val Gly Asp Tyr Ala Gln Ile Val Lys Glu Asn Ser Lys
        130                 135                 140
Gln Leu Glu Thr Lys Thr Pro Gly Gln Ile Gln Leu Glu Arg Tyr Gln
145                 150                 155                 160
Thr Tyr Gly Gln Leu Arg Gly Asp Phe Thr Val Glu Lys Asp Gly Lys
                165                 170                 175
Lys His Arg Leu Ile Asn Val Phe Pro Thr Ser Ala Tyr Arg Ser Glu
            180                 185                 190
```

```
Ala Leu Arg Ile Leu Gln Thr Gln Glu Phe Asn Pro Gln Ile Thr
            195                 200                 205
Asp Glu Phe Ile Asn Arg Tyr Leu Glu Ile Leu Thr Gly Lys Arg Lys
210                 215                 220
Tyr Tyr His Gly Pro Gly Asn Glu Lys Ser Arg Thr Asp Tyr Gly Arg
225                 230                 235                 240
Tyr Arg Thr Ser Gly Glu Thr Leu Asp Asn Ile Phe Gly Ile Leu Ile
                245                 250                 255
Gly Lys Cys Thr Phe Tyr Pro Asp Glu Phe Arg Ala Ala Lys Ala Ser
            260                 265                 270
Tyr Thr Ala Gln Glu Phe Asn Leu Leu Asn Asp Leu Asn Asn Leu Thr
            275                 280                 285
Val Pro Thr Glu Thr Lys Lys Leu Ser Lys Glu Gln Lys Asn Gln Ile
290                 295                 300
Ile Asn Tyr Val Lys Asn Glu Lys Ala Met Gly Pro Ala Lys Leu Phe
305                 310                 315                 320
Lys Tyr Ile Ala Lys Leu Leu Ser Cys Asp Val Ala Asp Ile Lys Gly
                325                 330                 335
Tyr Arg Ile Asp Lys Ser Gly Lys Ala Glu Ile His Thr Phe Glu Ala
                340                 345                 350
Tyr Arg Lys Met Lys Thr Leu Glu Thr Leu Asp Ile Glu Gln Met Asp
            355                 360                 365
Arg Glu Thr Leu Asp Lys Leu Ala Tyr Val Leu Thr Leu Asn Thr Glu
            370                 375                 380
Arg Glu Gly Ile Gln Glu Ala Leu Glu His Glu Phe Ala Asp Gly Ser
385                 390                 395                 400
Phe Ser Gln Lys Gln Val Asp Glu Leu Val Gln Phe Arg Lys Ala Asn
                405                 410                 415
Ser Ser Ile Phe Gly Lys Gly Trp His Asn Phe Ser Val Lys Leu Met
                420                 425                 430
Met Glu Leu Ile Pro Glu Leu Tyr Glu Thr Ser Glu Glu Gln Met Thr
            435                 440                 445
Ile Leu Thr Arg Leu Gly Lys Gln Lys Thr Thr Ser Ser Ser Asn Lys
450                 455                 460
Thr Lys Tyr Ile Asp Glu Lys Leu Leu Thr Glu Glu Ile Tyr Asn Pro
465                 470                 475                 480
Val Val Ala Lys Ser Val Arg Gln Ala Ile Lys Ile Val Asn Ala Ala
                485                 490                 495
Ile Lys Glu Tyr Gly Asp Phe Asp Asn Ile Val Ile Glu Met Ala Arg
            500                 505                 510
Glu Thr Asn Glu Asp Asp Glu Lys Lys Ala Ile Gln Lys Ile Gln Lys
            515                 520                 525
Ala Asn Lys Asp Glu Lys Asp Ala Ala Met Leu Lys Ala Ala Asn Gln
            530                 535                 540
Tyr Asn Gly Lys Ala Glu Leu Pro His Ser Val Phe His Gly His Lys
545                 550                 555                 560
Gln Leu Ala Thr Lys Ile Arg Leu Trp His Gln Gly Glu Arg Cys
                565                 570                 575
Leu Tyr Thr Gly Lys Thr Ile Ser Ile His Asp Leu Ile Asn Asn Pro
                580                 585                 590
Asn Gln Phe Glu Val Asp His Ile Leu Pro Leu Ser Ile Thr Phe Asp
            595                 600                 605
Asp Ser Leu Ala Asn Lys Val Leu Val Tyr Ala Thr Ala Asn Gln Glu
```

```
              610                 615                 620
Lys Gly Gln Arg Thr Pro Tyr Gln Ala Leu Asp Ser Met Asp Asp Ala
625                 630                 635                 640

Trp Ser Phe Arg Glu Leu Lys Ala Phe Val Arg Glu Ser Lys Thr Leu
                    645                 650                 655

Ser Asn Lys Lys Lys Glu Tyr Leu Leu Thr Glu Glu Asp Ile Ser Lys
                660                 665                 670

Phe Asp Val Arg Lys Lys Phe Ile Glu Arg Asn Leu Val Asp Thr Arg
                675                 680                 685

Tyr Ala Ser Arg Val Val Leu Asn Ala Leu Gln Glu His Phe Arg Ala
            690                 695                 700

His Lys Ile Asp Thr Lys Val Ser Val Val Arg Gly Gln Phe Thr Ser
705                 710                 715                 720

Gln Leu Arg Arg His Trp Gly Ile Glu Lys Thr Arg Asp Thr Tyr His
                725                 730                 735

His His Ala Val Asp Ala Leu Ile Ile Ala Ala Ser Ser Gln Leu Asn
                740                 745                 750

Leu Trp Lys Lys Gln Lys Asn Thr Leu Val Ser Tyr Ser Glu Asp Gln
            755                 760                 765

Leu Leu Asp Ile Glu Thr Gly Glu Leu Ile Ser Asp Asp Glu Tyr Lys
            770                 775                 780

Glu Ser Val Phe Lys Ala Pro Tyr Gln His Phe Val Asp Thr Leu Lys
785                 790                 795                 800

Ser Lys Glu Phe Glu Asp Ser Ile Leu Phe Ser Tyr Gln Val Asp Ser
                805                 810                 815

Lys Phe Asn Arg Lys Ile Ser Asp Ala Thr
                820                 825

<210> SEQ ID NO 268
<211> LENGTH: 20
<212> TYPE: RNA
<213> ORGANISM: Artificial Sequence
<220> FEATURE:
<223> OTHER INFORMATION: CRISPR nuclease recognition sequence

<400> SEQUENCE: 268
uaauuucuac ucuuguagau                                           20
```